US011739321B2

(12) United States Patent
Eberwine et al.

(10) Patent No.: US 11,739,321 B2
(45) Date of Patent: Aug. 29, 2023

(54) COMPOSITIONS AND METHODS FOR GENOMIC DNA AND GENE EXPRESSION ANALYSIS IN SINGLE CELLS

(71) Applicants: Agilent Technologies, Inc., Santa Clara, CA (US); The Trustees of the University of Pennsylvania, Philadelphia, PA (US)

(72) Inventors: James Eberwine, Philadelphia, PA (US); Jae-Hee Lee, Philadelphia, PA (US); Jifen Li, Philadelphia, PA (US); Stephen Fisher, Philadelphia, PA (US); Youtao Lu, Philadelphia, PA (US); Junhyong Kim, Philadelphia, PA (US); Jai-Yoon Sul, Philadelphia, PA (US); Jinchun Wang, Santa Clara, CA (US); Mimi Healy, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 395 days.

(21) Appl. No.: 16/736,085

(22) Filed: Jan. 7, 2020

(65) Prior Publication Data
US 2020/0216841 A1 Jul. 9, 2020

Related U.S. Application Data

(60) Provisional application No. 62/898,824, filed on Sep. 11, 2019, provisional application No. 62/789,073, filed on Jan. 7, 2019.

(51) Int. Cl.
*C12Q 1/6816* (2018.01)
*C12N 15/11* (2006.01)
*C07H 19/10* (2006.01)
*C07H 21/02* (2006.01)
*C07H 21/04* (2006.01)

(52) U.S. Cl.
CPC ............ *C12N 15/11* (2013.01); *C07H 19/10* (2013.01); *C12Q 1/6816* (2013.01); *C07H 21/02* (2013.01); *C07H 21/04* (2013.01); *C12Y 207/07006* (2013.01); *C12Y 207/07007* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 4,873,192 A | 10/1989 | Kunkel | |
| 6,713,294 B1 | 3/2004 | Krokan et al. | |
| 7,195,874 B2 | 3/2007 | Rothschild et al. | |
| 7,211,394 B2 | 5/2007 | Rothschild et al. | |
| 7,435,572 B2 | 10/2008 | Bitinaite | |
| 7,893,227 B2 | 2/2011 | Wu et al. | |
| 7,897,737 B2 | 3/2011 | Wu et al. | |
| 7,964,352 B2 | 6/2011 | Wu et al. | |
| 8,148,503 B2 | 4/2012 | Litosh et al. | |
| 8,198,029 B2 | 6/2012 | Wu et al. | |
| 8,361,727 B2 | 1/2013 | Wu et al. | |
| 8,497,360 B2 | 7/2013 | Litosh et al. | |
| 8,877,905 B2 | 11/2014 | Litosh et al. | |
| 8,889,860 B2 | 11/2014 | Stupi et al. | |
| 8,969,535 B2 | 3/2015 | Wu et al. | |
| 9,200,319 B2 | 12/2015 | Litosh et al. | |
| 9,383,371 B2 | 7/2016 | Lee et al. | |
| 9,399,798 B2 | 7/2016 | Stupi et al. | |
| 9,689,035 B2 | 6/2017 | Stupi et al. | |
| 10,041,115 B2 | 8/2018 | Stupi et al. | |
| 2005/0017191 A1 | 1/2005 | Montagu et al. | |
| 2008/0132692 A1 | 6/2008 | Wu et al. | |
| 2008/0299637 A1 | 12/2008 | Gee et al. | |
| 2009/0203023 A1 | 8/2009 | Johnson | |
| 2011/0311963 A1 | 12/2011 | Lafferty et al. | |
| 2011/0311966 A1 | 12/2011 | Hennig et al. | |
| 2013/0095471 A1 | 4/2013 | Wu et al. | |
| 2014/0120532 A1 | 5/2014 | Lee et al. | |
| 2015/0051088 A1 | 2/2015 | Kim et al. | |
| 2017/0052175 A1 | 2/2017 | Healy et al. | |
| 2019/0127790 A1 | 5/2019 | Stupi et al. | |

FOREIGN PATENT DOCUMENTS

| | | |
|---|---|---|
| CN | 101330931 A | 12/2008 |
| CN | 102230895 | 11/2011 |
| EP | 2728359 | 5/2014 |
| WO | WO 2003/006625 | 1/2003 |
| WO | WO 2005/084367 | 9/2005 |
| WO | WO 2008/070749 | 6/2008 |
| WO | WO 2009/152353 | 12/2009 |

(Continued)

OTHER PUBLICATIONS

Agasti et al., "Photocleavable DNA Barcode—Antibody Conjugates Allow Sensitive and Multiplexed Protein Analysis in Single Cells," *J. Am. Chem. Soc.*, 134:18499-18502, 2012.
Aoki et al., "Design and synthesis of a photocleavable biotin-linker for the photoisolation of ligand-receptor complexes based on the photolysis of 8-quinolinyl sulfonates in aqueous solution," *Bioord. Med. Chem.*, 17:3405-13, 2009.
Bai et al., "Design and synthesis of a photocleavable biotinylated nucleotide for DNA analysis by mass spectrometry," *Nuc. Acids Res.*, 32:535-41, 2004.
Barnes et al., "Crystal Structure of a Transcribing RNA Polymerase II Complex Reveals a Complete Transcription Bubble," *Mol. Cell*, 59:258-269, 2015.

(Continued)

*Primary Examiner* — Samuel C Woolwine

(57) ABSTRACT

Provided herein are compositions and methods to assess the genomic landscape of fixed cells using light activated oligonucleotides that can be directed to the nucleus, mitochondria, or cytoplasm of fixed cells and that, upon activation, can be extended for in situ copying of nuclear single-stranded DNA (i.e., open chromatin), open mitochondrial DNA, and/or cytoplasmic RNA into barcoded complementary DNA. These methods also provide for gene specific 3D chromatin structural niche analysis.

24 Claims, 47 Drawing Sheets
(34 of 47 Drawing Sheet(s) Filed in Color)
Specification includes a Sequence Listing.

(56) References Cited

FOREIGN PATENT DOCUMENTS

| WO | WO 2013/040257 | 3/2013 |
|---|---|---|
| WO | WO 2016/161177 | 10/2016 |
| WO | WO 2017/024298 | 2/2017 |
| WO | WO 2018/103025 | 6/2018 |
| WO | WO 2018/183538 | 10/2018 |

OTHER PUBLICATIONS

Berton et al., "Essential role of BDNF in the mesolimbic dopamine pathway in social defeat stress," *Science*, 311:864-868, 2006.

Bieberstein et al., "First exon length controls active chromatin signatures and transcription," *Cell Rep.*, 2:62-68, 2012.

Bjursell et al., "Long regions of single-stranded DNA in human cells," *Nature*, 280:420-423, 1979.

Borrelli et al., "Decoding the epigenetic language of neuronal plasticity," *Neuron*, 60:961-974, 2008.

Boyle et al., "High-resolution mapping and characterization of open chromatin across the genome," *Cell*, 132:311-322, 2008.

Buchhalter and Dichter, "Electrophysiological comparison of pyramidal and stellate nonpyramidal neurons in dissociated cell culture of rat hippocampus," Brain Res. Bull., 26:333-338, 1991.

Buenrostro et al., "Single-cell chromatin accessibility reveals principles of regulatory variation," *Nature*, 523:486-490, 2015.

Buenrostro et al., "Transposition of native chromatin for fast and sensitive epigenomic profiling of open chromatin, DNA-binding proteins and nucleosome position," *Nat. Methods*, 10:1213-1218, 2013.

Chen et al., "Double staining immunohistochemistry," *N. Am. J. Med. Sci.*, 2:241-245, 2010.

Chen et al., "Variant GADL1 and response to lithium therapy in bipolar I disorder," *N. Engl. J. Med.*, 370:119-128, 2014.

Choi et al., "Mapping a multiplexed zoo of mRNA expression," *Development*, 143:3632-3637, 2016.

Choi et al., "Programmable in situ amplification for multiplexed imaging of mRNA expression," *Nat. Biotechnol.*, 28:1208-1212, 2010.

Clark et al., "scNMT-seq enables joint profiling of chromatin accessibility DNA methylation and transcription in single cells," *Nat. Commun.*, 9:781, 2018.

Core et al., "Analysis of nascent RNA identifies a unified architecture of initiation regions at mammalian promoters and enhancers," *Nat. Genet.*, 46:1311-1320, 2014.

Cornelison and Wold, "Single-cell analysis of regulatory gene expression in quiescent and activated mouse skeletal muscle satellite cells," *Developmental Biology*, 191:270-283, 1997.

Costa et al., "Epigenetic targets in GABAergic neurons to treat schizophrenia," *Adv. Pharmacol.*, 54:95-117, 2006.

Crino et al., "Embryonic neuronal markers in tuberous sclerosis: single-cell molecular pathology," *Proc. Natl. Acad. Sci. U.S.A.*, 93:14152-14157, 1996.

Cusanovich et al., "Multiplex single cell profiling of chromatin accessibility by combinatorial cellular indexing," *Science*, 348:910-914, 2015.

Danko et al., "Identification of active transcriptional regulatory elements from GRO-seq data," *Nat. Methods*, 12:433-438, 2015.

De la Torre-Ubieta and Bonni, "Transcriptional regulation of neuronal polarity and morphogenesis in the mammalian brain," *Neuron*, 72:22-40, 2011.

De Wit and de Laat, "A decade of 3C technologies: insights into nuclear organization," *Genes Dev.*, 26:11-24, 2012.

Dekker et al., "Exploring the three-dimensional organization of genomes: interpreting chromatin interaction data," *Nat. Rev. Genet.*, 14:390-403, 2013.

Deng et al., "An integrated microfluidic chip system for single-cell secretion profiling of rare circulating tumor cells," *Scientific Reports*, 4:7499, 2014.

Dueck et al., "Deep sequencing reveals cell-type-specific patterns of single-cell transcriptome variation," *Genome Biol.*, 16:122, 2015.

Dueck et al., "Variation is function: Are single cell differences functionally important?: Testing the hypothesis that single cell variation is required for aggregate function," *Bioessays*, 38:172-180, 2016.

Duman, "Remodeling chromatin and synapses in depression," *Nat. Med.*, 19:267, 2013.

Duncan, "DNA glycosylases," In *The enzymes*, 3$^{rd}$ edition, part A (ed. P. Boyer), pp. 565-586, Academic Press, New York, 1981.

Eberwine et al., "Analysis of gene expression in single live neurons," *Proc. Natl. Acad. Sci. U.S.A.*, 89:3010-3014, 1992.

Eberwine et al., "Complementary DNA synthesis in situ: methods and applications," *Methods Enzymol.*, 216:80-100, 1992.

Ellis et al., "Transcriptome analysis of cortical tissue reveals shared sets of downregulated genes in autism and schizophrenia," *Transl. Psychiatry*, 6:e817, 2016.

Eng et al., "Glial fibrillary acidic protein: GFAP-thirty-one years (1969-2000)," *Neurochem. Res.*, 25:1439-1451, 2000.

Feng et al., "Identifying ChIP-seq enrichment using MACS, "*Nat. Protoc.*, 7:1728-1740, 2012.

Fishilevich et al., "GeneHancer: genome-wide integration of enhancers and target genes in GeneCards," Database (Oxford), 2017:bax028, 2017.

Fleischer et al., "Identification and characterization of three new components of the mSin3A corepressor complex," *Mol. Cell Biol.*, 23:3456-3467, 2003.

Frankie et al., "The synaptic hypothesis of schizophrenia," *Neuron*, 39:205-216, 2003.

Fullard et al., "Open chromatin profiling of human postmortem brain infers functional roles for non-coding schizophrenia loci," *Hum. Mol. Genet.*, 26:1942-1951, 2017.

Ghabriel et al., "Immunological targeting of the endothelial barrier antigen (EBA) in vivo leads to opening of the blood-brain barrier," *Brain Res.*, 878:127-135, 2000.

Gribble et al., "Cytogenetics of the chronic myeloid leukemia-derived cell line K562: karyotype clarification by multicolor fluorescence in situ hybridization, comparative genomic hybridization, and locus-specific fluorescence in situ hybridization," *Cancer Genet. Cytogenet.*, 118:1-8, 2000.

Guidotti et al., "Epigenetic GABAergic targets in schizophrenia and bipolar disorder," *Neuropharmacology*, 60:1007-1016, 2011.

Hashimshony et al., "CEL-Seq: single-cell RNA-Seq by multiplexed linear amplification," *Cell Rep.*, 2:666-673, 2012.

Hayles et al., "A genome-wide resource of cell cycle and cell shape genes of fission yeast," *Open Biol.*, 3: 130053, 2013.

Hegedus et al., "Endogenous single-strand DNA breaks at RNA polymerase II promoters in *Saccharomyces cerevisiae,*" *Nucleic Acids Res.*, 46:10649-10668, 2018.

Heinz et al., "Simple combinations of lineage-determining transcription factors prime cis-regulatory elements required for macrophage and B cell identities," *Mol. Cell.*, 38:576-589, 2010.

Heller et al., "Locus-specific epigenetic remodeling controls addiction- and depression-related behaviors," *Nat. Neurosci.*, 17:1720-1727, 2014.

Houser et al., "Immunocytochemical localization of choline acetyltransferase in rat cerebral cortex: a study of cholinergic neurons and synapses," *J. Comp. Neurol.*, 234:17-34, 1985.

Huang and Akbarian, "GAD1 mRNA expression and DNA methylation in prefrontal cortex of subjects with schizophrenia," *PLoS One*, 2:e809, 2007.

Huang et al., "A biotin label-based antibody array for high-content profiling of protein expression," *Cancer Genomics Proteomics*, 7:129-41, 2010.

Insel and Wang, "Rethinking mental illness," *JAMA*, 303:1970-1971, 2010.

Islam et al., "Characterization of the single-cell transcriptional landscape by highly multiplex RNA-seq," *Genome Res.*, 21:1160-1167, 2011.

Islam et al., "Highly multiplexed and strand-specific single-cell RNA 5' end sequencing," *Nat. Protoc.*, 7:813-828, 2012.

Izant and McIntosh, "Microtubule-associated proteins: a monoclonal antibody to MAP2 binds to differentiated neurons," *Proc. Natl. Acad. Sci. U.S.A.*, 77:4741-4745, 1980.

(56) References Cited

OTHER PUBLICATIONS

Kent et al., "The human genome browser at UCSC," *Genome Res.*, 12:996-1006, 2002.
Khan and Zhang, "dbSUPER: a database of super-enhancers in mouse and human genome," *Nucleic Acids Res.*, 44:D164-171, 2016.
Kim & Eberwine, "RNA: state memory and mediator of cellular phenotype," *Trends Cell Biol.*, 20:311-318, 2010.
Kolovos et al., "Targeted Chromatin Capture (T2C): a novel high resolution high throughput method to detect genomic interactions and regulatory elements," *Epigenetics Chromatin*, 7:10, 2014.
Kouzine et al., "Permanganate/S1 Nuclease Footprinting Reveals Non-B DNA Structures with Regulatory Potential across a Mammalian Genome," *Cell Syst.*, 4:344-356 e347, 2017.
Kozlenkov et al., "Differences in DNA methylation between human neuronal and glial cells are concentrated in enhancers andnon-CpG sites," *Nucleic Acids Res.*, 42:109-127, 2014.
Kozlenkov et al., "Substantial DNA methylation differences between two major neuronal subtypes in human brain," *Nucleic Acids Res.*, 44:2593-2612, 2016.
Kucej et al., "Mitochondrial nucleoids undergo remodeling in response to metabolic cues," *J. Cell Sci.*, 121:1861-1868, 2008.
Kumar et al., "Chromatin remodeling is a key mechanism underlying cocaine-induced plasticity in striatum," *Neuron*, 48:303-314, 2005.
Lai et al., "Integrator mediates the biogenesis of enhancer RNAs," *Nature*, 525:399-403, 2015.
Lee et al., "Fluorescent in situ sequencing (FISSEQ) of RNA for gene expression profiling in intact cells and tissues," *Nat. Protoc.*, 10:442-458, 2015.
Lladser et al., "RNA Pol II transcription model and interpretation of GRO-seq data," *J. Math Biol.*, 74:77-97, 2017.
Louder et al., "Structure of promoter-bound TFIID and model of human pre-initiation complex assembly," *Nature*, 531:604-609, 2016.
Marom et al., "mtDNA Chromatin-like Organization Is Gradually Established during Mammalian Embryogenesis," *iScience*, 12:141-151, 2019.
Martinowich et al., "DNA methylation-related chromatin remodeling in activity-dependent BDNF gene regulation," *Science*, 302:890-893, 2003.
Maurano et al., "Systematic localization of common disease-associated variation in regulatory DNA," *Science*, 337:1190-1195, 2012.
McCarthy et al., "De novo mutations in schizophrenia implicate chromatin remodeling and support a genetic overlap with autism and intellectual disability," *Mol. Psychiatry*, 19:652-658, 2014.
Miyashiro and Eberwine, "Identification of RNA cargoes by antibody-positioned RNA amplification," *Cold Spring Harb. Protoc.*, 2015:434-441, 2015.
Miyashiro et al., "On the nature and differential distribution of mRNAs in hippocampal neurites: implications for neuronal functioning," *Proc. Natl. Acad. Sci. USA*, 91:10800-10804, 1994.
Miyashiro et al., "RNA cargoes associating with FMRP reveal deficits in cellular functioning in Fmr1 null mice," *Neuron*, 37:417-431, 2003.
Mo et al., "Epigenomic Signatures of Neuronal Diversity in the Mammalian Brain," *Neuron*, 86:1369-1384, 2015.
Moffitt & Zhuang, "RNA Imaging with Multiplexed Error-Robust Fluorescence In Situ Hybridization (MERFISH)," *Methods Enzymol.*, 572:1-49, 2016.
Montefiori et al., "Reducing mitochondrial reads in ATAC-seq using CRISPR/Cas9," *Sci. Rep.*, 7:2451, 2017.
Olejnik et al., "Photocleavable biotin derivatives: a versatile approach for the isolation of biomolecules," *Proc. Natl. Acad. Sci. USA*, 92:7590-4, 1995.
PCT International Search Report and Written Opinion issued in International Application No. PCT/US2020/012482, dated Mar. 30, 2020.

Ramos et al., "Photocleavage of peptides and oligodeoxynucleotides carrying 2-nitrobenzyl groups," *Helv. Chim. Acta*, 92:613-622, 2009.
Rao et al., "A 3D map of the human genome at kilobase resolution reveals principles of chromatin looping," *Cell*, 159:1665-1680, 2014.
Renthal et al., "Histone deacetylase 5 epigenetically controls behavioral adaptations to chronic emotional stimuli," *Neuron*, 56:517-529, 2007.
Rotem et al., "Single-cell ChIP-seq reveals cell subpopulations defined by chromatin state," *Nat. Biotechnol.*, 33:1165-1172, 2015.
Roussos et al., "A role for noncoding variation in schizophrenia," *Cell Rep.*, 9:1417-1429, 2014.
Ruzicka et al., "Circuit- and Diagnosis-Specific DNA Methylation Changes at gamma-Aminobutyric Acid-Related Genes in Postmortem Human Hippocampus in Schizophrenia and Bipolar Disorder," *JAMA Psychiatry*, 72:541-551, 2015.
SantaLucia and Hicks, "The thermodynamics of DNA structural motifs," *Annu. Rev. Biophys. Biomol. Struct.*, 3 3:415-440, 2004.
Scheer et al., "High sensitivity immunolocalization of double and single-stranded DNA by a monoclonal antibody," *Eur. J. Cell Biol.*, 43:358-371, 1987.
Seifuddin et al., "Systematic review of genome-wide gene expression studies of bipolar disorder," *BMC Psychiatry*, 13:213, 2013.
Shah et al., "seqFISH Accurately Detects Transcripts in Single Cells and Reveals Robust Spatial Organization in the Hippocampus," *Neuron*, 94:752-758 e1, 2017.
Sharma et al., "Valproic acid and chromatin remodeling in schizophrenia and bipolar disorder: preliminary results from a clinical population," *Schizophr. Res.*, 88:227-231, 2006.
Sherwood et al., "Discovery of directional and nondirectional pioneer transcription factors by modeling DNase profile magnitude and shape," *Nat. Biotechnol.*, 32:171-178, 2014.
Simonis et al., "Nuclear organization of active and inactive chromatin domains uncovered by chromosome conformation capture-on-chip (4C)," *Nat. Genet.*, 38:1348-1354, 2006.
Spaethling et al., "Primary Cell Culture of Live Neurosurgically Resected Aged Adult Human Brain Cells and Single Cell Transcriptomics," *Cell Rep.*, 18:791-803, 2017.
Sun et al., "ACF chromatin-remodeling complex mediates stress-induced depressive-like behavior," *Nat. Med.*, 21:1146-1153, 2015.
Szlachta et al., "Alternative DNA secondary structure formation affects RNA polymerase II promoter-proximal pausing in human," *Genome Biol.*, 19:89, 2018.
Tay et al., "Single-cell NF-kappaB dynamics reveal digital activation and analogue information processing," *Nature*, 466:267-271, 2010.
Tecott et al., "In situ transcription: specific synthesis of complementary DNA in fixed tissue sections," *Science*, 240:1661-1664, 1988.
Thurman et al., "The accessible chromatin landscape of the human genome," *Nature*, 489:75-82, 2012.
Tomaska et al., "Mitochondrial single-stranded DNA-binding proteins: in search for new functions," *Biol. Chem.*, 382:179-186, 2001.
Tsankova et al., "Epigenetic regulation in psychiatric disorders," *Nat. Rev. Neurosci.*, 8:355-367, 2007.
Ullal et al., "Cancer Cell Profiling by Barcoding Allows Multiplexed Protein Analysis in Fine-Needle Aspirates," *Sci. Transl. Med.*, 6:219ra9, 2014.
Valley et al., "Sequential superresolution imaging of multiple targets using a single fluorophore," *PLoS ONE*, 10(4):E0123941, 2015.
Van Gelder et al., "Amplified RNA synthesized from limited quantities of heterogeneous cDNA," *Proc. Natl. Acad. Sci. U.S.A.*, 87:1663-1667, 1990.
Vanhooren et al., "Mammalian peroxisomal acyl-CoA oxidases. I. Molecular characterization of rat pristanoyl-CoA oxidase," *Ann. N. Y. Acad. Sci.*, 804:674-675, 1996.
Varodayan and Harrison, "HSF1 transcriptional activity mediates alcohol induction of Vamp2 expression and GABA release," *Front. Integr. Neurosci.*, 7:89, 2013.

(56) References Cited

OTHER PUBLICATIONS

Vasquez et al., "Manipulating the mammalian genome by homologous recombination," *Proc. Natl. Acad. Sci. U.S.A.*, 98:8403-8410, 2001.
Vialou et al., "Epigenetic mechanisms of depression and antidepressant action," *Annu. Rev. Pharmacol. Toxicol.*, 53:59-87, 2013.
Visel et al., "VISTA Enhancer Browser—a database of tissue-specific human enhancers," *Nucleic Acids Res.*, 35:D88-92, 2007.
Wang et al., "A source of the single-stranded DNA substrate for activation-induced deaminase during somatic hypermutation," *Nat. Commun.*, 5:4137, 2014.
Wei et al., "Functional consequences of bidirectional promoters," *Trends Genet.*, 27:267-276, 2011.
Wirkner et al., "Triggered cell release from materials using bioadhesive photocleavable linkers," *Adv. Mater.*, 23: 3907-10, 2011.
Wu et al., "Quantitative assessment of single-cell RNA-sequencing methods," *Nat. Methods*, 11:41-46, 2014.
Wu et al., "Termination of DNA Synthesis by $N^6$-alkylated, Not 3'-O-alkylated, Photocleavable 2'-deoxyadenosine Triphosphates," *Nucleic Acids Research*, 35(19):6339-6349, 2007.
Xiao et al., "The DNA methylome and transcriptome of different brain regions in schizophrenia and bipolar disorder," *PLoS One*, 9:e95875, 2014.
Xu et al., "Immunochemical characterization of inhibitory mouse cortical neurons: three chemically distinct classes of inhibitory cells," *J. Comp. Neurol.*, 518:389-404, 2010.
Yu et al., "Chromatin dynamics during the differentiation of long-term hematopoietic stem cells to multipotent progenitors," *Blood Adv.*, 1:887-898, 2017.
Zeisel et al., "Molecular Architecture of the Mouse Nervous System," *Cell*, 174:999-1014 e1022, 2018.
Zhang et al., "Increased Variability of Genomic Transcription in Schizophrenia," *Sci. Rep.*, 5:17995, 2015.
Zhao et al., "CrossMap: a versatile tool for coordinate conversion between genome assemblies," *Bioinformatics*, 30:1006-1007, 2014.
Zhou and Paull, "Direct measurement of single-stranded DNA intermediates in mammalian cells by quantitative polymerase chain reaction," *Anal Biochem.*, 479:48-50, 2015.
Zhu et al., "Genome-wide chromatin state transitions associated with developmental and environmental cues," *Cell*, 152:642-654, 2013.
Ziller et al., "Dissecting neural differentiation regulatory networks through epigenetic footprinting," *Nature*, 518:355-359, 2015.
Buenrostro et al., "Transposition of native chromatin for multimodal regulatory analysis and personal epigenomics," PMC author manuscript, PMCID: PMC3959825, published in final edited form as: *Nat. Methods*, 10:1213-1218, 2013.
Danko et al., "Identification of active transcriptional regulatory elements with GRO-seq," PMC author manuscript, PMCID: PMC4507281, published in final edited form as: *Nat. Methods*, 12:433-438, 2015.
Louder et al., "Structure of promoter-bound TFIID and insight into human PIC assembly," PMC author manuscript, PMCID: PMC4856295, published in final edited form as: *Nature*, 531:604-609, 2016.
Sherwood et al., "Discovery of non-directional and directional pioneer transcription factors by modeling DNase profile magnitude and shape," PMC author manuscript, PMCID: PMC3951735, published in final edited from as: *Nat. Biotechnol.*, 32:171-178, 2014.
Tay et al., "Single-cell NF-κB dynamics reveal digital activation and analog information processing in cells," PMC author manuscript, PMCID: PMC3105528, published in final edited from as: *Nature*, 466:267-271, 2010.

FIG. 3B

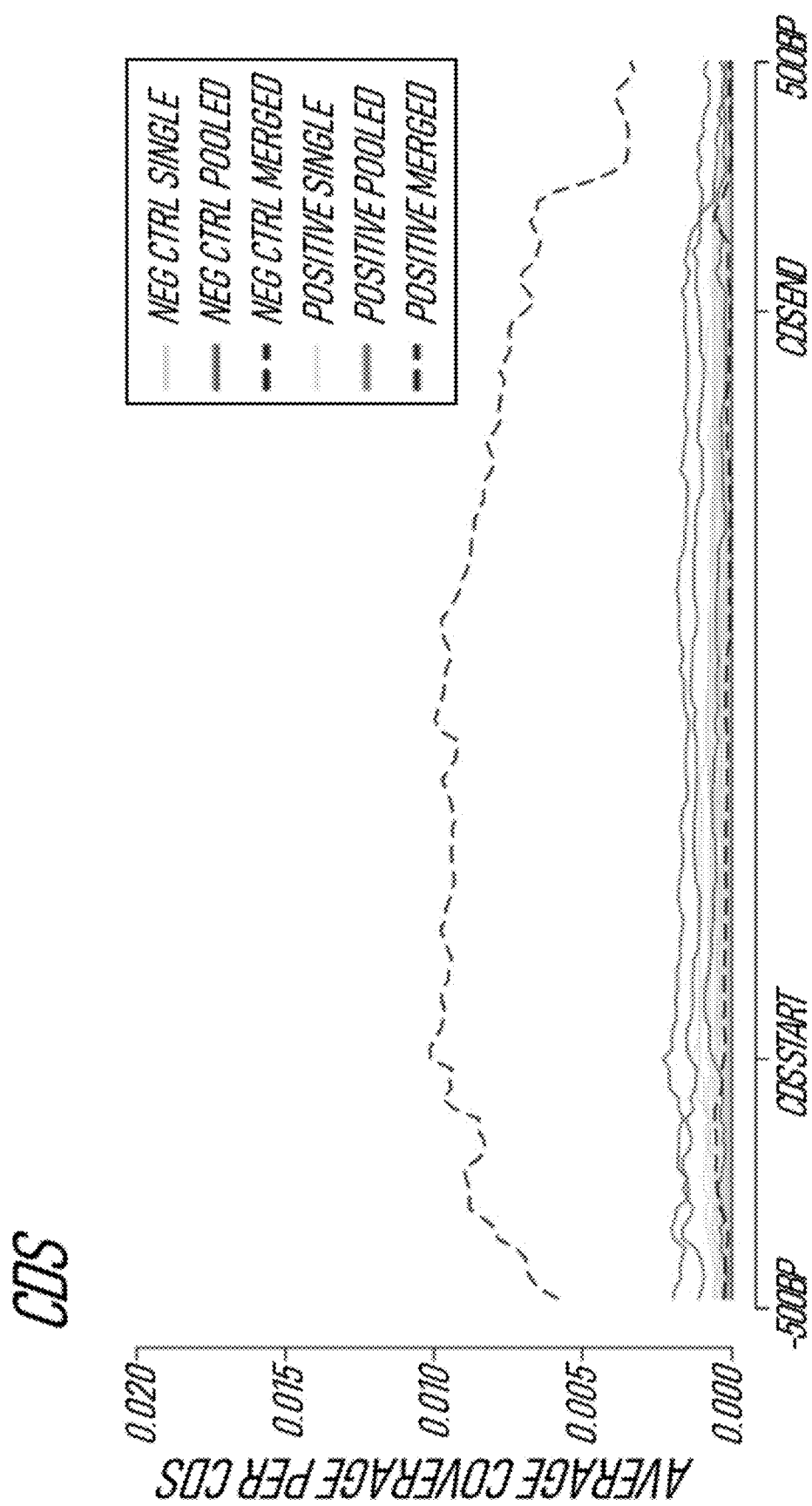
FIG. 10, cont.

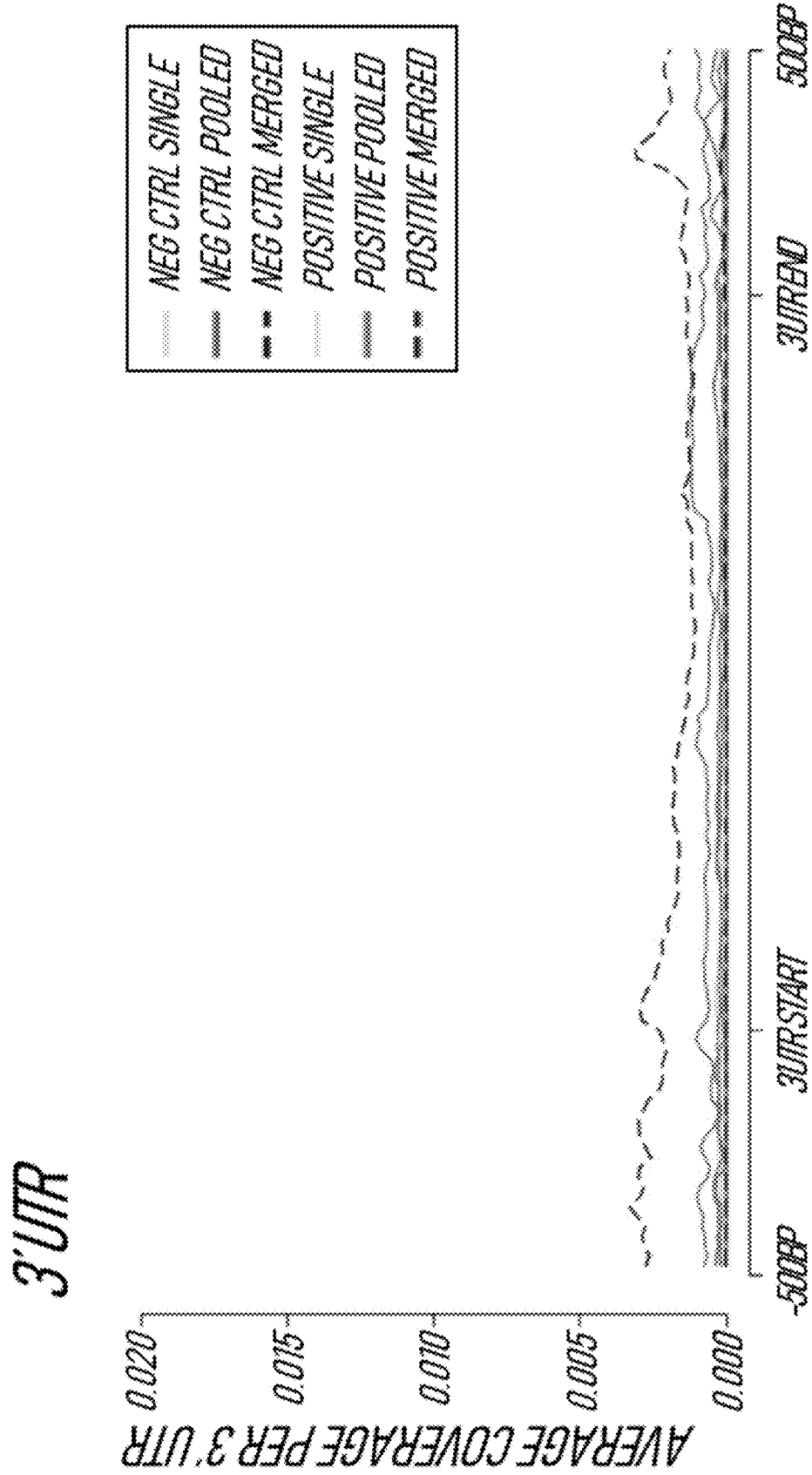
FIG. 10, cont.

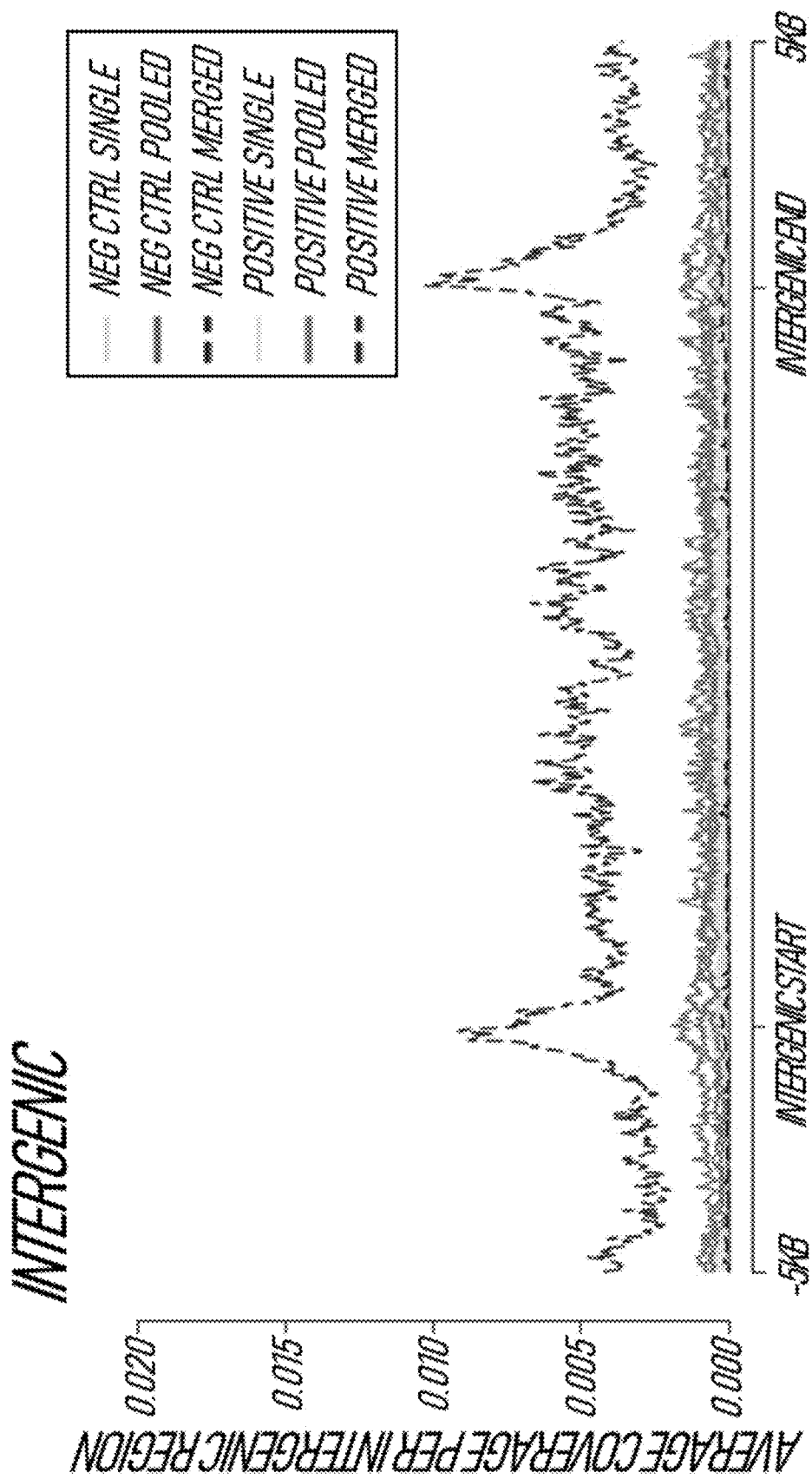
FIG. 10, cont.

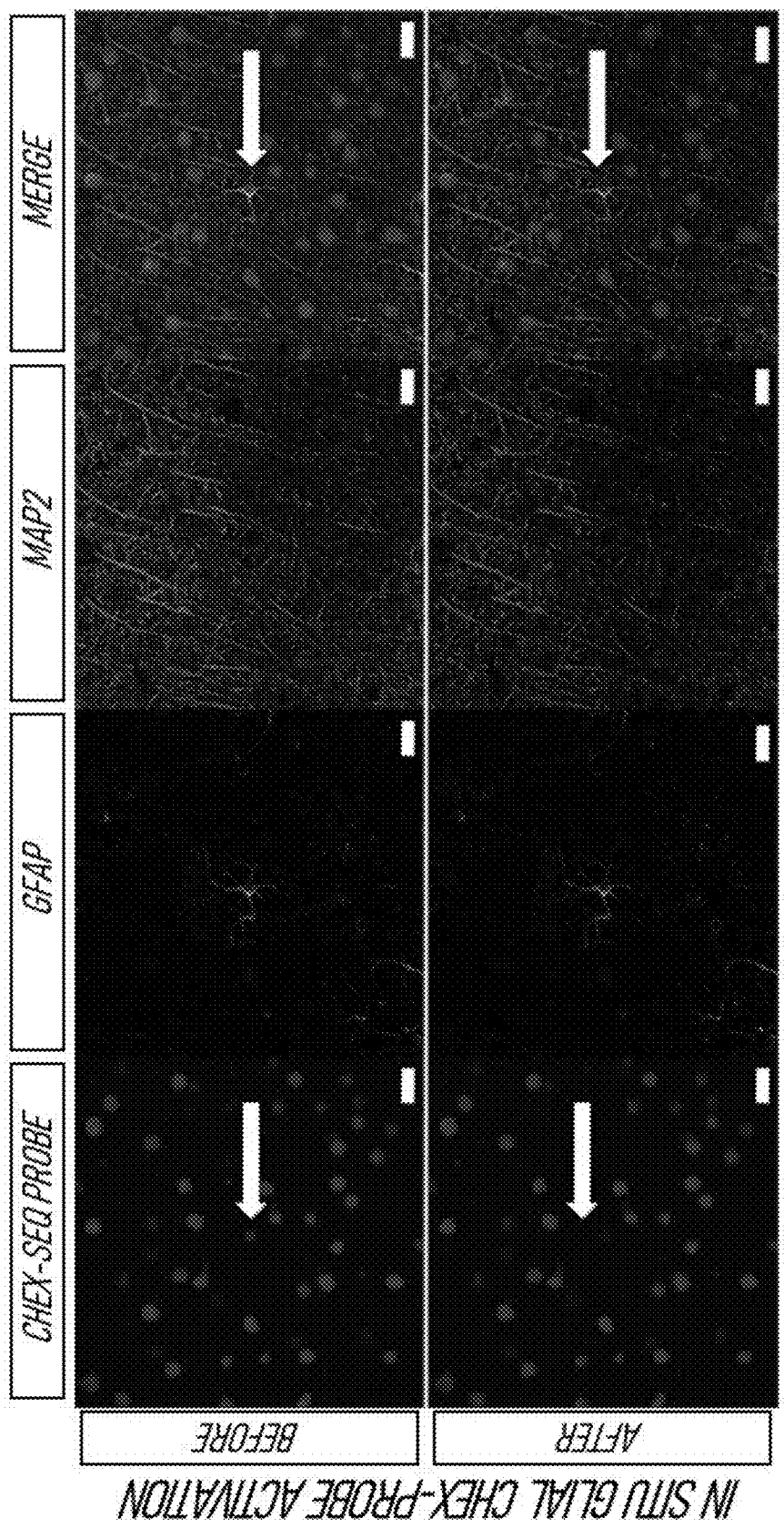
FIG. 11, cont.

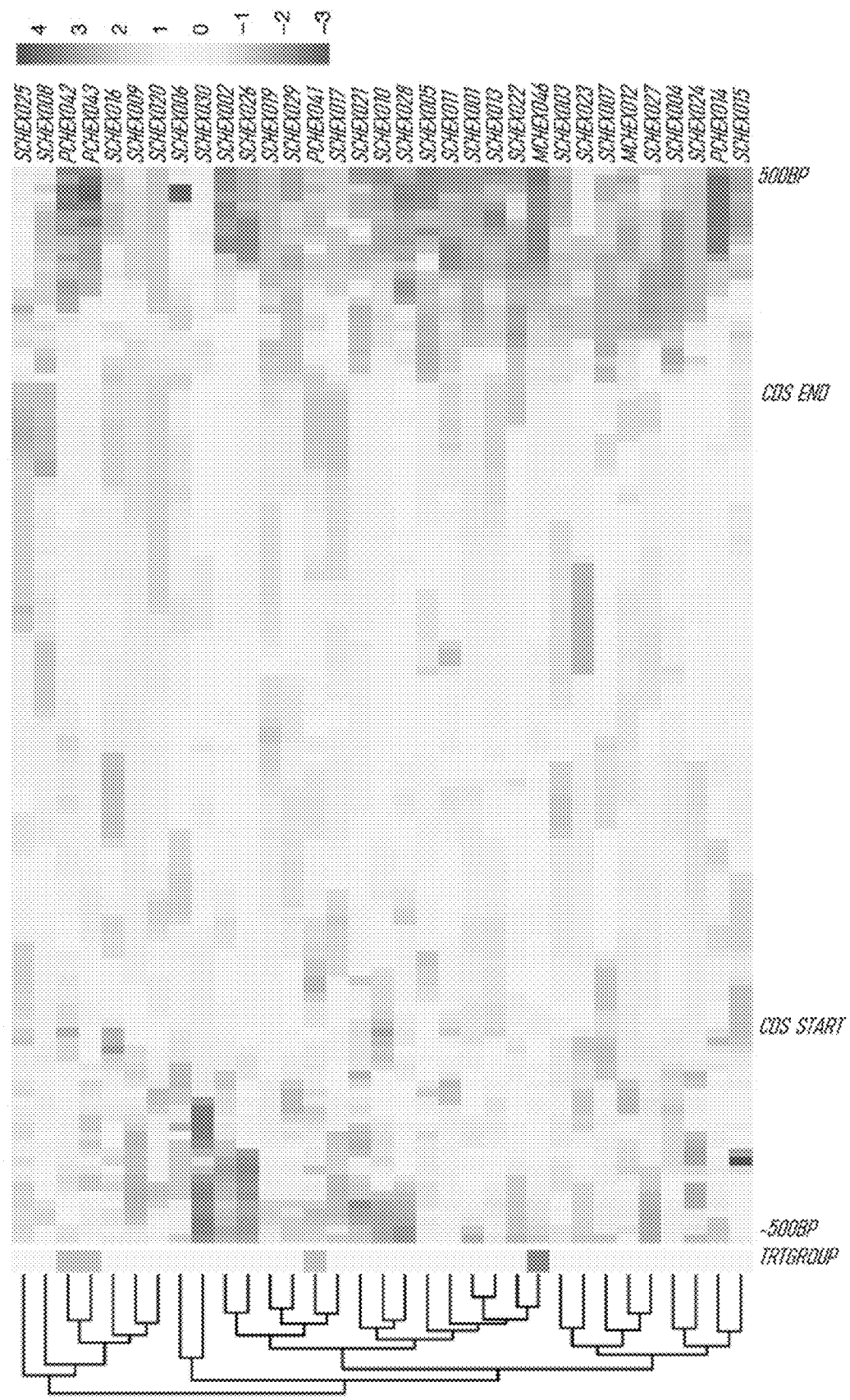
FIG. 13E, cont.

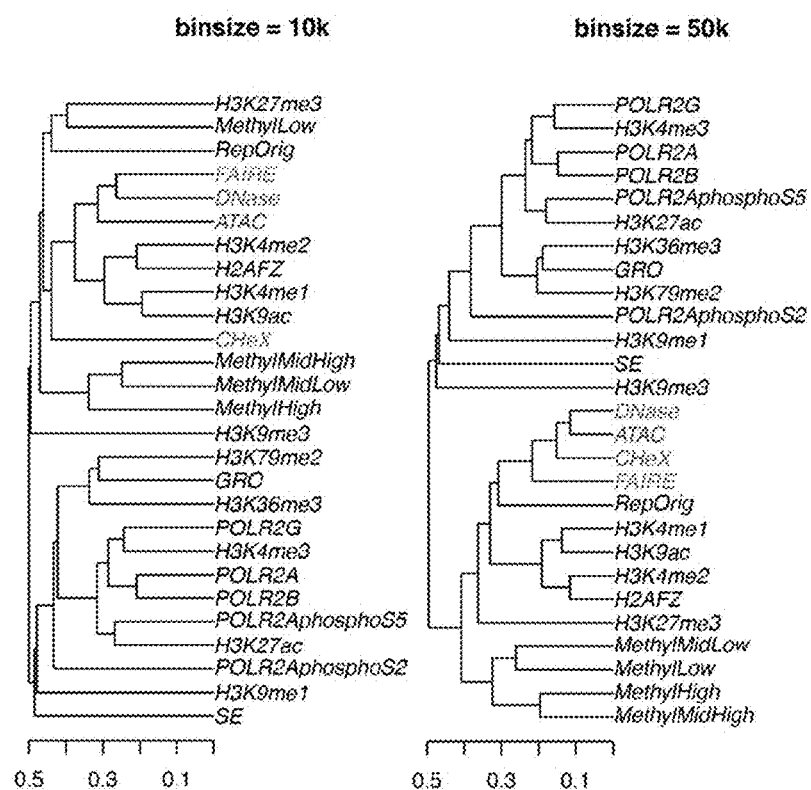
FIG. 14B
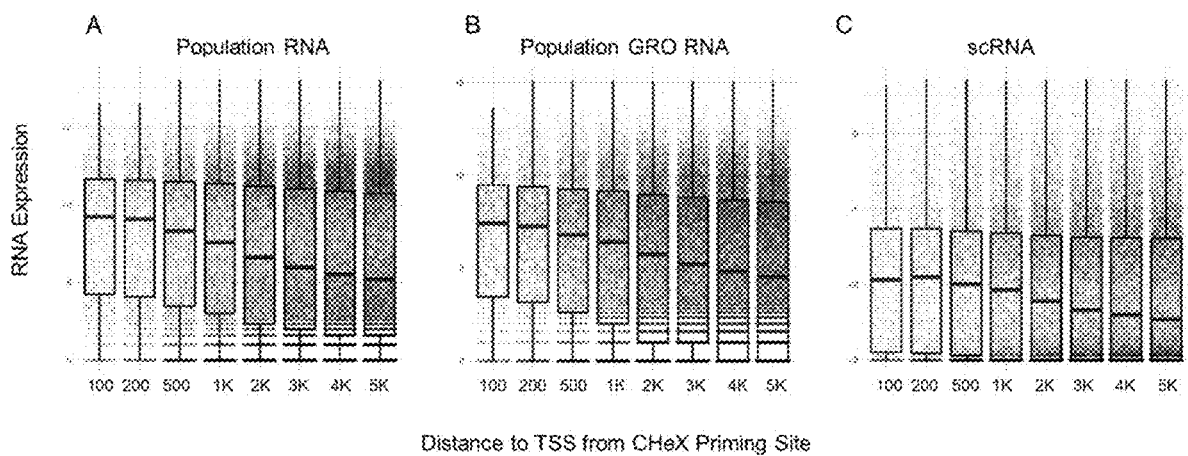
FIGS. 15A-C

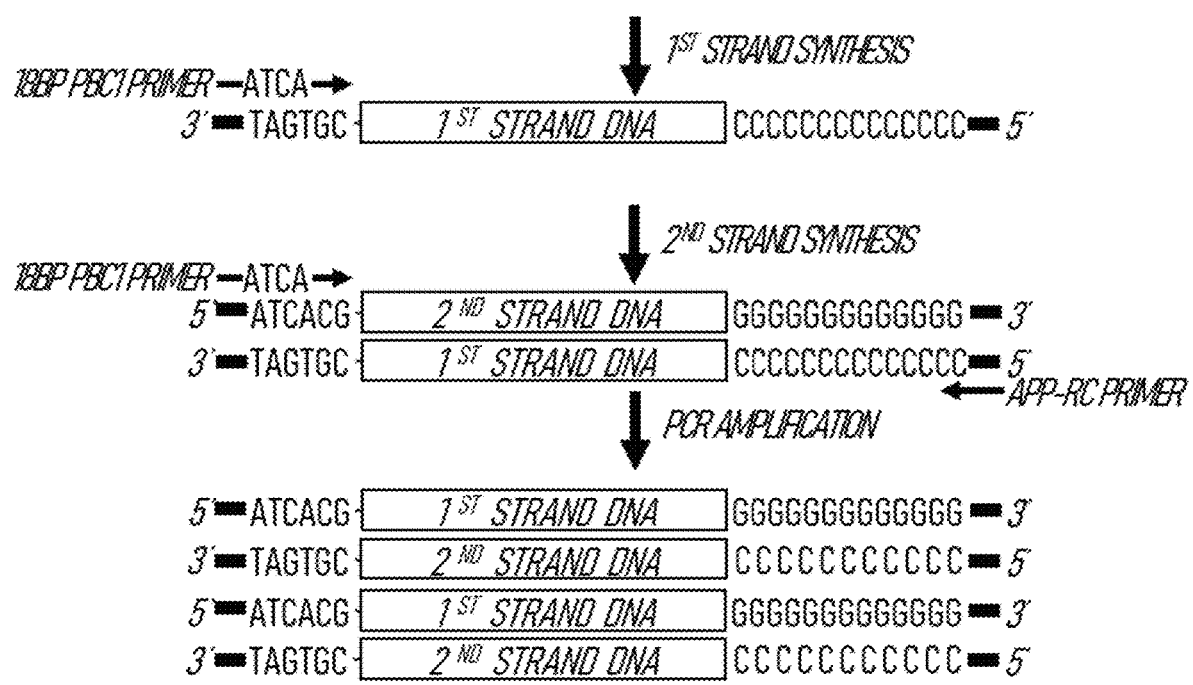
FIG. 19, cont.

continued …

SEQUENCE LISTING

```
<160> NUMBER OF SEQ ID NOS: 19

<210> SEQ ID NO 1
<211> LENGTH: 63
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (45)..(59)
<223> OTHER INFORMATION: n is any nucleotide
<220> FEATURE:
<221> NAME/KEY: misc_feature
<222> LOCATION: (45)..(59)
<223> OTHER INFORMATION: n is a, c, g, or t

<400> SEQUENCE: 1
ggagaattgt aatacgactc actataggga gacgcgtgat cacgnnnnnn nnnnnnnnt      60 gtg                                                                  63
```

```
<210> SEQ ID NO 2
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (45)..(59)
<223> OTHER INFORMATION: n is any nucleotide
<220> FEATURE:
<221> NAME/KEY: misc_feature
<222> LOCATION: (45)..(59)
<223> OTHER INFORMATION: n is a, c, g, or t

<400> SEQUENCE: 2
ggagaattgt aatacgactc actataggga gacgcgtgat cacgnnnnnn nnnnnnnnnt    60

<210> SEQ ID NO 3
<211> LENGTH: 62
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (4)..(18)
<223> OTHER INFORMATION: n is any nucleotide
<220> FEATURE:
<221> NAME/KEY: misc_feature
<222> LOCATION: (4)..(18)
<223> OTHER INFORMATION: n is a, c, g, or t

<400> SEQUENCE: 3
aaannnnnnn nnnnnnnncg tgatcacgcg tctccctata gtgagtcgta ttacaattct    60
cc                                                                  62

<210> SEQ ID NO 4
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 4
ggagaattgt aatacgactc actataggga gacgcgtgat cacgaca                 47

<210> SEQ ID NO 5
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 5
cgtgatcacg cgtctcccta gtgagtcg tattacaatt ctcc                      44

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (8)..(22)
<223> OTHER INFORMATION: n is any nucleotide
<220> FEATURE:
<221> NAME/KEY: misc_feature
<222> LOCATION: (8)..(22)
```

-continued

```
<223> OTHER INFORMATION: n is a, c, g, or t

<400> SEQUENCE: 6
atgaggannn nnnnnnnnnn nnt                                        23

<210> SEQ ID NO 7
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: N_region
<222> LOCATION: (4)..(18)
<223> OTHER INFORMATION: n is any nucleotide
<220> FEATURE:
<221> NAME/KEY: misc_feature
<222> LOCATION: (4)..(18)
<223> OTHER INFORMATION: n is a, c, g, or t

<400> SEQUENCE: 7
aaannnnnnn nnnnnnnntc ctcattgt                                   28

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
tagggagacg cgtgatca                                              18

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 9
tagggagacg cgtgagtt                                              18

<210> SEQ ID NO 10
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 10
gcgccattga ccaggatttt cccccccccc cccc                            34

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gcgccattga ccaggatttt c                                          21

<210> SEQ ID NO 12
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 12
tccttagctg ttgcagaaat                                                  20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
cgttcagttg atgcagagtg                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
agaagcagct tcaaacctgc                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
aagttagctt tacagtgggc                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
ggtgttggtt ctcttaatct                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
atttagttgg ggcatttcac                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ttatggtggg tcatacggta                                                  20
```

```
<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tagtgtaagg agtatgggggg                                              20
```

COMPOSITIONS AND METHODS FOR GENOMIC DNA AND GENE EXPRESSION ANALYSIS IN SINGLE CELLS

REFERENCE TO RELATED APPLICATIONS

The present application claims the priority benefit of U.S. provisional application No. 62/898,824, filed Sep. 11, 2019 and U.S. provisional application No. 62/789,073, filed Jan. 7, 2019, the entire contents of each of which is incorporated herein by reference.

STATEMENT REGARDING FEDERALLY SPONSORED RESEARCH

This invention was made with government support under Grant Nos. U01 MH098953, RM1 HG010023, and R01 MH110185 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Jan. 2, 2020, is named AGLTP0014US_ST25.txt and is 5 kilobytes in size.

BACKGROUND

1. Field

The present disclosure relates generally to methods and compositions for detecting open chromatin and/or RNA in a single cell as well as methods and compositions for detecting the 3D structure of chromatin at targeted locations.

2. Description of Related Art

The spatial arrangement of genes, the structure of chromatin, and the accessibility of regulator DNA elements control expression of the nuclear architecture of a cell (Sherwood et al., 2014). Chromatin structure, in turn, is controlled by epigenetic methylation of DNA, modification of DNA binding proteins, and the dynamics of distal cis- and trans-chromosomal regions. The organization of the genome is complex and dynamic. For example, through changes in chromatin folding, distal enhancers are brought into close proximity to the promoter of regulated genes with various groups estimating that millions of such potential enhancer interactions exist in the genome (Lai et al., 2015). Such chromatin interactions have been mapped for a number of genes mostly using populations of cells in which isolated nuclei are chemically cross-linked to preserve proximal promoter interactions. After cross-linking, the site of interest is often identified using antibodies to transcription factors or modified proteins (such as histones) or simply by PCR for particular sites of interest (Simonis et al., 2006). The analysis of higher-level chromatin structure has been made easier with the development of chromatin mapping procedures (chromosome-conformation-capture), including 3C, 4C, 5C, and HiC (de Wit & de Laat, 2012; Dekker et al., 2013). These procedures use restriction enzyme cutting of the cross-linked chromatin, various PCR amplification strategies, and ligating linkers onto the DNA followed by sequencing of the products. Each of these processes is made less selective by the extensive manipulation of the DNA. It is estimated that using populations of cells HiC captures only 20% to 70% of trans-chromosomal contacts. Further, while HiC is better for analysis of chromosome topology, it is less sensitive primarily due to low efficiency ligation processes.

A recent approach to identifying open chromatin in single cells exploits an assay for transposase-accessible chromatin (ATACseq) (Buenrostro et al., 2013). This methodology uses Tn5 transposase to tag accessible regions of the genome. While used on single cells, single cell ATACseq data is presented as merged data from multiple cells as each transposon insertion provides only for detection of a single allelic region for each transposon prohibiting it from being detected a second time except through summation of multiple cells data. This procedure allows for mapping of some regulatory sites but is reported to miss many previously identified by 3C/4C on larger numbers of cells. Indeed only 9.4% of promoters are represented in an ATAC. Further, the integration of Tn5 into the genome is not completely random, so some sequences will be missed. Finally, ATAC permits analysis on a genome wide scale with little ability to drive gene-specific analysis except through random discovery. To assess such 3D structures on a cellular level, methods are needed to assess the open-conformational status of an individual cell's genome.

SUMMARY

Some embodiments provided herein relate to methods to assess the multimodal genomics landscape of fixed cells using light activated oligonucleotides that can be directed to the nucleus or cytoplasm of fixed cells and that, upon activation, can be extended in situ, thereby copying nuclear single-stranded DNA (open chromatin) and/or cytoplasmic RNA into complementary DNA, such as barcoded complementary DNA. Isolation, amplification, and sequencing of these in situ transcribed cDNAs may provide information as to how RNAs are processed from the transcriptional potential of open genomic DNA to cytoplasmic steady-state RNA abundances in the context of individual cell's interactions with their microenvironment. These methods also provide for gene specific 3D chromatin structural niche analysis, which may be used to identify spatially-defined, biologically relevant, and functional gene-specific enhancers.

In one embodiment, provided are oligonucleotide molecules comprising, from 5' to 3', an amplification segment, a hybridization segment, and a reversibly terminating nucleotide. In some aspects, the amplification segment is an RNA polymerase promoter. In some aspects, the amplification segment is a primer binding site. In some aspects, the amplification segment comprises between about seven and about fifty nucleotides. In some aspects, the hybridization segment comprises a random nucleotide sequence. In some aspects, the hybridization segment comprises a known nucleotide sequence. In certain aspects, the known nucleotide sequence is complementary to a target genomic or mitochondrial DNA sequence. In certain aspects, the known nucleotide sequence is complementary to a target RNA sequence. In some aspects, the hybridization segment comprises a poly-T sequence. In some aspects, the hybridization segment comprises between about seven and about thirty nucleotides. In some aspects, the hybridization segment comprises about fifteen nucleotides. In some aspects, the oligonucleotides further comprise an index barcode segment positioned between the amplification segment and the hybridization segment. In certain aspects, the oligonucleotides further comprise a spacer segment positioned between the amplification segment and the index barcode segment. In some aspects, the reversibly terminating nucleotide comprises a nitrobenzyl group. In some aspects, the reversibly terminating nucleotide comprises a fluorescent label.
In some aspects, the photoactivatable terminating nucleotide comprises a structure of the formula:
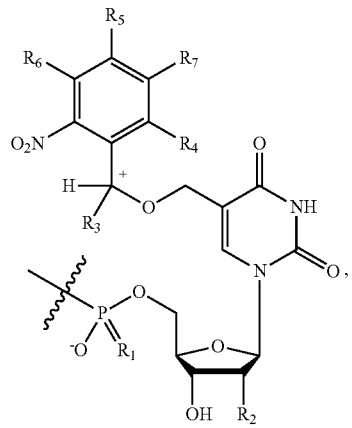
(I)
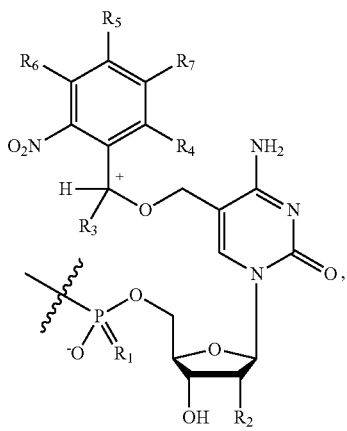
(II)
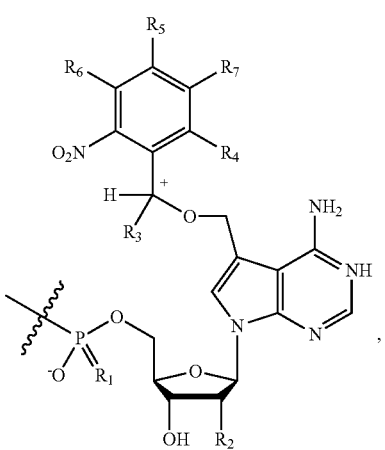
(III)
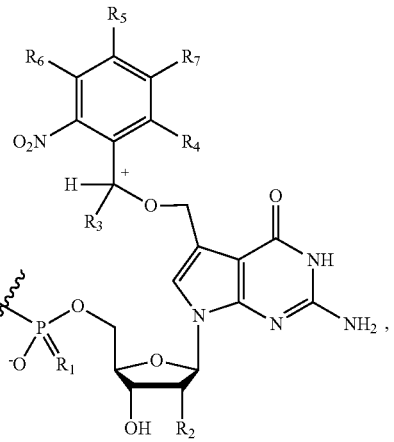
(IV)
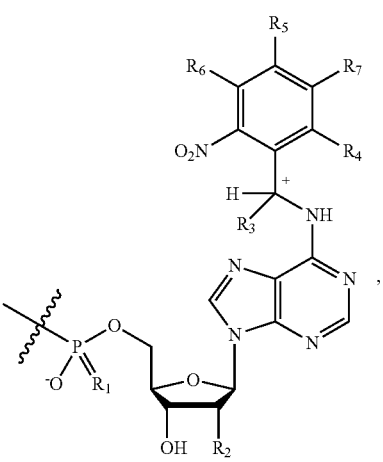
(V)
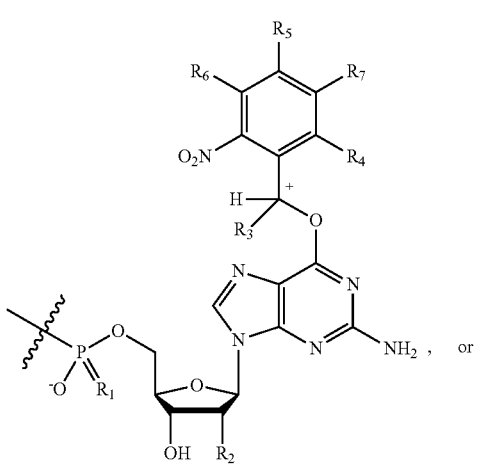
(VI)

-continued

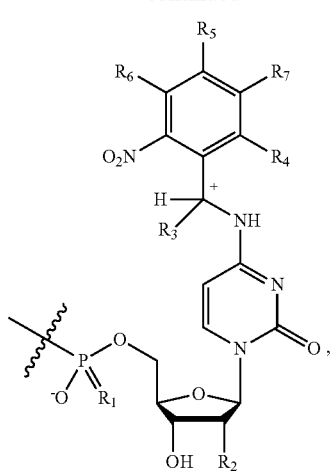

(VII)

wherein:
R₁ is O or S;
R₂ is hydrogen or hydroxy;
R₃ is alkyl$_{(C≤8)}$ or substituted alkyl$_{(C≤8)}$;
R₄ is
  hydrogen, hydroxy, halo, amino, nitro, cyano, azido or mercapto;
  alkyl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
R₅, R₆, and R₇ are each independently:
  hydrogen, hydroxy, halo, amino, nitro, cyano, azido or mercapto;
  alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
  a group of formula:

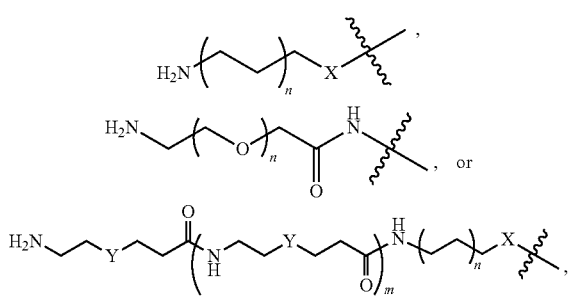

wherein
  X is
    —O—, —S—, or —NH—; or
    alkanediyl$_{(C≤12)}$, alkenediyl$_{(C≤12)}$, alkynediyl$_{(C≤12)}$, or a substituted version of any of these groups;
  Y is —O—, —NH—, alkanediyl$_{(C≤12)}$ or substituted alkane-diyl$_{(C≤12)}$;
  n is an integer from 0-6; and
  m is an integer from 0-6; or
  a -linker-reporter;
or a tautomer or optical isomer thereof.
In some aspects, R₇ is methoxy. In some aspects, the photoactivatable terminating nucleotide comprises a structure of the formula:

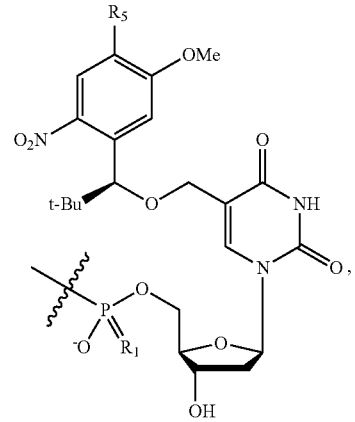

wherein R₅ is a -linker-reporter. In some aspects, the photoactivatable terminating nucleotide comprises a structure of the formula:

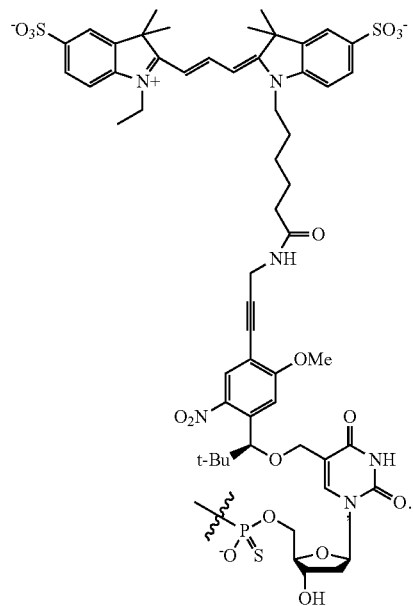

In one embodiment, provided herein are populations of oligonucleotide molecules each comprising, from 5' to 3', an amplification segment, a hybridization segment, and a reversibly terminating nucleotide. In some aspects, the amplification segment is an RNA polymerase promoter. In some aspects, the amplification segment is a primer binding site. In some aspects, the amplification segment comprises between about seven and about fifty nucleotides. In some aspects, the hybridization segments comprise a degenerate nucleotide sequence. In some aspects, each nucleic acid molecule in the population comprises a unique hybridization segment sequence. In some aspects, the hybridization segments comprise one or more known nucleotide sequence. In certain aspects, each known nucleotide sequence is complementary to a target genomic or mitochondrial DNA sequence. In certain aspects, each known nucleotide sequence is complementary to a target RNA sequence. In some aspects, the hybridization segments comprise a poly-T sequence. In some aspects, the hybridization segments comprise between about seven and about thirty nucleotides. In some aspects, the hybridization segments comprise about fifteen nucleotides. In some aspects, the oligonucleotides of the populations further comprise an index barcode segment positioned between the amplification segment and the hybridization segment. In some aspects, the oligonucleotides of the populations further comprise a spacer segment positioned between the RNA polymerase promoter segment and the index barcode segment. In some aspects, the reversibly terminating nucleotide comprises a nitrobenzyl group. In some aspects, the reversibly terminating nucleotide comprises a fluorescent label.

In some aspects, the photoactivatable terminating nucleotide comprises a structure of the formula:

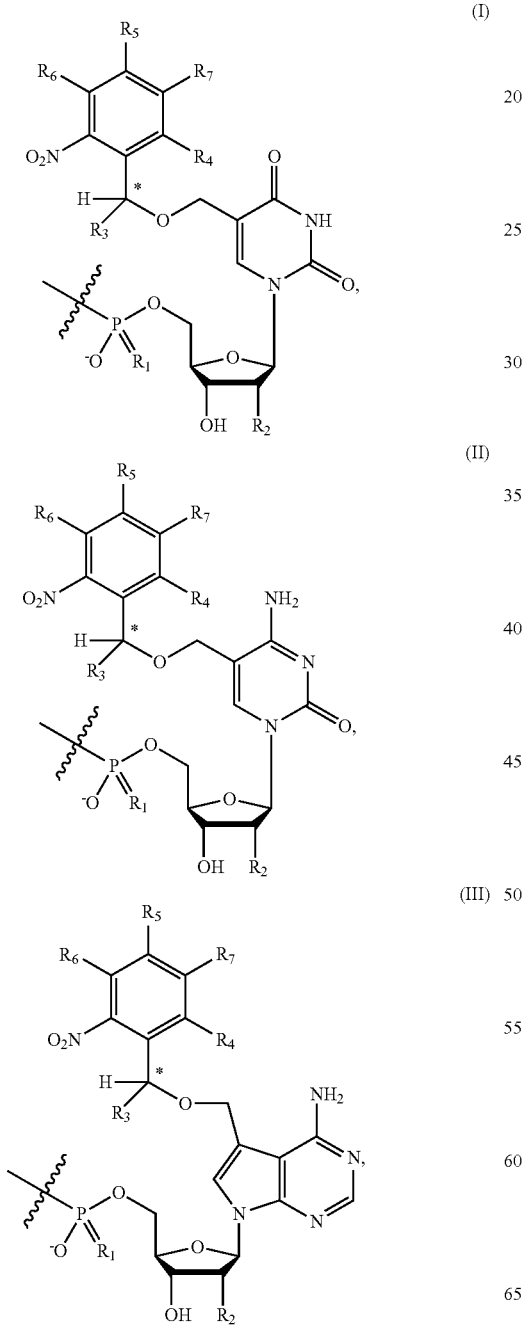

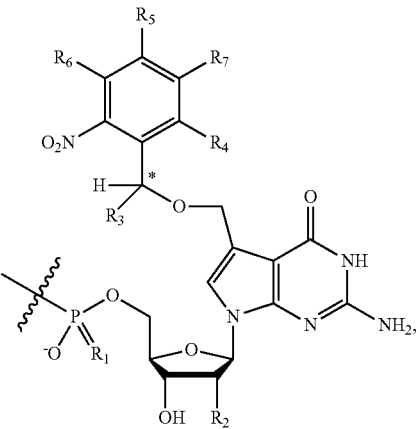

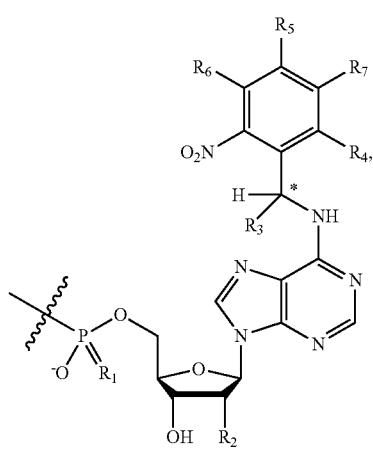

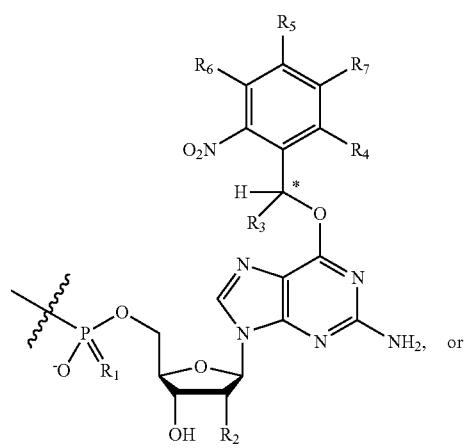

-continued

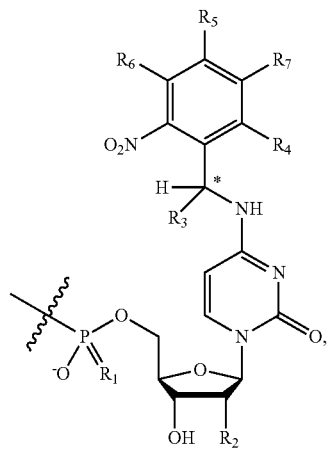
(VII)

wherein:
R₁ is O or S;
R₂ is hydrogen or hydroxy;
R₃ is alkyl$_{(C≤8)}$ or substituted alkyl$_{(C≤8)}$;
R₄ is
  hydrogen, hydroxy, halo, amino, nitro, cyano, azido or mercapto;
  alkyl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
R₅, R₆, and R₇ are each independently:
  hydrogen, hydroxy, halo, amino, nitro, cyano, azido or mercapto;
  alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkyl-amino$_{(C≤6)}$, amido$_{(C≤6)}$, or a substituted version of any of these groups;
  a group of formula:

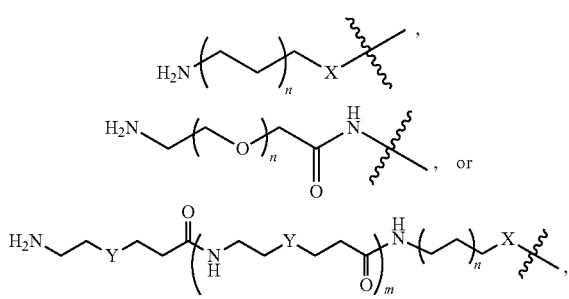

wherein
  X is
    —O—, —S—, or —NH—; or
    alkanediyl$_{(C≤12)}$, alkenediyl$_{(C≤12)}$, alkynediyl$_{(C≤12)}$, or a substituted version of any of these groups;
  Y is —O—, —NH—, alkanediyl$_{(C≤12)}$ or substituted alkane-diyl$_{(C≤12)}$;
  n is an integer from 0-6; and
  m is an integer from 0-6; or
  a -linker-reporter;
or a tautomer or optical isomer thereof.
In some aspects, R₇ is methoxy. In some aspects, the photoactivatable terminating nucleotide comprises a structure of the formula:

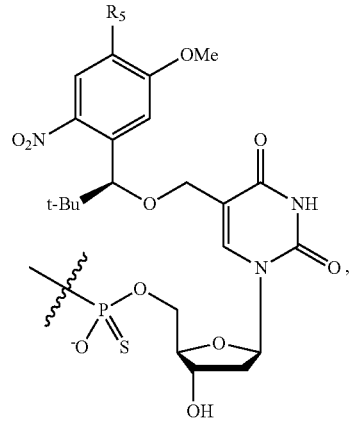

wherein R₅ is a -linker-reporter. In some aspects, the photoactivatable terminating nucleotide comprises a structure of the formula:

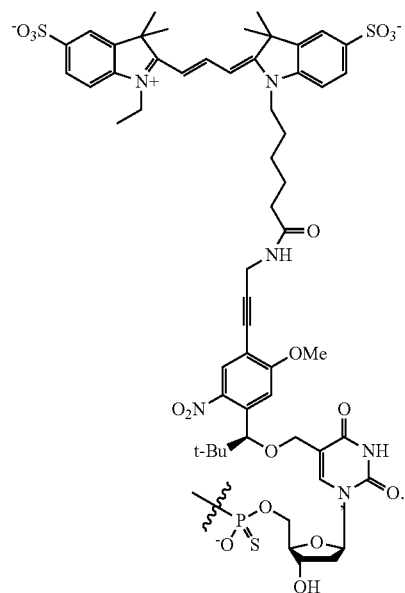

In one embodiment, provided herein are methods for identifying regions of open DNA in a cell, the method comprising: (a) introducing a population of oligonucleotide molecules into the cell, wherein each molecule comprises, from 5' to 3', an amplification segment, an index barcode segment, a hybridization segment, and a reversibly terminating nucleotide; (b) incubating the cell under conditions to allow for the hybridization segments of the population of oligonucleotide molecules to anneal to regions of open DNA; (c) activating at least a portion of the annealed oligonucleotide molecules to expose an extendable 3' hydroxy group; and (d) synthesizing cDNAs from the open DNA by extending the activated oligonucleotide molecules from their extendable 3' hydroxy groups.

In some aspects, the amplification segment is an RNA polymerase promoter. In some aspects, the amplification segment is a primer binding site. In some aspects, the amplification segment comprises between about seven and about fifty nucleotides. In some aspects, the hybridization segments of the population of oligonucleotides comprise a degenerate nucleotide sequence. In some aspects, each nucleic acid molecule in the population comprises a unique hybridization segment sequence. In some aspects, the hybridization segments comprise one or more known nucleotide sequence. In certain aspects, each known nucleotide sequence is complementary to a target genomic or mitochondrial DNA sequence. In some aspects, the hybridization segments comprise between about seven and about thirty nucleotides. In some aspects, the hybridization segments comprise about fifteen nucleotides. In some aspects, the oligonucleotides of the population further comprise a spacer segment positioned between the amplification segment and the index barcode segment. In some aspects, the photoactivatable terminating nucleotide comprises a structure of the formula:

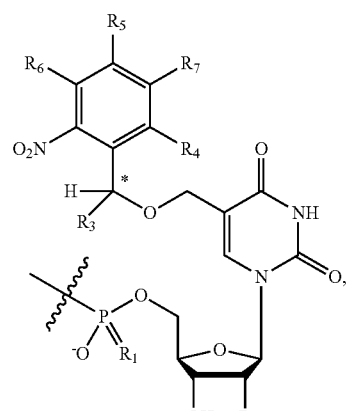

(I)

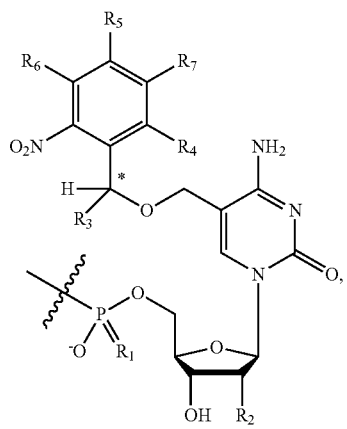

(II)

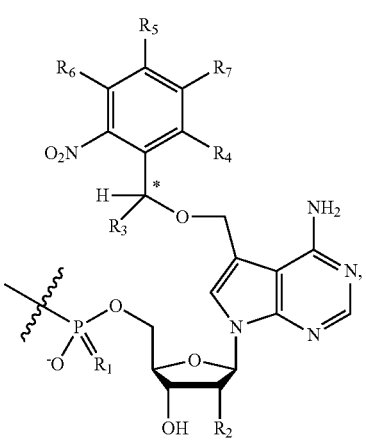

(III)

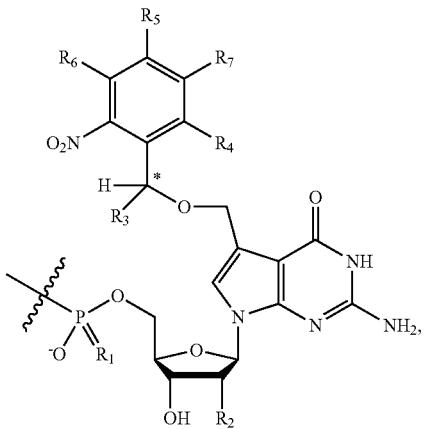

(IV)

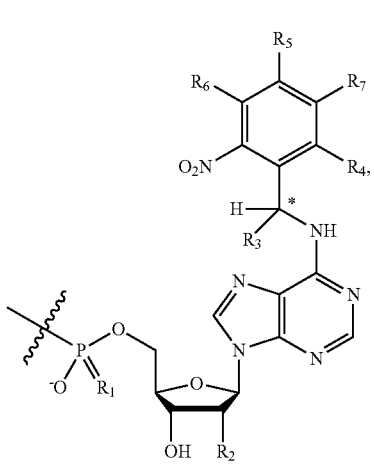

(V)

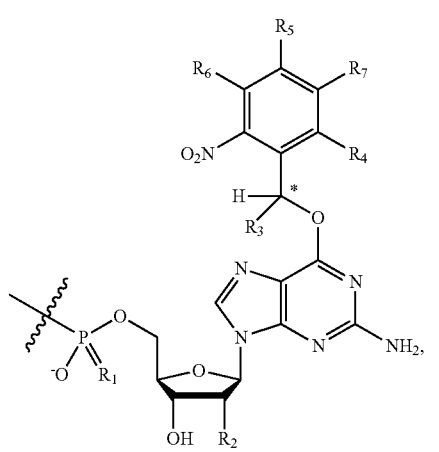

(VI)

-continued (VII)

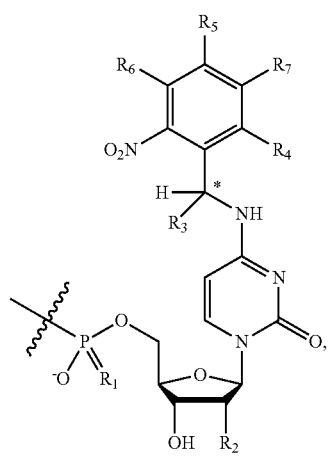

wherein:
R₁ is O or S;
R₂ is hydrogen or hydroxy;
R₃ is alkyl$_{(C≤8)}$ or substituted alkyl$_{(C≤8)}$;
R₄ is
  hydrogen, hydroxy, halo, amino, nitro, cyano, azido or mercapto;
  alkyl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
R₅, R₆, and R₇ are each independently:
  hydrogen, hydroxy, halo, amino, nitro, cyano, azido or mercapto;
  alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkyl-amino$_{(C≤6)}$, amido$_{(C≤6)}$, or a substituted version of any of these groups;
  a group of formula:

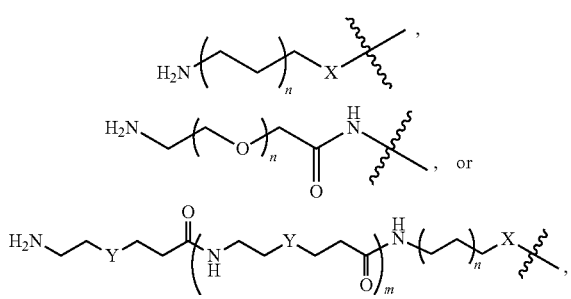

, or wherein
  X is
    —O—, —S—, or —NH—; or
    alkanediyl$_{(C≤12)}$, alkenediyl$_{(C≤12)}$, alkynediyl$_{(C≤12)}$, or a substituted version of any of these groups;
  Y is —O—, —NH—, alkanediyl$_{(C≤12)}$ or substituted alkane-diyl$_{(C≤12)}$;
  n is an integer from 0-6; and
  m is an integer from 0-6; or
  a -linker-reporter;
or a tautomer or optical isomer thereof.
In some aspects, R₇ is methoxy. In some aspects, the photoactivatable terminating nucleotide comprises a structure of the formula:

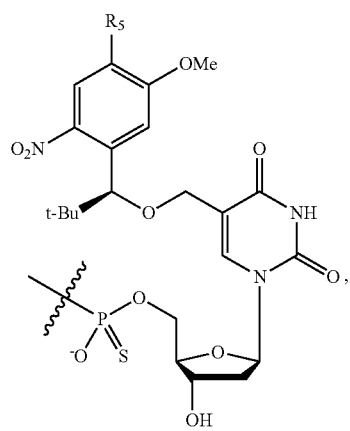

wherein R₅ is a -linker-reporter. In some aspects, the photoactivatable terminating nucleotide comprises a structure of the formula:

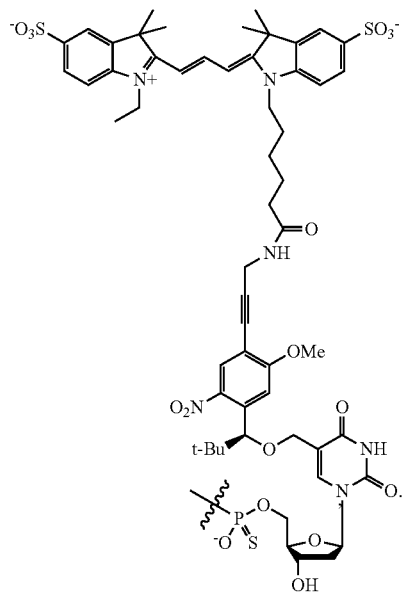

In some aspects, the population of oligonucleotide molecules introduced in process (a) are a population of oligonucleotide molecules of any one of the present embodiments.

In some aspects, the cell is fixed. In some aspects, activation comprises photoactivations. In some aspects, the open DNA is open chromatin and activation comprises exposing the nucleus to ultraviolet light. In some aspects, activation is performed throughout the nucleus. In some aspects, the open DNA is open mitochondrial DNA and activation comprises exposing at least one mitochondrion in the cell to ultraviolet light. In some aspects, activation is performed throughout more than one mitochondrion in the cell. In some aspects, activation is performed at a particular site within the nucleus or mitochondrion. In certain aspects, the particular site is identified based on localization of a gene of interest. In certain aspects, the particular site is the transcription start site of the gene of interest. In certain aspects, the particular site is localized using in situ hybridization. In certain aspects, activation at the particular site comprises exposing the particular site to multi-photon excitation based on the in situ hybridization signal.

In some aspects, synthesizing cDNAs comprises adding a DNA-dependent DNA polymerase. In some aspects, the methods further comprise processing the synthesized cDNAs to generate double-stranded cDNAs comprising the index barcode segment and the amplification segment of the oligonucleotides. In certain aspects, the methods further comprise amplifying the double-stranded cDNAs. In certain aspects, amplifying comprises PCR, rolling circle amplification, or RNA amplification. In certain aspects, the methods further comprise obtaining a sequence of at least a portion of the double-stranded cDNAs. In certain aspects, the methods further comprise aligning the sequences with genomic or mitochondrial sequences, thereby identifying regions of open DNA.

In some aspects, the methods are multiplex methods, wherein the methods are performed sequentially on two or more cells in a sample. In some aspects, the methods are multiplex methods, wherein the methods are performed sequentially on two or more particular sites in the cell. In certain aspects, the populations of oligonucleotide molecules introduced during each round of multiplexing comprise unique index barcode segments.

In some aspects, the methods are methods of categorizing a cell. In some aspects, the methods are methods of predicting or determining a subtype of a cell.

In some aspects, the methods further comprise determining whether regions of open DNA are transcriptionally active, wherein the method further comprises, after process (d): (e) incubating the cell under conditions which substantially allow only unextended oligonucleotides to denature from the open DNA; (f) inactivating or removing the denatured unextended oligonucleotides; (g) introducing a second population of oligonucleotide molecules into the cell, wherein each molecule comprises, from 5' to 3', an amplification segment, an index barcode segment that is distinct from the index barcode segment of the oligonucleotide molecules introduced in process (a), a hybridization segment, and a reversibly terminating nucleotide; (h) incubating the cell under conditions to allow for the hybridization segments of the population of oligonucleotide molecules to anneal to expressed RNAs; (i) activating at least a portion of the annealed oligonucleotide molecules to expose an extendable 3' hydroxy group; and (j) synthesizing cDNAs from the expressed RNAs by extending the activated oligonucleotide molecules from their extendable 3' hydroxy groups.

In some aspects, the amplification segment is an RNA polymerase promoter. In some aspects, the amplification segment is a primer binding site. In some aspects, the amplification segment comprises between about seven and about fifty nucleotides. In some aspects, the hybridization segments of the second population of oligonucleotide molecules comprise a poly-T sequence. In some aspects, the hybridization segments of the second population of oligonucleotide molecules comprise one or more known nucleotide sequence. In certain aspects, each known nucleotide sequence is complementary to a target RNA sequence.

In some aspects, the hybridization segments of the second population of oligonucleotide molecules comprise between about seven and about thirty nucleotides. In some aspects, the hybridization segments of the second population of oligonucleotide molecules comprise about fifteen nucleotides. In some aspects, the oligonucleotides of the population further comprise a spacer segment positioned between the amplification segment and the index barcode segment. In some aspects, the photoactivatable terminating nucleotide comprises a structure of the formula:

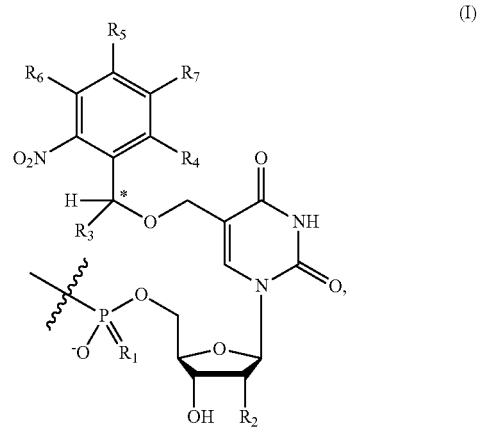

(I)

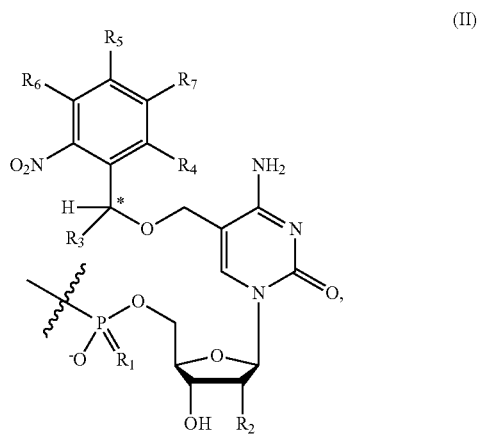

(II)

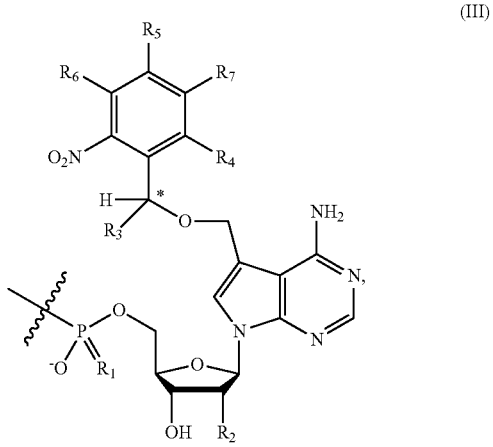

(III)

17
-continued (IV)

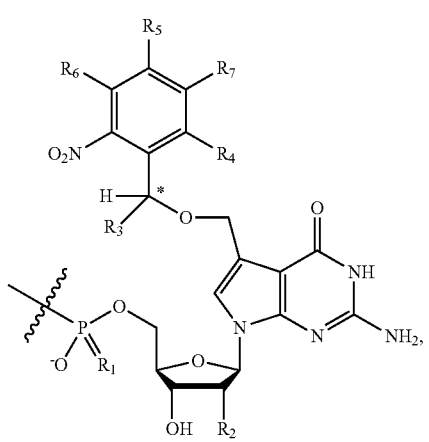

(V)

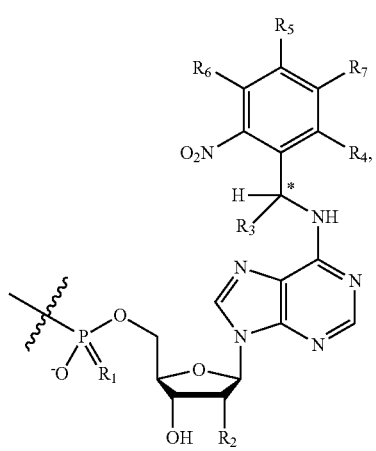

(VI)

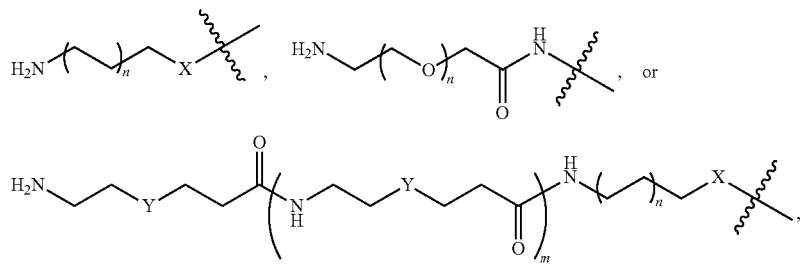

18
-continued (VII)

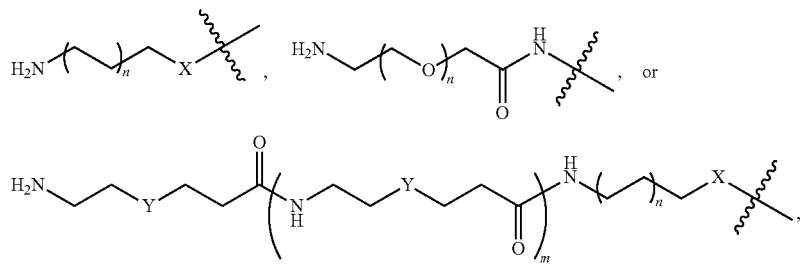

wherein:

$R_1$ is O or S;

$R_2$ is hydrogen or hydroxy;

$R_3$ is alkyl$_{(C\leq 8)}$ or substituted alkyl$_{(C\leq 8)}$;

$R_4$ is hydrogen, hydroxy, halo, amino, nitro, cyano, azido or mercapto;

alkyl$_{(C\leq 6)}$, acyl$_{(C\leq 6)}$, alkoxy$_{(C\leq 6)}$, acyloxy$_{(C\leq 6)}$, alkylamino$_{(C\leq 6)}$, dialkylamino$_{(C\leq 6)}$, amido$_{(C\leq 6)}$, or a substituted version of any of these groups;

$R_5$, $R_6$, and $R_7$ are each independently:

hydrogen, hydroxy, halo, amino, nitro, cyano, azido or mercapto;

alkyl$_{(C\leq 6)}$, alkenyl$_{(C\leq 6)}$, alkynyl$_{(C\leq 6)}$, aryl$_{(C\leq 6)}$, aralkyl$_{(C\leq 8)}$, heteroaryl$_{(C\leq 6)}$, acyl$_{(C\leq 6)}$, alkoxy$_{(C\leq 6)}$, acyloxy$_{(C\leq 6)}$, alkylamino$_{(C\leq 6)}$, dialkylamino$_{(C\leq 6)}$, amido$_{(C\leq 6)}$, or a substituted version of any of these groups;

a group of formula:

wherein
X is
—O—, —S—, or —NH—; or alkanediyl$_{(C\leq12)}$, alkenediyl$_{(C\leq12)}$, alkynediyl$_{(C\leq12)}$, or a substituted version of any of these groups;
Y is —O—, —NH—, alkanediyl$_{(C\leq12)}$ or substituted alkane-diyl$_{(C\leq12)}$;
n is an integer from 0-6; and
m is an integer from 0-6; or
a -linker-reporter;
or a tautomer or optical isomer thereof.

In some aspects, $R_7$ is methoxy. In some aspects, the photoactivatable terminating nucleotide comprises a structure of the formula:

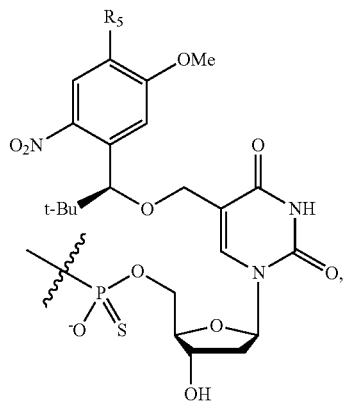

wherein $R_5$ is a -linker-reporter. In some aspects, the photoactivatable terminating nucleotide comprises a structure of the formula:

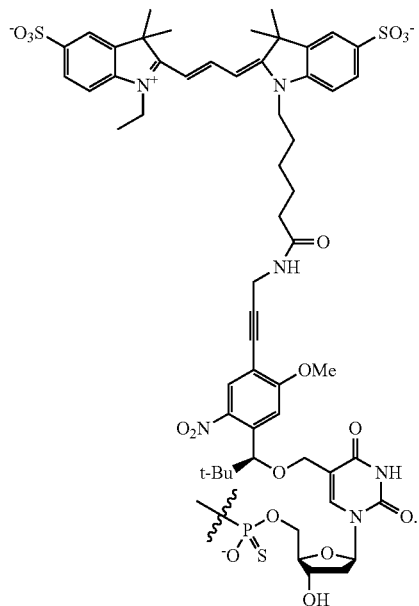

In some aspects, the second population of oligonucleotide molecules introduced in process (g) are a population of oligonucleotide molecules of any one of the present embodiments.

In some aspects, the cell is fixed. In some aspects, activation comprises photoactivation. In some aspects, activation comprises exposing the cytoplasm to ultraviolet light. In some aspects, activation is performed throughout the cytoplasm. In some aspects, activation is performed at a particular site within the cytoplasm. In certain aspects, the particular site is an axon or a dendrite. In some aspects, synthesizing cDNAs comprises adding an RNA-dependent DNA polymerase. In some aspects, the methods further comprise processing the synthesized cDNAs to generate double-stranded cDNAs comprising the index barcode segment and the promoter region segment of the oligonucleotides. In some aspects, the methods further comprise amplifying the double-stranded cDNAs. In certain aspects, amplifying comprises PCR, rolling circle amplification, or RNA amplification. In certain aspects, the methods further comprise obtaining a sequence of at least a portion of the double-stranded cDNAs, thereby identifying the expressed RNAs.

In some aspects, the methods are multiplex methods, wherein the methods are performed sequentially on two or more particular sites in the cell. In some aspects, the methods are multiplex methods, wherein the methods are performed sequentially on two or more cells in a sample. In certain aspects, the populations of oligonucleotide molecules introduced during each round of multiplexing comprise unique index barcode segments.

In one embodiment, provided herein are methods for identifying the expressed RNAs in a cell, the method comprising: (a) introducing a population of oligonucleotide molecules into the cell, wherein each molecule comprises, from 5' to 3', an amplification segment, an index barcode segment, a hybridization segment, and a reversibly terminating nucleotide; (b) incubating the cell under conditions to allow for the hybridization segments of the population of oligonucleotide molecules to anneal to expressed RNAs; (c) activating at least a portion of the annealed oligonucleotide molecules to expose an extendable 3' hydroxy group; and (d) synthesizing cDNAs from the expressed RNAs by extending the activating oligonucleotide molecules from their extendable 3' hydroxy groups.

In some aspects, the amplification segment is an RNA polymerase promoter. In some aspects, the amplification segment is a primer binding site. In some aspects, the amplification segment comprises between about seven and about fifty nucleotides. In some aspects, the hybridization segments comprise a poly-T sequence. In some aspects, the hybridization segments comprise one or more known nucleotide sequence. In certain aspects, each known nucleotide sequence is complementary to a target RNA sequence. In some aspects, the hybridization segments comprise between about seven and about thirty nucleotides. In some aspects, the hybridization segments comprise about fifteen nucleotides. In some aspects, the oligonucleotides of the population further comprise a spacer segment positioned between the amplification segment and the index barcode segment. In some aspects, the photoactivatable terminating nucleotide comprises a structure of the formula:

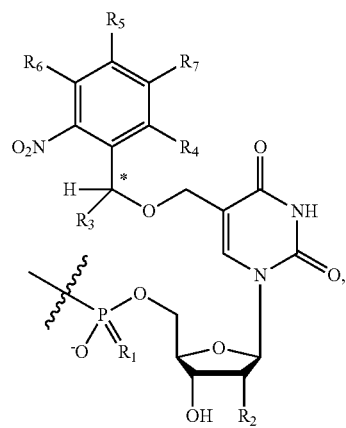
(I)
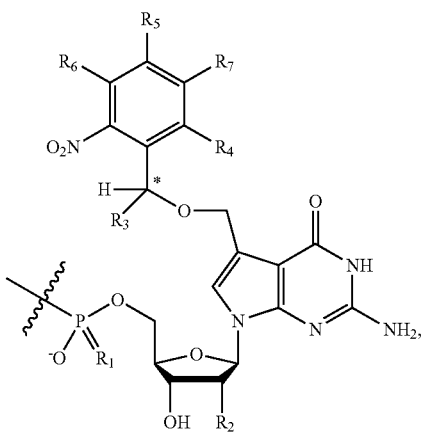
(IV)
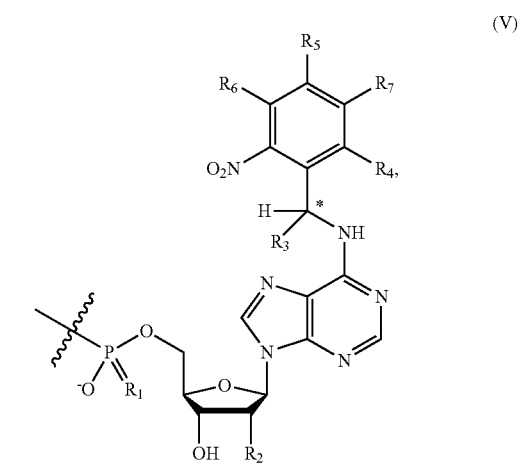
(II)
(V)
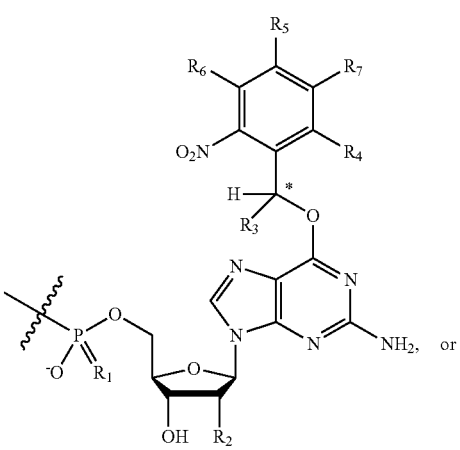
(III)
(VI)

-continued (VII)

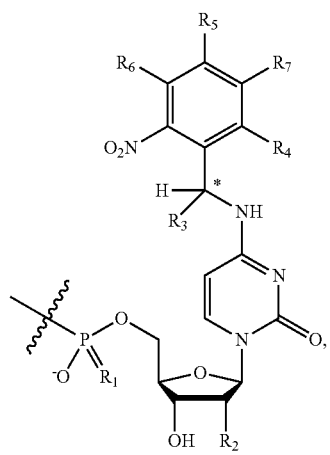

wherein:
R₁ is O or S;
R₂ is hydrogen or hydroxy;
R₃ is alkyl$_{(C≤8)}$ or substituted alkyl$_{(C≤8)}$;
R₄ is
  hydrogen, hydroxy, halo, amino, nitro, cyano, azido or mercapto;
  alkyl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
R₅, R₆, and R₇ are each independently:
  hydrogen, hydroxy, halo, amino, nitro, cyano, azido or mercapto;
  alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;
  a group of formula:

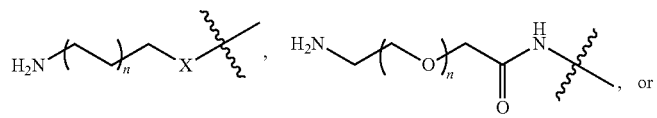

wherein
X is
  —O—, —S—, or —NH—; or
  alkanediyl$_{(C≤12)}$, alkenediyl$_{(C≤12)}$, alkynediyl$_{(C≤12)}$, or a substituted version of any of these groups;
Y is —O—, —NH—, alkanediyl$_{(C≤12)}$ or substituted alkane-diyl$_{(C≤12)}$;
n is an integer from 0-6; and
m is an integer from 0-6; or
a -linker-reporter;
or a tautomer or optical isomer thereof.

In some aspects, R₇ is methoxy. In some aspects, the photoactivatable terminating nucleotide comprises a structure of the formula:

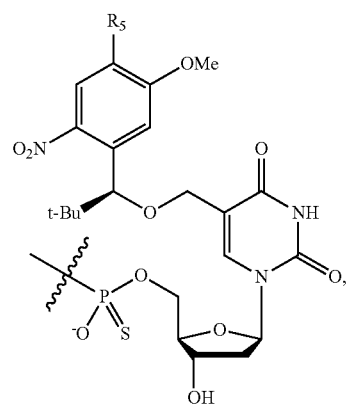

wherein R₅ is a -linker-reporter. In some aspects, the photoactivatable terminating nucleotide comprises a structure of the formula:

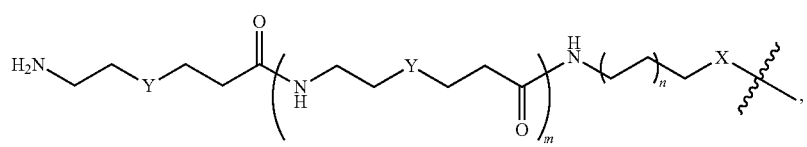

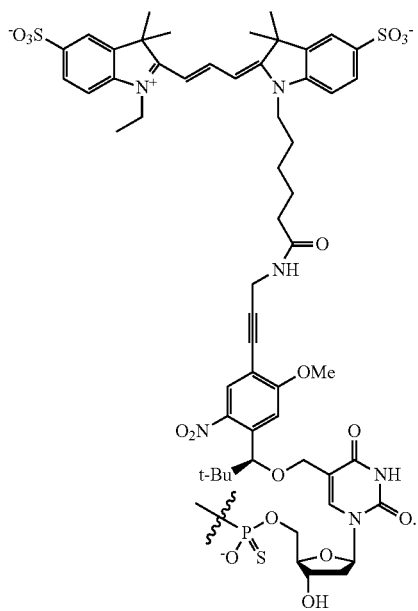

In some aspects, the population of oligonucleotide molecules introduced in process (a) are a population of oligonucleotide molecules of any one of the present embodiments.

In some aspects, the cell is fixed. In some aspects, activation comprises photoactivation. In some aspects, activation comprises exposing the cytoplasm to ultraviolet light. In some aspects, activation is performed throughout the cytoplasm. In some aspects, activation is performed at a particular site within the cytoplasm. In certain aspects, the particular site is an axon or a dendrite.

In some aspects, synthesizing cDNAs comprises adding an RNA-dependent DNA polymerase. In some aspects, the methods further comprise processing the synthesized cDNAs to generate a double-stranded cDNAs comprising the index barcode segment and the amplification segment of the oligonucleotides. In certain aspects, the methods further comprise amplifying the double-stranded cDNAs. In certain aspects, amplifying comprises PCR, rolling circle amplification, or RNA amplification. In certain aspects, the methods further comprise obtaining a sequence of at least a portion of the double-stranded cDNAs, thereby identifying the expressed RNAs.

In some aspects, the methods are multiplex methods, wherein the methods are performed sequentially on two or more particular sites in the cell. In some aspects, the methods are multiplex methods, wherein the methods are performed sequentially on two or more cells in a sample. In certain aspects, the populations of oligonucleotide molecules introduced during each round of multiplexing comprise unique index barcode segments.

In one embodiment, provided herein are kits comprising a population of oligonucleotides according to any one of the present embodiments and at least one of a DNA polymerase, an RNA polymerase, a reverse transcriptase, deoxyribonucleotides, and/or ribonucleotides.

The following numbered paragraphs describe additional and/or alternative aspects of the invention:

1. An oligonucleotide molecule comprising, from 5' to 3', an amplification segment, a hybridization segment, and a reversibly terminating nucleotide.
2. The oligonucleotide molecule of paragraph 1, wherein the amplification segment is an RNA polymerase promoter.
3. The oligonucleotide molecule of paragraph 1, wherein the amplification segment is a primer binding site.
4. The oligonucleotide molecule of any one of paragraphs 1-3, wherein the amplification segment comprises between about seven and about fifty nucleotides.
5. The oligonucleotide molecule of any one of paragraphs 1-4, wherein the hybridization segment comprises a random nucleotide sequence.
6. The oligonucleotide molecule of any one of paragraphs 1-4, wherein the hybridization segment comprises a known nucleotide sequence.
7. The oligonucleotide molecule of paragraph 6, wherein the known nucleotide sequence is complementary to a target genomic or mitochondrial DNA sequence.
8. The oligonucleotide molecule of paragraph 6, wherein the known nucleotide sequence is complementary to a target RNA sequence.
9. The oligonucleotide molecule of any one of paragraphs 1-4, wherein the hybridization segment comprises a poly-T sequence.
10. The oligonucleotide molecule of any one of paragraphs 1-9, wherein the hybridization segment comprises between about seven and about thirty nucleotides.
11. The oligonucleotide molecule of any one of paragraphs 1-10, wherein the hybridization segment comprises about fifteen nucleotides.
12. The oligonucleotide molecule of any one of paragraphs 1-11, further comprising an index barcode segment positioned between the amplification segment and the hybridization segment.
13. The oligonucleotide molecule of paragraph 12, further comprising a spacer segment positioned between the amplification segment and the index barcode segment.
14. The oligonucleotide molecule of any one of paragraphs 1-13, wherein the reversibly terminating nucleotide comprises a nitrobenzyl group.
15. The oligonucleotide molecule of any one of paragraphs 1-14, wherein the reversibly terminating nucleotide comprises a fluorescent label.
16. The oligonucleotide molecule of any one of paragraphs 1-15, wherein the reversibly terminating nucleotide is a photoactivatable terminating nucleotide.
17. The oligonucleotide molecule of paragraph 16, wherein the photoactivatable terminating nucleotide comprises a structure of the formula:

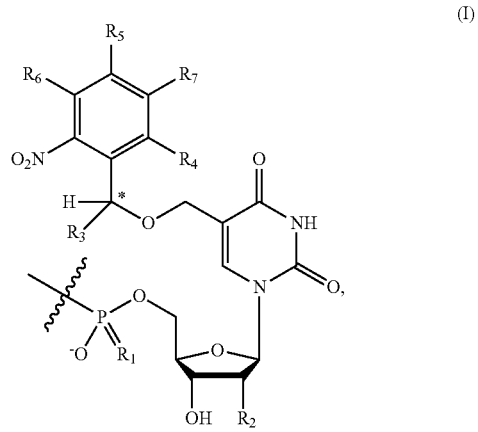

(I)

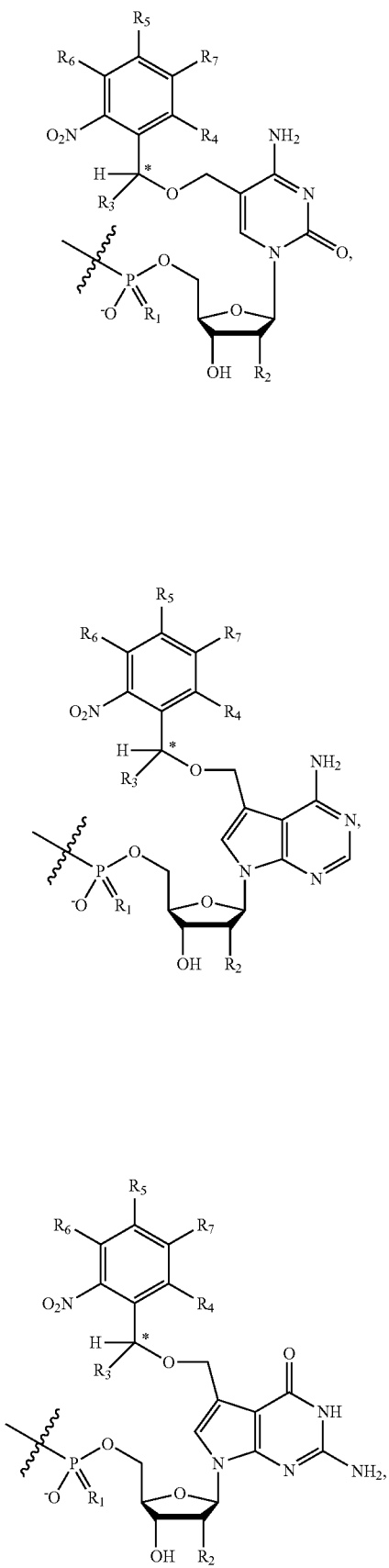
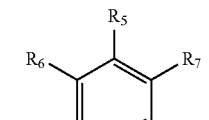
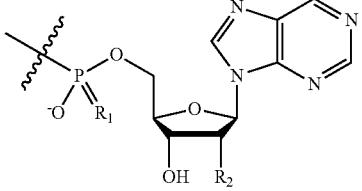
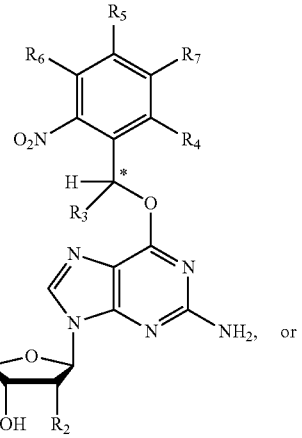
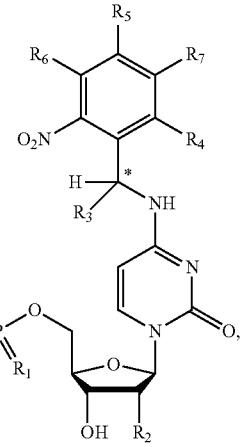

wherein:
$R_1$ is O or S;
$R_2$ is hydrogen or hydroxy;
$R_3$ is alkyl$_{(C \leq 8)}$ or substituted alkyl$_{(C \leq 8)}$;
$R_4$ is
  hydrogen, hydroxy, halo, amino, nitro, cyano, azido or mercapto;
  alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;
$R_5$, $R_6$, and $R_7$ are each independently:
  hydrogen, hydroxy, halo, amino, nitro, cyano, azido or mercapto;

alkyl$_{(C≤6)}$, alkenyl$_{(C≤6)}$, alkynyl$_{(C≤6)}$, aryl$_{(C≤6)}$, aralkyl$_{(C≤8)}$, heteroaryl$_{(C≤6)}$, acyl$_{(C≤6)}$, alkoxy$_{(C≤6)}$, acyloxy$_{(C≤6)}$, alkylamino$_{(C≤6)}$, dialkylamino$_{(C≤6)}$, amido$_{(C≤6)}$, or a substituted version of any of these groups;

a group of formula:

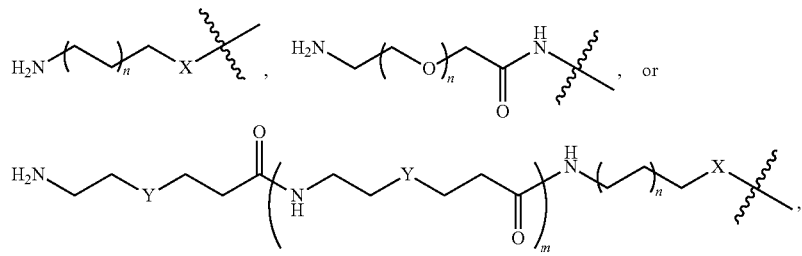

wherein

X is

—O—, —S—, or —NH—; or alkanediyl$_{(C≤12)}$, alkenediyl$_{(C≤12)}$, alkynediyl$_{(C≤12)}$, or a substituted version of any of these groups;

Y is —O—, —NH—, alkanediyl$_{(C≤12)}$ or substituted alkane-diyl$_{(C≤12)}$;

n is an integer from 0-6; and m is an integer from 0-6; or a -linker-reporter;

or a tautomer or optical isomer thereof.

18. The oligonucleotide molecule of paragraph 17, wherein $R_7$ is methoxy.

19. The oligonucleotide molecule of paragraph 18, wherein the photoactivatable terminating nucleotide comprises a structure of the formula:

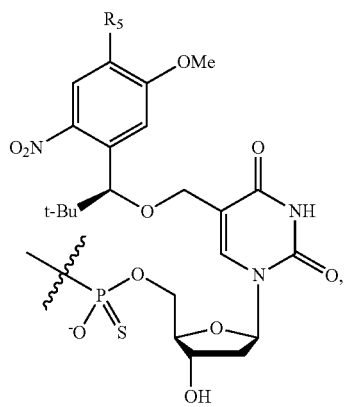

wherein $R_5$ is a -linker-reporter.

20. The oligonucleotide molecule of paragraph 19, wherein the photoactivatable terminating nucleotide comprises a structure of the formula:

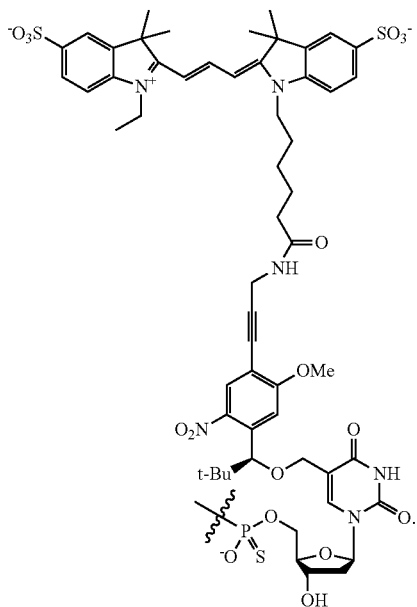

21. A population of oligonucleotide molecules each comprising, from 5' to 3', an amplification segment, a hybridization segment, and a reversibly terminating nucleotide.

22. The population of paragraph 21, wherein the amplification segment is an RNA polymerase promoter.

23. The population of paragraph 21, wherein the amplification segment is a primer binding site.

24. The population of any one of paragraphs 21-23, wherein the amplification segment comprises between about seven and about fifty nucleotides.

25. The population of any one of paragraphs 21-24, wherein the hybridization segments comprise a degenerate nucleotide sequence.

26. The population of any one of paragraphs 21-25, wherein each nucleic acid molecule in the population comprises a unique hybridization segment sequence.

27. The population of any one of paragraphs 21-24, wherein the hybridization segments comprise one or more known nucleotide sequence.

28. The population of paragraph 27, wherein each known nucleotide sequence is complementary to a target genomic or mitochondrial DNA sequence.

29. The population of paragraph 27, wherein each known nucleotide sequence is complementary to a target RNA sequence.
30. The population of any one of paragraphs 21-24, wherein the hybridization segments comprise a poly-T sequence.
31. The population of any one of paragraphs 21-30, wherein the hybridization segments comprise between about seven and about thirty nucleotides.
32. The population of any one of paragraphs 21-31, wherein the hybridization segments comprise about fifteen nucleotides.
33. The population of any one of paragraphs 21-32, further comprising an index barcode segment positioned between the amplification segment and the hybridization segment.
34. The population of paragraph 33, further comprising a spacer segment positioned between the RNA polymerase promoter segment and the index barcode segment.
35. The population of any one of paragraphs 21-34, wherein the reversibly terminating nucleotide comprises a nitrobenzyl group.
36. The population of any one of paragraphs 21-35, wherein the reversibly terminating nucleotide comprises a fluorescent label.
37. The population of any one of paragraphs 21-36, wherein the reversibly terminating nucleotide is a photoactivatable terminating nucleotide.
38. The population of paragraph 37, wherein the photoactivatable terminating nucleotide comprises a structure of the formula:

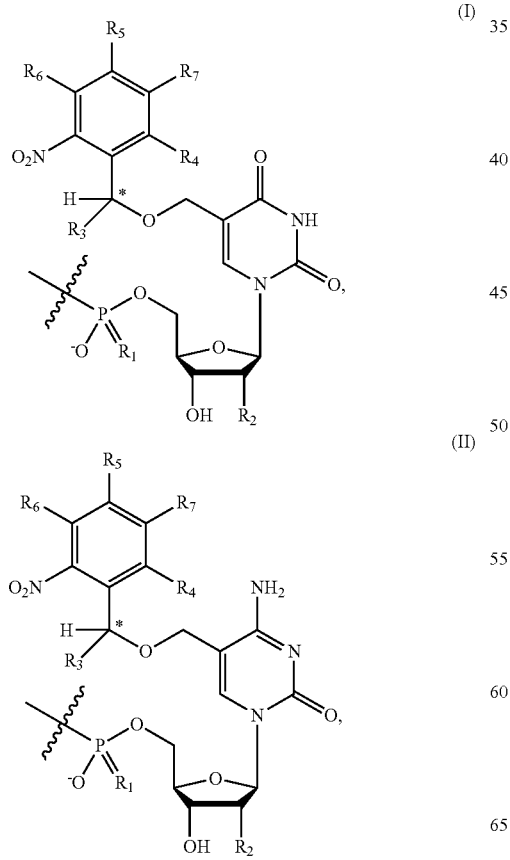

(I)

(II)

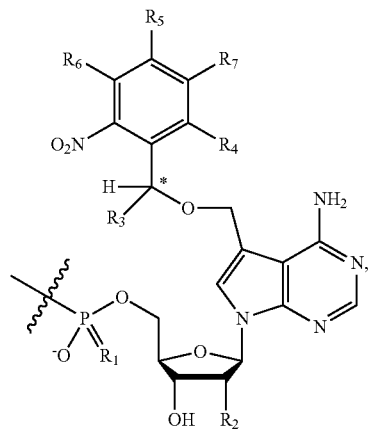

(III)

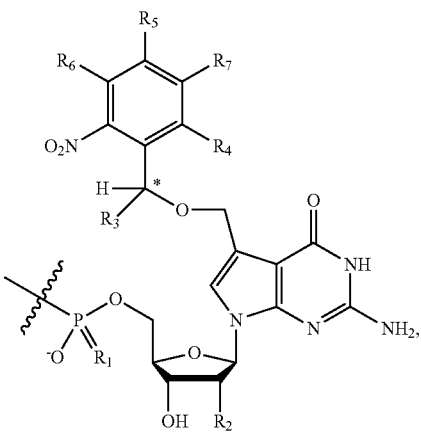

(IV)

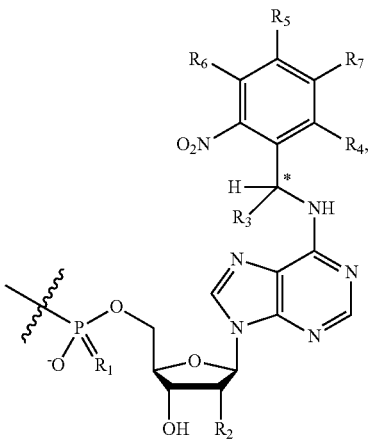

(V)

-continued

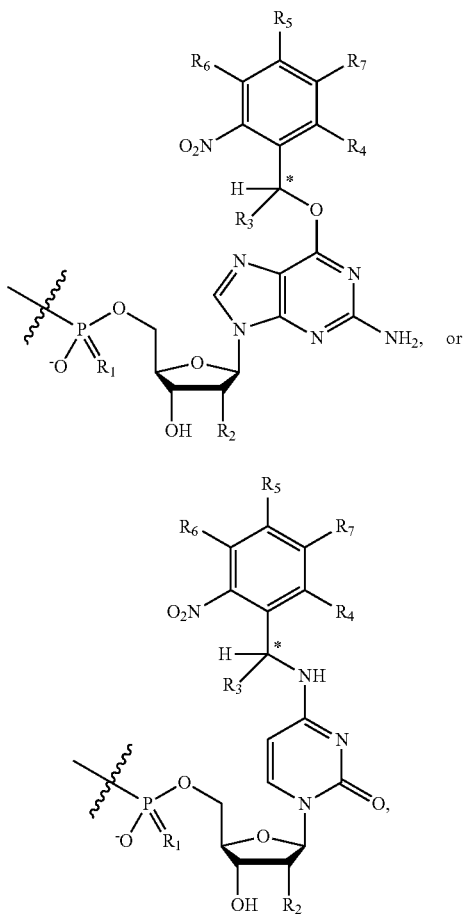

wherein:

$R_1$ is O or S;

$R_2$ is hydrogen or hydroxy;

$R_3$ is alkyl$_{(C \leq 8)}$ or substituted alkyl$_{(C \leq 8)}$;

$R_4$ is hydrogen, hydroxy, halo, amino, nitro, cyano, azido or mercapto;

alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;

$R_5$, $R_6$, and $R_7$ are each independently:

hydrogen, hydroxy, halo, amino, nitro, cyano, azido or mercapto;

alkyl$_{(C \leq 6)}$, alkenyl$_{(C \leq 6)}$, alkynyl$_{(C \leq 6)}$, aryl$_{(C \leq 6)}$, aralkyl$_{(C \leq 8)}$, heteroaryl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;

a group of formula:

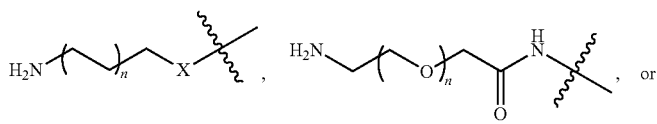

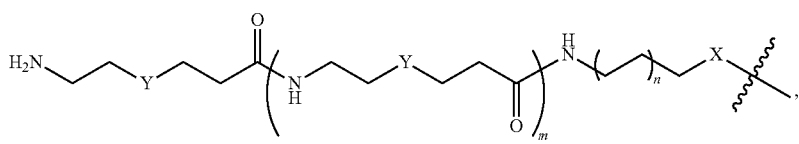

wherein
X is
—O—, —S—, or —NH—; or alkanediyl$_{(C≤12)}$, alkenediyl$_{(C≤12)}$, alkynediyl$_{(C≤12)}$, or a substituted version of any of these groups;

Y is —O—, —NH—, alkanediyl$_{(C≤12)}$ or substituted alkane-diyl$_{(C≤12)}$;

n is an integer from 0-6; and m is an integer from 0-6; or a -linker-reporter;

or a tautomer or optical isomer thereof.

39. The population of paragraph 38, wherein R$_7$ is methoxy.

40. The population of paragraph 39, wherein the photoactivatable terminating nucleotide comprises a structure of the formula:

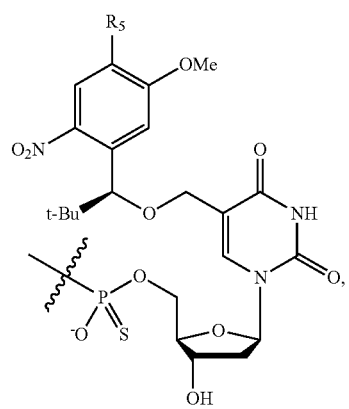

wherein R$_5$ is a -linker-reporter.

41. The population of paragraph 40, wherein the photoactivatable terminating nucleotide comprises a structure of the formula:

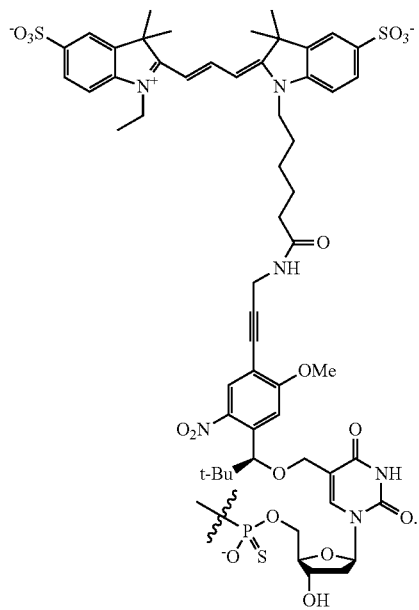

42. A method for identifying regions of open DNA in a cell, the method comprising:
    (a) introducing a population of oligonucleotide molecules into the cell, wherein each molecule comprises, from 5' to 3', an amplification segment, an index barcode segment, a hybridization segment, and a reversibly terminating nucleotide;
    (b) incubating the cell under conditions to allow for the hybridization segments of the population of oligonucleotide molecules to anneal to regions of open DNA;
    (c) activating at least a portion of the annealed oligonucleotide molecules to expose an extendable 3' hydroxy group; and
    (d) synthesizing cDNAs from the open DNA by extending the activated oligonucleotide molecules from their extendable 3' hydroxy groups.

43. The method of paragraph 42, wherein the amplification segment is an RNA polymerase promoter.

44. The method of paragraph 42, wherein the amplification segment is a primer binding site.

45. The method of any one of paragraphs 42-44, wherein the amplification segment comprises between about seven and about fifty nucleotides.

46. The method of any one of paragraphs 42-45, wherein the hybridization segments of the population of oligonucleotides comprise a degenerate nucleotide sequence.

47. The method of any one of paragraphs 42-46, wherein each nucleic acid molecule in the population comprises a unique hybridization segment sequence.

48. The method of any one of paragraphs 42-45, wherein the hybridization segments comprise one or more known nucleotide sequence.

49. The method of paragraph 48, wherein each known nucleotide sequence is complementary to a target genomic or mitochondrial DNA sequence.

50. The method of any one of paragraphs 42-49, wherein the hybridization segments comprise between about seven and about thirty nucleotides.

51. The method of any one of paragraphs 42-50, wherein the hybridization segments comprise about fifteen nucleotides.

52. The method of any one of paragraphs 42-51, wherein the population of oligonucleotide molecules further comprise a spacer segment positioned between the amplification segment and the index barcode segment.

53. The method of any one of paragraphs 42-52, wherein the reversibly terminating nucleotide is a photoactivatable terminating nucleotide.

54. The method of paragraph 53, wherein the photoactivatable terminating nucleotide comprises a structure of the formula:

(I)

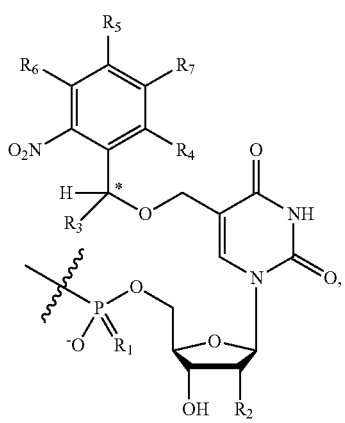

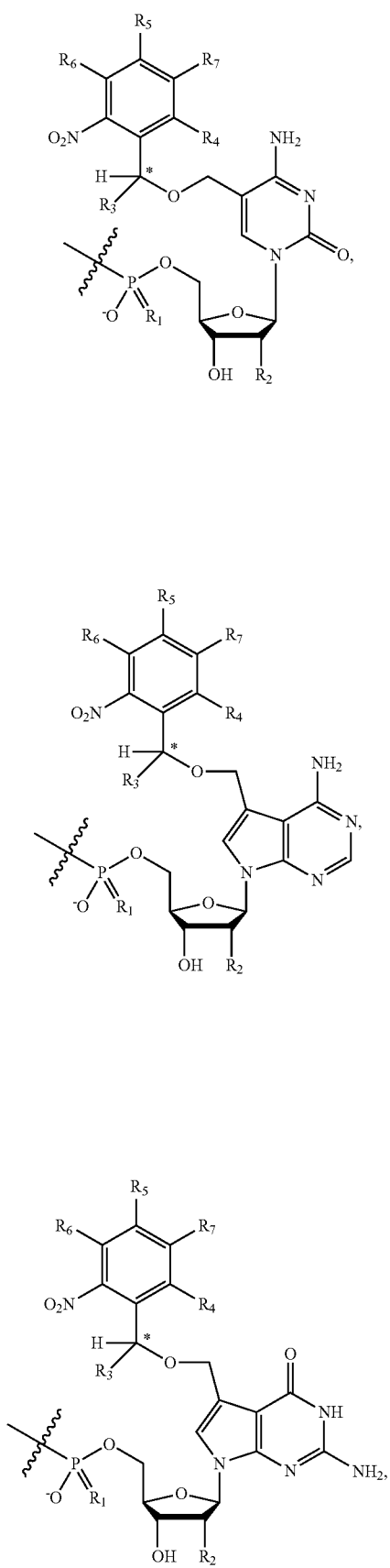
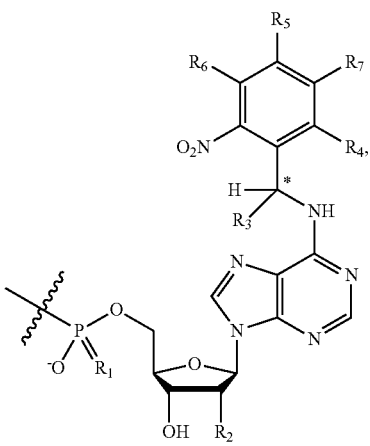
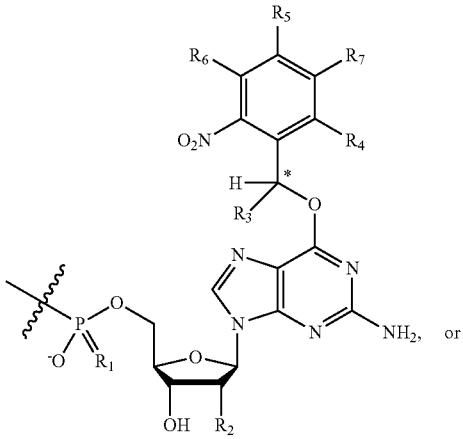
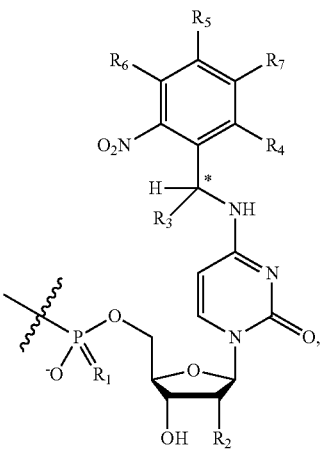

wherein:
R$_1$ is O or S;
R$_2$ is hydrogen or hydroxy;
R$_3$ is alkyl$_{(C \leq 8)}$ or substituted alkyl$_{(C \leq 8)}$;
R$_4$ is
    hydrogen, hydroxy, halo, amino, nitro, cyano, azido or mercapto;
    alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;
R$_5$, R$_6$, and R$_7$ are each independently:
    hydrogen, hydroxy, halo, amino, nitro, cyano, azido or mercapto;

alkyl$_{(C\leq 6)}$, alkenyl$_{(C\leq 6)}$, alkynyl$_{(C\leq 6)}$, aryl$_{(C\leq 6)}$, aralkyl$_{(C\leq 8)}$, heteroaryl$_{(C\leq 6)}$, acyl$_{(C\leq 6)}$, alkoxy$_{(C\leq 6)}$, acyloxy$_{(C\leq 6)}$, alkylamino$_{(C\leq 6)}$, dialkylamino$_{(C\leq 6)}$, amido$_{(C\leq 6)}$, or a substituted version of any of these groups;

a group of formula:

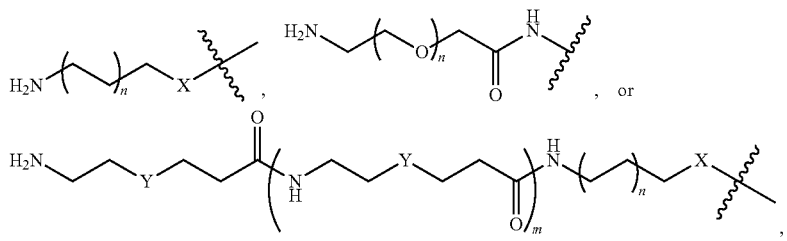

wherein
X is
—O—, —S—, or —NH—; or
alkanediyl$_{(C\leq 12)}$, alkenediyl$_{(C\leq 12)}$, alkynediyl$_{(C\leq 12)}$, or a substituted version of any of these groups;

Y is —O—, —NH—, alkanediyl$_{(C\leq 12)}$ or substituted alkane-diyl$_{(C\leq 12)}$;

n is an integer from 0-6; and m is an integer from 0-6; or a -linker-reporter;

or a tautomer or optical isomer thereof.

55. The method of paragraph 54, wherein $R_7$ is methoxy.
56. The method of paragraph 55, wherein the photoactivatable terminating nucleotide comprises a structure of the formula:

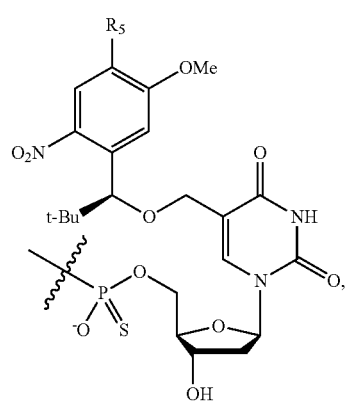

wherein $R_5$ is a -linker-reporter.

57. The method of paragraph 56, wherein the photoactivatable terminating nucleotide comprises a structure of the formula:

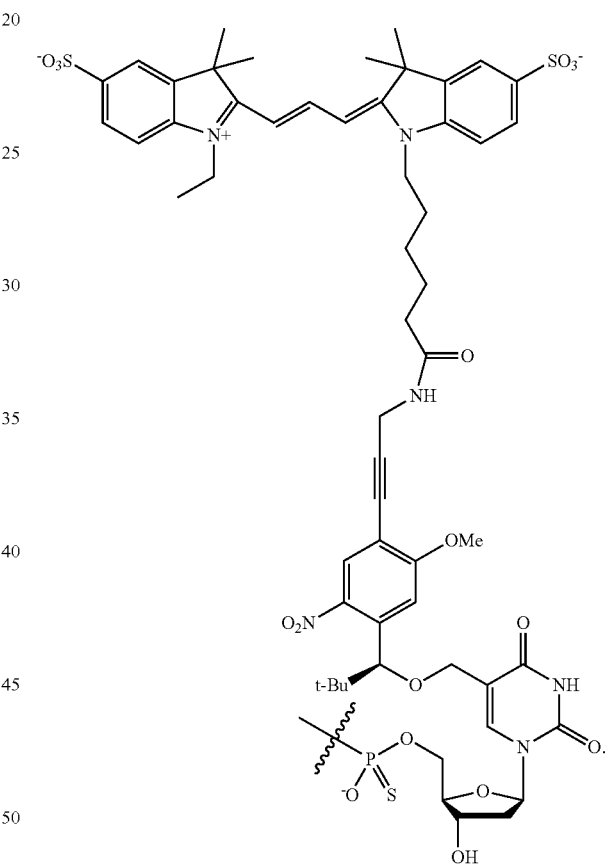

58. The method of any one of paragraphs 42-57, wherein the population of oligonucleotide molecules introduced in process (a) are a population of oligonucleotide molecules of any one of paragraphs 21-28 and 31-41.
59. The method of any one of paragraphs 42-58, wherein the cell is fixed.
60. The method of any one of paragraphs 42-59, wherein the open DNA is open chromatin, wherein activation comprises exposing the nucleus to ultraviolet light.
61. The method of any one of paragraphs 42-60, wherein activation is performed throughout the nucleus.
62. The method of any one of paragraphs 42-59, wherein the open DNA is open mitochondrial DNA, wherein activation comprises exposing at least one mitochondrion in the cell to ultraviolet light.

63. The method of any one of paragraphs 42-59 and 62, wherein activation is performed throughout more than one mitochondrion in the cell.
64. The method of any one of paragraphs 42-60 or 62, wherein activation is performed at a particular site within the nucleus or mitochondrion.
65. The method of paragraph 64, wherein the particular site is identified based on localization of a gene of interest.
66. The method of paragraph 65, wherein the particular site is the transcription start site of the gene of interest.
67. The method of paragraph 65 or 66, wherein the particular site is localized using in situ hybridization.
68. The method of paragraph 67, wherein activation at the particular site comprises exposing the particular site to multi-photon excitation based on the in situ hybridization signal.
69. The method of any one of paragraphs 42-68, wherein synthesizing cDNAs comprises adding a DNA-dependent DNA polymerase.
70. The method of any one of paragraphs 42-69, further comprising processing the synthesized cDNAs to generate double-stranded cDNAs comprising the index barcode segment and the amplification segment of the oligonucleotides.
71. The method of paragraph 70, further comprising amplifying the double-stranded cDNAs.
72. The method of paragraph 71, wherein amplifying comprises PCR, rolling circle amplification, or RNA amplification.
73. The method of paragraph 71 or 72, further comprising obtaining a sequence of at least a portion of the double-stranded cDNAs.
74. The method of paragraph 73, further comprising aligning the sequences with genomic or mitochondrial sequences, thereby identifying regions of open DNA.
75. The method of any one of paragraphs 42-74, wherein the method is a multiplex method, wherein the method is performed sequentially on two or more cells in a sample.
76. The method of any one of paragraphs 42-74, wherein the method is a multiplex method, wherein the method is performed sequentially on two or more particular sites in the cell.
77. The method of paragraph 75 or 76, wherein the populations of oligonucleotide molecules introduced during each round of multiplexing comprise unique index barcode segments.
78. The method of any one of paragraphs 42-77, wherein the method is further defined as a method of categorizing a cell.
79. The method of any one of paragraphs 42-77, wherein the method is further defined as a method of predicting or determining a subtype of a cell.
80. The method of any one of paragraphs 42-79, wherein the method further comprises determining whether regions of open DNA are transcriptionally active, wherein the method further comprises, after process (d):
    (e) incubating the cell under conditions which substantially allow only unextended oligonucleotides to denature from the open DNA;
    (f) inactivating or removing the denatured unextended oligonucleotides;
    (g) introducing a second population of oligonucleotide molecules into the cell, wherein each molecule comprises, from 5' to 3', an amplification segment, an index barcode segment that is distinct from the index barcode segment of the oligonucleotide molecules introduced in process (a), a hybridization segment, and a reversibly terminating nucleotide;
    (h) incubating the cell under conditions to allow for the hybridization segments of the population of oligonucleotide molecules to anneal to expressed RNAs;
    (i) activating at least a portion of the annealed oligonucleotide molecules to expose an extendable 3' hydroxy group; and
    (j) synthesizing cDNAs from the expressed RNAs by extending the activated oligonucleotide molecules from their extendable 3' hydroxy groups.
81. The method of paragraph 80, wherein the amplification segment is an RNA polymerase promoter.
82. The method of paragraph 80, wherein the amplification segment is a primer binding site.
83. The method of any one of paragraphs 80-82, wherein the amplification segment comprises between about seven and about fifty nucleotides.
84. The method of any one of paragraphs 80-83, wherein the hybridization segments of the second population of oligonucleotide molecules comprise a poly-T sequence.
85. The method of any one of paragraphs 80-84, wherein the hybridization segments of the second population of oligonucleotide molecules comprise one or more known nucleotide sequence.
86. The method of paragraph 85, wherein each known nucleotide sequence is complementary to a target RNA sequence.
87. The method of any one of paragraphs 80-86, wherein the hybridization segments of the second population of oligonucleotide molecules comprise between about seven and about thirty nucleotides.
88. The method of any one of paragraphs 80-87, wherein the hybridization segments of the second population of oligonucleotide molecules comprise about fifteen nucleotides.
89. The method of any one of paragraphs 80-88, wherein the population of oligonucleotide molecules further comprise a spacer segment positioned between the amplification segment and the index barcode segment.
90. The method of any one of paragraphs 80-89, wherein the reversibly terminating nucleotide is a photoactivatable terminating nucleotide.
91. The method of paragraph 90, wherein the photoactivatable terminating nucleotide comprises a structure of the formula:

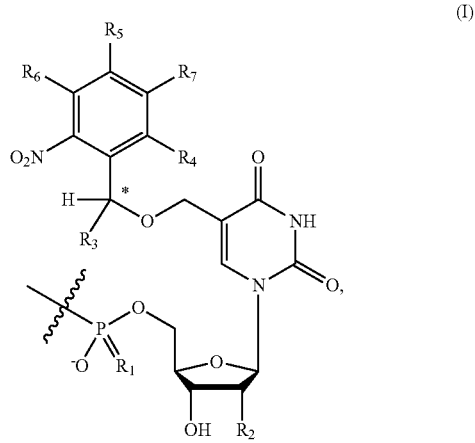

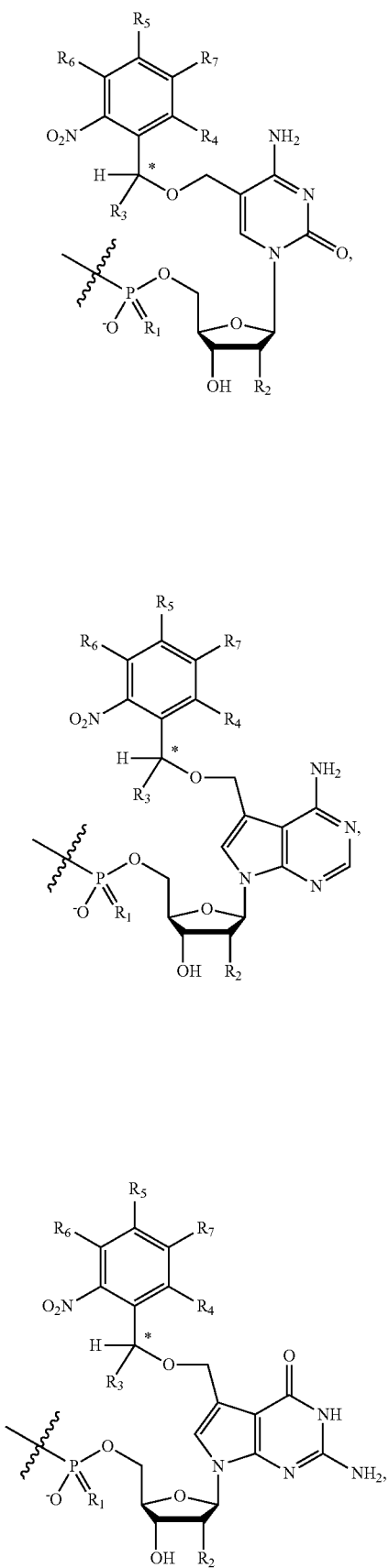
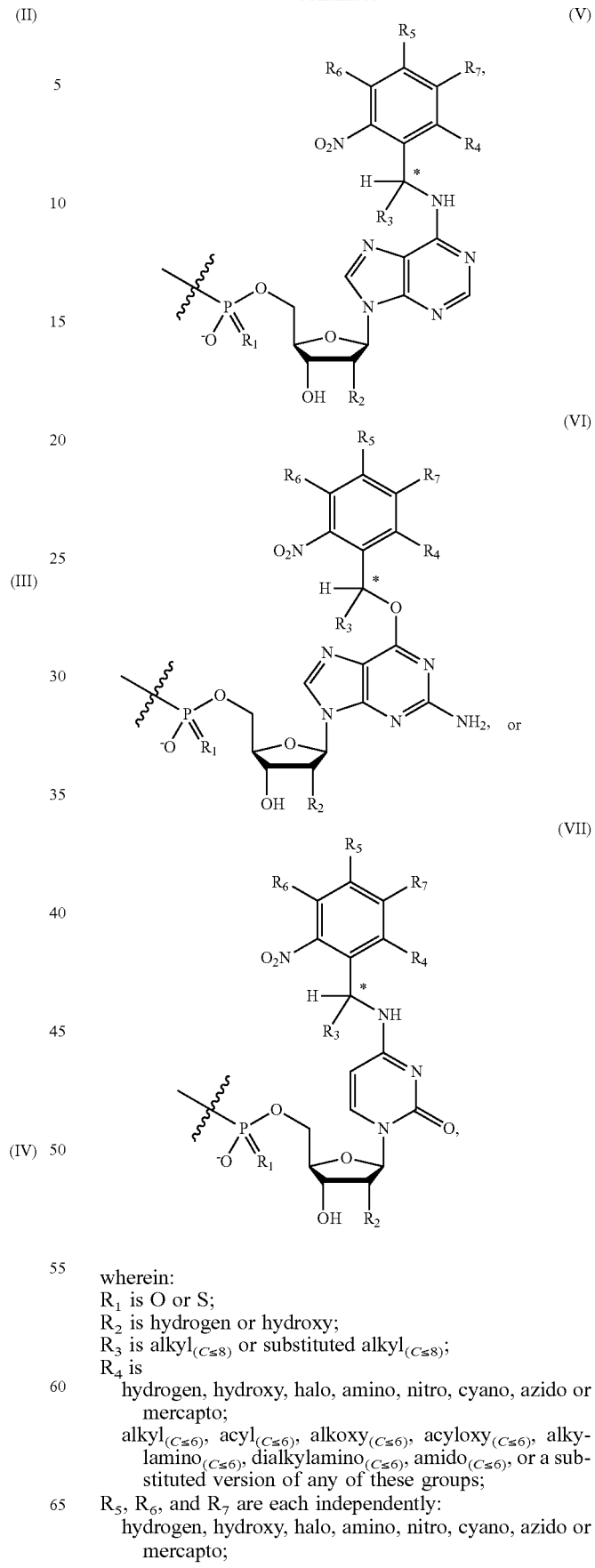

wherein:
R$_1$ is O or S;
R$_2$ is hydrogen or hydroxy;
R$_3$ is alkyl$_{(C \leq 8)}$ or substituted alkyl$_{(C \leq 8)}$;
R$_4$ is
  hydrogen, hydroxy, halo, amino, nitro, cyano, azido or mercapto;
  alkyl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;
R$_5$, R$_6$, and R$_7$ are each independently:
  hydrogen, hydroxy, halo, amino, nitro, cyano, azido or mercapto;

alkyl$_{(C \leq 6)}$, alkenyl$_{(C \leq 6)}$, alkynyl$_{(C \leq 6)}$, aryl$_{(C \leq 6)}$, aralkyl$_{(C \leq 8)}$, heteroaryl$_{(C \leq 6)}$, acyl$_{(C \leq 6)}$, alkoxy$_{(C \leq 6)}$, acyloxy$_{(C \leq 6)}$, alkylamino$_{(C \leq 6)}$, dialkylamino$_{(C \leq 6)}$, amido$_{(C \leq 6)}$, or a substituted version of any of these groups;

a group of formula:

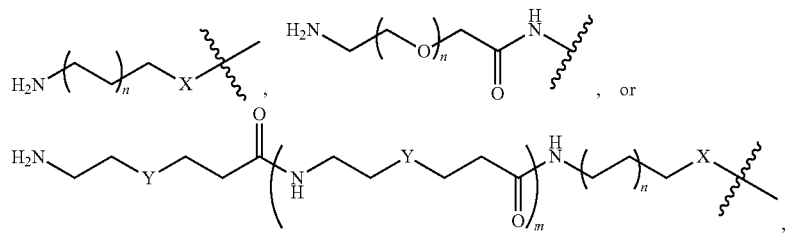

wherein

X is

—O—, —S—, or —NH—; or alkanediyl$_{(C \leq 12)}$, alkenediyl$_{(C \leq 12)}$, alkynediyl$_{(C \leq 12)}$, or a substituted version of any of these groups;

Y is —O—, —NH—, alkanediyl$_{(C \leq 12)}$ or substituted alkane-diyl$_{(C \leq 12)}$;

n is an integer from 0-6; and m is an integer from 0-6; or a -linker-reporter;

or a tautomer or optical isomer thereof.

92. The method of paragraph 91, wherein $R_7$ is methoxy.

93. The method of paragraph 92, wherein the photoactivatable terminating nucleotide comprises a structure of the formula:

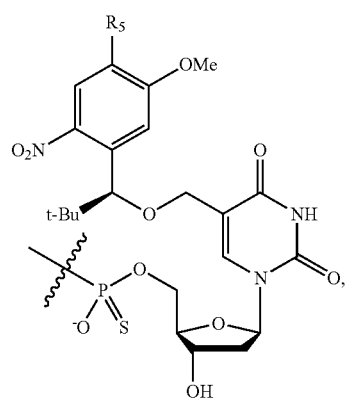

wherein $R_5$ is a -linker-reporter.

94. The method of paragraph 93, wherein the photoactivatable terminating nucleotide comprises a structure of the formula:

95. The method of any one of paragraphs 80-94, wherein the second population of oligonucleotide molecules introduced in process (g) are a population of oligonucleotide molecules of any one of paragraphs 21-27 and 29-41.

96. The method of any one of paragraphs 80-95, wherein the cell is fixed.

97. The method of any one of paragraphs 80-96, wherein activation comprises exposing the cytoplasm to ultraviolet light.

98. The method of any one of paragraphs 80-97, wherein activation is performed throughout the cytoplasm.

99. The method of any one of paragraphs 80-97, wherein activation is performed at a particular site within the cytoplasm.

100. The method of paragraph 99, wherein the particular site is an axon or a dendrite.

101. The method of any one of paragraphs 80-100, wherein synthesizing cDNAs comprises adding an RNA-dependent DNA polymerase.

102. The method of any one of paragraphs 80-101, further comprising processing the synthesized cDNAs to generate double-stranded cDNAs comprising the index barcode segment and the promoter region segment of the oligonucleotides.

103. The method of paragraph 102, further comprising amplifying the double-stranded cDNAs.
104. The method of paragraph 103, wherein amplifying comprises PCR, rolling circle amplification, or RNA amplification.
105. The method of paragraph 103 or 104, further comprising obtaining a sequence of at least a portion of the double-stranded cDNAs, thereby identifying the expressed RNAs.
106. The method of any one of paragraphs 99-105, wherein the method is a multiplex method, wherein the method is performed sequentially on two or more particular sites in the cell.
107. The method of any one of paragraphs 83-106, wherein the method is a multiplex method, wherein the method is performed sequentially on two or more cells in a sample.
108. The method of paragraph 106 or 107, wherein the populations of oligonucleotide molecules introduced during each round of multiplexing comprise unique index barcode segments.
109. A method for identifying the expressed RNAs in a cell, the method comprising:
  (a) introducing a population of oligonucleotide molecules into the cell, wherein each molecule comprises, from 5' to 3', an amplification segment, an index barcode segment, a hybridization segment, and a reversibly terminating nucleotide;
  (b) incubating the cell under conditions to allow for the hybridization segments of the population of oligonucleotide molecules to anneal to expressed RNAs;
  (c) activating at least a portion of the annealed oligonucleotide molecules to expose an extendable 3' hydroxy group; and
  (d) synthesizing cDNAs from the expressed RNAs by extending the activating oligonucleotide molecules from their extendable 3' hydroxy groups.
110. The method of paragraph 109, wherein the amplification segment is an RNA polymerase promoter.
111. The method of paragraph 109, wherein the amplification segment is a primer binding site.
112. The method of any one of paragraphs 109-111, wherein the amplification segment comprises between about seven and about fifty nucleotides.
113. The method of any one of paragraphs 109-112, wherein the hybridization segments comprise a poly-T sequence.
114. The method of any one of paragraphs 109-112, wherein the hybridization segments comprise one or more known nucleotide sequence.
115. The method of paragraph 114, wherein each known nucleotide sequence is complementary to a target RNA sequence.
116. The method of any one of paragraphs 109-115, wherein the hybridization segments comprise between about seven and about thirty nucleotides.
117. The method of any one of paragraphs 109-116, wherein the hybridization segments comprise about fifteen nucleotides.
118. The method of any one of paragraphs 109-117, wherein the population of oligonucleotide molecules further comprise a spacer segment positioned between the amplification segment and the index barcode segment.
119. The method of any one of paragraphs 109-118, wherein the reversibly terminating nucleotide is a photoactivatable terminating nucleotide.
120. The method of paragraph 119, wherein the photoactivatable terminating nucleotide comprises a structure of the formula:

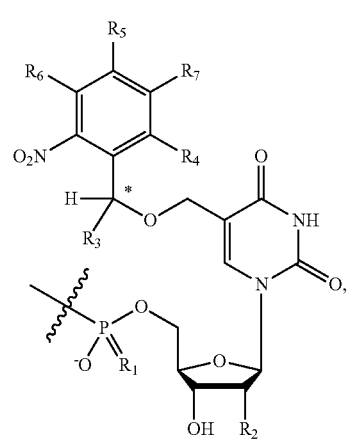
(I)

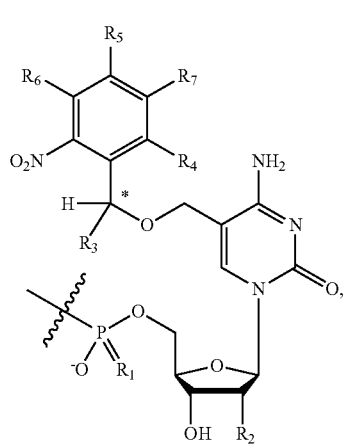
(II)

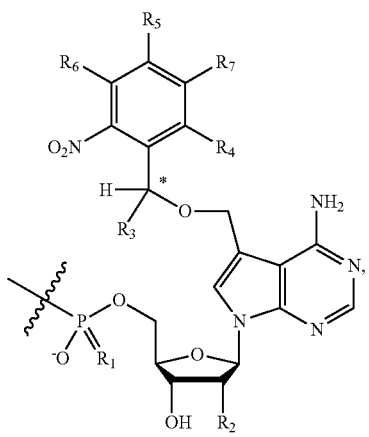
(III)

-continued

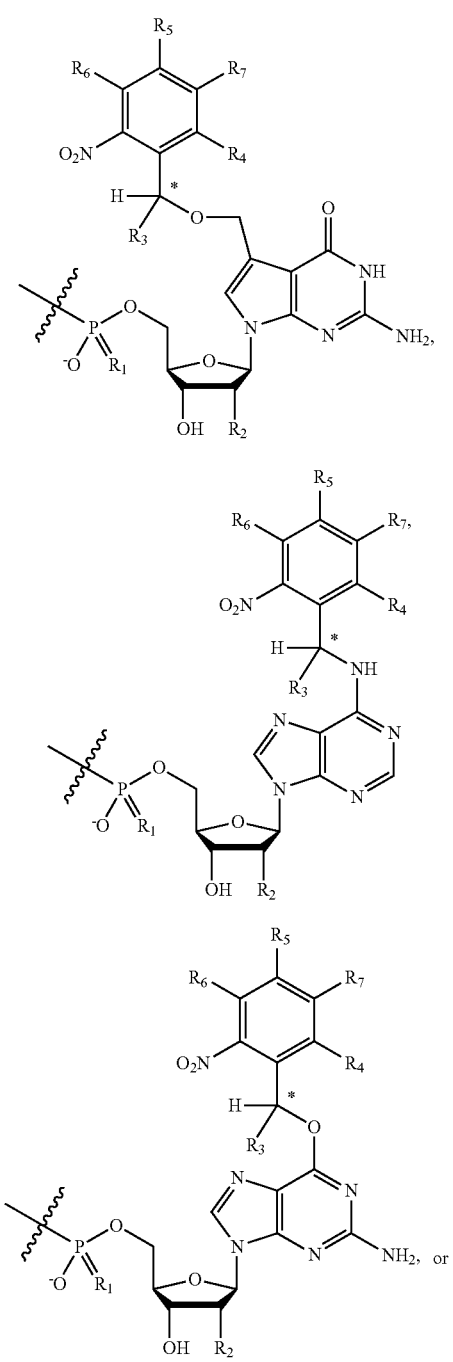

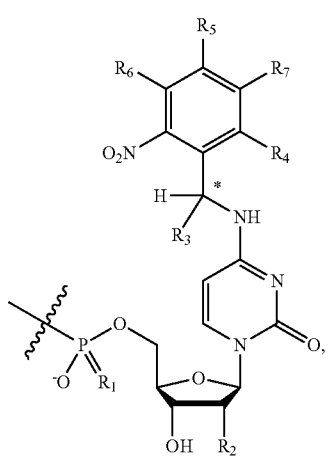

wherein:
R₁ is O or S;
R₂ is hydrogen or hydroxy;
R₃ is alkyl$_{(C\leq 8)}$ or substituted alkyl$_{(C\leq 8)}$;
R₄ is
  hydrogen, hydroxy, halo, amino, nitro, cyano, azido or mercapto;
  alkyl$_{(C\leq 6)}$, acyl$_{(C\leq 6)}$, alkoxy$_{(C\leq 6)}$, acyloxy$_{(C\leq 6)}$, alkylamino$_{(C\leq 6)}$, dialkylamino$_{(C\leq 6)}$, amido$_{(C\leq 6)}$, or a substituted version of any of these groups;
R₅, R₆, and R₇ are each independently:
  hydrogen, hydroxy, halo, amino, nitro, cyano, azido or mercapto;
  alkyl$_{(C\leq 6)}$, alkenyl$_{(C\leq 6)}$, alkynyl$_{(C\leq 6)}$, aryl$_{(C\leq 6)}$, aralkyl$_{(C\leq 8)}$, heteroaryl$_{(C\leq 6)}$, acyl$_{(C\leq 6)}$, alkoxy$_{(C\leq 6)}$, acyloxy$_{(C\leq 6)}$, alkylamino$_{(C\leq 6)}$, dialkylamino$_{(C\leq 6)}$, amido$_{(C\leq 6)}$, or a substituted version of any of these groups;
a group of formula:

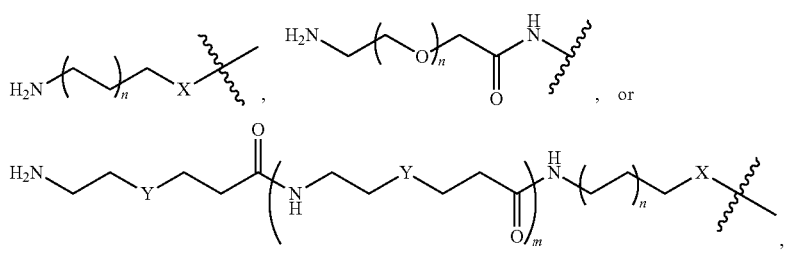

wherein
X is
—O—, —S—, or —NH—; or alkanediyl$_{(C \leq 12)}$, alkenediyl$_{(C \leq 12)}$, alkynediyl$_{(C \leq 12)}$, or a substituted version of any of these groups;
Y is —O—, —NH—, alkanediyl$_{(C \leq 12)}$ or substituted alkane-diyl$_{(C \leq 12)}$;
n is an integer from 0-6; and
m is an integer from 0-6; or
a -linker-reporter;
or a tautomer or optical isomer thereof.
121. The method of paragraph 120, wherein R$_7$ is methoxy.
122. The method of paragraph 121, wherein the photoactivatable terminating nucleotide comprises a structure of the formula:

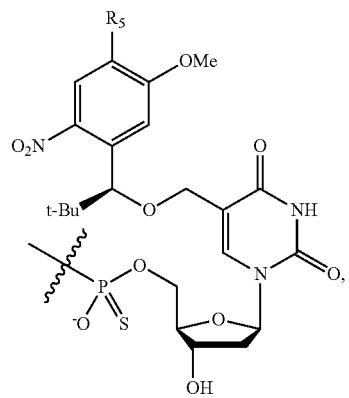

wherein R$_5$ is a -linker-reporter.
123. The method of paragraph 122, wherein the photoactivatable terminating nucleotide comprises a structure of the formula:

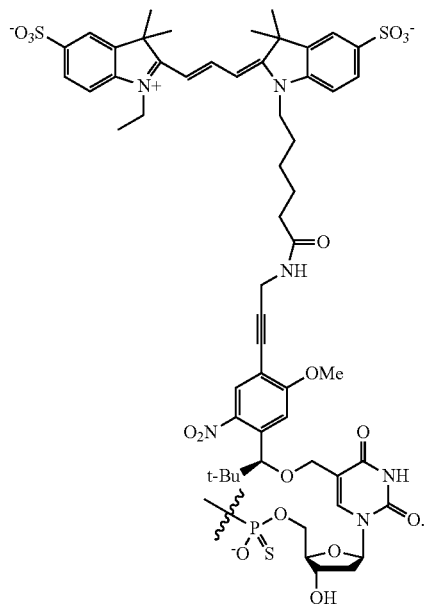

124. The method of any one of paragraphs 109-123, wherein the population of oligonucleotide molecules introduced in process (a) are a population of oligonucleotide molecules of any one of paragraphs 21-27 and 29-41.

125. The method of any one of paragraphs 109-124, wherein the cell is fixed.
126. The method of any one of paragraphs 109-125, wherein activation comprises exposing the cytoplasm to ultraviolet light.
127. The method of any one of paragraphs 109-126, wherein activation is performed throughout the cytoplasm.
128. The method of any one of paragraphs 109-126, wherein activation is performed at a particular site within the cytoplasm.
129. The method of paragraph 128, wherein the particular site is an axon or a dendrite.
130. The method of any one of paragraphs 109-129, wherein synthesizing cDNAs comprises adding an RNA-dependent DNA polymerase.
131. The method of any one of paragraphs 105-130, further comprising processing the synthesized cDNAs to generate a double-stranded cDNAs comprising the index barcode segment and the amplification segment of the oligonucleotides.
132. The method of paragraph 131, further comprising amplifying the double-stranded cDNAs.
133. The method of paragraph 132, wherein amplifying comprises PCR, rolling circle amplification, or RNA amplification.
134. The method of paragraph 132 or 133, further comprising obtaining a sequence of at least a portion of the double-stranded cDNAs, thereby identifying the expressed RNAs.
135. The method of any one of paragraphs 109-134, wherein the method is a multiplex method, wherein the method is performed sequentially on two or more particular sites in the cell.
136. The method of any one of paragraphs 109-135, wherein the method is a multiplex method, wherein the method is performed sequentially on two or more cells in a sample.
137. The method of paragraph 135 or 136, wherein the populations of oligonucleotide molecules introduced during each round of multiplexing comprise unique index barcode segments.
138. A kit comprising a population of oligonucleotides according to any one of paragraphs 21-41 and at least one of a DNA polymerase, an RNA polymerase, a reverse transcriptase, deoxyribonucleotides, and ribonucleotides.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 3A-B. Schematics of two exemplary CHeX-seq oligonucleotide synthesis method. FIG. 3A—The complete CHeX-seq probe (T7-BC1-N(15)-T-LTdU-Cy5) sequence is shown on the top. An oligo containing T7 promoter site, an Illumina 6 bp barcode1 (BC1, blue) and a 15 bp degenerate sequence, T7BC1-15N-T and its reverse complement oligo, T7BC1-15N-T-RC are synthesized and annealed to each other to generate double-stranded oligos. Cy5-labeled Lightning Terminator, LTdU-Cy5 is incorporated to its 3' end. The single-stranded CHeX-seq probe is harvested after denaturation of the double-stranded probe and HPLC purification. T7BC1-15-N-T is SEQ ID NO: 2 and T7BC1-15N-RC is SEQ ID NO: 3. FIG. 3B—T7BC1 is SEQ ID NO: 4; T7BC1-RC is SEQ ID NO: 5; 15N-T is SEQ ID NO: 6; and A-15N-RC is SEQ ID NO: 7. The sequences of the ligated pair are provided by SEQ ID NOs: 2 and 3.

FIG. 13A—Schematic of CHeX-seq assay rationale. FIG. 13B—CHeX-seq probe loading into K562 cell nuclei (DIC image) and fluorescence signal before and after activation of the CHeX-seq probe in a single nucleus (red arrow), scale bar=20 μm. FIG. 13C—Statistics of CHeX-seq priming sites with respect to genomic features. FIG. 13D—TSS proximal (+/−5 kb) coverage of K562 samples (all positive samples merged). FIG. 13E—z-scored coverage at TSS proximity (upper) and CDS (lower) at single-cell level. FIG. 13F—Overlap between CHeX-seq primed genes (whole gene body>0) and RNA-seq expressed genes (exon>median). FIG. 13G—GO functional enrichment results (top 20) of the CHeX-RNA overlapping genes (FIG. 13F, left).

FIGS. 14A-B. Genomic comparison of CHeX-seq with other open-chromatin assays. FIG. 14A—UCSC Genome Browser track view comparing the coverage of CHeX-seq (purple) against ATAC-seq (red), DNase-seq (blue), FAIRE-seq (green) at locus OTUD5. Below the four assays are regulatory interaction tracks (GeneCards genes TSS, Enhancers and Promoters, and GeneHancer Proximal-Distal Interactions) derived from the GeneHancer database (Fishilevich et al., 2017). The last four tracks are transcriptome and three histone marks (H3K27ac, H3K4me1, H3K4me3s). A regulatory interaction between OTUD5's promoter and one of its 3' introns is shared by all four open-chromatin assays (blue rectangle). FIG. 14B—Hierarchical clustering of open-chromatin assays, transcriptome, and epigenomes at 10 kb-bin (left) and 50 kb-bin (right) resolution, using binarized coverage and Jaccard distance.

FIGS. 15A-C. Correlation of CHeX-seq read distance from TSS with gene RNA abundance. FIG. 15A—Bulk K562 RNA-seq. FIG. 15B—Bulk K562 GRO-seq. FIG. 15C—K562 scRNA-seq, single cells averaged. Y-axes: gene expressions; x-axes: distance to TSS from CHeX priming sites.

FIG. 16A—Schematic showing the hypothesis that CHeX-seq priming-extending products should have opposite strandedness from sense-strand mRNA transcripts. FIG. 16B—Testing the hypothesis in FIG. 16A. X-axis: various genomic features where CHeX-seq priming events are counted and binarized; y-axis: ratio of number of antisense-stranded over sense-stranded CHeX-seq products.

FIG. 17A—Schematic of CHeX-seq analysis of paraformaldehyde-fixed tissue sections. FIG. 17B—Hippocampal section showing neurons immunolabeled for MAP2 (green). Red fluorescence indicates localization of the CHeX-seq probe. The right-most panels show reduced fluorescent signal in the single neuronal nucleus (white arrow) that was activated; scale bar=20 µm. FIG. 17C—Paraformaldehyde-fixed, cultured cortical neuron, shown by DIC microscopy (left panel) and nuclear fluorescence for the CHeX-seq primer (middle panel). This signal is diminished after probe activation (right panel; quantified in the right panel insert); scale bar=20 µm. FIG. 17D—CHeX-transcriptome comparison. Left, mouse fixed tissue section; right, mouse dispersed neurons. Rows are scRNA-seq average expression in exonic or intronic region, columns are CHeX-seq binarized priming signal in whole gene body, exonic or intronic region. FIG. 17E—Correlation in intronic regions between CHeX-seq priming frequency and transcriptional activity in hippocampal sections. FIG. 17F—Correlation in intronic regions between CHeX-seq priming frequency and transcriptional variability in mouse slice tissue.

FIG. 20A—The UCSC Genome Browser track view for a portion of chromosome 1. The CheX-seq track is similar to the ATAC-seq track showing that this chromosomal area is open. This is distinct from DNAse-seq and FAIRE-seq data. FIG. 20B—The left panel is the DAPI staining of the K562 cell nuclei. The right panel shows the fluorescence in situ hybridization signal using 8 fluorescently labeled oligonucleotides. These data show highly specific chromosome 1 trisomy in the K562 cells' nuclei. Scale bar=20 µm.

FIG. 22A—K562. FIG. 22B—human astrocyte. FIG. 22C—human neuron. FIG. 22D—mouse astrocyte. FIG. 22E—mouse neuron. FIG. 22F—in situ mouse neuron.

FIG. 23A—Images of human astrocytes on top and mouse on bottom. DIC (left) and DAPI images (left and middle panels, respectively) before CHeX-seq probe activation, and DAPI image after activation (right panels; quantification of DAPI signal in insert). Scale bar=20 µm. FIG. 23B—Quantification of CHeX-seq priming sites with respect to genomic features in astrocytes (left) and neurons (right). Key for CHeX-seq read site of localization relative to gene structure.

DETAILED DESCRIPTION

The process of RNA transcription requires a cell's genomic DNA to be in an open-chromatin conformation, where there is less nucleosome packing, so that the transcription regulatory proteins can bind and function. Likewise, mitochondrial DNA must be in an open conformation for transcription to occur. It is clear that chromatin structure is dynamic and regulated by a number of factors including development, stress and pharmacological challenge (Fullard et al., 2017; Kozlenkov et al., 2014; Kozlenkov et al., 2016). Most chromatin modeling studies have relied upon the use of multiple cells to generate genomic DNA/chromatin for analysis. Included among chromatin analysis procedures are DNase-seq, FAIRE-seq, and ChIP-seq as well as other approaches. Recently, these methods have been extended to single cells (Cusanovich et al., 2015; Buenrostro et al., 2015; Rotem et al., 2015; Clark et al., 2018). For example, the recent ATAC-seq approach to mapping chromatin in single cells exploits an assay for detecting transposase-accessible chromatin (Buenrostro et al., 2013). This methodology uses Tn5 transposase to tag and purify accessible nucleosome-free double-stranded DNA regions in the genome. Each of these procedures has specific advantages and disadvantages, with the most significant being that they all assess chromatin in nuclei isolated from the tissue of interest, thereby losing spatial location information and the cellular microenvironment context. To overcome these issues, CHeX-seq (CHromatin eXposed) has been developed to assess chromatin conformation in fixed single cells, including neurons and astrocytes.

CHeX-seq is complimentary to ATAC-seq as CHeX-seq queries single-stranded DNA while ATAC-seq assesses double-stranded DNA. Open chromatin is composed of both double- and single-stranded DNA (Bjursell et al., 1979; Scheer et al., 1987; Kouzine et al., 2017). The open state of chromatin is necessary for many cell functions, such as replication, homologous recombination, DNA repair as well as transcription. While the open state of chromatin is necessary for transcription to occur, "openness" may not correlate directly with transcription, as other trans-acting factors are also required (Yu et al., 2017). Single-stranded DNA is necessary for transcription in the form of the single-stranded "transcription bubble" which has been reported to be as large as ~200 bases (Barnes et al., 2015; Bieberstein et al., 2012). Further in concert with the transcription bubble, transcriptionally active chromatin contains long stretches of single-stranded areas greater than a kilobase in length (Kouzine et al., 2017; Bieberstein et al., 2012; Zhou & Paull, 2015). The amount of single-stranded DNA in the genome is estimated to vary from ~0.2% to 2.5%, depending upon the physiological state of the cell (Zhou & Paull, 2015).

Figure 3A:
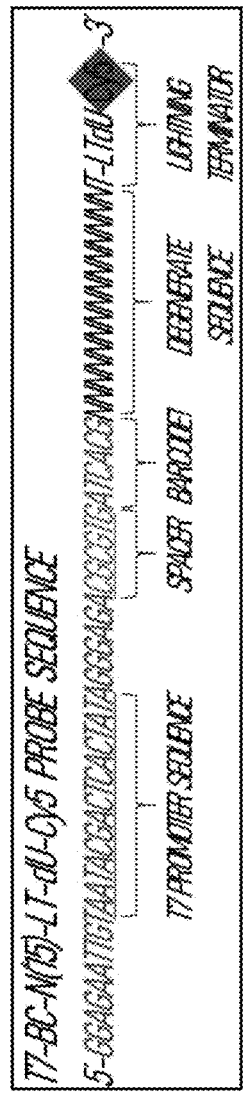
Figure 13A:
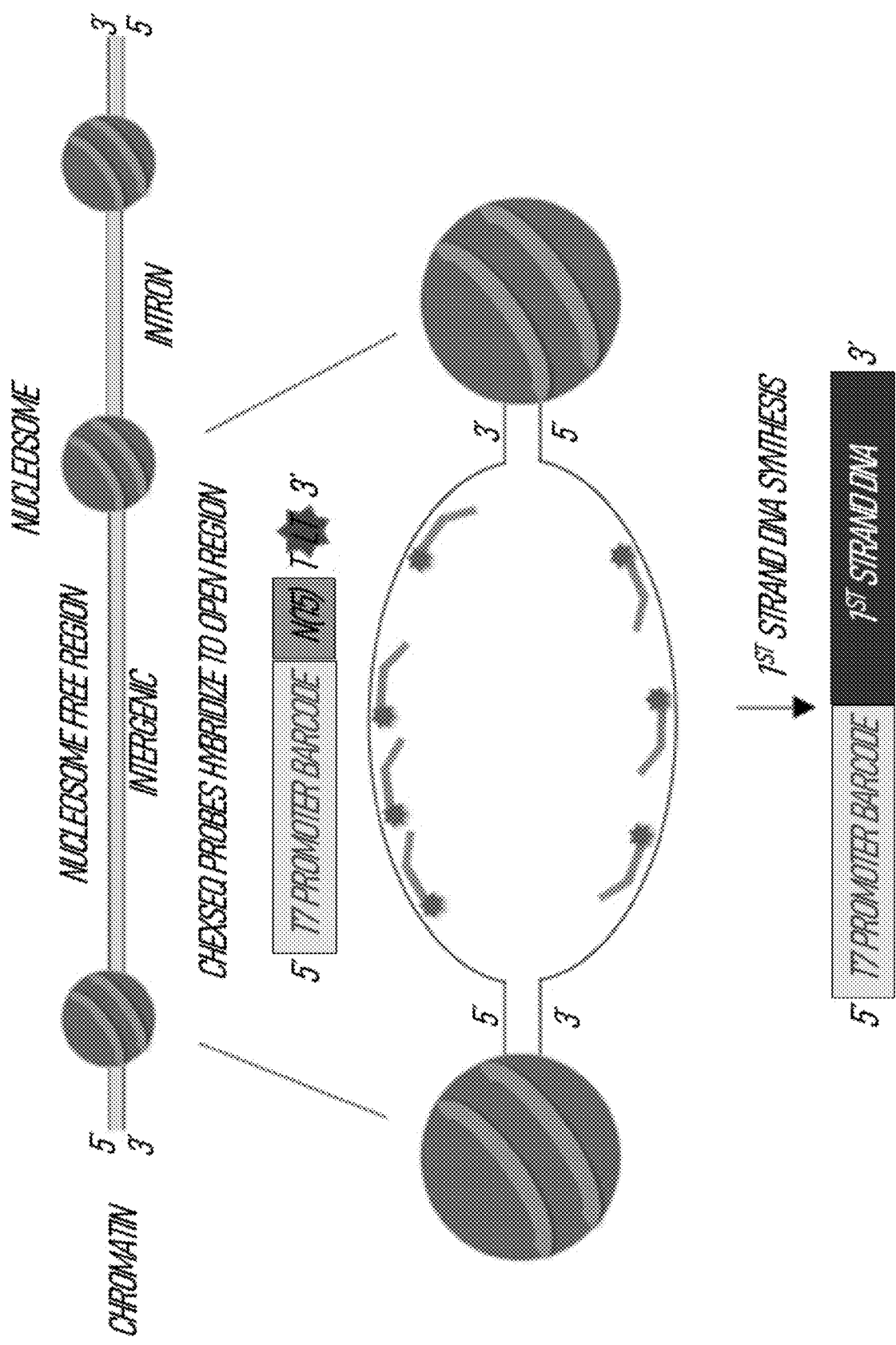
FIGS. 13A-G. K562 CHeX-seq Benchmarking.
Figure 19:
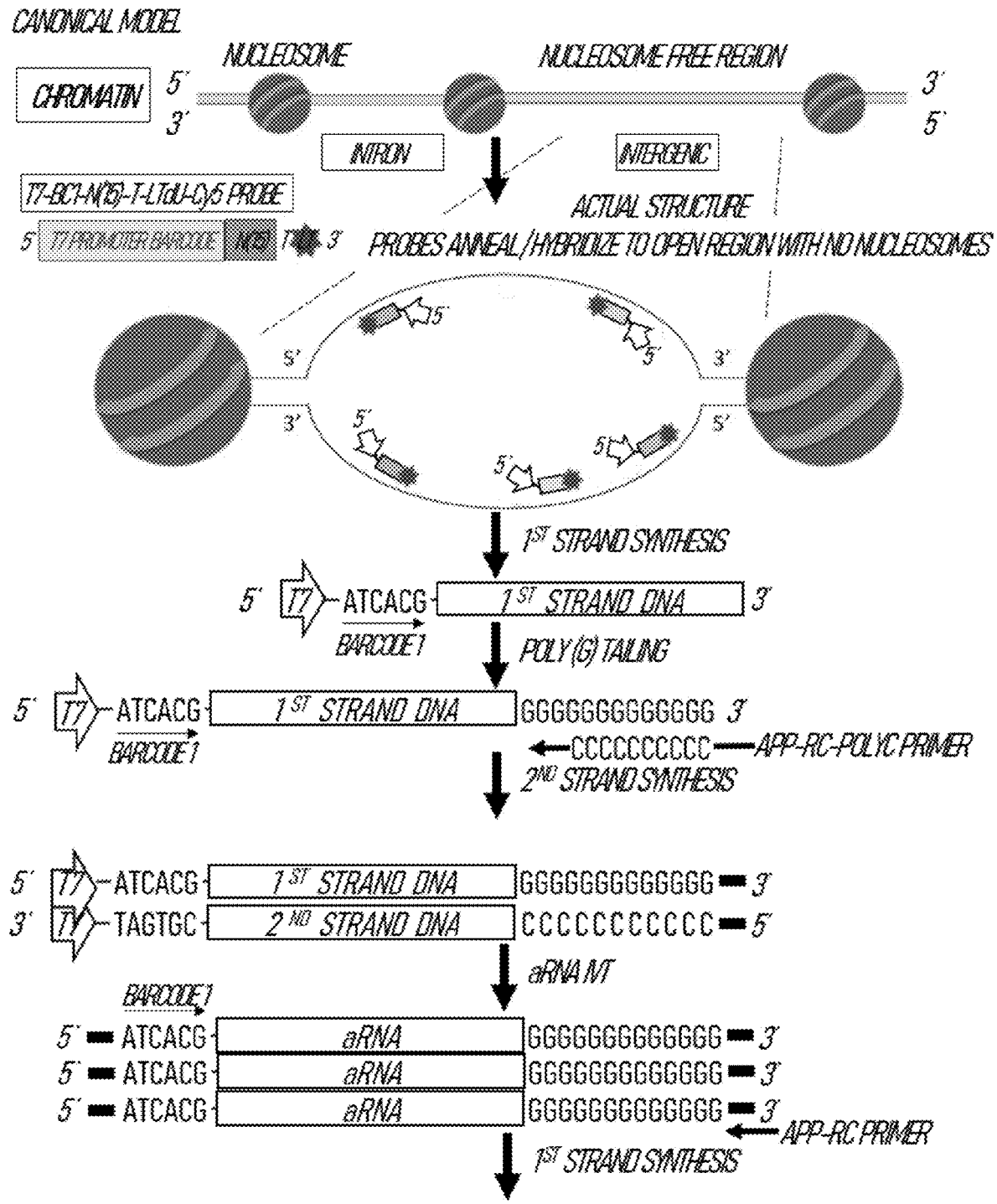
FIG. 19. A schematic of the CHeX-seq aRNA amplification protocol. Upon applying the CHeX-seq probe, T7-BC1-N(15)-T-LTdU-Cy5, to the PFA fixed, Triton X-100 permeabolized cells, the degenerate N(15) sequence hybridizes to single-stranded nucleosome-depleted genomic DNA found within open chromatin regions. After laser-mediated photocleavage of the termination group of the CHeX oligonucleotide first strand DNA synthesis is primed by DNA polymerase I. Second strand DNA is primed and synthesized using custom App-RC-polyC primer (Table 1) after poly (G) tailing of 3' end of $1^{st}$ strand DNA. Finally, RNA is amplified using linear in vitro transcription from the T7 RNA polymerase promoter incorporated into the double-stranded DNA. $2^{nd}$ round $1^{st}$ and $2^{nd}$ strand DNA subsequently are synthesized and amplified by PCR.

To assay single-stranded DNA at single-cell resolution in situ, CHeX-seq utilizes the resolution of light to limit reagent action and chromatin analysis to an individual cell's nucleus. To accomplish this, an oligonucleotide (FIG. 13A) has been designed that can anneal randomly to single-stranded genomic DNA and remain inactive until light-activation. After photoactivation, the oligonucleotide serves as a primer for DNA polymerase-mediated complementary DNA synthesis (FIG. 13A). This is DNA-directed in situ transcription (Eberwine et al., 1992; Tecott et al., 1988). The resolution of primer activation is determined by the diffraction limit of the activating light's wavelength and the numerical aperture of the lens. To facilitate analysis, the CHeX-seq oligonucleotide was engineered to contain a sample-specific barcode: a T7 RNA polymerase promoter site along with a degenerate DNA sequence that is terminated with a fluorescently tagged, photo-reversibly blocked nucleotide (FIGS. 3A&13A). After DNA synthesis, the complementary DNA is removed with 0.1 N NaOH, copied into double-stranded DNA, and linearly amplified using T7 RNA polymerase (aRNA amplification) (Van Gelder et al., 1990; Eberwine et al., 1992). The aRNA is subsequently reverse transcribed to $1^{st}$ and $2^{nd}$ strand DNA with custom primers, converted into a sequencing library, and sequenced (FIGS. 3A&19).

CHeX-seq has been benchmarked against the ENCODE-analyzed human K562 cells, which demonstrated its utility in dispersed mouse and human primary brain cells. These data highlight significant correlations between open-chromatin status and mRNA expression. These data show a DNA strand preference that suggests protein binding domains in single-stranded chromatin. CHeX-seq also provides evidence for genomic DNA regions that exhibit single-strandedness but are not transcribed, potentially including areas of DNA repair and sites of replication in dividing cells (Yu et al., 2017; Vasquez et al., 2001). In addition, human neurons and astrocytes were generally found to have more open chromatin than their mouse counterparts. Further, CHeX-seq can be used with single immunostained cells in fixed brain tissue sections. As CHeX-seq queries single-stranded DNA, the openness of mitochondria in single cells was able to be examined and the DNA in mitochondria present in in situ neurons was found to be more open than those in dispersed cells, suggesting a difference in metabolic status. The chromosomal landscape of single-stranded open-chromatin can be used to categorize cells and to predict subtypes of cells. CHeX-seq enables the analysis of chromatin structure in fixed immunostained single cells, opening up new avenues for examining the role of neuronal circuitry in modulating an individual cell's chromatin landscape in the natural tissue context.

Some embodiments provided herein relate to methods that allow for the study of the dynamics of chromatin structure and its correspondence with cytoplasmic RNA pools simultaneously in single cells. Also provided are methods to assess higher order chromatin structural dynamics around any single gene or multiple genes in anatomically and spatially defined single cells. Integration of chromatin structure determination with the same cell's cytoplasmic transcriptome in response to external (e.g., pharmacological) stimulation will enable the dynamics of the cell's transcriptional responses to be quantified.

I. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Amplification" refers to any means by which a polynucleotide sequence is copied and thus expanded into a larger number of polynucleotide molecules, for example, by reverse transcription, T7 RNA amplification, polymerase chain reaction, and ligase chain reaction, among other methods.

"Sense" refers to the nucleic acid sequence of the coding strand of a double stranded DNA molecule encoding a protein, or to a sequence which is substantially homologous to the coding strand. As defined herein, a sense sequence is complementary to the sequence of an expressed RNA molecule encoding a protein. It is not necessary that the sense sequence be complementary solely to the coding portion of the expressed RNA molecule. The sense sequence includes regulatory sequences specified on the coding strand of a DNA molecule encoding a protein, which regulatory sequences control expression of the coding sequences.

"Binding" is used herein to mean that a first moiety interacts with a second moiety.

"Biological sample," as that term is used herein, means a sample obtained from a single-cellular or multi-cellular organism that can be used to assess the level of expression of a nucleic acid, the status of a chromatin state, or both. Such a sample includes, but is not limited to, a cell, a blood sample, a tissue sample, a neural tissue sample, a brain sample, and a cerebrospinal fluid sample.

As used herein, a "pathological sample" is a biological sample from a subject having or suspected of having a disease, disorder, or condition. Pathological samples, include, but are not limited to, histological tissue sections and/or other biological preparations, such as tissue culture cells. Pathological samples are commonly used in diagnostic pathology.

As used herein, a "fixed sample" is a sample that has been treated so as to preserve the structural organization of cells and tissues in the sample in as close a life-like state as possible for subsequent examination, for instance, by light microscope. Fixation typically arrests autolysis and bacterial decomposition and stabilizes the structural organization of cellular and tissue constituents so that they withstand the subsequent stages of tissue processing.

"Complementary" as used herein refers to the broad concept of subunit sequence complementarity between two nucleic acids, e.g., two DNA molecules or a DNA molecule and an RNA molecule. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "coding region" of a gene includes the nucleotide residues of the coding strand of the gene and the nucleotides of the non-coding strand of the gene that are homologous with or complementary to, respectively, the coding region of an mRNA molecule that is produced by transcription of the gene.

A "coding region" of an mRNA molecule also includes the nucleotide residues of the mRNA molecule that are matched with an anticodon region of a transfer RNA molecule during translation of the mRNA molecule or that encode a stop codon. The coding region may thus include nucleotide residues corresponding to amino acid residues that are not present in the mature protein encoded by the mRNA molecule (e.g. amino acid residues in a protein export signal sequence).

As used herein, a "degenerate sequence" refers to sequence in which at one or more of the nucleotide positions in a polynucleotide, there are two or more types of nucleotides. In the context of a single polynucleotide, a "degenerate sequence" may be a "random" or "unknown" sequence.

An "isolated cell" refers to a cell which has been separated from other components and/or cells that naturally accompany the isolated cell in a tissue or organism.

An "isolated nucleic acid" refers to a nucleic acid (or a segment or fragment thereof) that has been separated from sequences that flank it in a naturally occurring state, for example, an RNA fragment that has been removed from the sequences that are normally adjacent to the fragment. The term also applies to nucleic acids that have been substantially purified from other components that naturally accompany the nucleic acid, e.g., RNA or DNA or proteins, in the cell.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "polynucleotide" means a single strand or parallel and anti-parallel strands of a nucleic acid. Thus, a polynucleotide may be either a single-stranded or a double-stranded nucleic acid. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Watson/Crick base-pairing" and "Watson/Crick complementarity" refer to the pattern of specific pairs of nucleotides, and analogs thereof, that bind together through hydrogen bonds, for example A pairs with T or U, and G pairs with C. The act of specific base-pairing is "hybridization" or "hybridizing." A hybrid forms when two, or more, complementary strands of nucleic acids undergo base-pairing.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, a "permeabilization agent" is a chemical that enables an oligonucleotide or other molecule access to the intracellular constituents of a cell.

A "photocleavable moiety" or "photoactivatable moiety" refers to a moiety that is cleaved or activated upon irradiation of the moiety with light energy. Light energy useful for activating such labels includes, but is not limited to, visible light, ultraviolet (UV) light, infrared (IR) light, among others. A photocleavable moiety or photoactivatable moiety is "incorporated into" a nucleic acid when the moiety is attached to, incorporated within, integrated into, or linked to the nucleic acid. This includes coupling of a moiety to the terminus of a nucleic acid as well as incorporating the moiety into a nucleic acid by including a nucleobase that contains such a label.

"Primer" refers to a polynucleotide that is capable of specifically hybridizing to a polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single stranded, but may be double stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A "genomic DNA" is a DNA strand that has a nucleotide sequence homologous with a gene as it exists in the natural host. By way of example, a chromosome or a fragment of a chromosome is a genomic DNA. In addition, mitochondrial DNA is a genomic DNA.

"Homologous" as used herein, refers to the subunit sequence similarity between two polymeric molecules, e.g., between two nucleic acid molecules, e.g., two DNA molecules or two RNA molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means=NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the structure

includes the structures

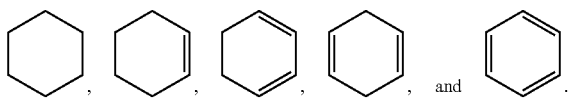

As will be understood by a person of skill in the art, no one such ring atom forms part of more than one double bond. The symbol "⁓", when drawn perpendicularly across a bond indicates a point of attachment of the group. It is noted that the point of attachment is typically only identified in this manner for larger groups in order to assist the reader in rapidly and unambiguously identifying a point of attachment. The symbol "◤" means a single bond where the group attached to the thick end of the wedge is "out of the page." The symbol "◣" means a single bond where the group attached to the thick end of the wedge is "into the page". The symbol "⁓" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

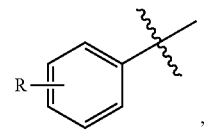

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

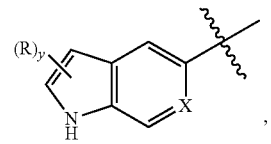

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n)

and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). Where the term "aliphatic" is used without the "substituted" modifier, then only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

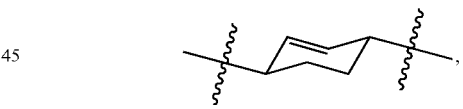

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —CCH, —CCCH$_3$, and —CH$_2$CCCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

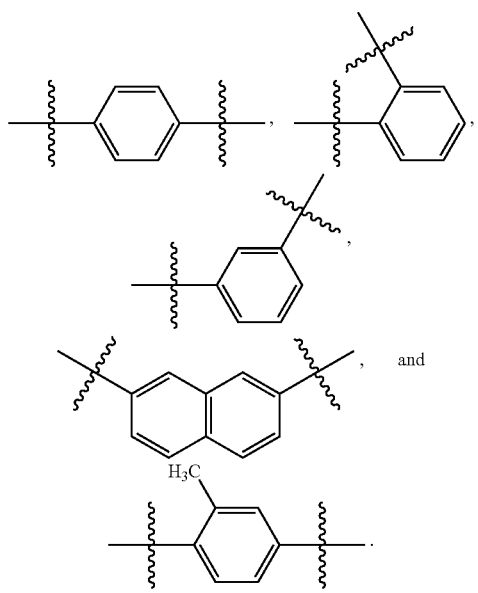

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

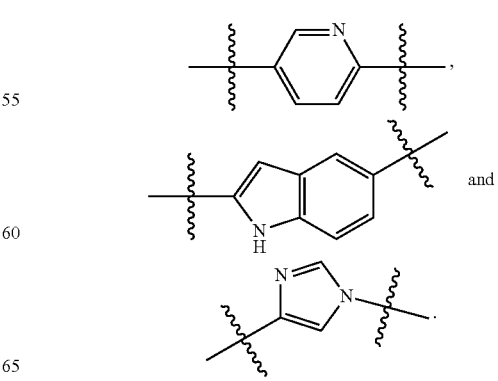

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. As used herein, the term does not preclude the presence of one or more double bonds in the ring or ring system, provided that the resulting groups remains non-aromatic. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O— alkanediyl-, —O—alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH— alkanediyl-, —NH— alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "aryl sulfonyl", "aralkyl sulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

An "isomer" of a first compound is a separate compound in which each molecule contains the same constituent atoms as the first compound, but where the configuration of those atoms in three dimensions differs.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

II. Compositions and Methods for Detecting Open Genomic DNA (CHeX-seq)

The accessibility of chromatin underlies a cells ability to transcriptionally respond to its local microenvironment and stimulation. This is important for normal cellular function as well as modulated changes in function. Knowledge of these subcellular sites of transcriptional regulation is required to understand a cells ability to respond to stimuli as well as the actual response.

Transcriptional analysis of single cells shows that a significant degree of cell-to-cell heterogeneity is influenced by the cell's microenvironment. These variations in the transcriptional states depend in part upon the open-chromatin status of nuclear genomic DNA or the open conformation of mitochondrial genomic DNA. While there are single cell approaches for analysis of chromatin structure, they require isolation of chromatin from the cell, at which point nearest neighbor chromosomal interactions are lost. For example, ATACseq has been used to assess open chromatin in multiple single cells (population studies at the single cell level, not just a single cell), but it is not very sensitive and assesses only ~3% of the open chromatin sites in any particular cell. Furthermore, ATACseq requires chromatin to be isolated from the cells of interest.

To overcome these issues with ATACseq and other chromosome-conformation-capture methods, provided herein are methods for high-resolution, single cell chromatin analysis that is reflective of the cellular functional state. These methods, termed CHeX-seq (Chromatin eXposed), do not require the genomic DNA to be isolated from the cell and can be used for identifying regions of open genomic DNA in single fixed cells.

Figure 1:
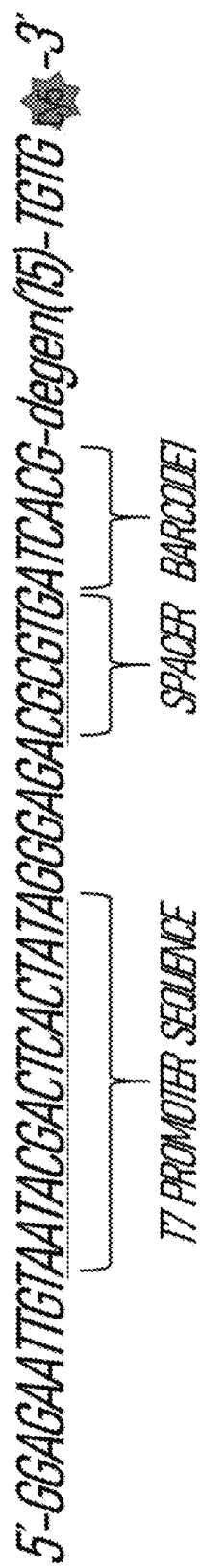
FIG. 1. Exemplary CHeX-seq multifunctional oligonucleotide (SEQ ID NO: 1). There is a photoactivatable non-extendable nucleotide containing a Cy5 fluorescent moiety at the 3' end of the oligonucleotide. Upon light activation the Cy5 fluorescence is lost and a free 3'-OH is formed such that the oligonucleotide can be extended in situ, thereby providing for DNA synthesis.

High-resolution CHeX-seq uses the resolution of light to limit chromatin analysis to an individual cell's nucleus. To accomplish this, CHeX-seq oligonucleotides have been engineered to contain index barcodes, an amplification segment, and a light-activated reporter-tagged reversibly terminating nucleotide (FIG. 1). These oligonucleotides can anneal, via their hybridization segment, in either a random or targeted fashion, to single-stranded genomic DNA but remain inactive until triggered. In situ activation of the light-activated reporter-tagged reversibly terminating nucleotide by laser in selected cells allows the CHeX-seq oligonucleotides to act as primers. This primer is used to prime DNA copying of single-stranded DNA in situ in those specific cells, which is then amplified and sequenced.

To provide for random annealing, the oligonucleotides contain short degenerate sequences that can anneal anywhere they can hybridize with the genomic DNA. This provides many more oligos in the degenerate mix that can bind, effectively increasing the oligonucleotide concentration over the course of the annealing time (e.g., 45 sec). In some embodiments, the annealing time may be about 10 sec, about 15 sec, about 20 sec, about 25 sec, about 30 sec, about 35 sec, about 40 sec, about 45 sec, about 50 sec, about 55 sec, about 60 sec, about 65 sec, about 70 sec, about 75 sec, about 80 sec, about 85 sec, about 90 sec, about 2 min, about 3 min, about 4 min, about 5 min, about 6 min, about 7 min, about 8 min, about 9 min, about 10 min, about 15 min, about 20 min, about 25 min, or about 30 min. The progression of annealing can be monitored using fluorescence microscopy to detect the fluorescent signal of the fluorescent tag in the nucleus of the cells.

The hybridization between the degenerate sequence in the oligonucleotides and genomic DNA may not be stringent. For example, there may be one or more, two or more, three or more, four or more, five or more, six or more, seven or more, eight or more, nine or more, or ten or more mismatches between the degenerate sequence in the oligonucleotide and the genomic DNA region to which it hybridizes. The number of mismatches that can be tolerated while still allowing for hybridization to any given genomic DNA sequence depends on the length of the degenerate sequence, the thermodynamics of the hybridization as dictated by the sequence of the degenerate sequence, and the annealing temperature. The thermodynamics of a hybridization event can be estimated using the methods described in SantaLucia & Hicks (2004). The mismatches may be in one or more continuous stretch(es), or the mismatches may be spaced out throughout the hybridized region in any configuration. For example, the hybridized region may comprise a stretch of two, three, four, five, six, seven, or eight mismatches in a row that create a bubble in the hybridized region. The hybridized region may comprise both a bubble in a first part and a single mismatch in a second part. The hybridized region may comprise both a first bubble in a first part and a second bubble in a second part.

The length of the degenerate sequence may vary. For example, the generate sequence in any given CHeX-seq oligonucleotide may have a sequence that is at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. A population of CHeX-seq oligonucleotides may consist of oligonucleotides all having the same length degenerate sequence. Alternatively, a population of CHeX-seq oligonucleotides may comprise oligonucleotides having degenerate sequences of various lengths.

In addition to providing for hybridization to the genomic DNA, the degenerate sequence will remain in the later amplified polynucleotide pool that is analyzed using sequencing, such as next-generation sequencing. As such, the degenerate sequence associated with each detected hybridization event may be used as a molecular barcode, or unique molecular identifier (UMI), to allow for analysis of whether only one locus of a gene is in an open chromatin state or whether both loci of that gene are in an open chromatin state.

To provide for targeted annealing, the oligonucleotides contain short, known sequences in place of the short degenerate sequences. The short, known sequences can be designed to anneal to any location in the genomic DNA where it is desirable to analyze whether the chromatin is in an open or closed state. For example, a panel of oligonucleotides may be designed to comprise short known sequences that are defined for one or more specific gene(s). For example, a panel of oligonucleotides may be designed to comprise short known sequences that can hybridize to genomic regions near all known SNPs or open genomic DNA regions that correlate with schizophrenia. Such a panel may be used in diagnostic methods. In designing a panel of targeted oligonucleotides, it may be desirable to select short known sequences having a certain G/C content and length so that each oligonucleotide will hybridize at a similar annealing temperature.

Figure 3B:
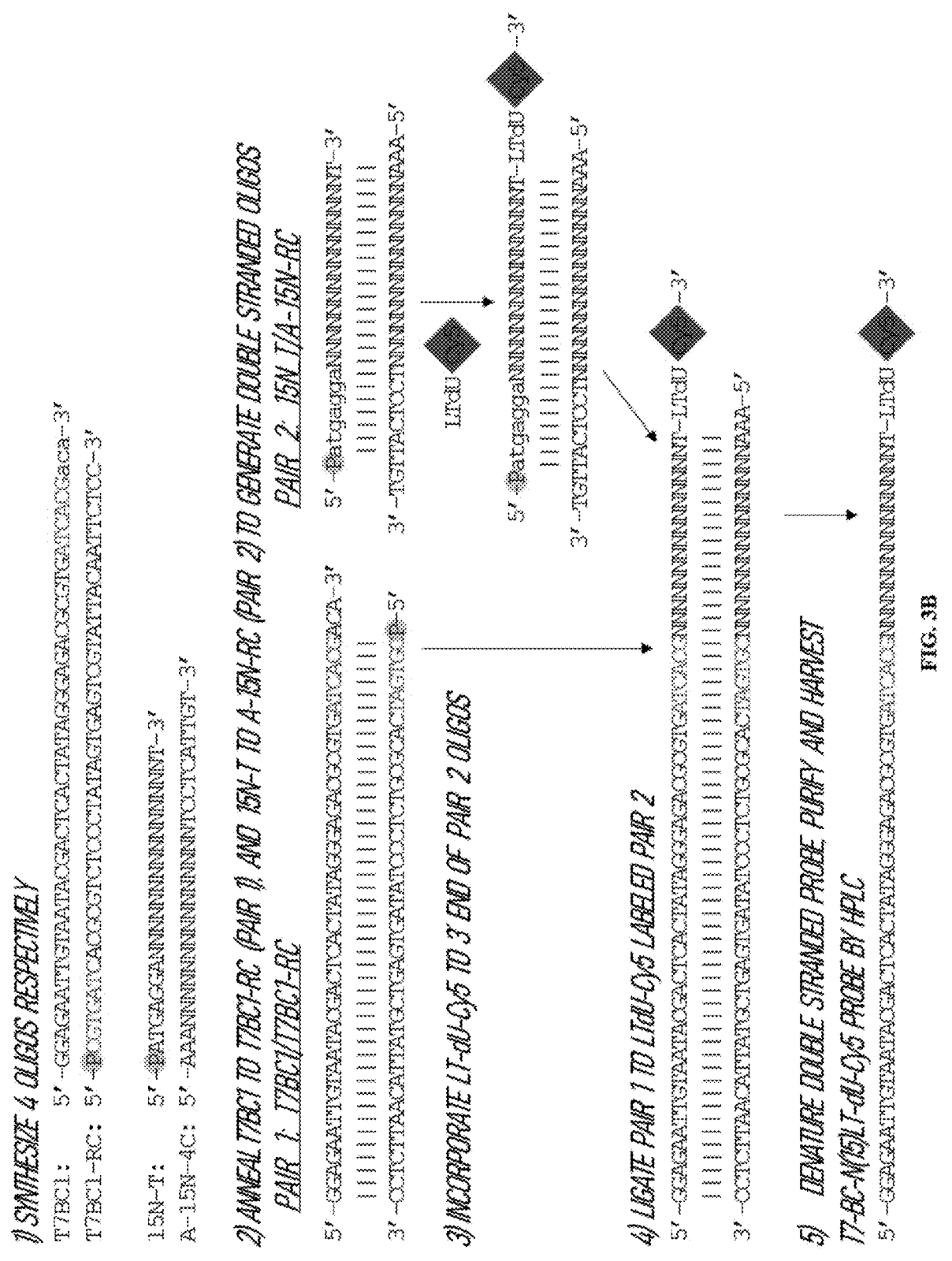
Figure 4:
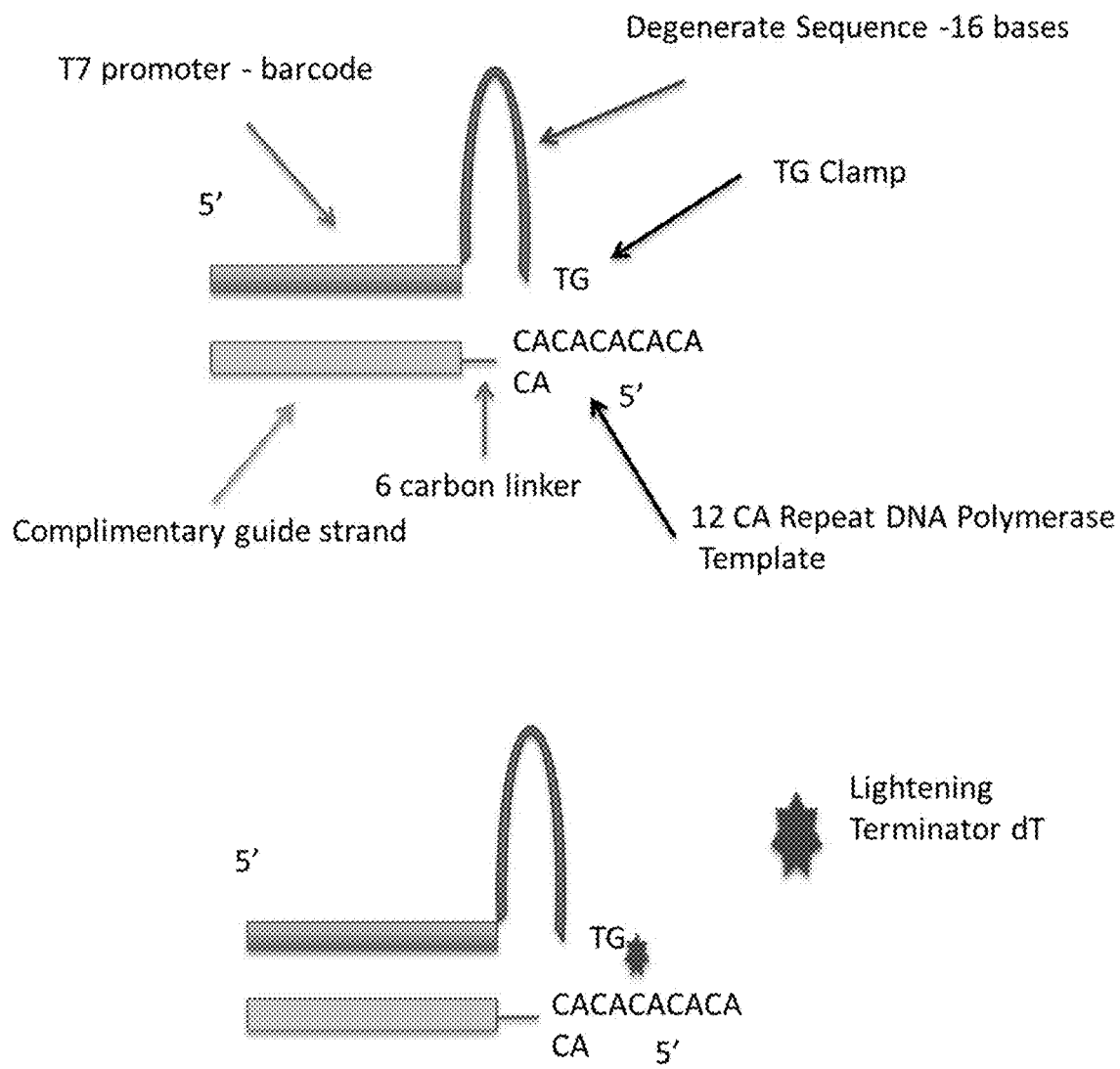
FIG. 4. Schematic of an exemplary CHeX-seq oligonucleotide synthesis method.

The CHeX-seq oligonucleotides may have a reporter-tagged reversibly terminating nucleotide on their 3' ends. Two exemplary embodiments of methods to enzymatically synthesize an oligonucleotide comprising the reporter-tagged reversibly terminating nucleotide are shown in FIGS. 3A, 3B, & 4. These methods comprise annealing the oligonucleotide to its reverse complement, where the reverse complement comprises a poly-A tail on its 5' end. Once annealed, the duplex is incubated with a fluorescently tagged photoactivatable terminating deoxyuridine analog that is incorporated into the oligonucleotide by DNA polymerase. The synthesized oligonucleotide can then be denatured from its reverse complement and purified. The method can be performed with the full oligonucleotide and its full reverse complement (FIG. 3A). Alternatively, it can be performed with a segment comprising the degenerate sequence following by ligation of the double-stranded degenerate sequence with a segment comprising the amplification segment, spacer, and barcode (FIG. 3B). This method allows for the generation of many different populations each comprising a unique barcode without having to synthesize the double-stranded degenerate sequence for each population. To this end, only the segment comprising the amplification segment, spacer, and barcode needs to be generated for each population, and then each unique barcode can be ligated to the double-stranded degenerate sequence thereby producing each uniquely barcoded, degenerate population. A further alternative method uses a reverse complement that has a 6 carbon linker in place of the degenerate sequence (FIG. 4). In this method, the oligonucleotide has a TG clamp in its 3' end in order to facilitate hybridization with the reverse complement strand in order to allow addition of the photoactivatable terminating nucleotide.

Figure 5:
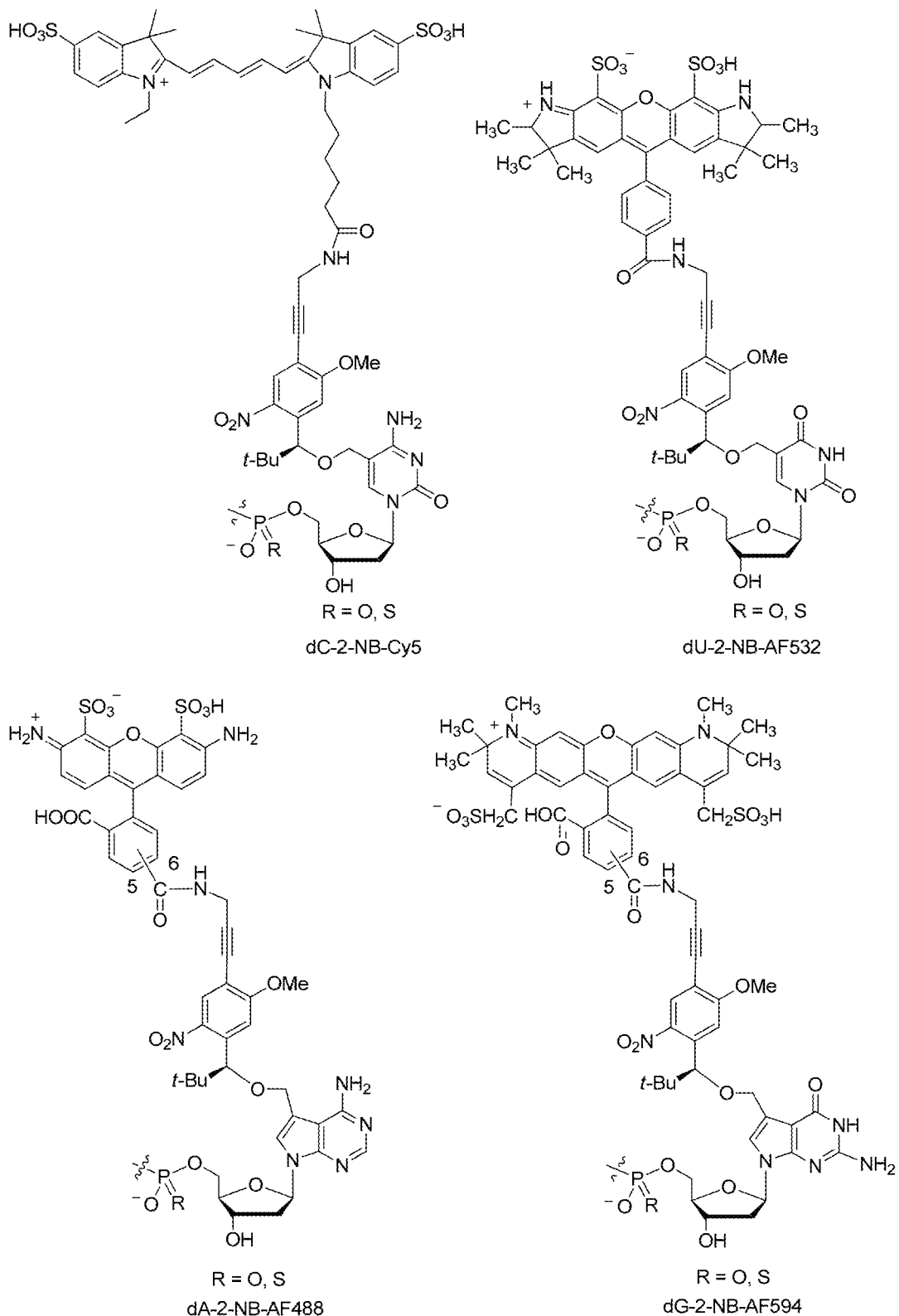
FIG. 5. Exemplary fluorescently tagged photoactivatable terminating nucleotide compounds.

In some embodiments, the reporter-tagged reversibly terminating nucleotide compounds comprise a nucleotide with a photocleavable group labeled with a reporter group, such as a fluorescent dye group, colorimetric dye group, radioactive label, or groups affecting a signal through chemiluminescent or bioluminescent means. As used herein, the term "reporter" or "label" refers to a chemical moiety that is able to produce a detectable signal directly or indirectly. The terminating nucleotides comprise removable protecting groups that are designed to terminate DNA synthesis. Examples of such nucleotide compounds include those disclosed in PCT Publn. Nos. WO 2003/006625, WO 2005/084367, WO 2008/070749, WO 2009/152353, WO 2013/040257, which are each incorporated herein by reference in their entirety. Specific examples of such nucleotide compounds include those shown in FIG. 5. Examples of indirectly detectable reporters include small tags, such as biotin, haptens (for example, digoxigenin), or magnetic particles, which may be detected by the binding of another protein or antibody, such that the reporter may be detected and visualized under a microscope. Examples of directly detectable reporters include fluorescent dye groups. Examples of fluorescent dye groups include xanthene derivate dyes (e.g., fluorescein and its derivatives, fluorescein isothiocyanate [FITC], carboxyfluorescein succinimidyl ester [CFSE], carboxyfluorescein diacetate succinimidyl ester [CFDA-SE], eosin Y, eosin B, rhodamine B, rhodamine 6G, rhodamine 123, rhodamine red-X [RRX], carboxytetramethylrhodamine [TAMRA], tetramethylrhodamine [TMR], isothiocyanate-derivative of rhodamine [TRITC], sulforhodamine 101, sulfonyl chloride derivative of sulforhodamine 101 [Texas Red], Oregon Green), BODIPY derivative dyes (e.g., BODIPY FL, BODIPY R6G, BODIPY TMR, BODIPY 581/591, BODIPY TR, BODIPY 630/650, BODIPY 650/665), coumarin derivative dyes (e.g., aminomethylcoumarin [AMCA]), allophycocyanin [APC], pyrene derivative dyes (e.g., Cascade Blue), 4',6-diaminidino-2-phenylindole [DAPI], DyLight dyes (e.g., DyLight™ 350, DyLight™ 405, DyLight™ 488, DyLight™ 550, DyLight™ 594, DyLight™ 633, DyLight™ 650, DyLight™ 680, DyLight™ 755, DyLight™ 800), phycoerythrin [PE], PI, peridinin-chlorophyll-protein [PerCP], cyanine derivative dyes (e.g., Cy® 5.5, indodicarbocyanine (Cy® 5), cyanine (Cy® 2), indocarbocyanine (Cy® 3), Cy® 3B, Cy® 3.5, Cy® 7, Cy® 7Q, oxacarbocyanine, thiacarbocyanine, merocyanine, phthalocyanine), anthracene derivative dyes (e.g., Draq-5, Draq-7, CyTRAK Orange, IRIS 2, IRIS 3, IRIS 3.5, IRIS 5, IRIS 5.5, IRIS 7G), eFluor dyes (e.g., eFluor® 450, PEeFluor® 615, eFluor® 660, eFluor® 710, PE-eFluor® 610, PerCP-eFluor® 710, APC-eFluor® 780), FluoProbes dyes (FluoProbes 390, FluoProbes 488, FluoProbes 532, FluoProbes 547H, FluoProbes 594, FluoProbes 647H, FluoProbes 682, FluoProbes 752, FluoProbes 782), GFP, IRDye 800, Pacific Blue, Pacific Green, Pacific Orange, pyrene, phycobiliprotein, Quasar® dyes (e.g., Quasar® 570, Quasar® 670, Quasar® 705), SNAFL, sulfocyanine derivative dyes (e.g., sulfo-Cy3, sulfo-Cy5, sulfo-Cy7), Tokyo Green, Alexa Fluor® dyes (e.g., ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 635, ALEXA FLUOR® 647, ALEXA FLUOR® 660, ALEXA FLUOR® 680, ALEXA FLUOR® 700, ALEXA FLUOR® 750, ALEXA FLUOR® 790), squaraine dyes (e.g., Seta™ dyes, SeTau dyes, Square dyes), or combinations thereof.

The first process in performing CHeX-seq is obtaining and fixing a sample to be assayed, which may be a cell line, a primary cell culture, or a tissue section. The sample may comprise any type of cell, such as a eukaryotic cell or a prokaryotic cell. When the cell is a eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. A cell may be a differentiated cell and/or a non-dividing cell. The cell may also be a progenitor cell or a stem cell. Preferably, the cell is a tissue-specific cell, more preferably a mammalian tissue-specific cell and more preferably still, a human tissue-specific cell. Non-limiting examples of cells suitable as a recipient cell include epithelial cells, neurons, fibroblasts, embryonic fibroblasts, keratinocytes, adult stem cells, embryonic stem cells, and cardiomyocytes. The methods provided herein may be performed on a cell comprising a cellular process. Such a cellular process includes, but is not limited to, a dendrite, an axon, a microvilli, a cilia, a stereocilia, a process, an astrocytic process, and the like. Any tissue sample from a subject may be used in the method of the invention. Examples of tissue that may be used include, but are not limited to, breast, prostate, ovary, colon, lung, endometrium, stomach, salivary gland and pancreas. The tissue sample can be obtained by a variety of procedures including, but not limited to surgical excision, aspiration or biopsy. The tissue may be embedded in paraffin or frozen. The tissue sample may be stained to differentiate between cell types within the sample, such as, for example, between neurons and glia in a brain sample.

In some embodiments, the sample may be exposed to a permeabilization agent to allow for entry of the oligonucleotides into the cell. Exemplary permeabilization agents include, but are not limited to Triton X-100, Tween-20, saponin, SDS, NP40, streptolysin O, proteinase K, pronase and triethanolamine, and organic solvents, such as methanol and acetone.

One technical consideration in performing CHeX-seq is getting the CHeX-seq oligonucleotides into the nucleus and having them hybridize to genomic DNA. Nuclear DNA accessibility is, in part, dictated by fixation conditions. For example, the use of low percentage fixative (for example, 0.25%, 0.5%, 0.75%, 1%, 2%, 3%, 4%, 5%, 6%, 7%, or 8%) for 30 sec, 45 sec, 1 min, 1.5 min, 2 min, 2.5 min, 3 min, 3.5 min, 4 min, 4.5 min, 5 min, 5.5 min, 6 min, 6.5 min, 7 min, 7.5 min, 8 min, 8.5 min, 9 min, 9.5 min, or 10 min may provide for the detection of open genomic DNA for ~80% of expressed RNAs, which is ~8× better than reported for ATACseq coverage. The fixative may be formalin, glutaraldehyde, xylene a precipitating fixative (for example, methanol or ethanol), or a chemically and light reversible cross-linking agent.

Once the CHeX-seq oligonucleotides are present in the nucleus, the oligonucleotides are given time to anneal to regions of open genomic DNA. In some embodiments, the annealing time may be about 10 sec, about 15 sec, about 20 sec, about 25 sec, about 30 sec, about 35 sec, about 40 sec, about 45 sec, about 50 sec, about 55 sec, about 60 sec, about 65 sec, about 70 sec, about 75 sec, about 80 sec, about 85 sec, or about 90 sec. In some embodiments, the annealing temperature may be about 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. The progression of annealing can be monitored using fluorescence microscopy to detect the fluorescent signal of the fluorescent tag in the nucleus of the cells.

The hybridized oligonucleotides are then imaged using their reporter tag. In some embodiments, reporter-tagged reversibly terminating oligonucleotides are reversibly terminating due to the presence of a site that can be photocleaved, resulting in an extendable 3' hydroxy group. In some embodiments, the photocleavable moiety may comprise a 2-nitrobenzyl or substituted 2-nitrobenzyl group, which may be efficiently photochemically cleaved, for example, with UV light. See U.S. Patent Appl. Publ. 2010/0041041, which is incorporated herein by reference in its entirety. It is generally understood that wavelengths >300 nm are used to minimize damage to DNA and proteins (Corrie, 2005) with several specific exemplary wavelengths other than 365 nm being 340 nm and 355 nm (Seo, 2005). As such, the terms "photocleaving" or "photocleave," as used herein, are meant to refer generally to the act of exposing a sample to a wavelength of light >300 nm, e.g., 365 nm, 370 nm, 375 nm, 380 nm, 385 nm, 390 nm, 395 nm, 400 nm, 405 nm, 410 nm, or 415 nm, so as to effect the cleavage of the photocleavable bond.

In some aspects, a photoactivatable terminating nucleotide has a structure of the formula:

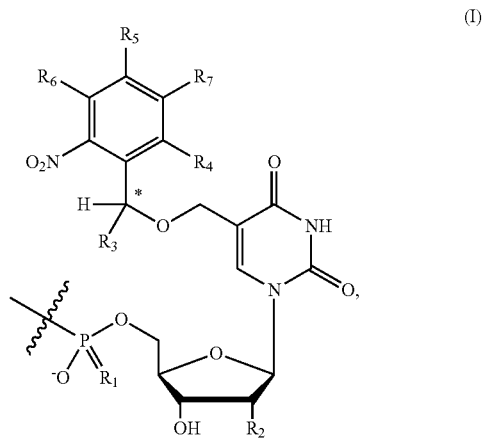

(I)

-continued
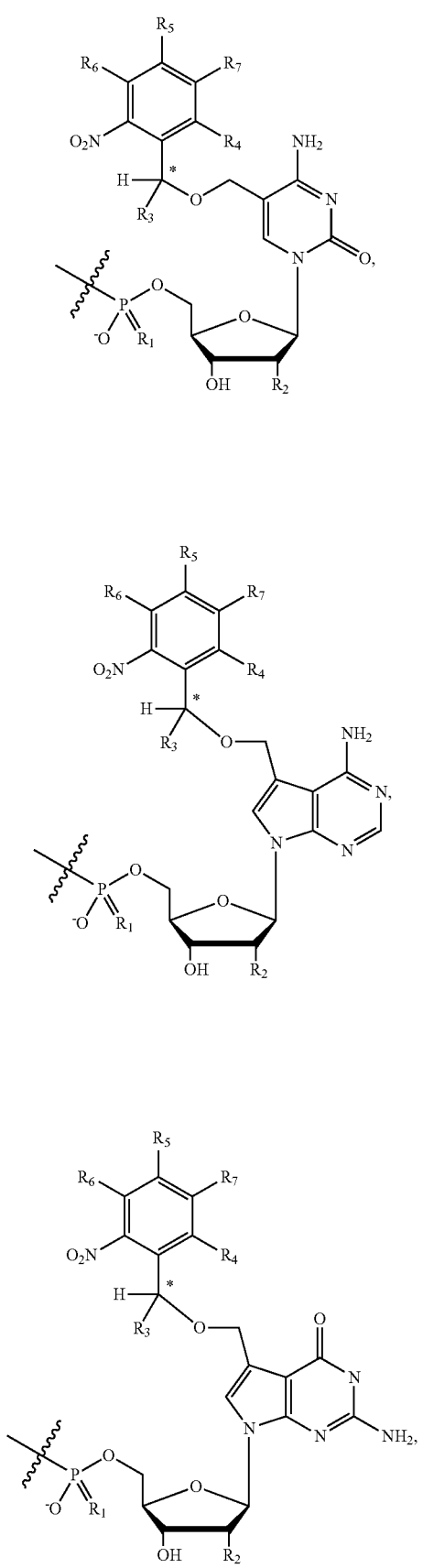
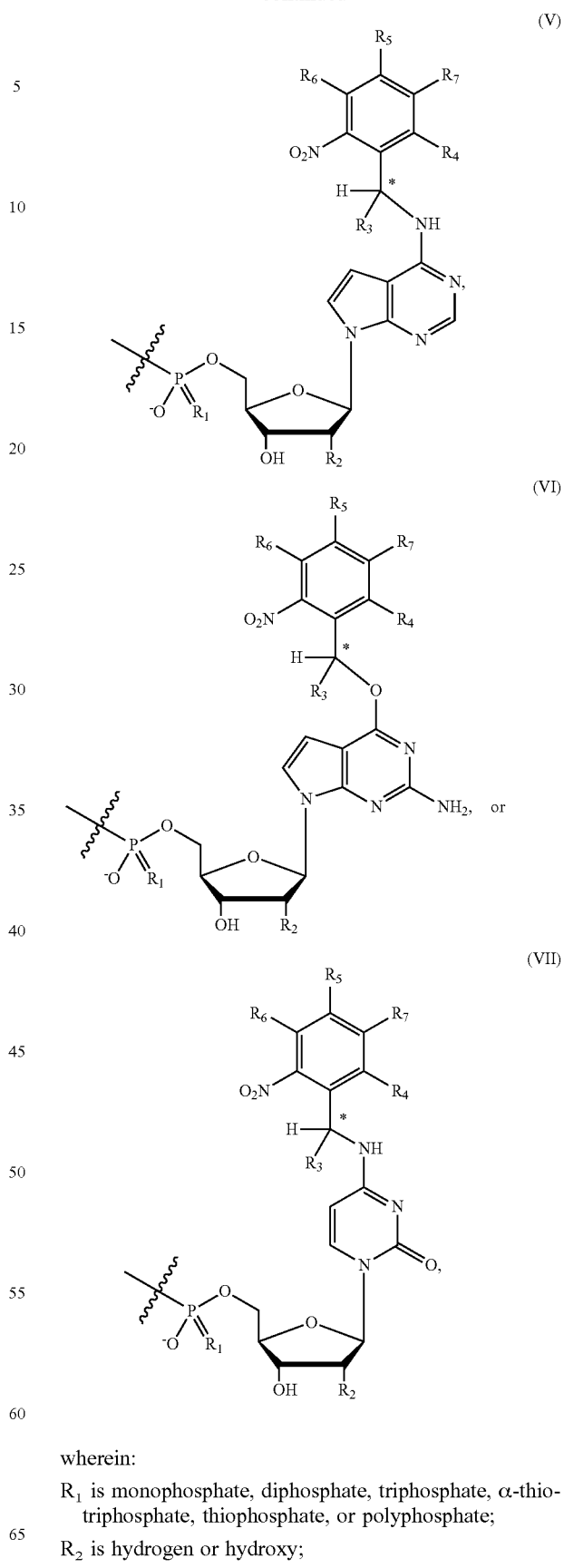
wherein:
R₁ is monophosphate, diphosphate, triphosphate, α-thio-triphosphate, thiophosphate, or polyphosphate;
R₂ is hydrogen or hydroxy;
R₃ is alkyl$_{(C \leq 8)}$ or substituted alkyl$_{(C \leq 8)}$;

$R_4$ is hydrogen, hydroxy, halo, amino, nitro, cyano, azido or mercapto;

alkyl$_{(C\leq6)}$, acyl$_{(C\leq6)}$, alkoxy$_{(C\leq6)}$, acyloxy$_{(C\leq6)}$, alkylamino$_{(C\leq6)}$, dialkylamino$_{(C\leq6)}$, amido$_{(C\leq6)}$, or a substituted version of any of these groups;

$R_5$, $R_6$, and $R_7$ are each independently:

hydrogen, hydroxy, halo, amino, nitro, cyano, azido or mercapto;

alkyl$_{(C\leq6)}$, alkenyl$_{(C\leq6)}$, alkynyl$_{(C\leq6)}$, aryl$_{(C\leq6)}$, aralkyl$_{(C\leq8)}$, heteroaryl$_{(C\leq6)}$, acyl$_{(C\leq6)}$, alkoxy$_{(C\leq6)}$, acyloxy$_{(C\leq6)}$, alkylamino$_{(C\leq6)}$, dialkylamino$_{(C\leq6)}$, amido$_{(C\leq6)}$, or a substituted version of any of these groups;

a group of formula:

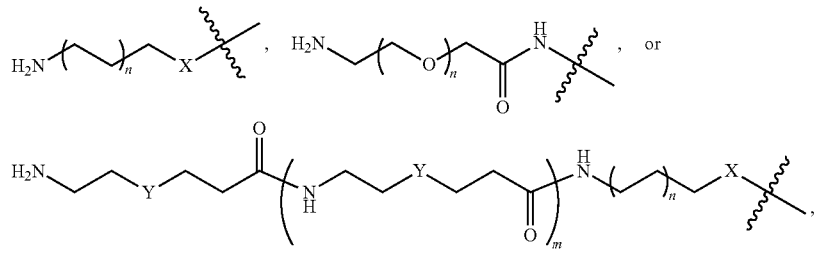

wherein

X is

—O—, —S—, or —NH—; or alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, or a substituted version of any of these groups;

Y is —O—, —NH—, alkanediyl$_{(C\leq12)}$ or substituted alkanediyl$_{(C\leq12)}$;

n is an integer from 0-6; and m is an integer from 0-6; or a -linker-reporter;

or a salt, tautomer, or optical isomer thereof.

In some embodiments, the photoactivatable terminating nucleotides are further defined as a compound of formulas I, II, III, IV, V, VI or VII. In some embodiments, $R_1$ is hydroxy, monophosphate, diphosphate, triphosphate, α-thiotriphosphate, or polyphosphate. In some embodiments, $R_2$ is hydrogen, hydroxy. In some embodiments, $R_3$ is alkyl$_{(C\leq8)}$, for example, alkyl$_{(C3-4)}$, including isopropyl or tert-butyl. In some embodiments, $R_4$ is hydrogen, nitro. In some embodiments, $R_5$ is hydrogen, iodo, or alkoxy$_{(C\leq6)}$, including, for example, methoxy. In some embodiments, $R_5$ is a group of formula:

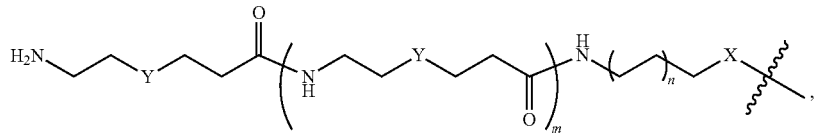

wherein

X is

—O—, —S—, or —NH—; or alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, or a substituted version of any of these groups; and n is an integer from 0-6.

In some embodiments, X is alkynediyl$_{(C2-8)}$, for example, —C≡C—. In some embodiments, n is zero.

In some embodiments, $R_5$ is a group of formula:

wherein

X is

—O—, —S—, or —NH—; or alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, or a substituted version of any of these groups;

Y is —O—, —NH—, alkanediyl$_{(C\leq12)}$ or substituted alkanediyl$_{(C\leq12)}$;

n is an integer from 0-6; and m is an integer from 0-6.

In some embodiments, X is alkynediyl$_{(C2-8)}$, for example, —C≡C—. In some embodiments, Y is —CH$_2$—. In some embodiments, n is zero. In some embodiments, m is zero. In some embodiments, $R_5$ is a -linker-reporter. In some embodiments, the linker is:

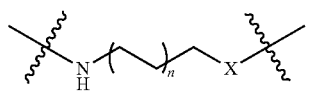

wherein
X is
—O—, —S—, or —NH—; or
alkanediyl$_{(C≤12)}$, alkenediyl$_{(C≤12)}$, alkynediyl$_{(C≤12)}$, arenediyl$_{(C≤12)}$, heteroarenediyl$_{(C≤12)}$, or a substituted version of any of these groups; and
n is an integer from 0-6.

In some embodiments, X is alkynediyl$_{(C2-8)}$, for example, —C≡C—. In some embodiments, n is zero.

In some embodiments, the linker is:

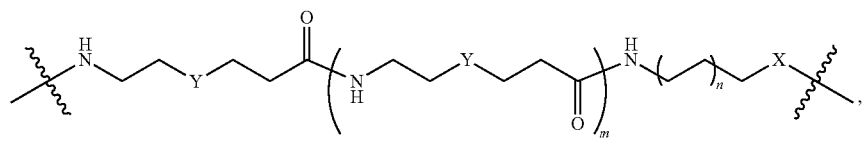

wherein
X is
—O—, —S—, or —NH—; or
alkanediyl$_{(C≤12)}$, alkenediyl$_{(C≤12)}$, alkynediyl$_{(C≤12)}$, arenediyl$_{(C≤12)}$, heteroarenediyl$_{(C≤12)}$, or a substituted version of any of these groups;
Y is —O—, —NH—, alkanediyl$_{(C≤12)}$ or substituted alkanediyl$_{(C≤12)}$;
n is an integer from 0-6; and
m is an integer from 0-6.

In some embodiments, X is alkynediyl$_{(C2-8)}$, for example, —C≡C—. In some embodiments, Y is —CH$_2$—. In some embodiments, n is zero. In some embodiments, m is zero. In some embodiments, the reporter is based on a dye, wherein the dye is zanthene, fluorescein, rhodamine, BODIPY, cyanine, coumarin, pyrene, phthalocyanine, phycobiliprotein, or a squaraine dye.

In some embodiments, $R_6$ is hydrogen. In some embodiments, the starred carbon atom is in the S configuration. In some embodiments, the starred carbon atom is in the R configuration. In some embodiments, $R_7$ is methoxy.

In some embodiments, the photoactivatable terminating nucleotide is further defined as:

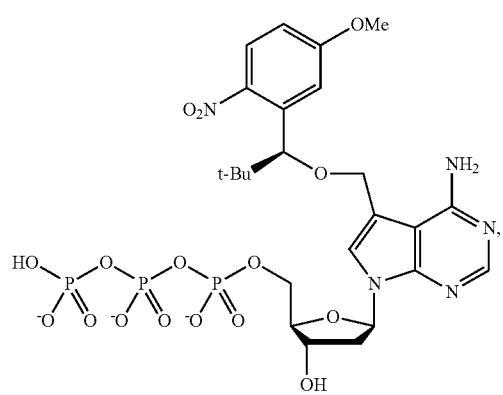

-continued

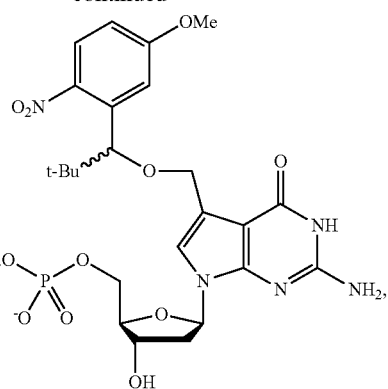

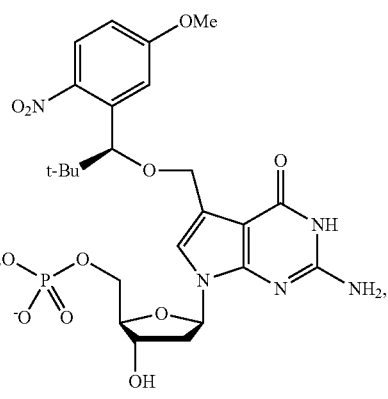

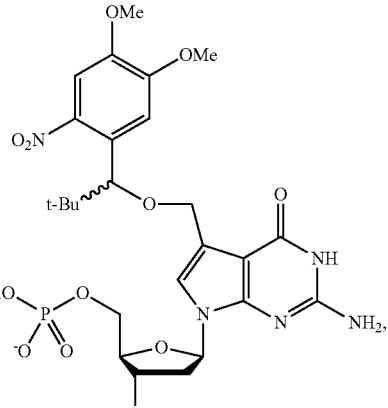

-continued
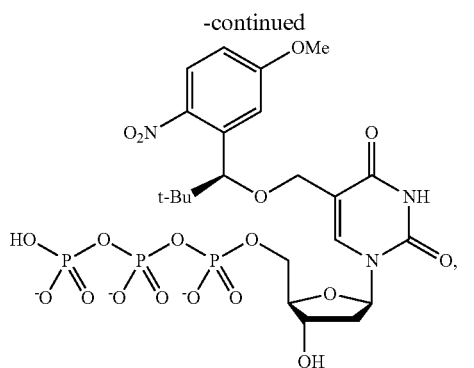
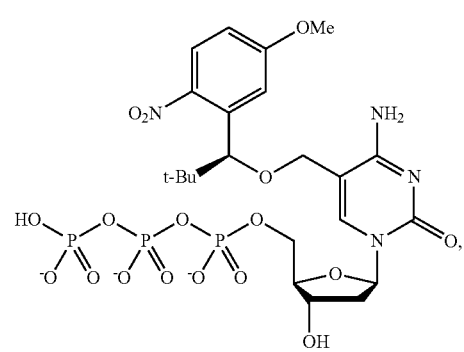
or a salt and/or protonated form of any of these formulas.
In some embodiments, the photoactivatable terminating nucleotide is further defined as:
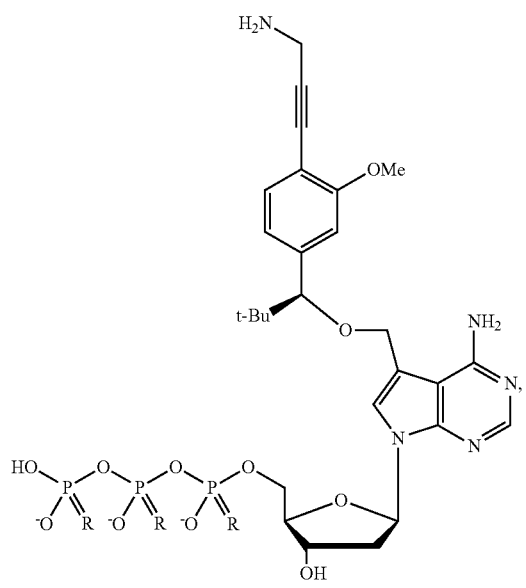
-continued
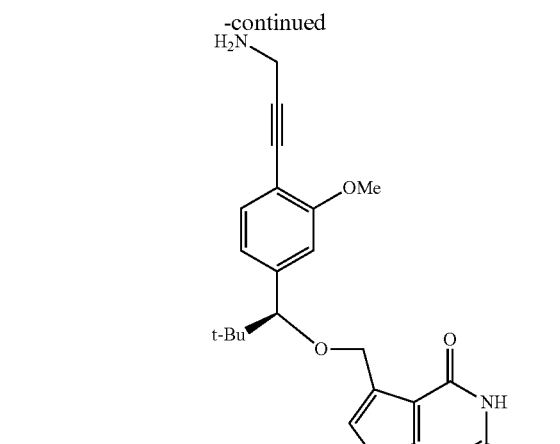
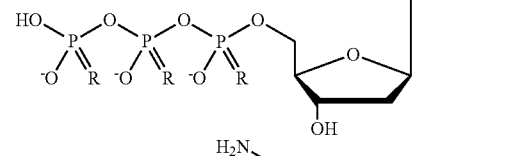
wherein R is =O or =S, or a salt and/or protonated form of any of these formulas.
In some embodiments, the photoactivatable terminating nucleotide is further defined as:

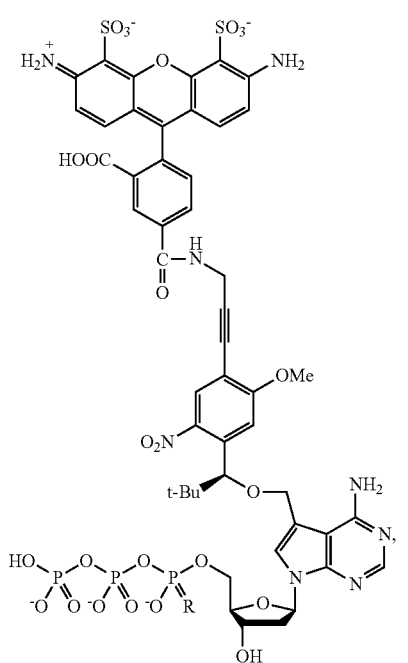
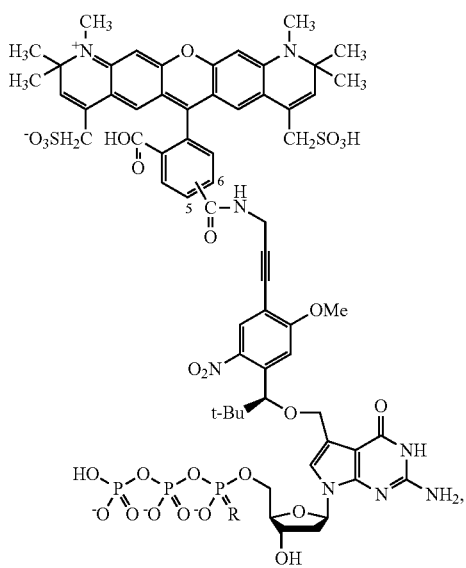
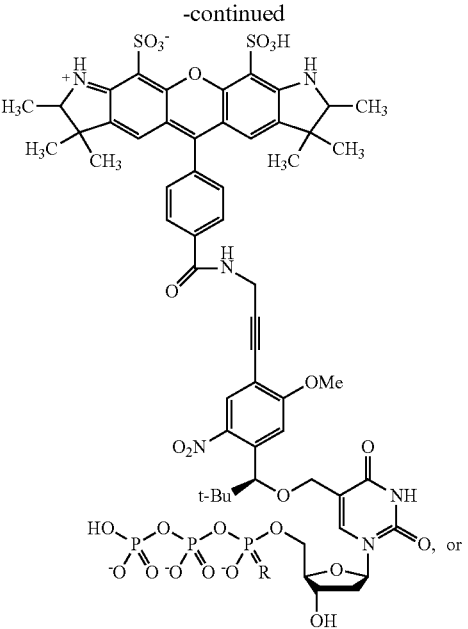
wherein R is =O or =S, or a salt and/or protonated form of any of these formulas.
In some embodiments, the photoactivatable terminating nucleotide is further defined as:

85
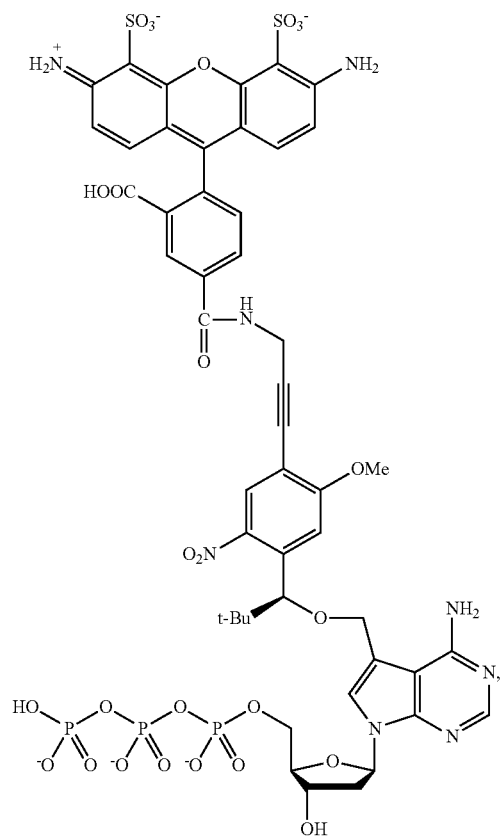
86
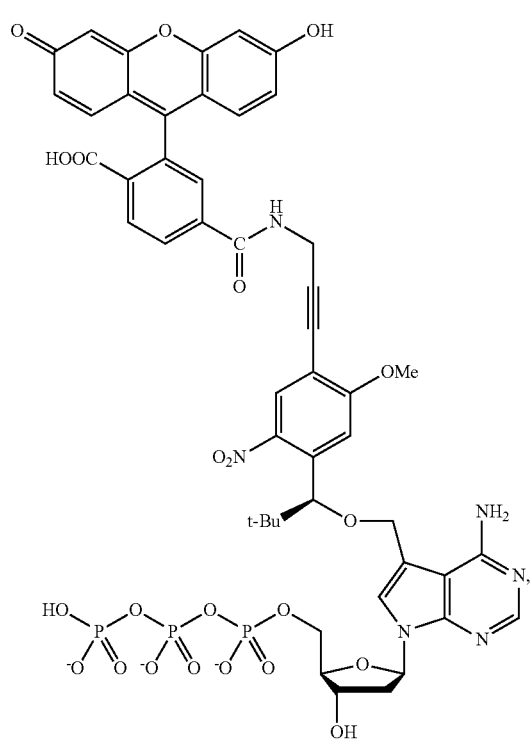
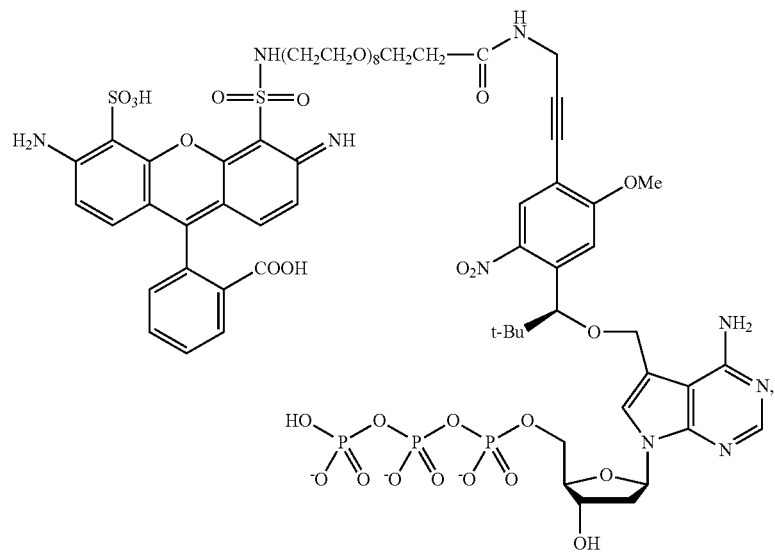

87
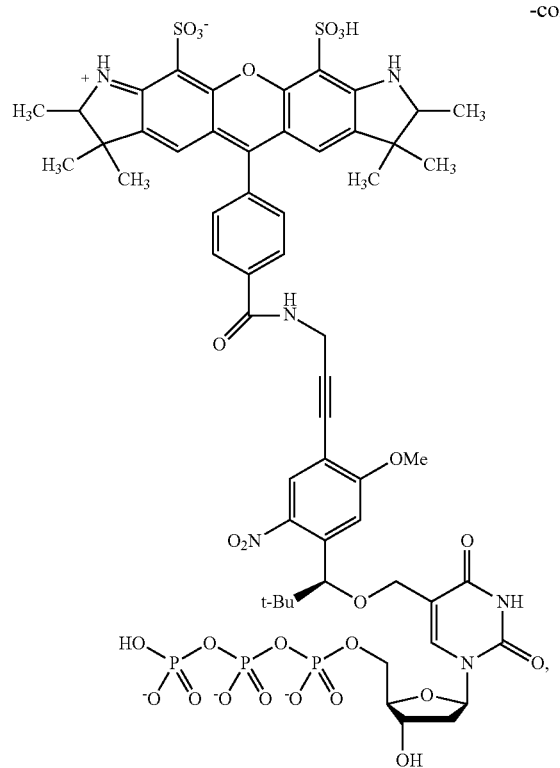
88
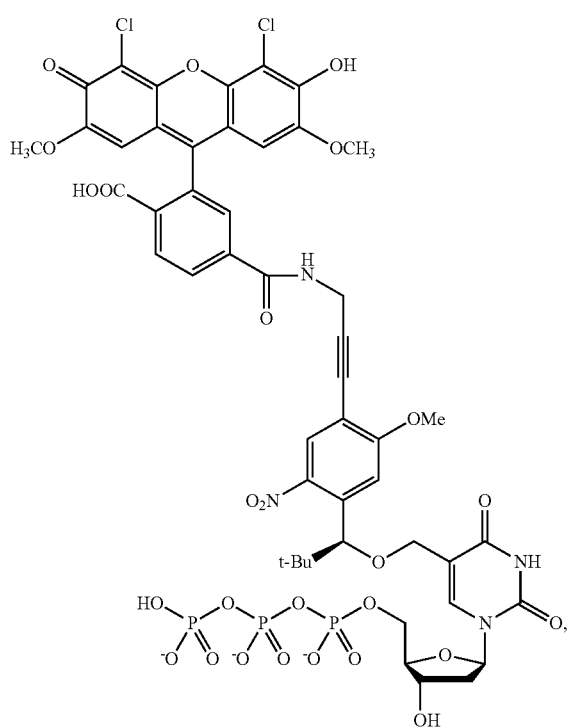
-continued
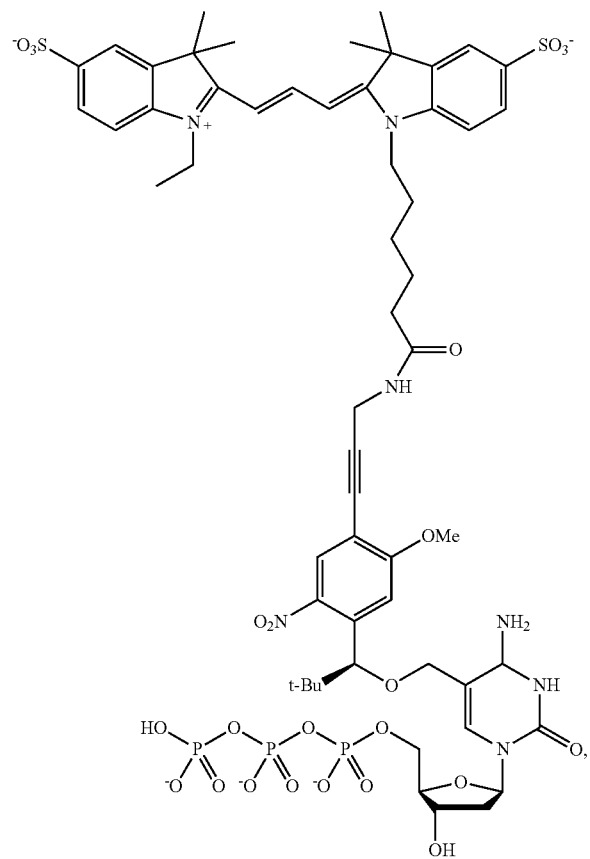

-continued
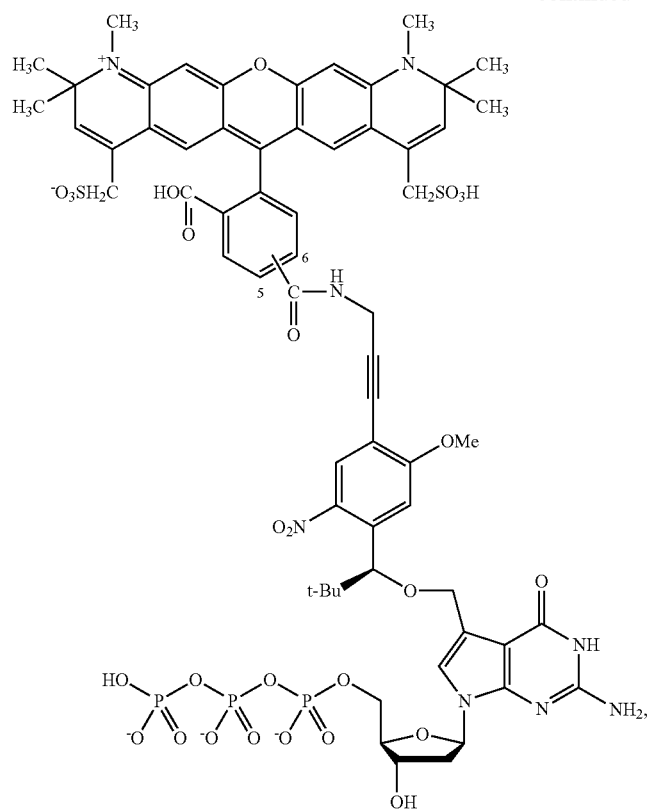
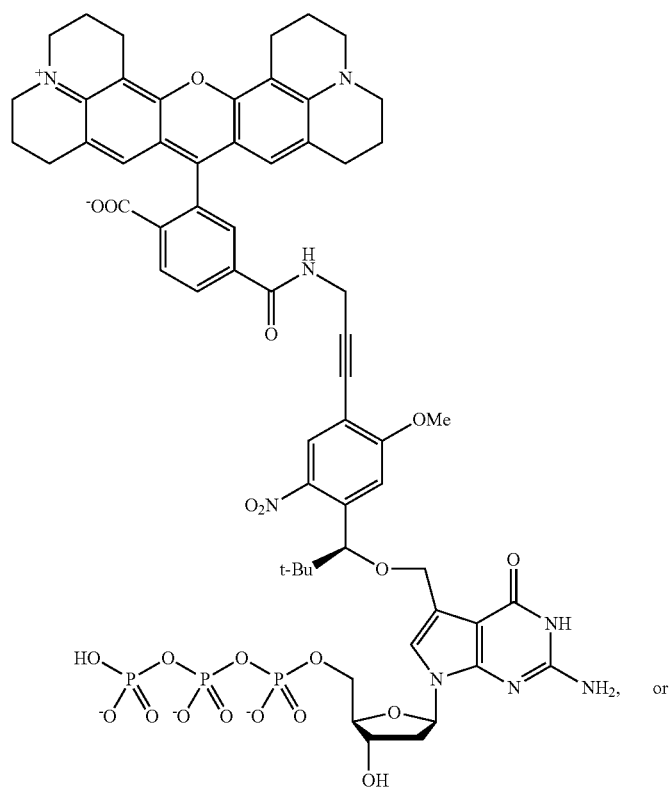
or

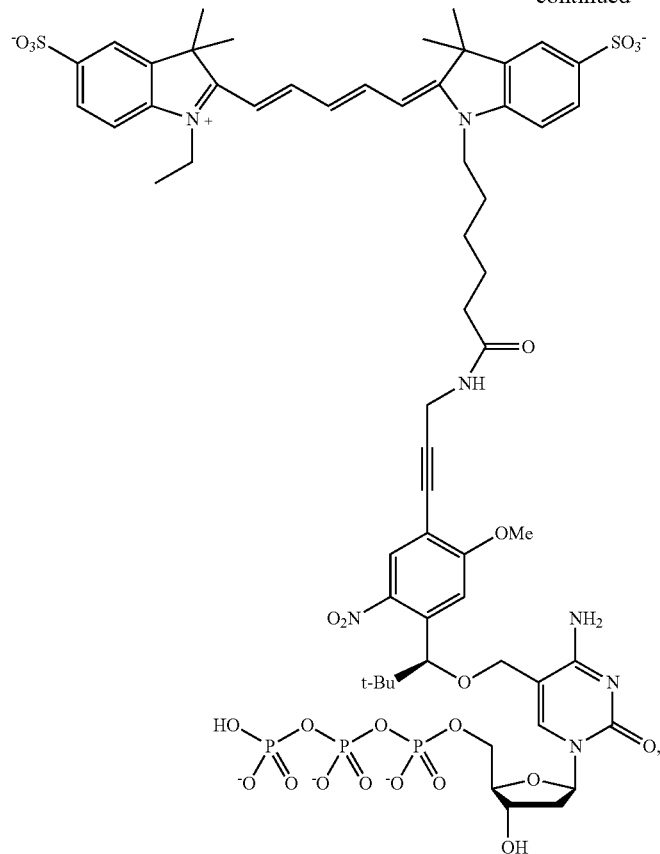

or a salt and/or protonated form of any of these formulas.

In some embodiments, following imaging, the reporter-tagged photoactivatable terminating oligonucleotides, either in a specific region or in the entire nucleus, are photoactivated with a laser at, for example, 405 nm. The resolution of photoactivation, which is removal of the terminating moiety on the nucleotide compounds, is determined by the diffraction limit of the activating-light wavelength and the numerical aperture of the lens. For example, the area to be photoactivated can be a 10 nm sphere (see FIG. 6) when using multi-photon activation. In contrast to the spatial confinement of multi-photon activation, single-photon activation results in effective photon distribution through the entire z-axis of illumination, therefore the power and duration of laser illumination may be carefully controlled to minimize unwanted activation of the CHeX-seq oligonucleotides outside of the desired activation area. Furthermore, ultra-high-resolution activation in fixed cells may be accomplished using an evanescence wave from near-field fiber optics providing a 10-50 nm resolution.

To get the full chromatin complement of a single cell, the laser photoactivation will have to occur throughout the volume of the nucleus, which may be achieved by moving the photoactivation laser to different positions within the nucleus. If activation of the CHeX-seq oligonucleotides occurs outside of the nucleus, there should be little effect as the CHeX-seq polymerase is DNA polymerase, which will only make a DNA copy if DNA is the template. As such, CHeX-seq oligonucleotides that anneal to RNA, in either the nucleus or the cytoplasm, will not be extended to generate complementary DNA.

In some embodiments, reporter-tagged reversibly terminating oligonucleotides are reversibly terminating due to the presence of a site that can be enzymatically cleaved, resulting in removal of a non-extendable 3' end and creation of an extendable 3' hydroxy group. The non-extendable 3' end may be a 3' terminal phosphate, a 2',3'-cyclic phosphate, a 2'-O-methyl group, a base modification, or a backbone sugar or phosphate modification. The cleavable site may be positioned towards the 3' end of the oligonucleotide The site that can be enzymatically cleaved may be a specific sequence that is known to be a target of an endonuclease enzyme. Incubation with the endonuclease may cause the annealed oligonucleotide to be cleaved at the site. The site may be a specific nucleotide, such as a cleavable base. "Cleavable base," as used herein, refers to a nucleotide that is generally not found in a sequence of DNA. For most DNA samples, deoxyuridine is an example of a cleavable base. Although the triphosphate form of deoxyuridine, dUTP, is present in living organisms as a metabolic intermediate, it is rarely incorporated into DNA. When dUTP is incorporated into DNA, the resulting deoxyuridine is promptly removed in vivo by normal processes, e.g., processes involving the enzyme uracil-DNA glycosylase (UDG) (U.S. Pat. No. 4,873,192; Duncan, 1981; both references incorporated herein by reference in their entirety). Thus, deoxyuridine occurs rarely or never in natural DNA. Non-limiting examples of other cleavable bases include deoxyinosine, bromodeoxyuridine, 7-methylguanine, 5,6-dihyro-5,6 dihydroxydeoxythymidine, 3-methyldeoxadenosine, etc. (see, Duncan, 1981).

The term "DNA glycosylase" refers to any enzyme with glycosylase activity that causes excision of a modified nitrogenous heterocyclic component of a nucleotide from a polynucleotide molecule, thereby creating an abasic site. DNA N-glycosylases include the following enzymes and their homologues in higher eukaryotes, including human homologues: uracil-DNA glycosylase (UDG), 3-methyladenine DNA glycosylase II (e.g., AlkA), TagI glycosylase, and MUG glycosylase. Uracil-DNA glycosylases recognize uracils present in single-stranded or double-stranded DNA and cleave the N-glycosidic bond between the uracil base and the deoxyribose of the DNA sugar-phosphate backbone, leaving an abasic site. See, e.g., U.S. Pat. No. 6,713,294. The loss of the uracil creates an apyrimidinic site in the DNA. The enzyme does not, however, cleave the phosphodiester backbone of the DNA molecule. Uracil-DNA glycosylases, abbreviated as "UDG" or "UNG" include mitochondrial UNG1, nuclear UNG2, SMUG1 (single-strand-selective uracil-DNA glycosylase), TDG (TU mismatch DNA glycosylase), MBD4 (uracil-DNA glycosylase with a methyl-binding domain), and other eukaryotic and prokaryotic enzymes. An enzyme possessing this activity does not act upon free dUTP, free deoxyuridine, or RNA. An additional example of UDG enzymes for creating one or more abasic sites is a thermostable homolog of the *E. coli* UDG from *Archaeoglobus fulgidus*. Afu UDG catalyzes the release of free uracil from uracil-containing DNA. Afu UDG efficiently hydrolyzes uracil from single-stranded or double-stranded DNA. Another example includes Antarctic thermolabile UDG, which catalyzes the release of free uracil from uracil-containing single-stranded or double-stranded DNA. The Antarctic thermolabile UDG enzyme is sensitive to heat and can be rapidly and completely inactivated at temperatures above 50° C.

Non-limiting examples of additional cleavable bases and their respective nicking agents are as follows: AlkA glycosylase recognizes and cleaves deoxyinosine residues; DNA-7-methylguanine glycosylases recognize and cleave 7-methylguanine residues; hypoxanthine-NDA glycosylase recognizes and cleaves hypoxanthine residues; 3-methyladenine-DNA glycosylase I (e.g., TagI) and 3-methyladenine-DNA glycosylase II (e.g., AlkA) recognize and cleave 3-methyladenine residues; Fpg recognizes and cleaves 8-oxo-guanine residues; and Mug recognizes and cleaves 3,N(4)-ethenocytosine and uracil residues from DNA.

As used herein, the term "abasic DNA" or "DNA with an abasic site" refers to a DNA molecule, either single-stranded or double-stranded, that contains at least one abasic nucleotide, sometimes called an "abasic site." An "abasic nucleotide" is a nucleotide that lacks a base in the 1' position of the deoxyribose. As used herein, the term "AP endonuclease" or "AP lyase" means an enzyme capable of breaking a phosphodiester backbone of a nucleic acid at an abasic site. The term includes enzymes capable of breaking the backbone both 5' and 3' of the abasic site.

The DNA sugar-phosphate backbone that remains after, for example, UDG cleavage of the glycosidic bond can then be cleaved, for example, by alkaline hydrolysis, elevated temperature, tripeptides containing aromatic residues between basic ones, such as Lys-Trp-Lys and Lys-Tyr-Lys, and AP endonucleases, such as endonuclease IV, endonuclease V, endonuclease III, endonuclease VI, endonuclease VII, human endonuclease II, and the like. Therefore, an enzyme such as APE I may be used in conjunction with UDG to remove dU resides from and then nick a nucleic acid molecule. Examples of enzymes for creating a nick at an abasic site include apurinic/apyrimidinic (AP) endonucleases, such as APE 1 (also known as HAP 1 or Ref-1), which shares homology with *E. coli* exonuclease III protein.

APE 1 cleaves the phosphodiester backbone immediately 5' to an AP site, via a hydrolytic mechanism, to generate a single-strand DNA break leaving a 3'-hydroxyl and 5'-deoxyribose phosphate terminus.

An artificial nicking agent may be created by combining a DNA N-glycosylase and an AP endonuclease, for example by combining UDG glycosylase with APE I endonuclease or AlkA glycosylase with EndoIV endonuclease to achieve single-stranded cleavage at a cleavable nucleotide. Examples of nicking agents described herein that are capable of excising modified nucleotides include: (i) for excising deoxyuridine—UDG glycosylase in a mixture with EndoIV endonuclease; UDG glycosylase in a mixture with FPG glycosylase/AP lyase; UDG glycosylase in a mixture with EndoVIII glycosylase/AP lyase; a mixture containing UDG glycosylase, EndoIV endonuclease, and EndoVIII glycosylase/AP lysase; (ii) for excising 8-oxo-guanine and deoxyuridine—a mixture containing UDG glycosylase, FPG glycosylase/AP lyase, and EndoIV endonuclease; UDG glycosylase in a mixture with FPG glycosylase/AP lyase; and (iii) for excising deoxyinosine—AlkA glycosylase in a mixture with EndoVIII glycosylase/AP lyase or AlkA glycosylase in a mixture with FPG glycosylase/AP lyase.

Endonuclease VIII from *E. coli* acts as both an N-glycosylase and an AP lyase. The N-glycosylase activity releases degraded pyrimidines from double-stranded DNA, generating an abasic site. The AP lyase activity cleaves 3' to the abasic site leaving a 5' phosphate and a 3' phosphate. Degraded bases recognized and removed by Endonuclease VIII include urea, 5,6-dihydroxythymine, thymine glycol, 5-hydroxy-5-methylhydantoin, uracil glycol, 6-hydroxy-5, 6-dihydrothymine, and methyltartronylurea. While Endonuclease VIII is similar to Endonuclease III, Endonuclease VIII has β and δ lyase activity while Endonuclease III has β lyase activity.

Fpg (formamidopyrimidine [fapy]-DNA glycosylase) (also known as 8-oxoguanine DNA glycosylase) acts both as an N-glycosylase and an AP lyase. The N-glycosylase activity releases degraded purines from double stranded DNA, generating an apurinic site. The AP lyase activity cleaves both 3' and 5' to the apurinic site thereby removing the apurinic site and leaving a one base gap. Some of the degraded bases recognized and removed by Fpg include 7,8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine, and 5-hydroxy-uracil.

Also contemplated are the nicking agents referred to as the USER™ Enzyme, which specifically nicks target molecules at deoxyuridine, and the USER™ Enzyme 2, which specifically nicks target molecules at both deoxyuridine and 8-oxo-guanine both leaving a 5' phosphate at the nick location (see, U.S. Pat. No. 7,435,572). USER™ Enzyme is a mixture of uracil-DNA glycosylase (UDG) and the DNA glycosylase-lyase Endonuclease VIII. UDG catalyzes the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released.

Figure 2:
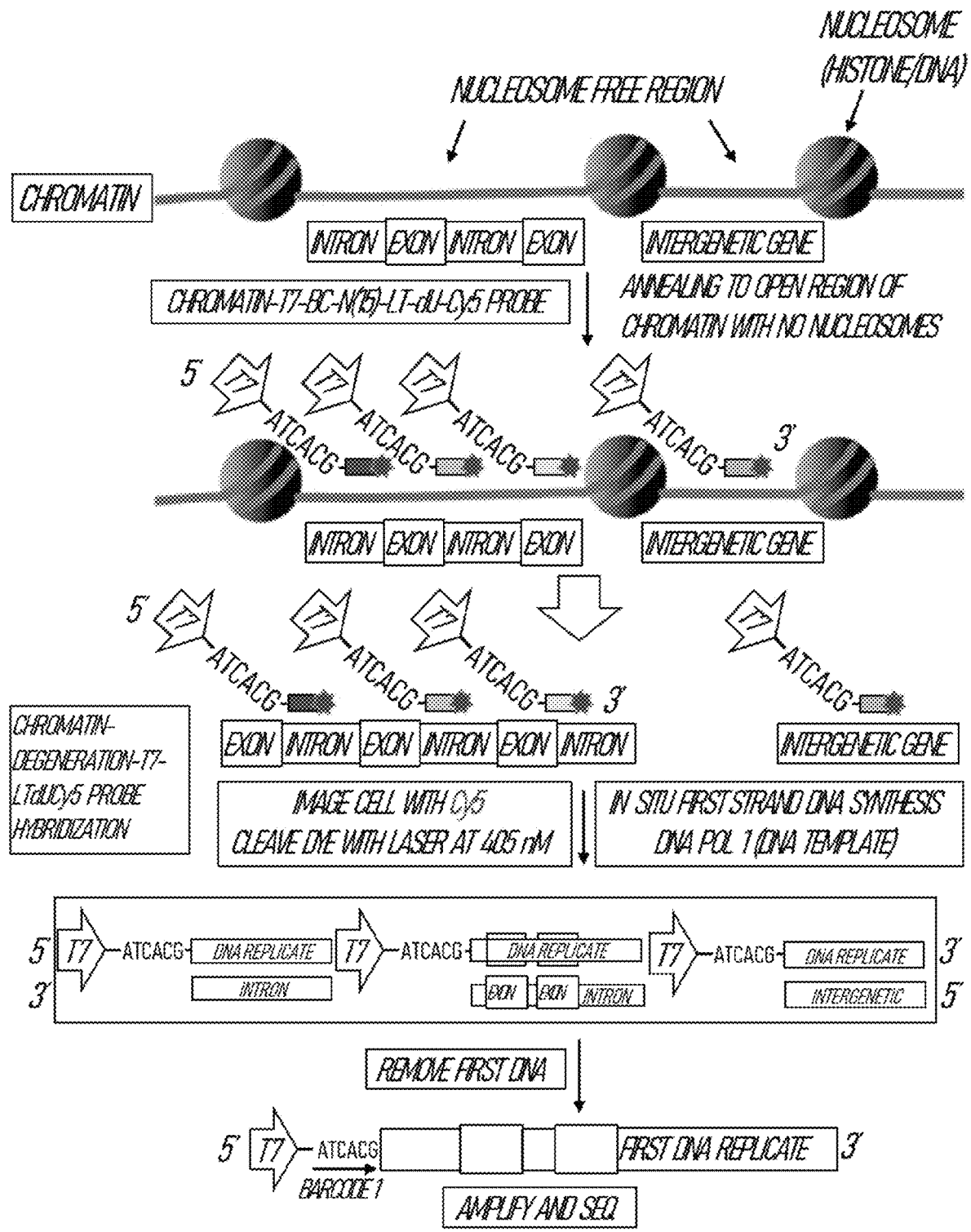
FIG. 2. Schematic of CHeX-seq protocol for assaying transcriptionally-active chromatin.

After photoactivation, the 3'-end of the oligonucleotide can be extended in situ, allowing for subsequent DNA polymerase-mediated complementary DNA synthesis using the genomic DNA as a template (FIG. 2). For this, DNA Polymerase I can use the terminal 3' hydroxy of each annealed oligonucleotide to in situ synthesize complementary DNA from the open genomic DNA. After DNA synthesis, the complementary DNA is dehybridized from the genomic DNA (for example, by heating the sample), removed, copied into double-stranded DNA, and amplified. Amplification may comprise PCR amplification, rolling circle amplification, or RNA amplification. In the case of PCR amplification, the CHeX-seq oligonucleotides may comprise a first primer binding site in their amplification segments, and a second primer binding site may be added to the 3' end of the extended cDNA by ligation of a single-stranded primer sequence. In the case of RNA amplification, the CHeX-seq oligonucleotides may comprise, for example, an Sp6, T3, or T7 promoter sequence and amplification performed using Sp6, T3, or T7 RNA polymerase, respectively.

The amplified polynucleotides can then be made into a cDNA library that can be sequenced, for example using next-generation sequencing. It is also possible to multiplex CHeX-seq oligonucleotides by synthesizing multiply barcoded oligonucleotides that can be iteratively diffused into the fixed cells. This would allow the assay to be adapted for high throughput analysis.

III. Compositions and Methods for Detecting Cytoplasmic RNA (LT-TISA)

Molecular profiling of individual cells has described endogenous transcriptome variability within and between cells using various techniques, including targeted amplification (Cornelison & Wold, 1997; Tay et al., 2010; Miyashiro et al., 1994), florescence in-situ hybridization (FISH), and whole transcriptome assays. In addition to variability in expression levels, RNA sequencing from single cells has revealed heterogeneity across different cells in transcript forms, such as splice products and 5' sequences (Dueck et al., 2015). This variability suggests that regulatory control processes that govern an individual cell's fate may be obscured when measured using pools of cells, even if the cell phenotypes are homogeneous. This individual cell variability may be necessary for tissue level system function (e.g., creating and maintaining neuronal diversity) (Dueck et al., 2016).

Over the past seven years, researchers have worked to create a versatile toolkit for genomics analysis of single live cells residing in their natural microenvironment, which enables RNA analysis in live cells for studies where live tissue is available. However, for many human studies live tissue is not available so methods for analysis of the transcriptome in fixed cells must be developed and optimized. There are protocols for doing this starting with in situ transcription methodology (Tecott et al., 1988; Crino et al., 1996; Miayshiro et al., 2003) and more recently Mer-FISH (Moffitt & Zhuang, 2016), Seq-FISH (Shah et al., 2017) and FISSEQ (Lee et al., 2015). Briefly Mer-FISH permits iterative hybridization of oligonucleotide FISH probes that permit localization of transcripts to many cells to be identified. Seq-FISH is similar to Mer-FISH with the exception that an iterative HCR (Choi et al., 2016; Choi et al., 2010) hybridization probe protocol is used, which provides a much stronger signal. Published Mer-FISH protocols permit identification of hundreds of RNAs in cells while Seq-FISH has been used to identify ~100 RNAs. As hybridization-based detection protocols they cannot easily report on splice variants or be easily quantified as background increases with each annealing. FISSEQ is an approach for sequencing RNA directly in fixed tissue sections where the RNA has been in situ copied into cDNA (using in situ transcription technology (Crino et al., 1996)) and linearly amplified with rolling circle amplification. The protocol is limited to ~400 RNAs by virtue of rolling circle amplification issues. However, the first unbiased process in FISSEQ is in situ transcription, which requires the hybridization of an oligonucleotide to the RNA to initiate cDNA synthesis, which can then be removed from the fixed cell, amplified, and sequenced. Provided herein are methods that modify, optimize, and utilize in situ transcription to assess the RNA complement of fixed cells. This may be performed simultaneously with CHeX-seq in the same cell.

While TISA can be performed with any oligonucleotide that has a free 3'-OH to achieve specific cell or subcellular activation, it is preferable to activate the oligonucleotide only at the subcellular site where cDNA synthesis is wanted. This may be achieved by using reporter-tagged reversibly terminating nucleotides, as discussed above in the context of CHeX-seq oligonucleotides. In this version of TISA, called LT-TISA, oligonucleotides may be synthesized that will bind to the polyA tail of RNA. As such, the oligonucleotide may have an amplification segment, such as a primer binding site or an RNA polymerase promoter, on the 5' end, a specific barcode, and a poly-dT stretch that has a photoactivatable 3' terminating nucleotide on the 3' end (LT-TISA oligonucleotides). In this scenario, the oligonucleotides are added to the fixed cells as an in situ hybridization oligonucleotides and anneal to the 3' poly-A tail of single-stranded RNA in the cell (Tecott et al., 1988; Crino et al., 1996; Lee et al., 2015; Miyashiro & Eberwine, 2015). Alternatively, the LT-TISA oligonucleotide may comprise a target-specific hybridization segment in place of the poly-dT stretch. As such, a panel of LT-TISA oligonucleotides may be generated that specifically hybridize to any desired selection of target RNAs. For cytoplasmic RNA characterization, the LT-TISA oligonucleotides are laser activated in the cytoplasm of the fixed cell (thereby eliminating genomic DNA contamination) and reverse transcriptase is added allowing the activated LT-TISA oligonucleotide to prime cDNA using the annealed RNA as a template.

In some embodiments, this iteration of TISA will be multiplexed so that multiple cells can be separately analyzed by synthesizing LT-TISA degenerate sequence oligonucleotides with different barcodes (BCs) (also used for multiplexing cells see below). For example, LT-TISA oligonucleotide with BC1 is annealed to fixed cells and activated in the cellular cytoplasm of a single cell (or type of cell, such as inhibitory neuron), the unactivated LT-TISA oligonucleotide is removed from other cells by optical washing (see discussion of optical washing). Next a second LT-TISA oligonucleotide with BC2 is annealed to cells and activated only in the cytoplasm of a second cell. Once this has been iterated for as many cells as desired, the enzyme reverse transcriptase is added and cDNA is synthesized by extension of the 3' hydroxy group and using the annealed RNA as a template. After cDNA synthesis, all of the cDNAs can be removed by alkaline denaturation, simultaneously amplified, and made into sequencing libraries. Each cell's transcriptome is uniquely identified by the presence of the BC on the reads associated with that particular subcellular region.

The LT-TISA methodology may be optimized for simultaneous detection of pools of RNA from different subcellular regions by testing cellular fixation conditions (types of fixatives, time of fixation, etc), photoactivation parameters (optimal wavelength determination, energy requirements), and molecular biological processes to create subregion-specific TISA libraries.

IV. Methods for Detecting Both Open Genomic DNA and Cytoplasmic RNA in a Single Cell Provided herein are methods to quantitate the landscape of open genomic DNA in fixed cells simultaneously with their cytoplasmic-localized transcriptome. Previous approaches for studying the landscape of open genomic DNA of cells required organelle isolation, such as isolation of the nucleus for Nuc-seq to assess nuclear RNA surrogate for cytoplasmic RNA or ATACseq for open chromatin analysis, but at the sacrifice of cellular spatial location. Extant hybridization techniques such as Mer-FISH or SeqFISH retain spatial information but permit only a subset of the cytoplasmic RNAs to be assessed. Further these approaches do not permit simultaneous chromatin and RNA characterization from the same cell while retaining tissue-associated spatial resolution.

To understand how cells respond to their local environment one needs to assess not only cytoplasmic RNA abundances but also the structural dynamics of the chromatin that gives rise to the RNA. To be ultimately informative, these measures must occur in the same cell so that dynamic processes influencing the flow of information from the chromatin to cytoplasmic RNA can be assessed without the dilution effect of other non- or differentially responsive cells. Quantitative assessment of all three in the same cell may be used to provide a detailed view of the transcriptional regulatory pathways that may be useful in manipulating the pathway to enhance cellular responses to various local stimuli including those leading to disease.

Also, while openness is necessary for transcription to occur it is important to see the product of transcription, namely the cytoplasmic RNA, in order to assess how the open state correlates with cytoplasmic RNA abundances. Simultaneous measurement of chromatin dynamics with cytoplasmic RNA populations in the same cell will detail the fine-tuning of transcriptome regulatory pathways across co-regulated genes.

As such, methods are provided that harmonize LT-TISA procedures with CHeX-seq procedures, which both use in situ cDNA synthesis and aRNA amplification, so that chromatin landscape determination and cytoplasmic RNA pool characterization can be accomplished in single fixed cells.

As, in some embodiments, CHeX-seq will be performed first with DNA polymerase it may be preferable to remove unactivated CHeX-seq oligonucleotides prior to LT-TISA so that LT-TISA oligonucleotides can anneal to the RNA. Any unactivated CHeX-seq oligonucleotides will be removed using, for example, heat denaturation such that short 16 base annealed sequences will unhybridized while the longer double-stranded CHeX-seq oligonucleotide-primed DNA will remain annealed. This will allow the extended CHeX-seq oligonucleotides to stay associated with the chromatin until after the subsequent LT-TISA reactions.

In some embodiments, the optical washing protocol and on microscope stage multiplexing of CHeX-seq and LT-TISA analysis in immuno-specified cells can be performed. Time estimates for performing CHeX-seq and LT-TISA oligonucleotide addition and optical washing to place specifically barcoded oligonucleotides in the nucleus and cytoplasm of multiple individual cells is 1 min per population of barcoded oligonucleotides. This suggests that 300 individual immuno-identified cells with different barcodes in the nucleus (CHeX-seq) and cytoplasm (LT-TISA) can be completed in 10 hrs. This may be sped up by, for example, using a multi-barrel pipet spritzer with six barrels so that six different oligonucleotides can be applied in a space-limited fashion thus targeting 1,800 cells all with different barcoded oligonucleotides in each cell's nucleus and cytoplasm over 10 hrs.

V. Methods for Analyzing the 3D Structure of Open Genomic DNA Around Selected Genes Provided herein are methods for the structural analysis of the chromatin niche around specific genes. The methods allow for the promoter regulatory mechanisms, including locally utilized enhancers in spatially defined single cells and other genomic/chromatin regulatory regions that modulate the selected genes, to be identified in vivo because such regulatory elements are expected to be close to the gene being regulated. As chromosome packing can position genes from distant chromosomal areas including different chromosomes near a gene of interest it is important to define the chromosomal areas near a gene of regulatory interest. The chromatin landscape for the expressed genome and 3D "chromatin niche" around specific genes may be variable from cell to cell but more similar in cells resident in similar microenviroments. Furthermore, monitoring of chromatin niche dynamics over time may be used to detail how these important regulatory niches change over time and in response to external stimuli.

Figure 6:
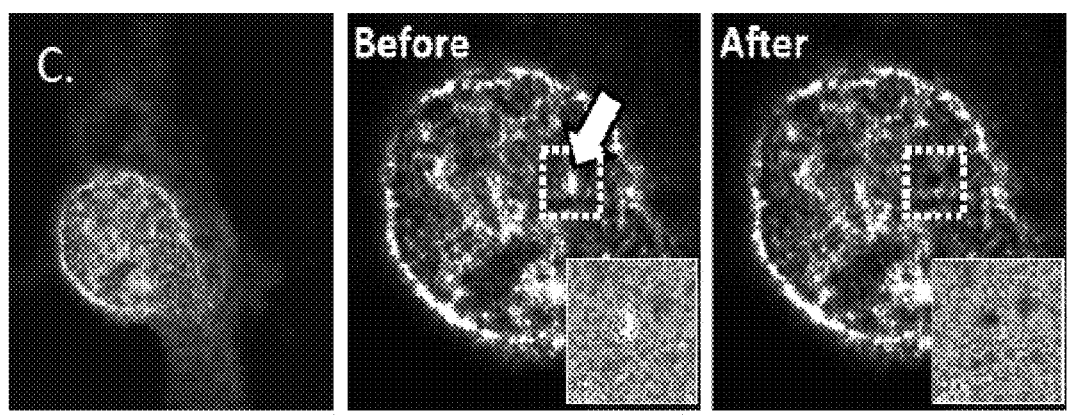
FIG. 6. Photoactivation at a specific site in the nucleus of a cell. To illustrate the ability to focally activate in the nucleus of a cell the nucleus is stained with an antibody to a transcription factor that is localized in the nucleus. One particular site (dotted box) is photoactivated with the 405 nm laser showing that such sites (analogous to HCR in situ hybridization site) can be photo addressed.

In this gene-specific iteration of CHeX-seq, fixed cells/tissue may be used for fluorescent in situ hybridization to detect the location of the specific gene(s). This specific gene FISH signal will be used to target the nucleus using multi-photon activation of the CHeX-seq oligonucleotides only at the FISH spotlighted gene(s). For example, a FISH probe directed to the open genomic DNA region near the transcription start site (TSS) of the selected gene may be used to produce a fluorescent signal at the gene's TSS, which can be imaged. These probes may be sense in direction so that the genomic DNA sequence is annealed to rather than the RNA. Then the CHeX-seq oligonucleotide may be added, which will diffuse throughout the fixed cells/tissue and bind to open areas of the cellular chromatin. To specifically assess the chromatin structure around the selected gene's TSS, the FISH probe signal will be used to direct multi-photon irradiation to locally activate the CHeX-seq oligonucleotides at the site of the gene's TSS (FIG. 6). The CHeX-seq oligonucleotide activated near the selected gene can be extended for cDNA synthesis at single stranded open genomic DNA sites near the gene's TSS. This gene niche specific CHeX-seq procedure can identify sequences, corresponding to chromatin regions near the site of the FISH probe, which may be genomic modulator elements (including enhancers) of the selected gene's transcription. These methods may be used to study any specified genomic DNA site. Furthermore, these methods may be made higher throughput using optical washing.

VI. Multiplexing

The methods for characterizing chromatin and cytoplasmic RNA, as provided herein, may be transitioned to a moderate/high throughput data production platform. To make the analysis of chromatin and cytoplasmic RNA into a moderate/high throughput procedure, methods that allows iterative addressing of specific oligonucleotides are provided. In Mer-FISH and Seq-FISH this was achieved by chemical dehybridization and more recently photobleaching. However, these methods are inadequate for differentially removing unactivated oligonucleotides from between cells and within a cell for subcellular analysis.

Figure 7:
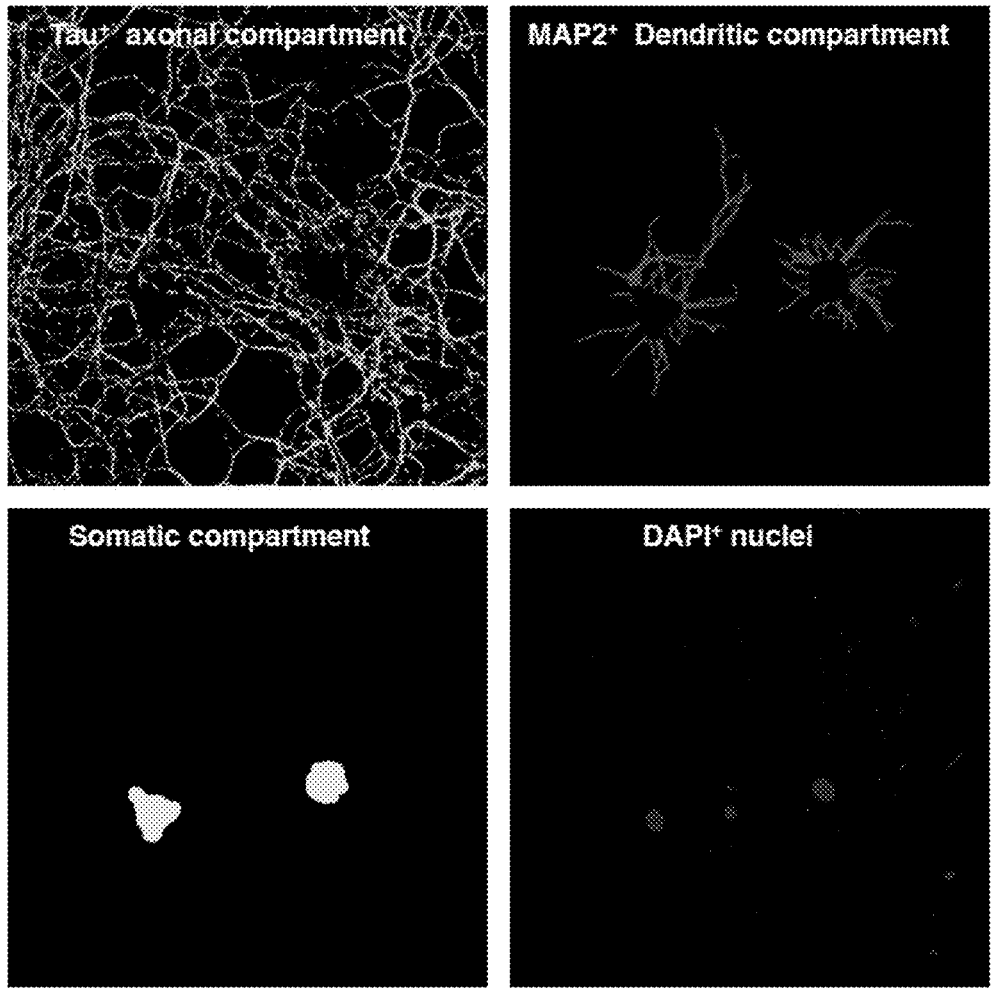
FIG. 7. Immunofluorescence image-based automated cell compartment analysis for use in optical washing. Raw image is separated into immunofluorescence signals of selective compartments with Tau for axons, MAP2 for dendrites and DAPI for nucleus. Each compartmental image is computed as a binary image for automatic quantification of average intensity per pixel and regional distribution pattern. The somatic compartment is computed based on DAPI/MAP2 signal and cell morphological contours.

As such, provided herein are methods of optical washing. These methods use an IR laser to locally heat the solution on a fixed tissue section to denature unwanted oligonucleotide binding. This is useful because the oligonucleotides used for CHeX-seq and LT-TISA are short and their hybridization can be easily controlled. In order to hybridize in the cell of interest, a fully automated picospritzer and aspiration system can be used to locally apply the oligonucleotides with selected barcodes to a limited space over the fixed cells or in a tissue. A cell of interest can be identified by immunofluorescence and oligonucleotide hybridization in that cell can be monitored by increased fluorescence signals as the CHeX-seq and LT-TISA oligonucleotides hybridizes and becomes fluorescently labeled by the addition of a fluorescently tagged photoactivatable terminating nucleotide (e.g., lightening terminator). Depending on the oligonucleotide size, temperature manipulation can be optimized, and the theoretical irradiation and heated area can be estimated by Fourier's law of heat conduction ($p=-Ak(dT/dL)$, $p$=thermal power, $A$=heated area, $k$=thermal conductivity, $dT$=temperature gradient, and $dL$=distance). For example, for a CHeX-seq oligonucleotide that has a degenerate annealing sequence of 15 bases, the Tm will range from 35-42° C., and for a LT-TISA (15 base polyA) oligonucleotide, the Tm will be 35° C. Heating of the solution surrounding the annealed oligonucleotide to 50° C. will dehybridize >95% of the unactivated oligonucleotides. A 50° C. temperature can be achieved instantaneously at focused pixels using 30 mW energy. Dehybridization and the efficiency of oligonucleotide clearing (for example, by washing) may be easily monitored by fluorescence signal decrease. However, these methods are also applicable without a picospritzer-bath application of oligonucleotide to the entire tissue can be performed (however, oligonucleotide hybridization will be slower) and denaturing of all areas except the cells of interest can be achieved by optical washing based upon immunofluorescence image masking that protects areas from heating thereby allowed selective heating of unstained cells (FIG. 7). This process may be incorporated into custom imaging software.

Within these experimental paradigms, in the future there is considerable flexibility to target different cellular compartments, to achieve multiplexing, for example, to assess initial rapid nuclear transcriptional response as well as steady-state cytoplasmic RNA abundances in selected cells that are in synaptic connectivity with one another in their natural microenvironment (tissue sections) (de la Torre-Ubieta & Bonni, 2011; Spaethling et al., 2017), and to analyze different RNA populations (e.g., mRNA, noncoding RNA, total RNA).

VII. Exemplary Application of the Present Methods—Chromatin Remodeling in Neurodevelopment and Psychiatric Illness The pharmacology of chromatin remodeling has been relatively understudied when contrasted with its important role in neurodevelopment and age-related plasticity (Borrelli et al., 2008; Ziller et al., 2015). In neurons an important plasticity modulator of these biologies is BDNF whose influence upon neuronal differentiation and local protein synthesis has been well documented (Martinowich et al., 2003; Berton et al., 2006). Other plasticity related phenomena that have been linked to chromatin changes include the influence of strong depolarizing stimuli upon dendritic morphology (Ellis et al., 2016; de la Torre-Ubieta & Bonni, 2011; Seifuddin et al., 2013). In genome wide association studies (GWAS) of autism spectrum disorders (ASD), as well as in chronic alcohol addiction, changes in chromatin remodeling and dendritic morphology have been linked to activation of NMDA glutamate receptors, voltage sensitive Ca++ channels and GABAb receptors (Varodayan & Harrison, 2013; Costa et al., 2006; Guidotti et al., 2011), which under normal conditions mediate hyperpolarization. These data on chromatin remodeling derive from analysis of large numbers of cells.

Genome wide association studies have identified multiple genetic loci associated with schizophrenia and depression, yet many of these loci have not yielded mechanistic insight into the causality of the illnesses (Maurano et al., 2012). As such, it is important to think beyond the genetics with an eye towards how the genome is regulated (Insel & Wang, 2010). There is accumulating evidence that there is significant variation in cellular susceptibility to illnesses such as depression and consequently there will be variation in therapeutic responsiveness. Transcriptome variability has been observed for schizophrenia (Zhang et al., 2015) and depression including in noncoding RNA populations (Roussos et al., 2014). The process of RNA transcription requires DNA of a particular conformation (i.e., open) where there is less nucleosome packing so that the transcription regulatory enzymes can function. Chromatin variation has also been noted between neurons and other cell types (Fullard et al., 2017) specifically including differences in genomic DNA methylation between neurons and astrocytes (Kozlenkov et al., 2014; Kozlenkov et al., 2016). Such epigenetic methylation differences have been seen between cells in other cell types as well (Mo et al., 2015). There has been some effort to correlate transcriptome and chromatin variability in the belief that having both sets of data would enable a better understanding of the regulatory mechanisms that underlie cellular dysfunction in these illnesses (Xiao et al., 2014). The plasticity of chromatin responsiveness has been highlighted in developmental changes (Zhu et al., 2013), cocaine pharmacological manipulation (Kumar et al., 2005), and changes in emotional status (Renthal et al., 2007). These studies show chromatin variation between cell types and subtypes even from populations of enriched cells. Such variation emphasizes the need to assess this variation at the level of single cells where mechanistic insight is more readily attainable. The literature that reports on chromatin reorganization uses almost exclusively acute and robust pharmacological manipulation of cultured cell lines—with limited exploration of the more subtle modulatory roles of synaptic transmitters (which are clinically significant) or their pharmacological equivalents like receptor or channel modulators in the slice preparation. To address the question of how psychoactive drugs effect the chromatin structure around specific genes, one needs to be able to assess the chromatin structure locally at these subgenomic single gene sites (Kolovos et al., 2014; Heller et al., 2014).

The molecular actions of synaptic stimulation upon chromatin remodeling follow the established receptor and calcium binding protein-mediated routes (Frankle et al., 2003). In neurons from the mouse hippocampus and cerebral cortex, chromatin remodeling has been mechanistically linked to the chromatin remodeling proteins, AXTR, HSF1 and H3.3 (Varodayan & Harrison, 2013). These proteins are also affected by 5HT receptor-mediated stimulation (involved in mood disorders). This links mood disorders to other psychiatric disorders through chromatin remodeling mechanisms (Duman, 2013; Sun et al., 2015; McCarthy et al., 2014). Mood disorders are therapeutically influenced by the SSRIs which are the most prevalent antidepressants and similarly synaptically-mediated fine tuning is also observed by D2 antagonists that are the most commonly used antipsychotics (Vialou et al., 2013).

Background on Transcriptome Variability:

Recent technological advancements have enabled increasingly high-resolution measurements of gene expression in single cells, resulting in a growing appreciation for the extent of expression variability across cells. This variability has been examined as: 1) an indicator of the vast diversity of cell types in multicellular organism; 2) a by-product of redundancy in regulatory networks; 3) a temporal snapshot of asynchronous dynamic processes; 4) the product of molecular dynamics; or 5) as evidence that RNA abundances may be irrelevant for cell phenotype. An alternative perspective is to consider whether single cell transcriptome, proteome and other molecular variability might be critical for cell population-level function. Are individual cells in a multi-cellular tissue similar to individual organisms in a cooperative community, where each cell's behavior contributes to an emergent higher-level ensemble function?

This variability reflects a many-to-one relationship between transcriptome states and a cell's phenotype (Kim & Eberwine, 2010). In this relationship, the molecular ratios of the subsets of RNA are determined by the cell systems' stoichiometric constraints, which underdetermine the transcriptome state. By analogy, transcriptome phenotypes are defined as subsets of RNAs comprising selected RNA systems, which exist in balance with each other to produce the associated cellular function. There is considerable evidence that individual cells in a tissue adopt a heterogeneous state, either through relaxation of their physiological dynamics or by active signaling and maintenance of an aggregate state.

Figure 8:
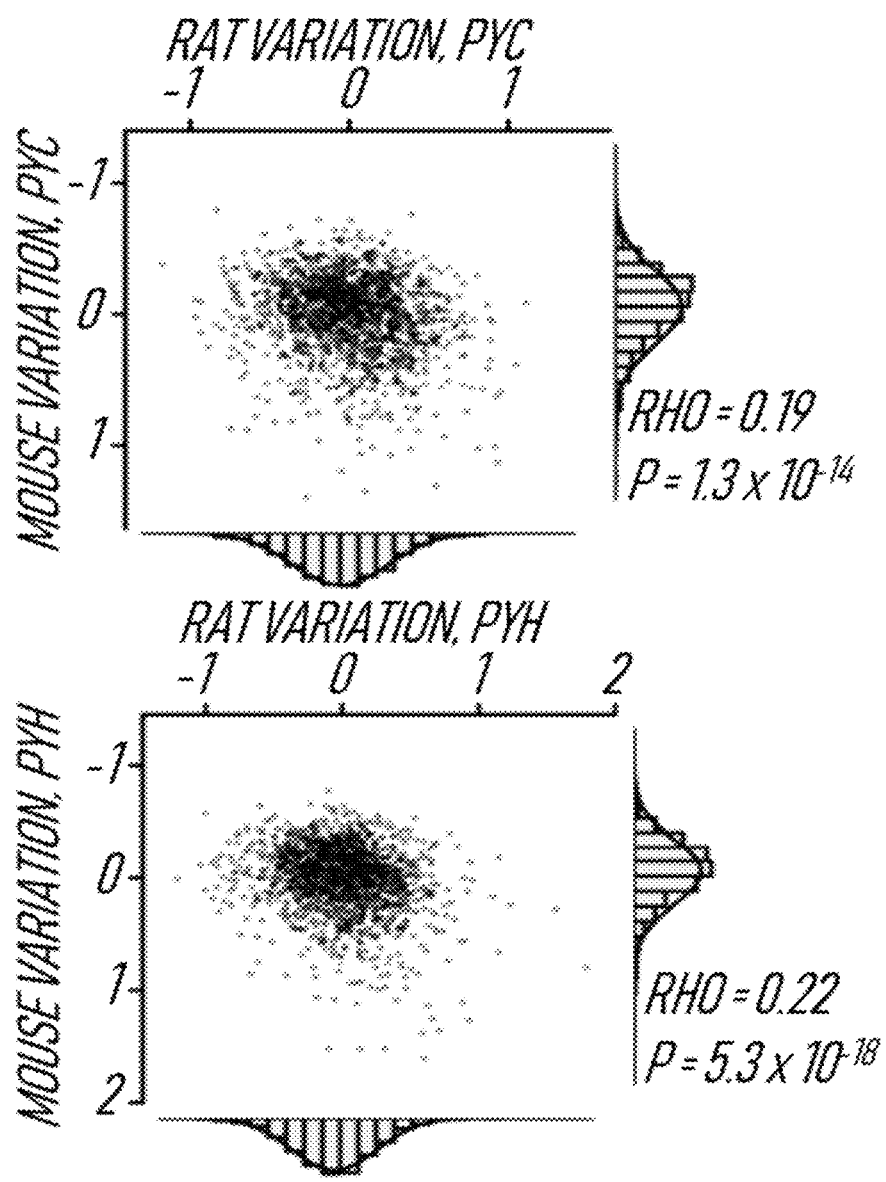
FIG. 8. Partial correlation of F-statistic across species, controlling for gene expression level, for cortical (left) and hippocampal (right) pyramidal neurons. Axes are a measure of variation, controlled for gene expression level. "rho" indicates the partial correlation coefficient. P-values are from a two-sided T-test of association. Marginal histograms are shown overlaid with a normal curve.

Furthermore, if gene expression variation amongst individual cells is important for tissue function, the degree of variation itself may be conserved across species. As a proof of principle, the F-statistic for cortical and hippocampal pyramidal neurons in rat and mouse was calculated. For each cell type, the partial correlation of the F-statistic across species was computed, controlling for gene expression levels to ensure that correlation was not simply due to shared levels of gene expression. The partial correlation coefficient across species is significant for both cell types examined (two-sided T-test of association $p<10^{-13}$, FIG. 8), indicating conservation of gene expression variation across species. These data support the hypothesis that gene expression variation is regulated, at least for some genes, and that the pattern of expression across a population of cells is likely important for tissue function.

Provided herein are methods that enable the determination of whether the positioning of chromosomes relative to the cell signaling inputs (in part due to the polarity and location of the cell) produces cellular transcriptome variability and facilitates the "many to one" elaboration of similar cellular physiological states (Kim & Eberwine, 2010).

Figure 9:
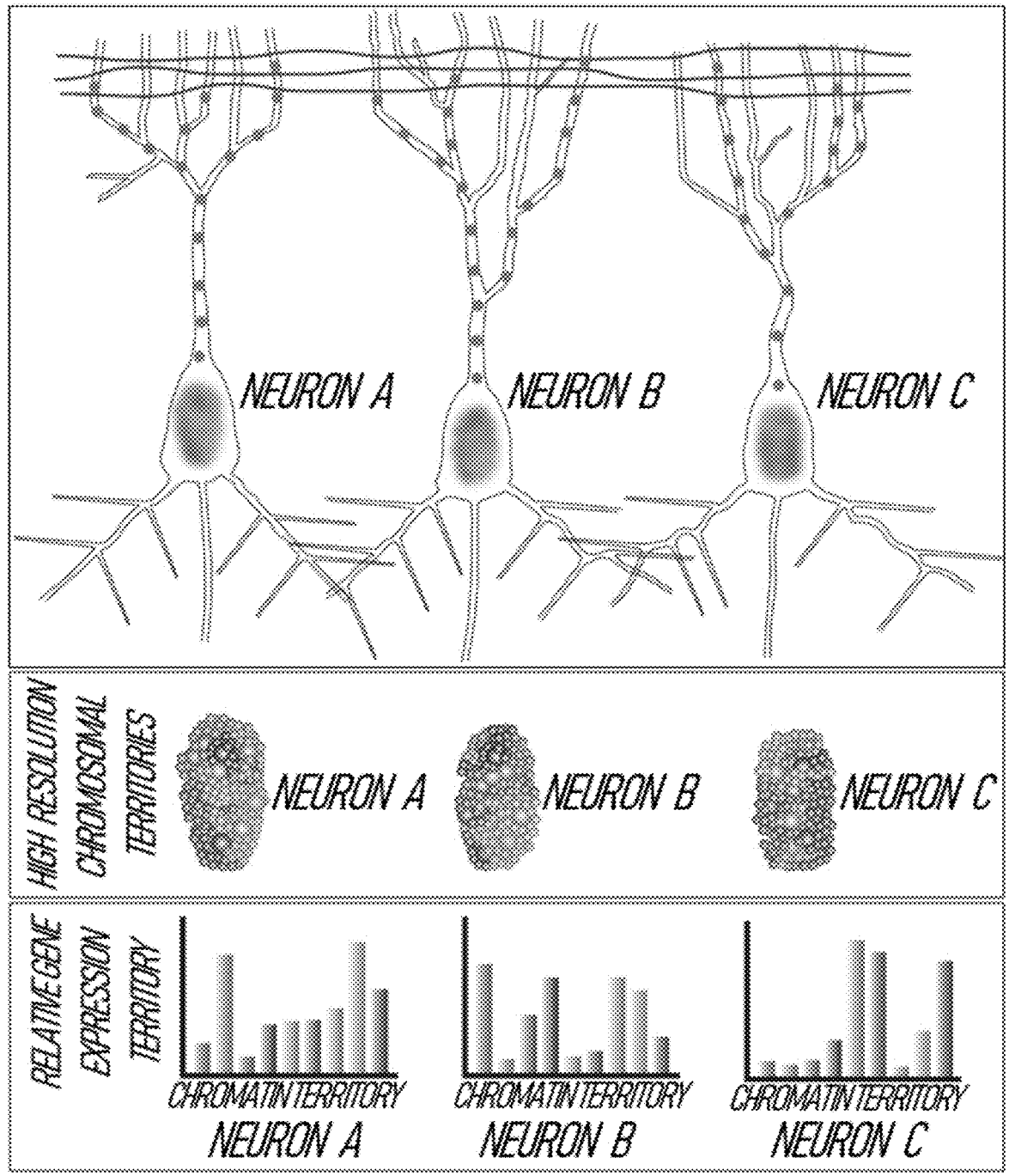
FIG. 9. A model of chromatin variability. Signals are received by the neurons in the top panels that activate a second messenger system (green dots) that activates the nucleus. Each neuron has a different arrangement of chromosomes in the nucleus (middle panel), which upon receiving the vectorial signal activates transcription of genes to differing extents (bottom panels).

Impact of the Morphological Geometry of the Neuron Upon the Nucleus:

CNS neurons are situated in brain structures where they receive synaptic input from many presynaptic neurons. During neuronal development the neurons migrate to the position where they become "hard-wired" or interconnected both synaptically and stearically with surrounding cells (FIG. 9, top). These neurons can modify their synaptic connectivity but are limited in their ability to move or reposition themselves. The nucleus in the neuron is relatively immobile, with neuronal cytoskeleton associations holding the nucleus in place. As these neurons are postmitotic, there is little gross movement of chromosomes, for example: chromosome one cannot acutely change position with chromosome five (FIG. 9, middle). However, cis- and trans-regulatory regions that control chromatin openness and expression do move. Any two neighboring cells may have overlapping higher order chromatin structures giving rise to common cellular characteristics as well as variable structures giving rise to cellular distinctness.

Model for Generation of Transcriptome Variability:

Such morphological constraints suggest that as different neurons receive input from presynaptic neurons, the activation occurs in a vectorial manner from the site of stimulation. When the signal cascade reaches the nucleus, the open chromatin regions closest to the site of stimulation will receive the strongest and quickest stimulation (FIG. 9, where neuron A has green- and purple-colored chromatin at the side of the nucleus closest to the stimulation; neuron B has black and purple chromatin; and neuron C has blue and green chromatin). Given the predicted differences in chromosomal localization, it is further suggested that chromatin interactions will also be largely distinct with different enhancer and target gene interactions in selected cells. The differences in proximity to vectorial stimulation and differences in chromosomal/chromatin interactions would then give rise to transcriptional variability (FIG. 9, bottom panels).

The methods provided herein may be used to identify changes in chromatin state and/or the cytoplasmic transcriptome resulting from clinically relevant manipulation, for example antidepressant drug action (Tsankova et al., 2007; Sharma et al., 2006; Ellis et al., 2016). Clinical depression is a psychiatric illness for which therapeutic treatment can be difficult because of long onboard time for the drugs to be effective and the need to adjust dosages to be effective. The molecular basis for these issues likely results in part from the genomic variability that exists between cells as well as the need to change the epigenetic state of the adult neuronal genome. To this end, drugs that treat depression may be tested for their ability to modulate chromatin structure and cytoplasmic RNA abundances in the context of the variability that exists between cells. Because "cell to cell" differences in chromosomal organization may underlie cell-to-cell variability in transcriptional responses to antidepressant drug, analysis of the 3D structure of open chromatin around selected genes may provide further insight. This knowledge may promote development of new methods to manipulate higher order chromatin structure to enhance the therapeutic efficacy of these drugs.

To this end, the CHeX-seq protocol may be used to generate single neuron open chromatin datasets for dispersed mouse and human cortical neurons. In addition, the combined CHeX-seq and LT-TISA protocol may be used to generate quantitative single neuron transcriptional biology datasets from open chromatin analysis to steady state levels of cytoplasmic RNA pools for dispersed mouse and human cortical neurons. Simultaneous measurement of cytoplasmic RNA pools with chromatin structure may show what areas of the transcriptional pathway are most closely associated with antidepressant pharmaco-responsiveness. Finally, the time course of chromatin niche remodeling around specific genes will provide the first insights into how conserved a process chromatin remodeling is for genes associated with psychiatric illnesses. This information will be useful in assessing the functional interplay between time for niche development and phenotypic outcome.

Specifically, the present methods may be used to assess on the "regulated transcriptome" effects of single cell cortical neuronal chromatin remodeling in response to the antidepressant fluoxetine. Simultaneous measurement of cytoplasmic RNA pool with chromatin structure can be used to reveal what areas of the transcriptional pathway are most closely associated with antidepressant pharmaco-responsiveness (Tsankova et al., 2007). As a corollary to these genomics level responses, the time course of chromatin niche remodeling around specific genes can be examined to provide the first insights into how conserved of a process chromatin remodeling is for genes associated with psychiatric illnesses. This information will be useful in assessing the functional interplay between time for niche development and phenotypic outcome. The single gene chromatin niche analysis can concentrate upon pharmacological modulation of the chromatin structure around genes encoding chromatin remodeling proteins, such as AXTR, HSF1 and H3.3 (which must be active during remodeling), as well as pharmacologically responsive target genes, including the glutamate and GABAb receptors and members of the CREB 2' messenger activation system, which are involved in GPCR mediated cellular events (Ruzicka et al., 2015; Huang & Akbarian, 2007; Chen et al., 2014).

An experimental system that is often used to assess cell biological mechanisms is primary dispersed CNS cell culture. Long-term (2-3 months) mouse cultures require that the neurons come from fetal/newborn mice since mature neurons do not usually remain viable in culture for extended times. Short-term mouse primary cell culture from adult brain can be done acutely for up to 3 days. Previously it was assumed that the same would be true for human neuronal cells, but to test this, the inventors have collected and characterized live human brain tissue from patients. The brain tissues were obtained from consented patients undergoing neurosurgery (typically for tumor removal). The laboratory staff waits during the surgical process and delivers the appropriate tissue to the lab, typically within 20 minutes of resection. The cells have been enzymatically dissociated from small amounts of tissue and dispersed adult neuronal primary cell culture has successfully been performed for 3 months and longer. Primary cell culture models are useful in predicting and isolating the factors involved in various physiological events including RBP interactions with mRNA, which can subsequently be tested in vivo. The utility of these long-term human cell cultures is reflected in that cells of a particular type tend to reveal their distinct class only within a subset of genes. For example, RNAseq analysis of ~300 human brain-derived cells followed by pathway analysis showed the presence of neurons, astrocytes, endothelial cells, microglia, and oligodendrocytes in the human brain cell cultures. Identifying sub-cell types from single cell samples requires careful application of noise control, pathway/gene selection, and machine learning methods. These data show that the human primary cell culture methodology works well for various transcriptionally defined cell types including neurons that will be utilized in these studies (Thurman et al., 2012).

VIII. Kits

Kits according to the invention provide at least one component that is useful for practicing at least one embodiment of a method of the invention. Thus, a kit may provide some or all of the components necessary to practice at least one embodiment of a method according to the invention. A kit may comprise at least one container that contains an oligonucleotide of the invention. A kit may comprise all of the oligonucleotides needed to perform at least one embodiment of a method according to the invention, such as, for example, a panel of oligonucleotides for the analysis of open genomic DNA and/or expression for selected genes or a panel of degenerate oligonucleotides for genome-wide analysis of open genomic DNA.

Kits are generally defined as packages containing one or more containers containing one or more oligonucleotides or compositions of the invention. The kits themselves may be fabricated out of any suitable material, including, but not limited to, cardboard, metal, glass, plastic, or some other polymeric material known to be useful for packaging and storing biological samples, research reagents, or substances. The kits may be designed to hold one or more containers, each of such containers being designed to hold one or more nucleic acids, compositions, or samples of the invention. The containers may be fabricated out of any suitable material including, but not limited to, glass, metal, plastic, or some other suitable polymeric material. Each container may be selected independently for material, shape, and size. Non-limiting examples of containers include tubes (e.g., microfuge tubes), vials, ampules, bottles, jars, bags, and the like. Each container may be sealed with a permanent seal or a reclosable seal, such as a screw cap. One or more of the containers in the kit may be sterilized prior to or after inclusion in the kit.

The kits of the invention may include one or more other components or substances useful in practicing the methods of the invention, such as sterile water or aqueous solutions, buffers for performing the various reactions involved in the methods of the invention, and/or reagents for detection of amplification products. Thus, a kit may comprise one or more polymerase for amplification of a cDNA or RNA molecule. A kit may comprise one or more reverse transcriptases for cDNA synthesis from a RNA template. It also can comprise some or all of the components, reagents, and supplies for performing reverse transcription and amplification according to embodiments of the invention. For example, in some embodiments, in addition to one or more oligonucleotides comprising the photoactivatable terminator, the kits may include nucleotides for reverse transcription and/or amplification with or without one or more polymerases. In embodiments, it includes some or all of the reagents necessary for library preparation and next-generation sequencing analysis.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—CHeX-Seq Oligonucleotide Terminator Addition

HPLC-purified oligonucleotides and their complementary oligonucleotides were purchased from Integrated DNA Technologies (IDT). A template-dependent DNA polymerase incorporation assay was employed to incorporate a fluorescently tagged photoactivatable terminating nucleotide analog onto the 3' end of oligonucleotide: (1) 5 μM of oligonucleotide, 25 μM of complementary oligonucleotide, 50 μM of a fluorescently tagged photoactivatable terminating nucleotide analog, 4 mM $MgSO_4$, and 0.1 U/μL of Terminator (New England Biolabs) were mixed in 1× ThermoPol buffer, (2) the mix was heated to 80° C. for 45 seconds, and (3) the mix was incubated for 5 minutes at each of 60° C., 55° C., 50° C., 45° C., 40° C., 35° C., 30° C., and 2555° C. The incorporation product was purified on the Agilent 1260 Infinity reverse phase HPLC using the XTerra MS C18 Prep column (Waters). The purified product solution volume was concentrated to approximately 250 μL using the Eppendorf Vacufuge followed by denaturation into single-stranded oligonucleotides with an equal volume of 0.2 M NaOH. HPLC purification and concentration were repeated using the same conditions for collection of the oligonucleotides. The final product was dissolved into 1×PBS, and concentration was determined by measuring fluorescent dye absorbance.

Example 2—CHeX-seq

Figure 10:
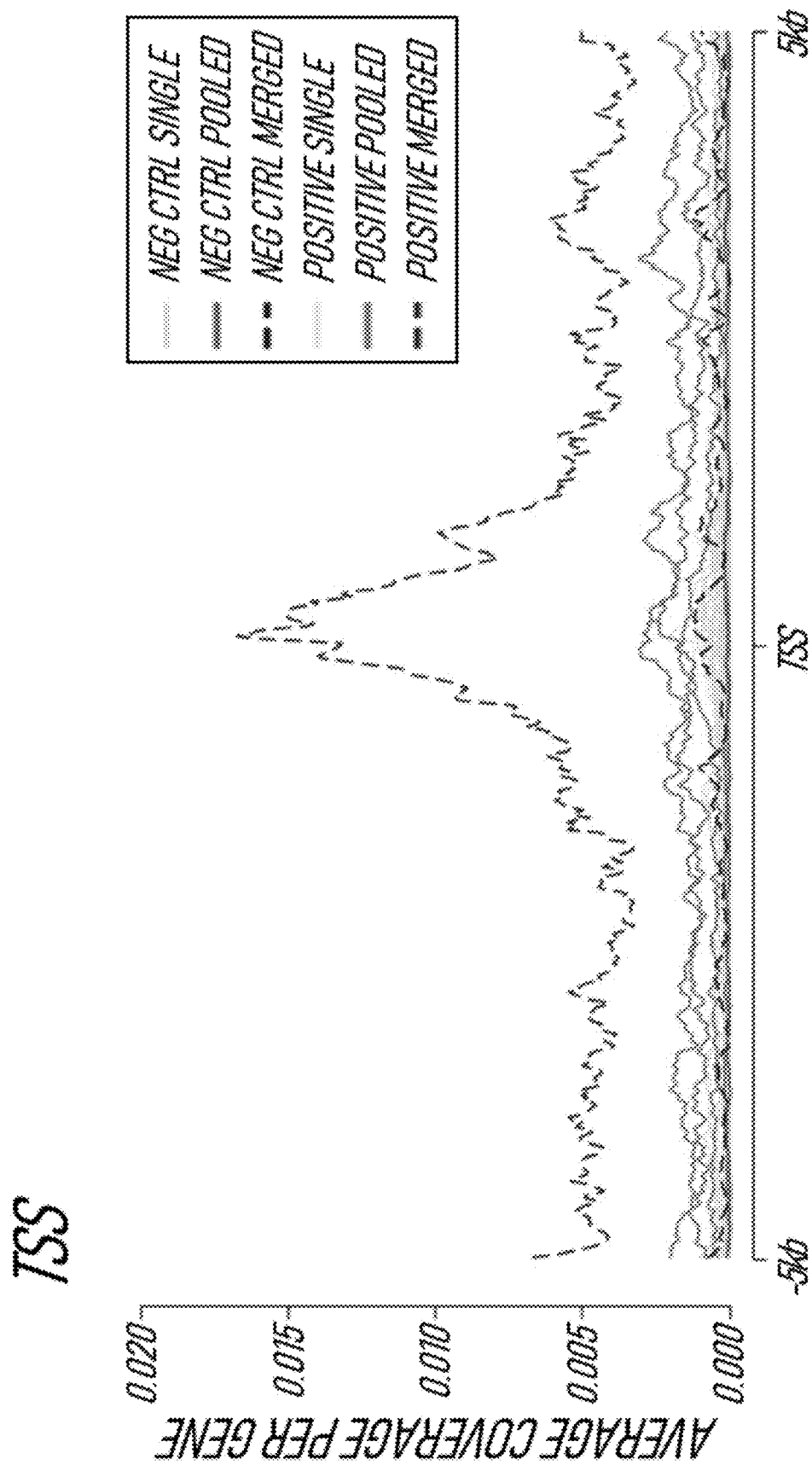
FIG. 10. CHeX-seq preliminary data. Reads were quantified relative to genomic feature start and stop locations for both positive and control samples: transcription starting site, gene coding region, 3'UTR, and intergenic region. Single cell samples are shown as separate traces and are also "merged" into a single trace. Pooled samples are shown as separate traces.

CHeX-seq was performed using cells fixed in 3% formalin for 3 mins. For this experiment, CHeX-seq oligonucleotides targeting single nuclei of cortical neurons were used. FIG. 10 shows a summary of alignments of the reads for individual cells. The alignments are mapped in relation to different genomic features, transcription start sites (TSS), coding sequences (CDS), 3'UTR, and intergenic regions. The reads showed peaks at expected proximity to the TSS and across coding sequences. Interestingly, peaks were also seen at both ends of intergenic regions.

Example 3—Materials & Methods for Examples 4-7

Human Brain Tissue.

Human brain tissue was collected at the Hospital of the University of Pennsylvania (IRB #816223) using standard operating procedures for enrollment and consent of patients. Briefly, an en bloc sample of brain (typically 5×5×5 mm) was obtained from cortex that was resected as part of neurosurgical procedures for the treatment of epilepsy or brain tumors. This tissue was immediately transferred to a container with ice-cold oxygenated artificial CSF (in mM: KCl 3, $NaH_2PO_4$ 2.5, $NaHCO_3$ 26, glucose 10, $MgCl_2$-$6H_2O$ 1, $CaCl_2$-$2H_2O$ 2, sucrose 202, with 5% $CO_2$ and 95% $O_2$ gas mixture) for transfer to the laboratory. Tissues arrived in the laboratory ~10 minutes post excision. The brain tissues were then processed for cell culturing and fixation.

Cell Culturing/Preparation and Fixation.

K562 cells were obtained from ATCC and cultured in RPMI 1640 medium (Invitrogen) with 10% FBS and penicillin-streptomycin in a T75 flask at 37° C. in 5% $CO_2$ for 2-3 days. The cultured cells were transferred to a 50 ml tube and 16% paraformaldehyde (final 1%) was added for 10 mins at room temperature to fix the cells. After fixation, 1 M glycine (final 200 mM) with RPMI 1640 medium was used to quench for 10 mins followed by centrifugation at 300×g for 5 mins. The supernatant was discarded and 3 mL of PBS were added to the pellet and then mixed by gently pipetting up and down 10-15 times using a fire-polished glass-pipette, to prevent cell clumping, and centrifuged at 300 rpm for 5 mins. The 100 μl cell pellet was attached to 18 mm gridded coverslips by incubating them for 2 h at room temperature. The samples were treated with PBS (w/o $Ca^{++}$, $Mg^{++}$) containing 0.01% Triton X-100 for 10 mins and then washed with PBS (w/o $Ca^{++}$, $Mg^{++}$) 3 times for 3 mins. To prepare human neuronal cell cultures, adult human brain tissue was placed in the papain (20 U, Worthington Biochemical) solution to dissociate at 37° C. for 30 to 40 mins and followed by ovomucoid (a papain inhibitor, 10 mg/ml, Worthington Biochemical) to stop the enzymatic dissociation (Spaethling et al., 2017). The tissue was triturated with a fire-polished glass Pasteur pipette. The cloudy cell suspension was carefully transferred to a new tube and centrifuged at 300×g for 5 mins at room temperature. The cells were counted in an Autocounter (Invitrogen). Cells were plated on poly-L-lysine-coated (0.1 mg/ml, Sigma-Aldrich) 12-mm coverslips at a density of $3\times10^4$ cells/coverslip. Cultures were incubated at 37° C., 95% humidity, and 5% $CO_2$ in neuronal basal medium (Neurobasal A, Gibco), serum-free supplement (B-27, Gibco) and 1% penicillin/streptomycin (Thermo-Fisher Scientific). Dispersed mouse neuron/astrocyte cultures were prepared following published protocols (Buchhalter & Dichter, 1991). Dispersed cells were fixed using 4% paraformaldehyde for 10 min at room temperature. This was followed by three washes with 1×PBS. The cells were permeabilized with 0.1% Triton-X100 for 10 min at room temperature followed by three washes with 1×PBS.

Mouse Brain Tissue Section Preparation.

A 3-month old male mouse was anaesthetized with halothane, euthanized by thoracotomy, then subjected to cardiac perfusion with 5 ml PBS followed by 20 ml PBS/4% paraformaldehyde. The brain was removed and post fixed at 4° C. for 16 h, then rinsed in PBS and sectioned in the coronal plane at 100 μm on a vibratome (Leica VT-1000s). Sections including the hippocampus were then subjected to immunofluorescence labeling with chicken anti-MAP2 antisera (1:1000; Ab 5392; Abcam) followed by Alexa 488 conjugated goat anti-chicken secondary antibody (1:400; ab150169; Abcam).

CHeX-Seq Probe Synthesis:

HPLC-purified probe oligo and its complimentary oligo were purchased from Integrated DNA Technologies (IDT). A template-dependent DNA polymerase incorporation assay was employed to extend Cy5-dye-labeled Lightning Terminator™ (Agilent, Inc.) to the 3' end of probe oligo: (1) 5 μM of probe oligo, 25 μM complimentary oligo, 50 μM of Cy5-labeled Lightning Terminator™, 4 mM $MgSO_4$, and 0.1 U/μL of Therminator (New England Biolabs) were mixed in 1× ThermoPol buffer, (2) the mix was heated to 80° C. for 45 sec and (3) then incubated for 5 mins at each of 60° C., 55° C., 50° C., 45° C., 40° C., 35° C., 30° C. and 25° C. The incorporation product was purified on the 1260 Infinity reverse phase HPLC (Agilent Technologies) using the XTerra MS C18 Prep column (Waters). The purified product solution was concentrated to approximately 250 μL using the Vacufuge (Eppendorf) followed by denaturation into single-stranded oligo with equal volume of 0.2 M NaOH. HPLC purification and concentration were repeated using the same conditions for collection of the Lighting Terminator-labeled single-stranded probe. The final product was dissolved into 1×PBS and the concentration was determined by measuring Cy5 absorbance at 647 nm (FIG. S1).

CHeX-Seq Probe Application.

After fixation and permeabilization, the cells and brain slices were incubated with CHeX-seq probe (170 nM) in TES buffer (10 mM Tris, 1 mM EDTA, 150 mM NaCl) for 1 h at room temperature. The samples were then washed with 1×PBS (w/o $Ca^{++}$, $Mg^{++}$) 3 times for 3 min.

Imaging and Photoactivation.

After CHeX-seq probe annealing and washing, the samples were transferred to the imaging chamber with 1×PBS (w/o $Ca^{++}$, $Mg^{++}$). All images and photoactivations were performed using a Carl Zeiss 710 Meta confocal microscope (20× water-immersion objectives, NA 1.0). CHeX-seq probe annealing was confirmed by exciting at 633 nm and emission was detected at 640-747 nm. The photoactivation was performed using the 405 nm (UV) laser at 60% power and 6.30 µs per pixel.

First Strand DNA Synthesis In Situ and Single Cell Harvest.

After photoactivation in each individual cell's nucleus, a master mix containing DNA polymerase I and 1st strand DNA synthesis buffer was added to the cells and incubated for 1 h at room temperature. Subsequently, the single cells containing synthesized complementary DNA were harvested using a glass micropipette under using a Zeiss 710 confocal microscope (Carl Zeiss) for visualization.

Linear Amplification of Nucleosome Free Area of Chromatin.

(A) 1st strand DNA synthesis and poly G tailing at 3' end: After harvesting single cells, the in situ synthesized cDNA was removed by adding fresh prepared 0.1 N NaOH and incubating the sample for 5 min at RT followed by neutralization with 1 M Tris (pH 7.5). After ethanol precipitation, the 1st strand DNA was resuspended in nuclease free water. Subsequently, poly(G) was added to the 3' end using terminal deoxynucleotidyl transferase (TdT) (Invitrogen). (B) 2nd strand DNA synthesis and round 1 linear RNA amplification: 2nd strand DNA was synthesized using DNA polymerase I for 2 h at 16° C. after priming with custom App-RC-polyC primer (Table 1). RNA was amplified using linear in vitro transcription from T7 RNA polymerase promoter incorporated into the double-stranded DNA with Ambion MEGAscript T7 In Vitro Transcription (IVT) Kit. (C) Round 2 1st and 2nd strand DNA synthesis and PCR amplification: After cleanup IVT reaction, 1st strand DNA was reverse transcribed from aRNA using Superscript III using a custom App-RC primer (Table 1) 2nd strand DNA was synthesized using DNA Polymerase 1 with a custom 18bpPBC1 primer (Table 1). Subsequently, the double-stranded blunt ended DNA was amplified using custom primers 18bpPBC1/App-RC (Table 1) following PCR condition: 98° C. for 30 sec; thermocycling at 98° C. for 10 sec, 50° C. for 30 sec, 72° C. for 30 sec for 27 cycles; extension at 72° C. for 2 mins, and was then used for library construction. Samples for the control experiments were processed with the same procedure except no CHeX-seq probe was applied, and 2nd round 2nd strand DNA PCR amplification was performed with custom primers 18bpPBC14/App-RC (Table 1).

TABLE 1

List of primers and oligonucleotide sequences used in these studies.

| Name | Sequence (5'→3') |
|---|---|
| T7-BC1-N(15)-T-LTdU-Cy5 | GGAGAATTGTAATACGACTCACTATAG GGAGACGCGTGATCACGNNNNNNNNNN NNNNNT-LTdU-Cy5 (SEQ ID NO: 2) |
| 18bpPBC1 | TAGGGAGACGCGTGATCA (SEQ ID NO: 8) |
| 18bpPBC14 | TAGGGAGACGCGTGAGTT (SEQ ID NO: 9) |

TABLE 1-continued

List of primers and oligonucleotide sequences used in these studies.

| Name | Sequence (5'→3') |
|---|---|
| App-RC-polyC | GCGCCATTGACCAGGATTTTCCCCCCC CCCCCCC (SEQ ID NO: 10) |
| App-RC | GCGCCATTGACCAGGATTTTC (SEQ ID NO: 11) |
| FISH 5ATTO590NChr1_1 | TCCTTAGCTGTTGCAGAAAT (SEQ ID NO: 12) |
| FISH 5ATTO590NChr1_2 | CGTTCAGTTGATGCAGAGTG (SEQ ID NO: 13) |
| FISH 5ATTO590NChr1_4 | AGAAGCAGCTTCAAACCTGC (SEQ ID NO: 14) |
| FISH 5ATTO590NChr1_6 | AAGTTAGCTTTACAGTGGGC (SEQ ID NO: 15) |
| FISH 5ATTO590NChr1_7 | GGTGTTGGTTCTCTTAATCT (SEQ ID NO: 16) |
| FISH 5ATTO590NChr1_8 | ATTTAGTTGGGGCATTTCAC (SEQ ID NO: 17) |
| FISH 5ATTO590NChr1_9 | TTATGGTGGGTCATACGGTA (SEQ ID NO: 18) |
| FISH 5ATTO590NChr1_10 | TAGTGTAAGGAGTATGGGGG (SEQ ID NO: 19) |

Sequencing Library Preparation.

Illumina TruSeq Nano DNA Library Preparation Kit was used with modifications. All of the second round PCR amplified double-stranded DNA was used as input. After converting DNA fragment into blunt ends with End Repair Mix, base "A" was added; sequence adapters were ligated. DNA inserts were amplified with PCR.

External Data.

GRO-seq: K562 GRO-seq was downloaded from SRA (accession GSE60454) (Core et al., 2014) in FASTQ format; raw reads were processed using the SCAP-T pipeline (available on the world wide web at scap-t.org); POL2 engaged transcripts were inferred by HOMER (Heinz et al., 2010); ATAC-seq: 1. Single-cell untreated K562 ATAC-seq data were downloaded from SRA (accession GSE65360) (Buenrostro et al., 2015 in raw FASTQ format. The alignment and peak calling methods in Buenrostro et al. (2015) were followed; 2. Mouse brain ATAC-seq data were downloaded from ENCODE (Davis et al. 2018) in BAM format; narrow and broad peaks were called using MACS2 (Feng et al., 2012); DNase-seq: 1. K562 DNase-seq narrow and broad peaks were downloaded from ENCODE in bigBed format; 2. Human brain DNase-seq data were downloaded from ENCODE in BAM format; FAIRE-seq: K562 FAIRE-seq narrow peaks were downloaded from ENCODE (accession ENCFF000TLT) in BED format; the original hg19 genome build was lifted over to hg38 by CrossMap (Zhao et al., 2014); Reduced representation bisulfite sequencing (RRBS): K562 DNA methylation RRBS data were downloaded from UCSC ENCODE track in BEDMethyl format; the original hg19 genome build was lifted over to hg38 by CrossMap. ChIP-seq: K562 ChIP-seq data were downloaded from ENCODE in genome build hg38. They were further organized in three categories: transcription factor binding sites (TFBSs) and narrow and broad histone modifications (H3K27ac, H3K4me3, H3K9ac, H3K4me2, H2AFZ; H3K4me1, H3K27me3, H3K36me3, H3K9me3, H3K79me2, H3K9me1). Only replicated peaks were used for histone modifications. Hi-C: K562 Hi-C data were downloaded from GSE63535 (Rao et al., 2014) in genome build hg19. In order to compare it with hg38 while minimizing potential artifacts caused by lifting over Hi-C data, CHeX-seq from hg38 was lifted over to hg19 using CrossMap. Enhancer and super-enhancer: Human and mouse experimentally validated enhancers were downloaded from the VISTA database (Visel et al., 2007); Super-enhancer data were downloaded from dbSUPER (Khan et al., 2016); DNA replication origin: K562 DNA replication origin data was downloaded from GEO (accession GSE46189), in BED format with pre-called peaks by the authors. The original genome build is hg19, which was converted to hg38 by CrossMap. Enhancer/promoter interactions: in UCSC Genome Browser, enhancers, promoters and regulatory interactions were loaded from database GeneHancer v4.11 (Fishilevich et al., 2017), using only high-confidence ("double elite") data.

Example 4—Benchmarking CHeX-Seq in Human K562 Cells

Figure 13B:
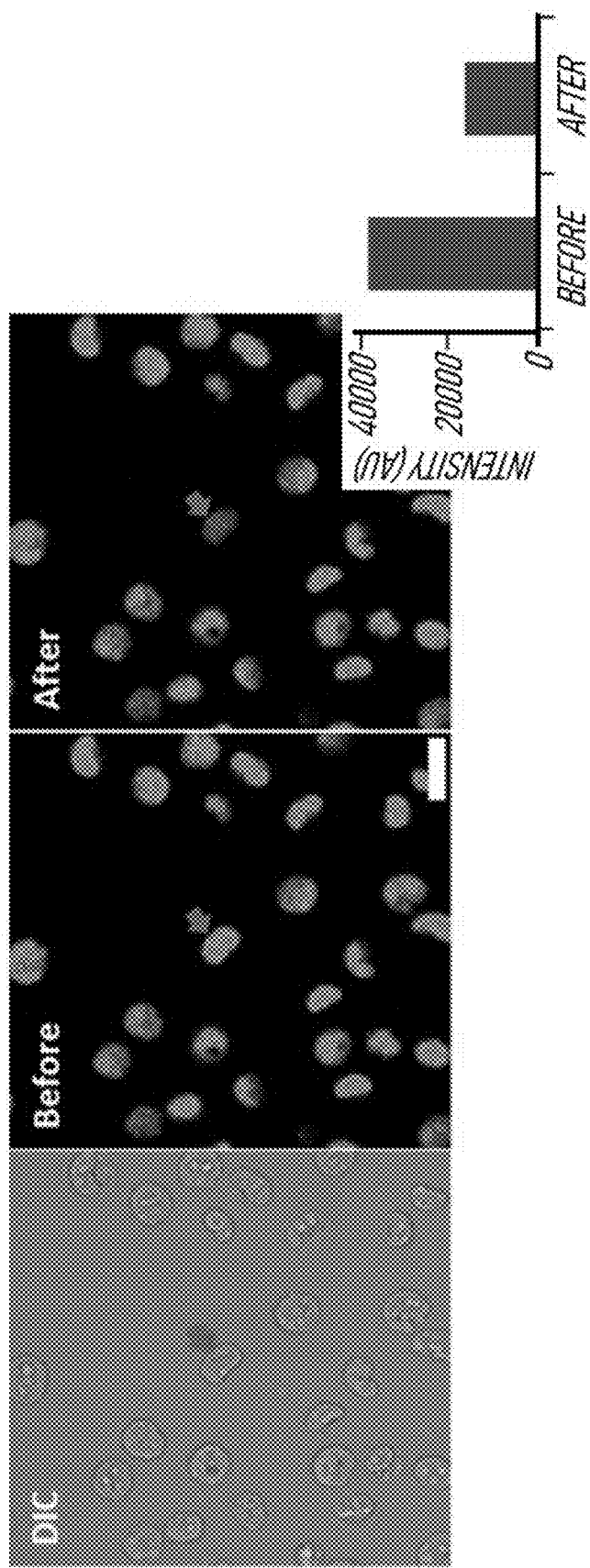

HK562 cells were selected for benchmarking, the CHeX-seq procedure as this cell line was chosen by ENCODE for extensive analyses (The ENCODE Project Consortium, 2012). After fixation, K562 cells were gravity deposited onto poly-L-lysine-coated cover slips and then permeabilized and washed in PBS. Annealing of the CHeX-seq fluorescently labeled primer to the chemically fixed cells shows the probe concentrating in the nucleus of the cell (FIG. 13B). The CHeX-seq primer was activated by illuminating with 405 nm (UV) laser at 60% power and 30 µs per pixel, whereupon a 45~80% decrease in fluorescence was observed (FIG. 13B inset). This decrease is due to the loss of the fluorescent moiety and freeing of a 3'-hydroxy I group to prime DNA synthesis.

Figure 13C:
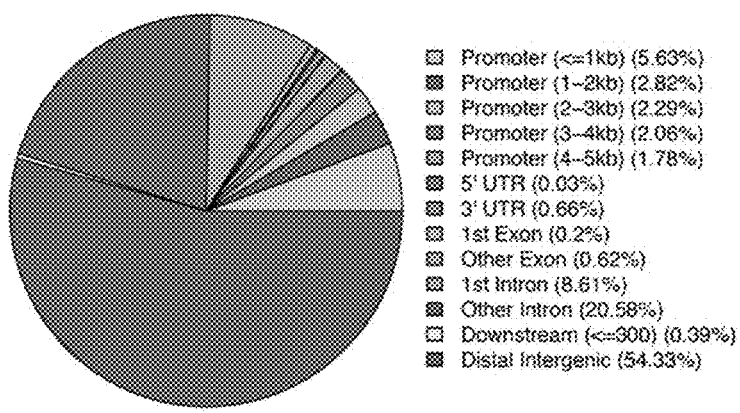
Figure 13D:
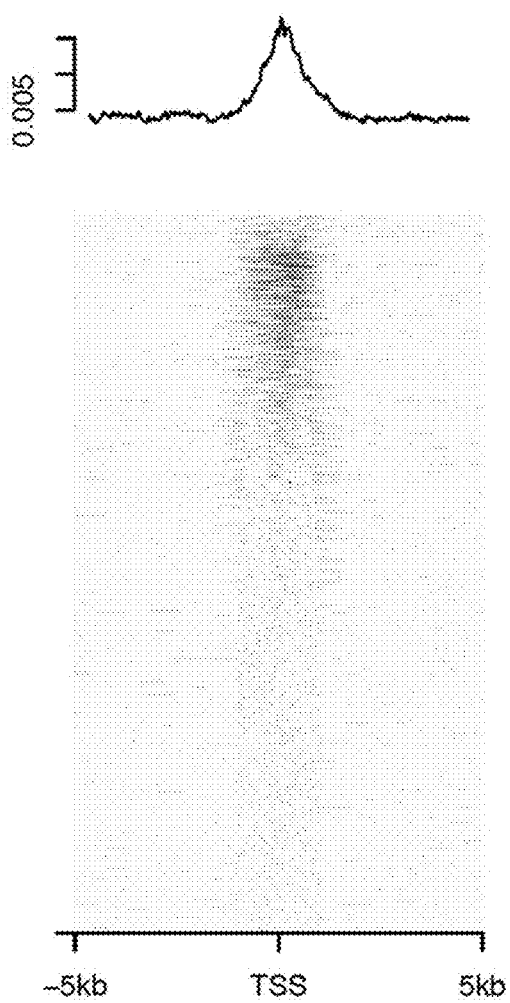
Figure 13E:
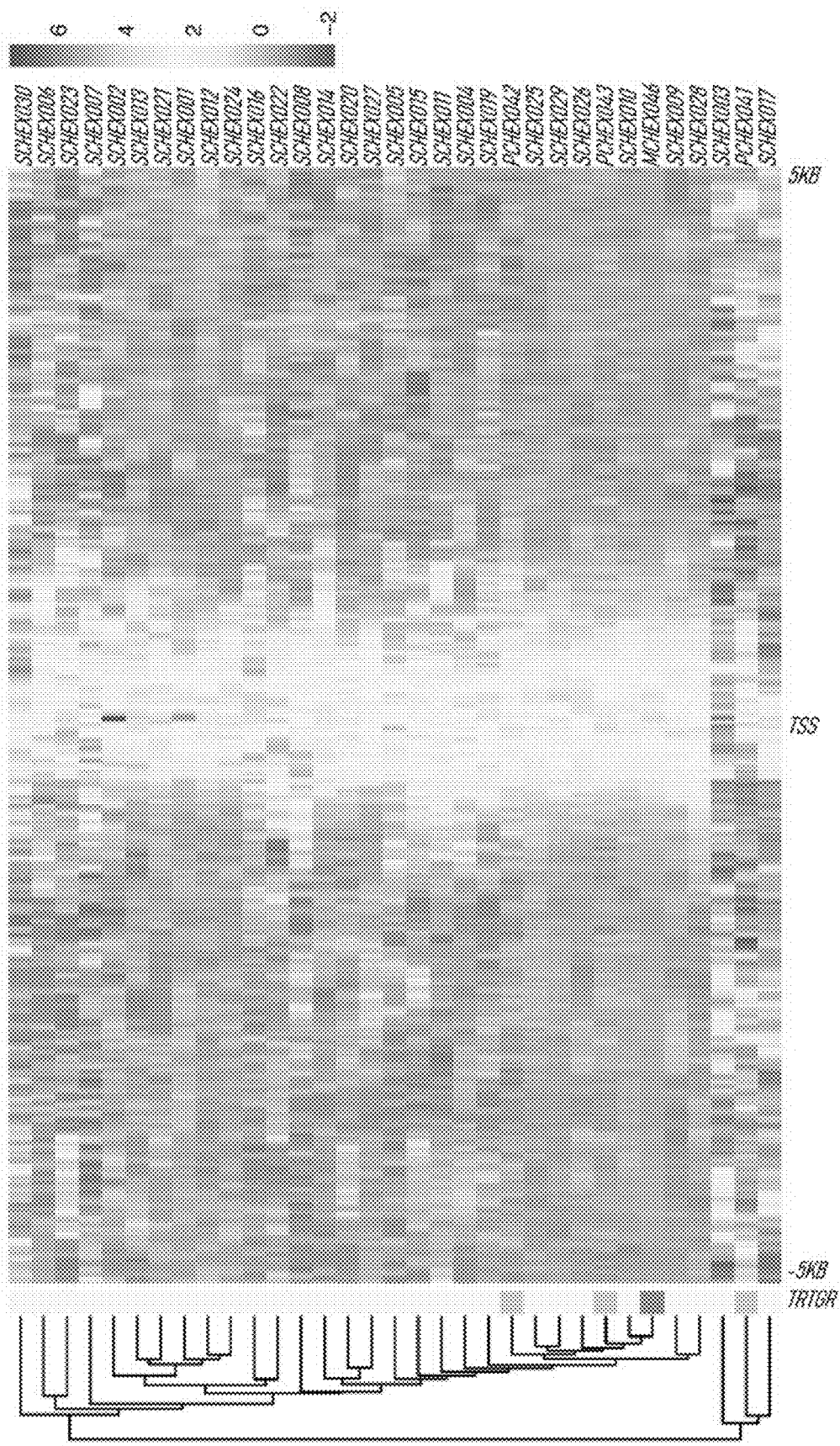

CHeX-seq reads were first preprocessed by a customized SCAP-T Next Generation Sequencing pipeline (available at github.com/safisher/ngs), then mapped back to the UCSC hg38 (human) or UCSC mm10 (mouse) genome. Finally, an additional QC procedure was applied to filter for good-quality reads. The percentage of CHeX-seq reads that map to various regions of the gene models were assessed along the length of the gene and its flanking regions, starting with the 5' promoter region, through the transcription start sites (TSS), the 5' untranslated region (UTR), the exons and introns, the 3' UTR, and 3'-proximal areas of all genes (FIG. 13C). K562 cells show the highest proportion of CHeX-seq reads in the intergenic regions (>50%), then to introns (~30%) and then proximal promoters less then 1 kb from the transcriptional start site (TSS) (~6%). The promoter proximal region (<1 kb) of genes had 3 times more reads than distal regions (4-5 kb), consistent with the opening of chromatin near the TSS. More specifically, TSS enrichment was observed in most single-cell samples, with weak or no enrichment in negative controls. Combining the signal across all non-control samples shows a distinct peak centered at TSS (FIG. 13D), much resembling the TSS peaks observed in ATAC-seq or DNase-seq assays (Buenrostro et al., 2013; Boyle et al., 2008). ATAC-seq data shows a peak of sequencing reads around the TSS, while the CHeX-seq data has a similar peak with a slightly extended slope after the peak in the 5' to 3' direction. FIG. 13E shows within-cell CHeX-seq signals from individual cells, pooled for annotated features. These data suggest a propensity for chromatin to be open near the start of the CDS (coding sequence) with a higher density of CHeX reads with a lower density within the CDS. This may be due to the observed high G-C content of CDS regions that may maintain the double-stranded state of DNA within an open genomic region. It may also reflect the dynamics of single-strand opening during transcriptional activity.

Figure 13F:
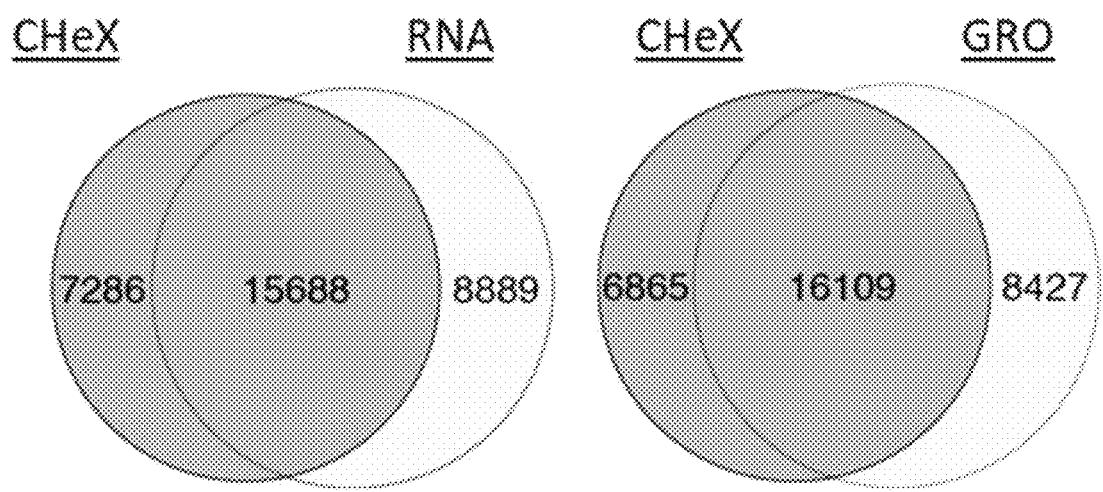
Figure 13G:
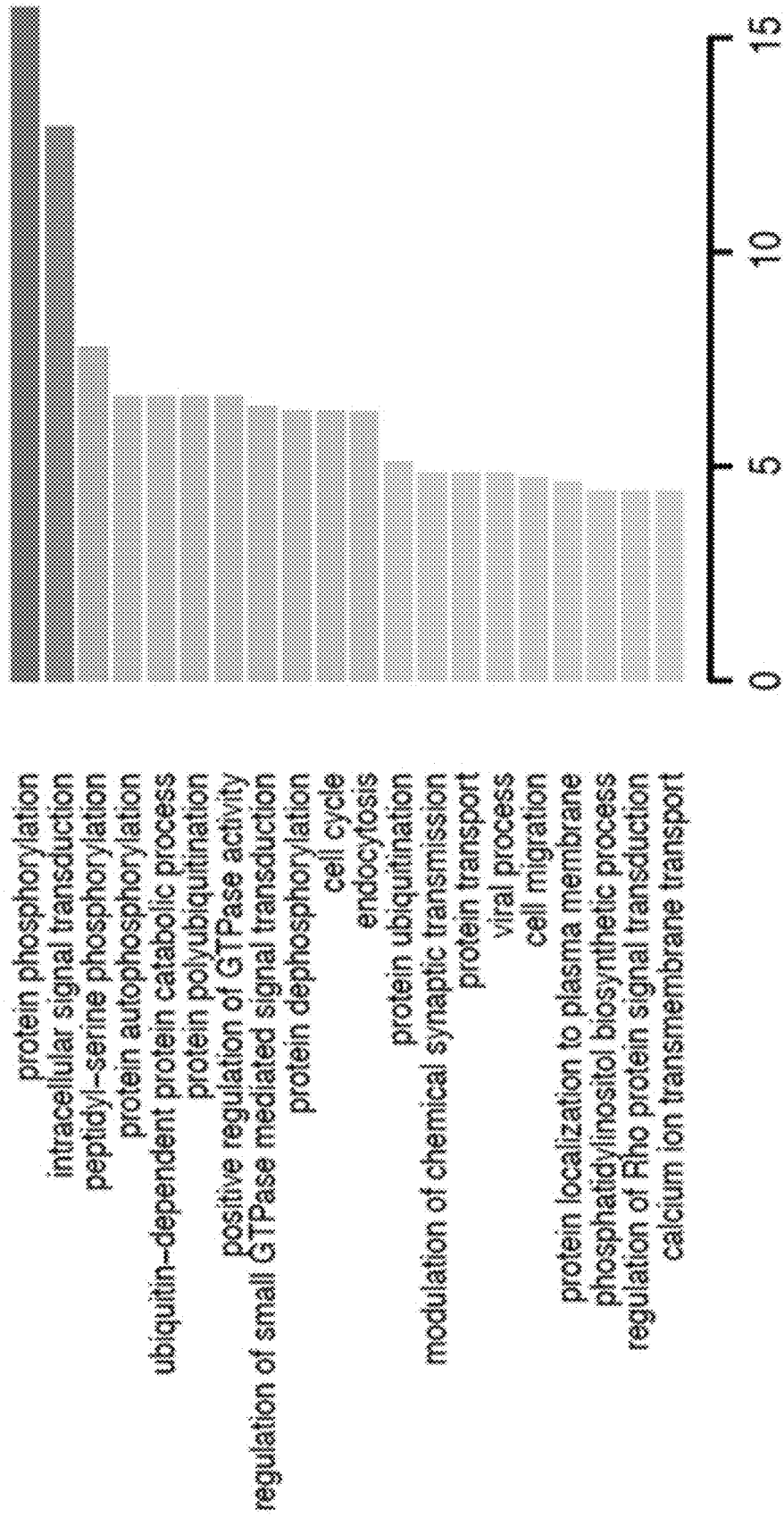

To assess how many of the K562 CHeX-seq sites correspond to expressed mRNA, the CHeX-seq data were compared with published K562 transcriptome datasets (FIG. 13F). These data showed that ~64% of the transcriptome (15,688 genes) had corresponding CHeX-seq sites with the expressed transcriptome. Even with this relatively large overlap, there were still 7,286 CHeX-seq genic regions (~32% of CHeX-seq genes) that did not have evidence of transcription in public transcriptome data. In comparing CHeX-seq data to GRO-seq transcripts (a real-time transcription runoff assay (Danko et al., 2015; Lladser et al., 2017)), there was a similar number of overlapping genes (~66%) while showing a decrease in the CHeX-seq unique genes. Since GRO-seq data are not dramatically influenced by RNA stability, it is a more accurate reflection of genes that are being actively transcribed from open-chromatin regions. In assessing the gene ontology (GO) of K562 cell mRNAs for which CHeX-seq sites are enriched, the cell signaling, cell cycle, and GTPase regulatory pathways were identified (FIG. 13G, top 20 are shown). These data are consistent with the fact that K562 cells are a transformed cell line in which these pathways are functional.

Figure 14A:
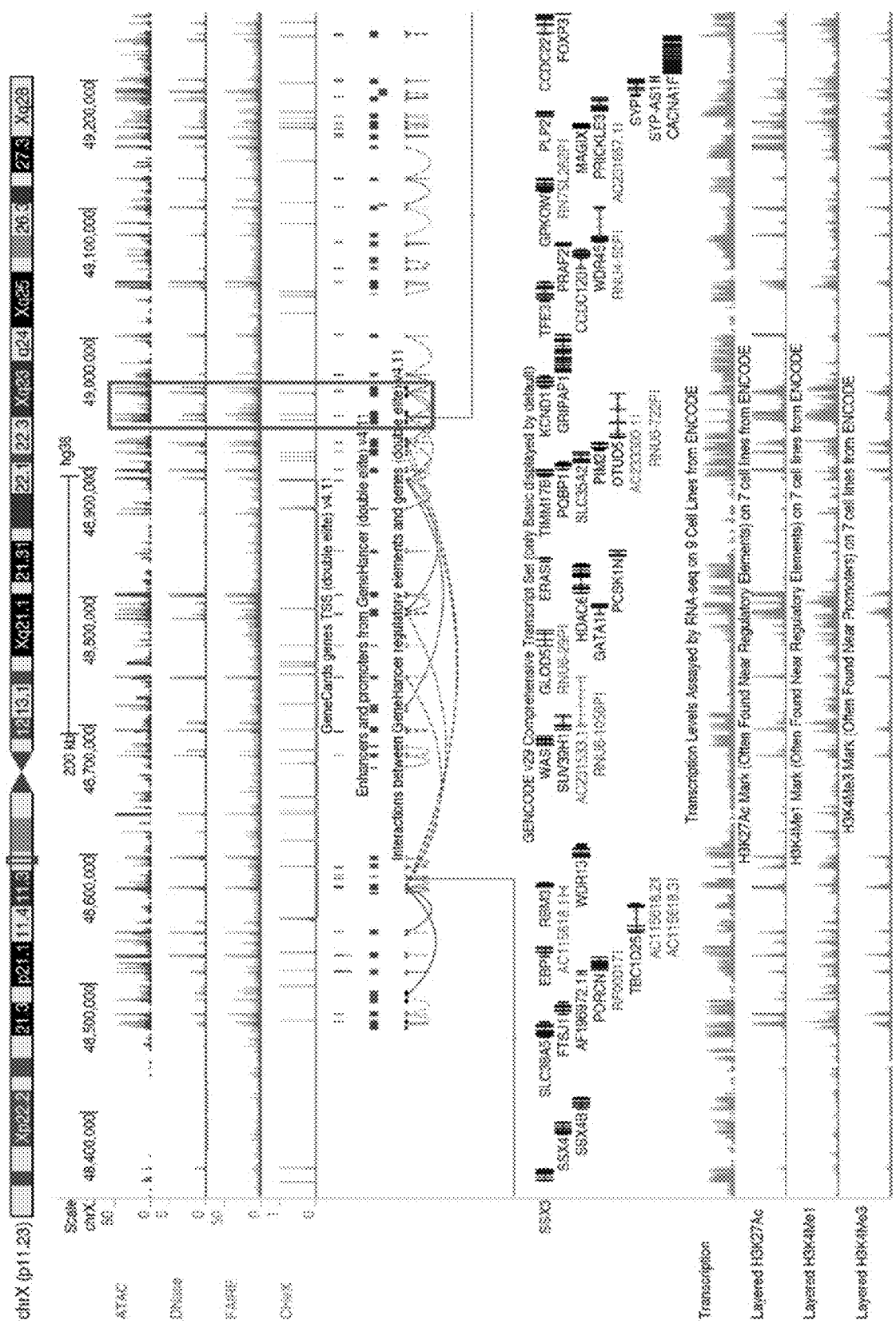

The genome coverage of CHeX-seq data compared with other open-chromatin as well as epigenome assays is presented in UCSC Genome Browser (Kent et al., 2002) (FIGS. 14A-B), As an example, the OTUD5 gene region shows the mapping of CHeX-seq reads to three open-chromatin assays (ATAC-, DNase-, FAIRE-seq), highlighting that each assay has both overlapping open-chromatin regions as well as regions unique to the method of analysis (FIG. 14A). There were 32 cells mapped for the CHeX-seq samples, versus ensemble mapping of more than 200 cells for the other assays. In this particular view of the gene, OTUD5, a regulatory interaction between OTUD5's promoter and one of its 3' introns is noted, which is shared by all four open chromatin assays (purple rectangle). Different epigenomic assays have different genomic scales due to both the biological nature of the signals detected by each technique and to the different chemistry of the assays. To assess the relationship between different epigenomic assays, signal concordance was computed in two different window sizes for 27 different assays and the results clustered (FIG. 14B). At the size scale of 10 kb windows, the open-chromatin assays (FAIRE-, DNase-, and ATAC-seq) cluster together, while CHeX-seq is in the same cluster but at a larger distance; this cluster also includes histone methylation assays and the replication of origin assay. At a window size of 50 kb, CHeX-seq, ATAC-seq, and DNase-seq assays form a tight cluster with FAIRE-seq outside the cluster. As the average size of a human gene is ~42 kb and the functional transcriptional chromatin unit is ~50 kb (Hegedus et al., 2018), these data suggest that the same open-chromatin associated genes are identified with each of these procedures, but the single-stranded open-chromatin CHeX-seq positions are likely displaced from those of the other procedures. A direct overlap would not be expected, as the other procedures have a target bias for double-stranded DNA (ATAC- and FAIRE-seq) or are indiscriminate (DNase-seq)

as compared to CHeX-seq's single-stranded DNA requirement. The CHeX-seq signals may be sparser due to limited numbers of analyzed cells, but these data highlight that both double-stranded and single-stranded DNA exist within the open-chromatin region and complement each other in the open-chromatin landscape of a cell.

Figure 20A:
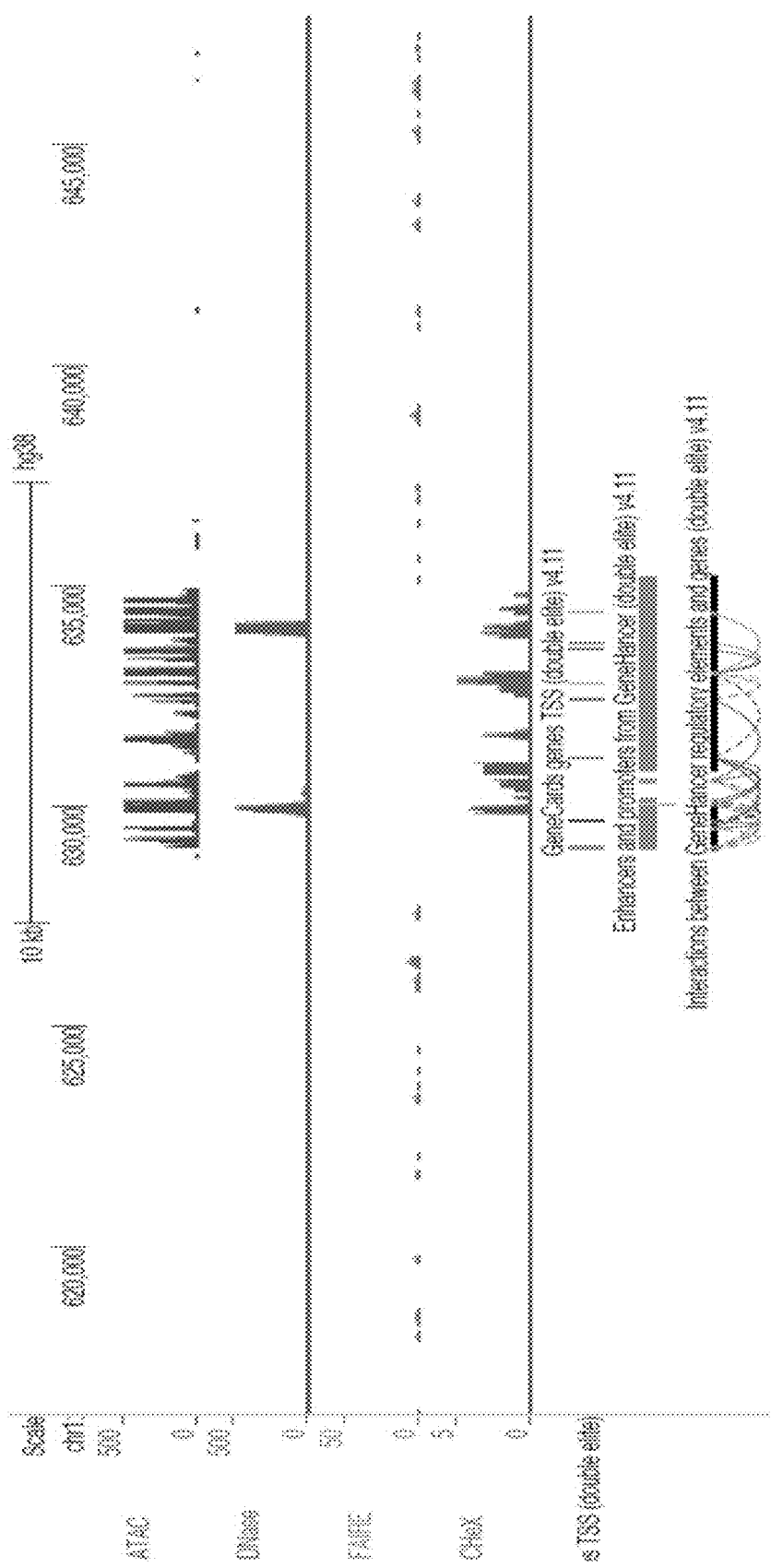
FIGS. 20A-B. In situ hybridization to region 630737-633960 of chromosome 1 (hg38).
Figure 20B:
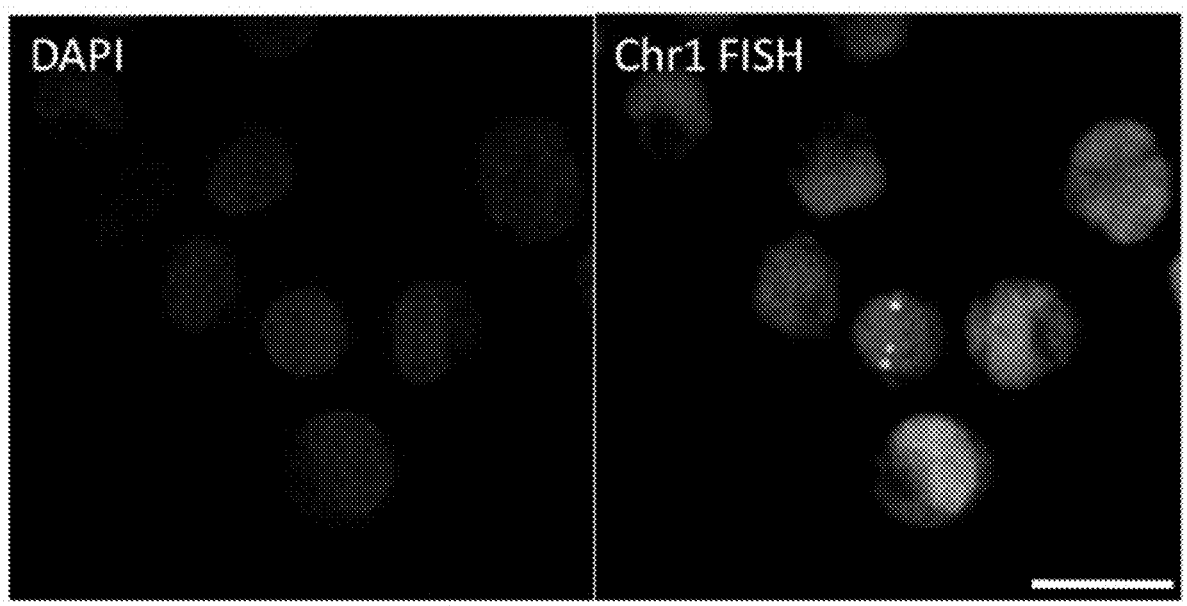

To confirm the single-stranded nature of some of the CHeX-seq predicted loci, single molecule FISH was performed for a CheX-seq predicted K562 single-stranded open-chromatin site on Chromosome 1 (630737-633960) (FIG. 20A), in addition to CheX-seq identification of the open-chromatin status of this genic region, ATAC-seq predicts it to be open, while in contrast, DNase shows limited openness and FAIRE predicts that it is not open. Eight 20-mer oligonucleotide probes were synthesized to this target area human Chromosome 1. These probes were labeled at the 5'-end with the ATTO 590 fluorophore. Upon performing FISH, generally 3 strong positive spots are observed in single cell nuclei (FIG. 20B). This trisomy signal is due to the complicated K562 cell karyotype where some cells have 3 copies of Chromosome 1 (Gribble et al., 2000).

Figure 16A:
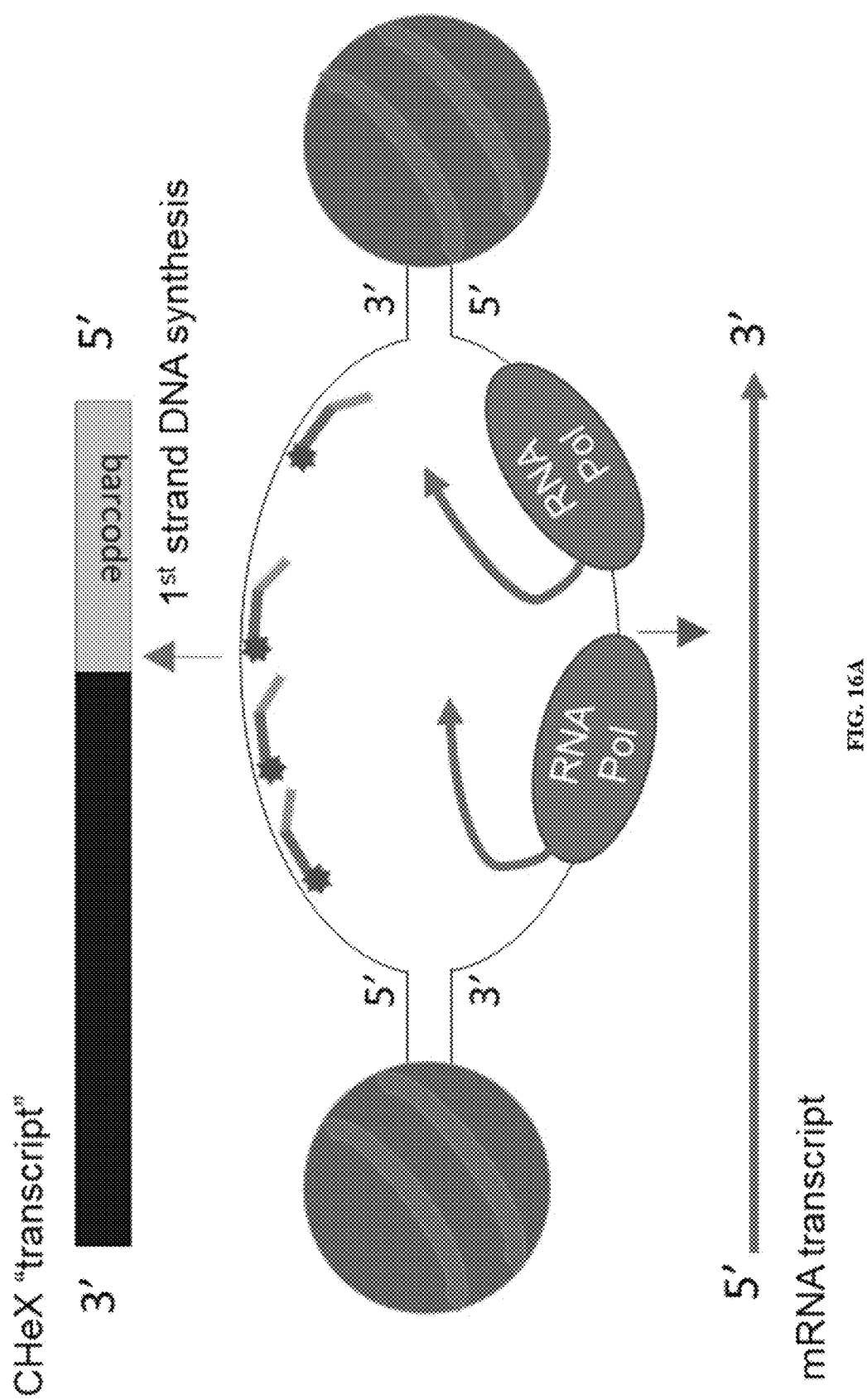
FIGS. 16A-B. CHeX-seq Strandedness: detecting open chromatin's strandedness.
Figure 16B:
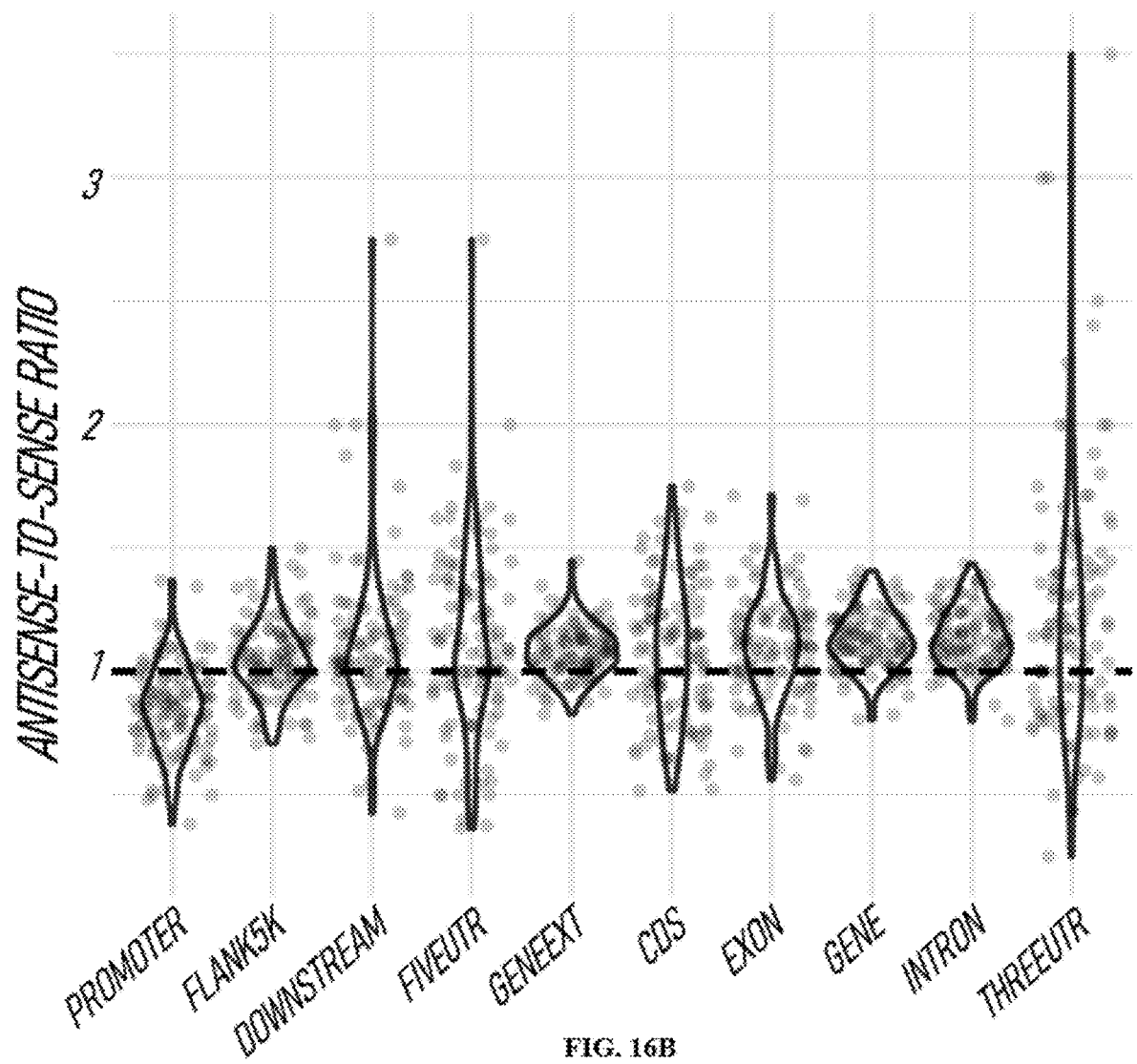
Figure 21:
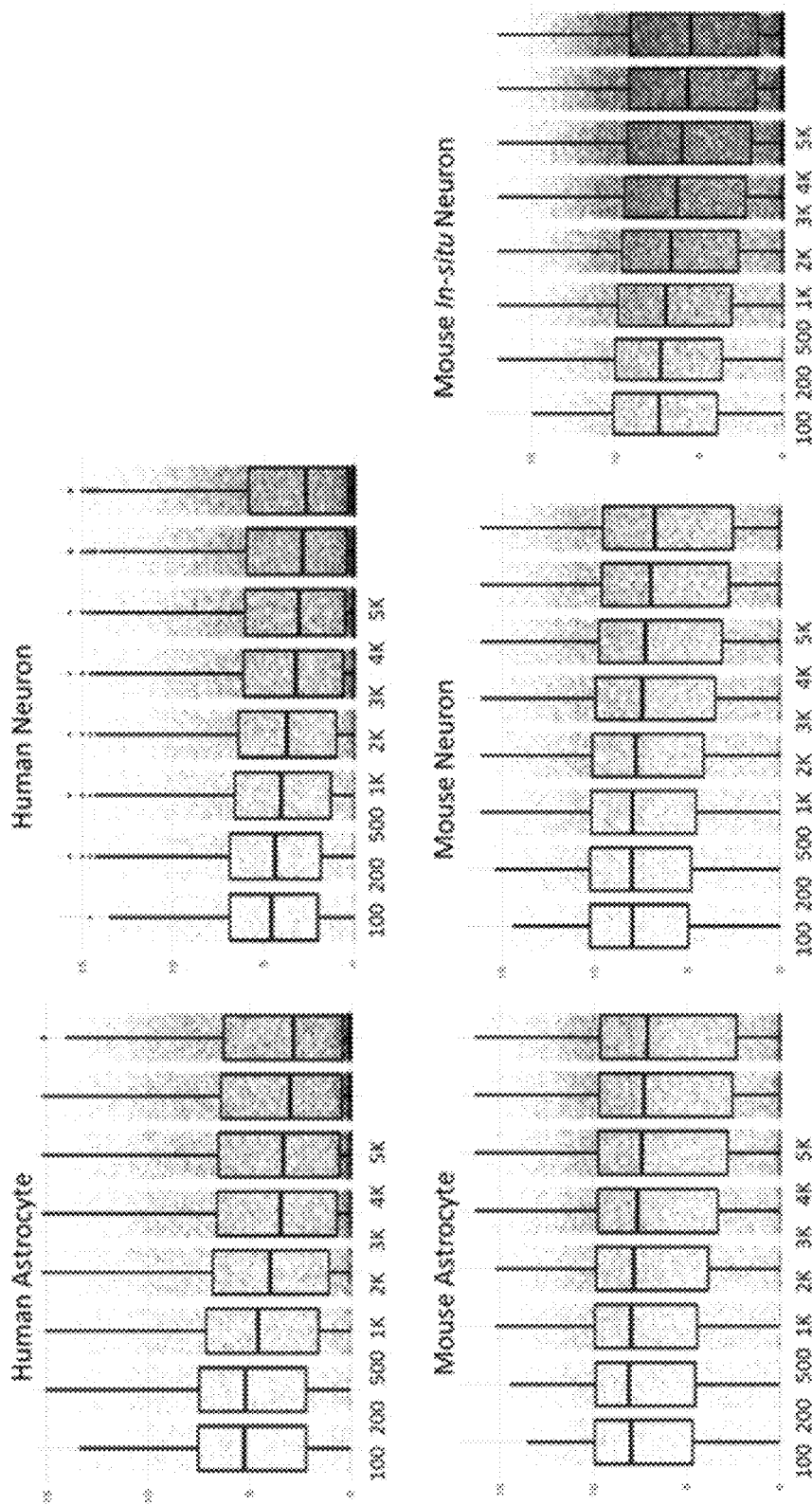
FIG. 21. Correlation of CHeX-seq read distance from TSS with RNA abundance in neurons and astrocytes.
Figure 22A:
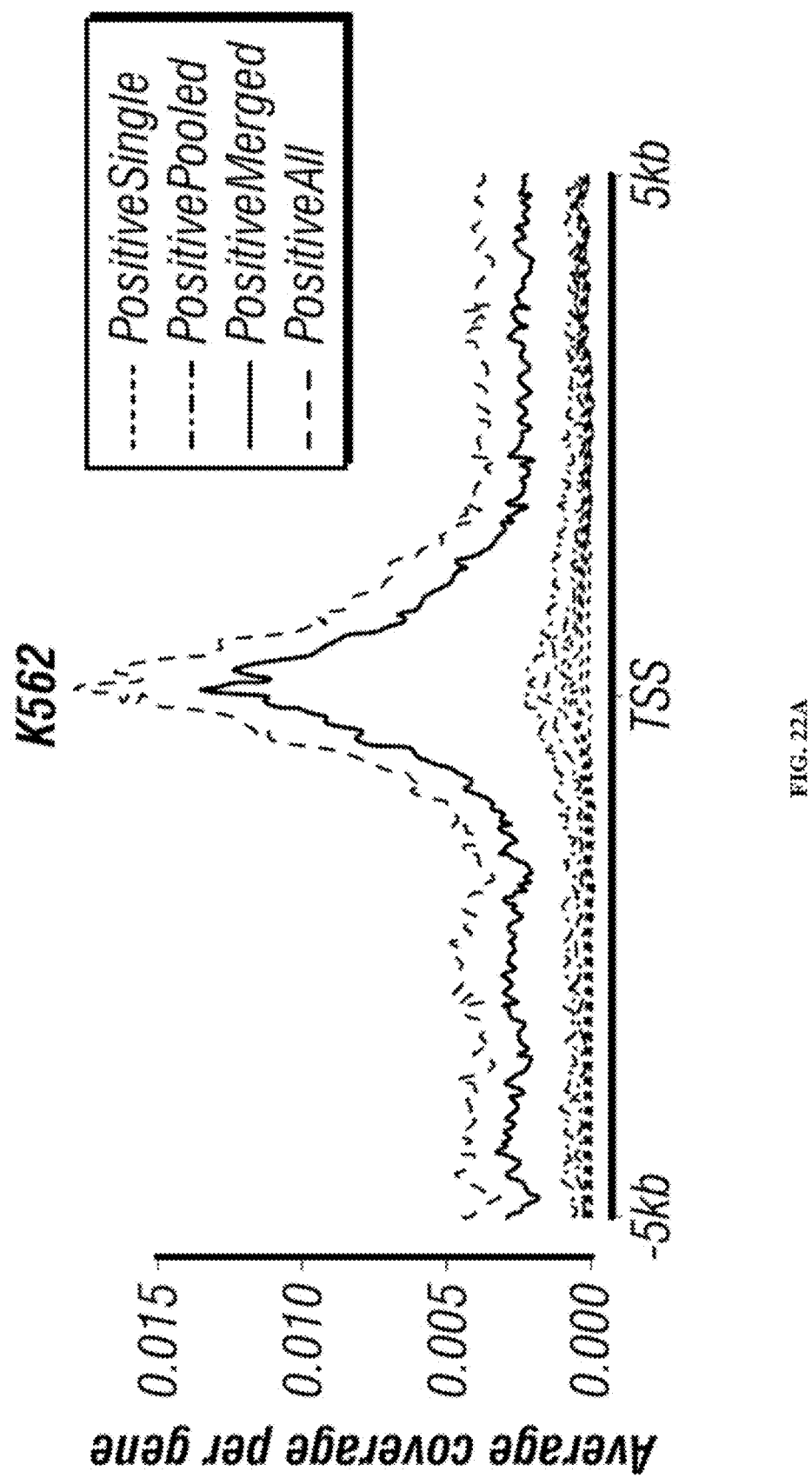
FIGS. 22A-F. Chex-seq reads mapping to the Transcriptional Start Sites for K562 cells, human and mouse dispersed neurons and astrocytes and mouse brain section localized neurons.
Figure 22B:
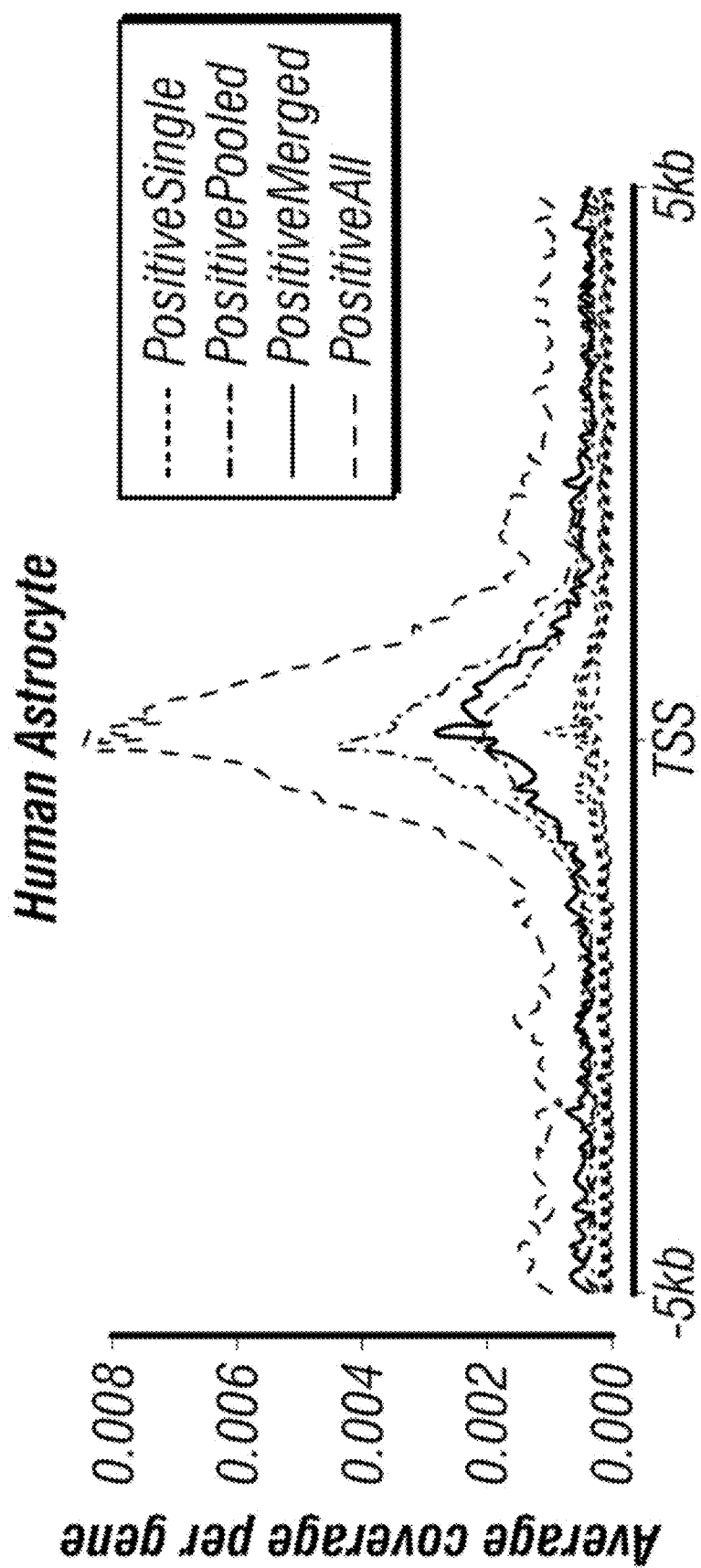
Figure 22C:
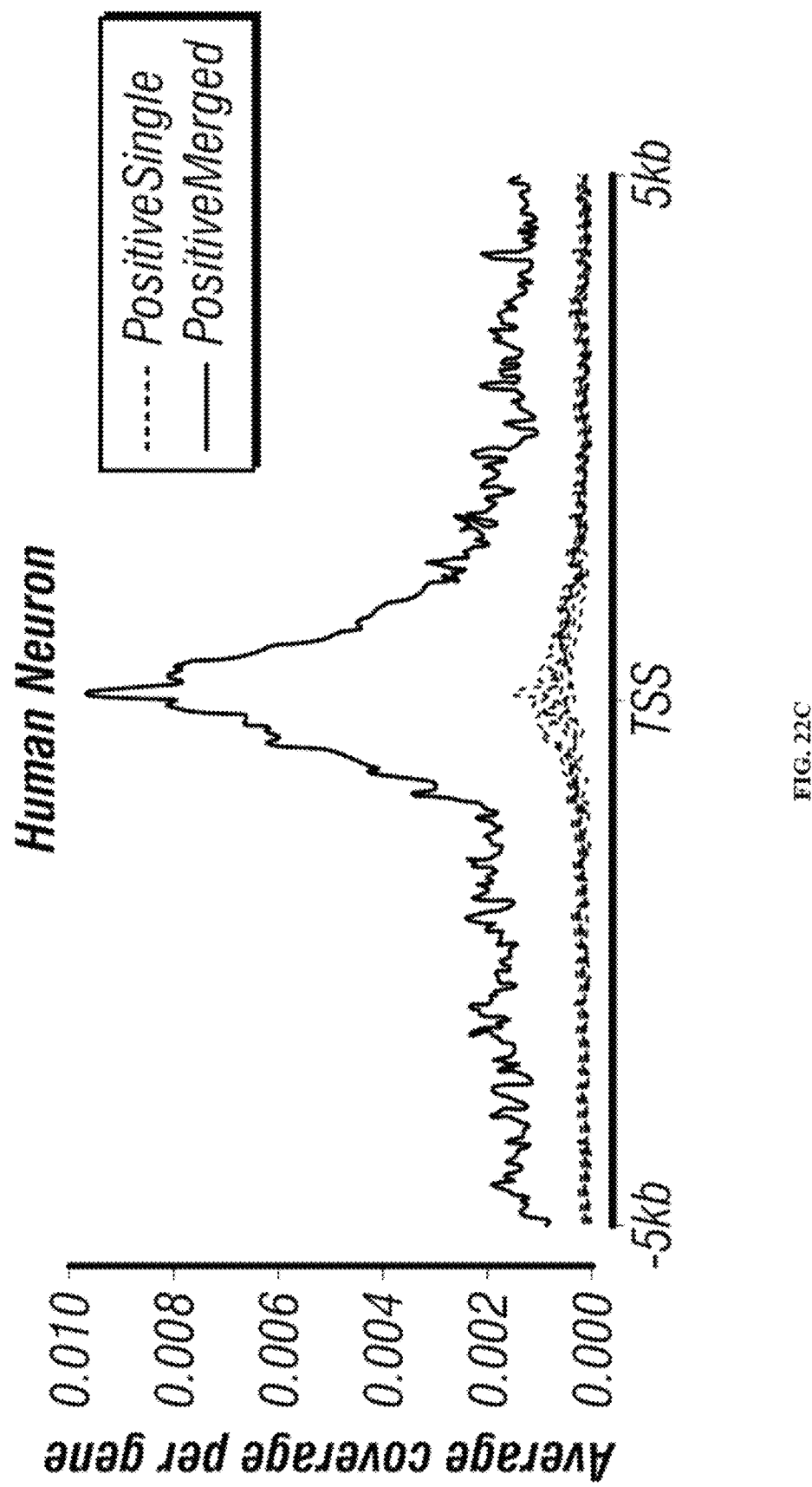
Figure 22D:
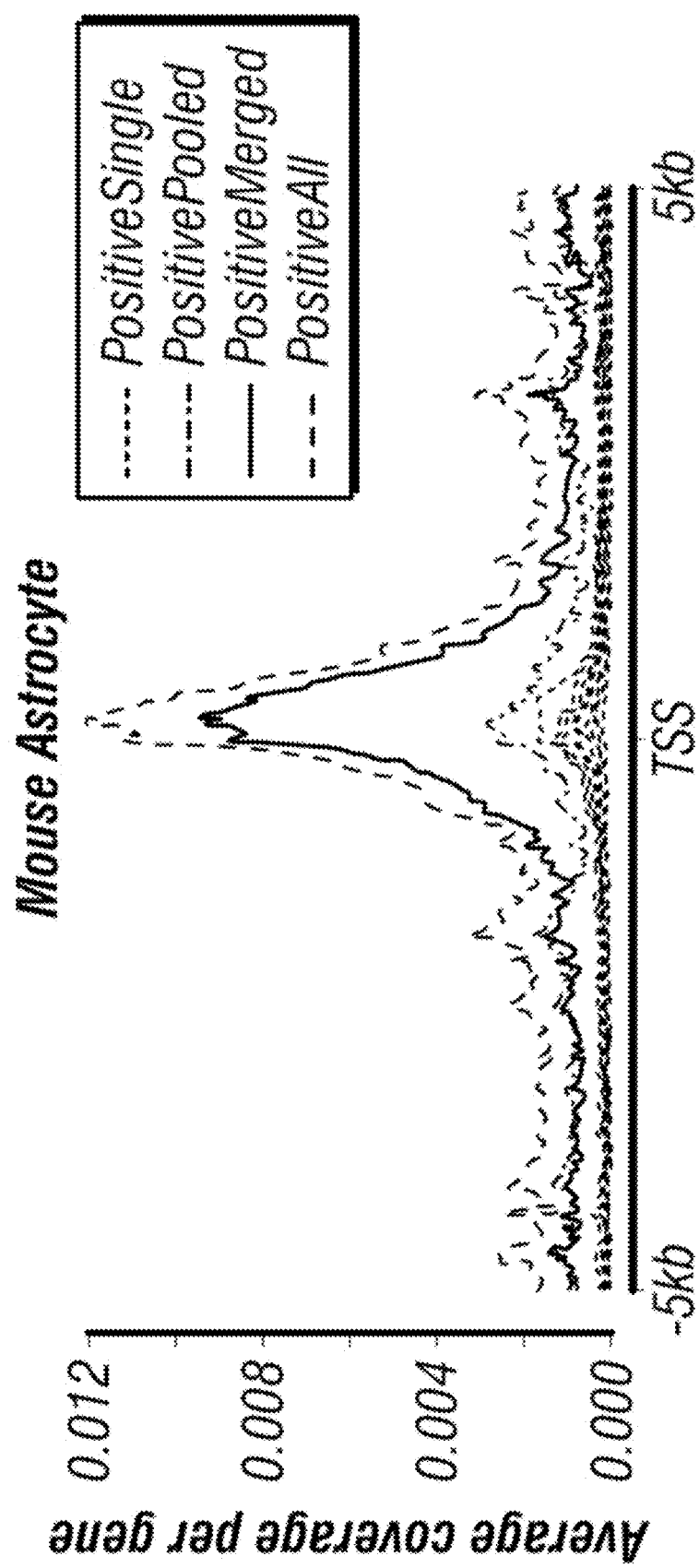
Figure 22E:
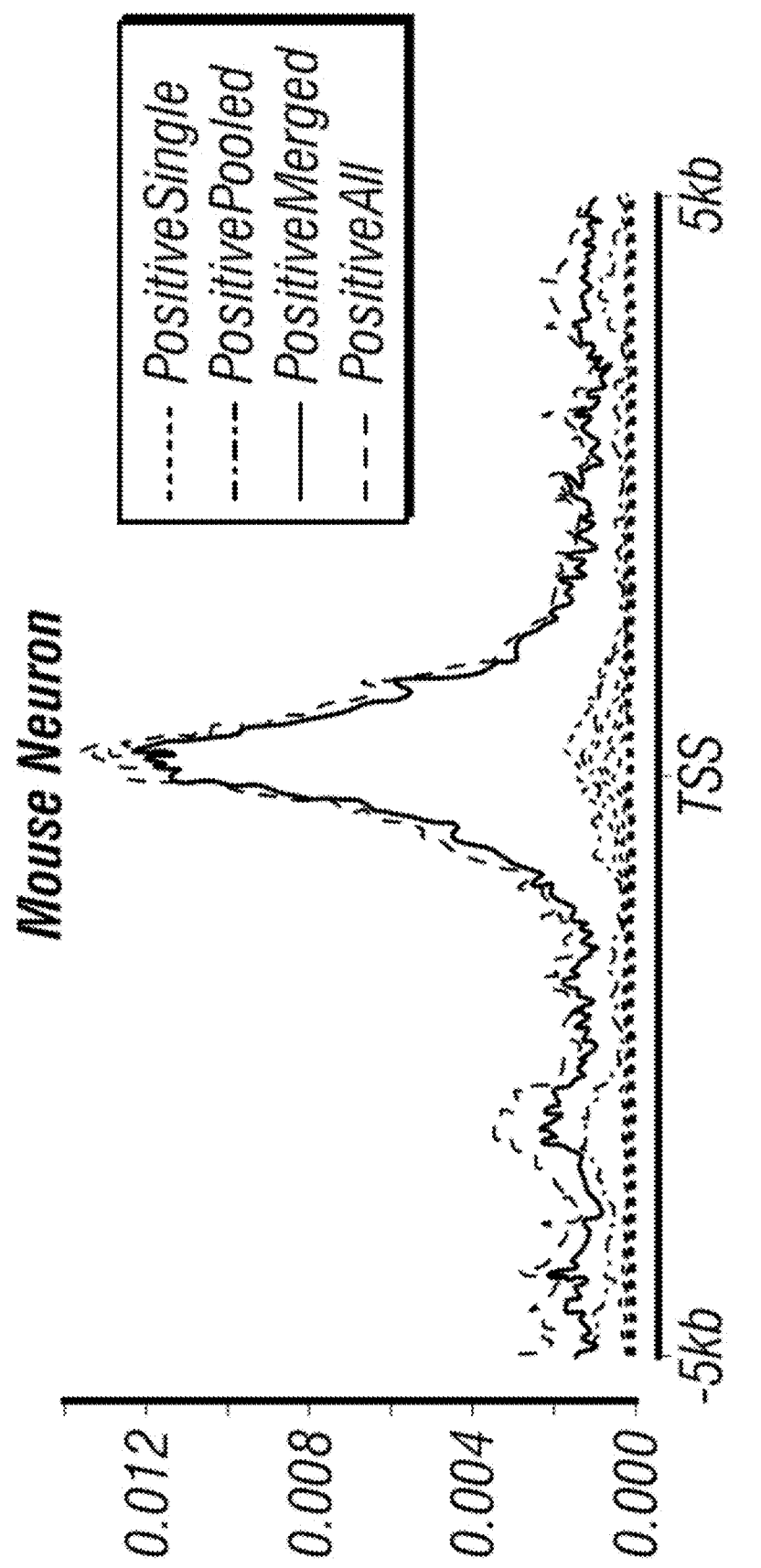
Figure 22F:
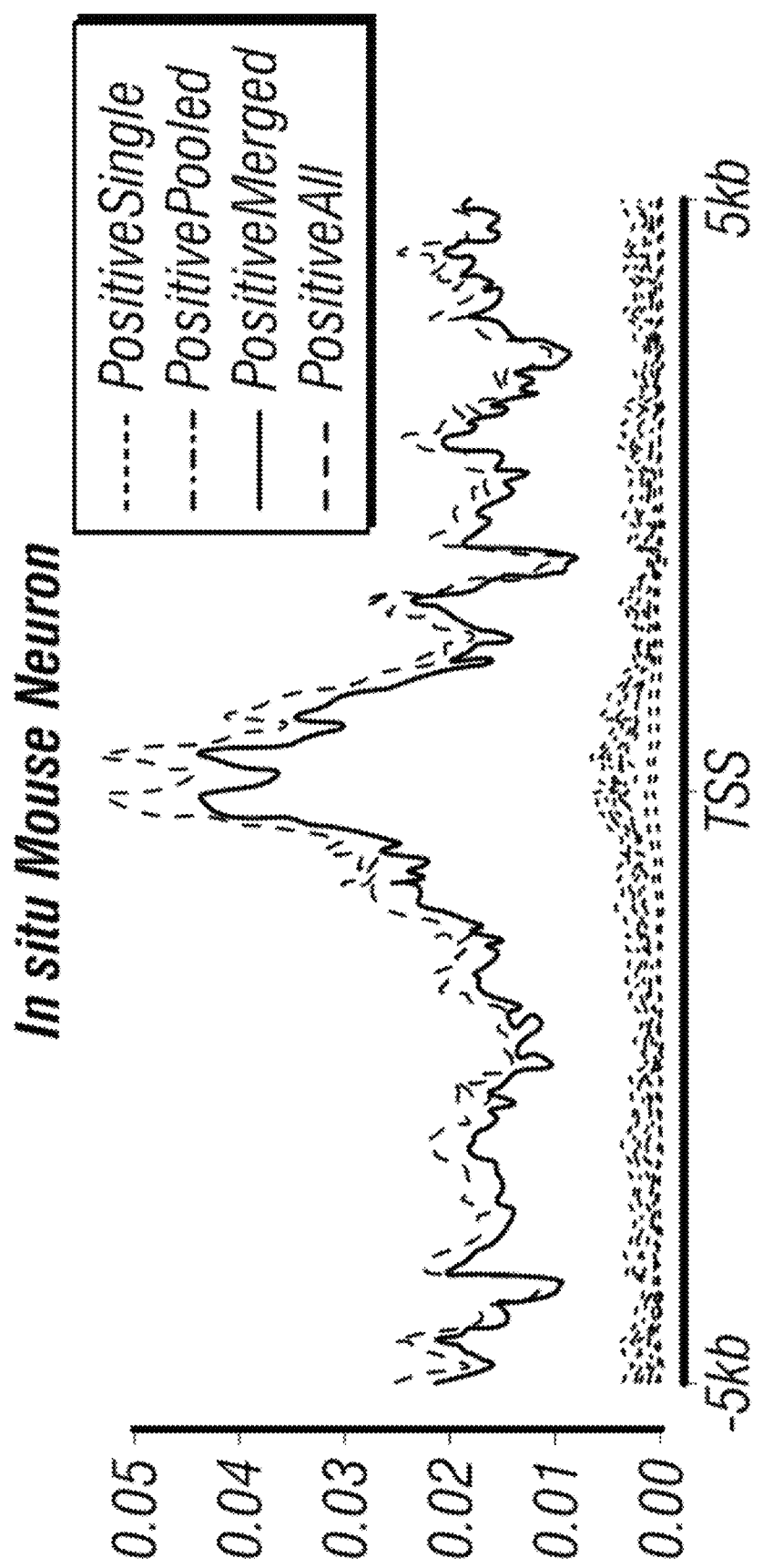

Next, K562 CHeX-sect priming sites were stratified with respect to their distance to the cognate genes' TSS and this distance was compared with RNA expression level, from the same gene (FIG. 15). Using three different RNA sources—population RNA (GSE32213), GRO-sect RNA (GSE60454), and single-cell RNA (scRNA, GSE90063) it can be seen that when the CHeX-seq priming sites are closer to the TSS, the corresponding RNAs are generally present in higher abundance (Szlachta et al., 2018). This pattern is found in human and mouse neurons and astrocytes and mouse section-localized neurons (FIG. 21). These data suggest a regulated plasticity with regard to single-stranded DNA within a gene: i.e., as transcription moves along the length of the gene, the 5'-open sites become unavailable for hybridization, perhaps due to reannealing of the single-stranded regions. In this model, detectable CHeX-seq priming sites have varying half-lives, and those that are proximal to the TSS remain single-stranded for a longer time and correspond to high levels of transcription. Thus CHeX-seq priming closer to the TSS would be more predictive of highly transcribed genes. These data are not simply due to differences in the rate of RNA stability, as GRO-seq RNA is newly synthesized nuclear RNA. One model is that the TSS proximal single-strandedness is associated with gene expression, whose accessibility decays with precession of transcription, while more distal regions' single-stranded accessibility might be related to other conformational regulation of the DNA, Since the RNA Pol2 transcriptional complex binds to the template DNA and synthesizes RNA transcripts in a 5' to 3' direction by transcribing the antisense strand, whether or not CHeX-seq probes might be preferentially bound to the potentially more accessible sense strand, giving rise to an excess of "antisense-strand" reads, was assessed (see schematic in FIG. 16A). FIG. 16B shows the ratio of antisense to sense reads for different annotated regions of the gene model. The results show a bias towards a higher ratio of reads in the transcribed as opposed to nontranscribed regions of the genome, with slightly increasing bias from 5' UTR towards 3' UTR. Interestingly, the promoter region exhibited an opposite bias towards sense-strand CHeX-seq products (FIG. 16B). This may be reflective of the antisense-strand being bound to proteins including Pol2 as it copies the antisense template, leaving the sense-strand more available for CHeX-seq primer binding (Wang et al., 2014; Louder et al., 2016). This opposite trend in promoters may be related to bidirectional promoter activity (Wei et al., 2011).

Figure 17A:
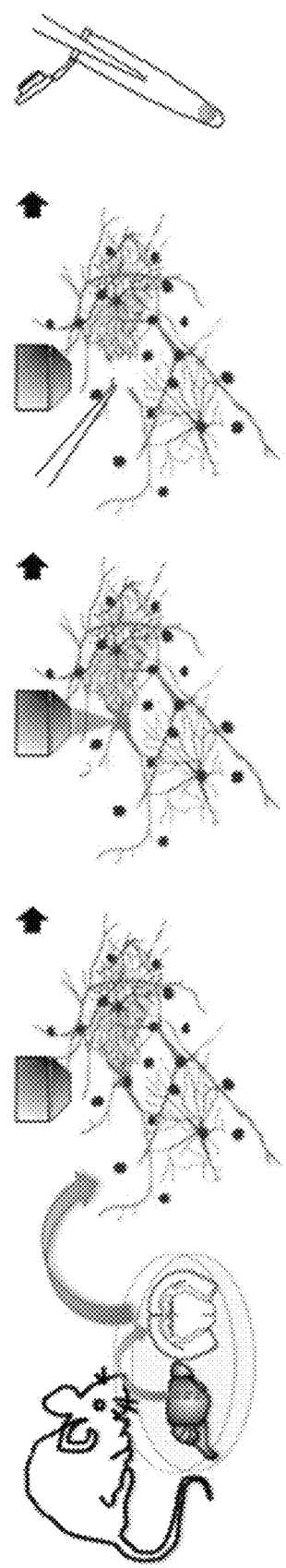
FIGS. 17A-F. CHeX-seq analysis of single neurons in fixed mouse tissue sections and dispersed cell culture.
Figure 17B:
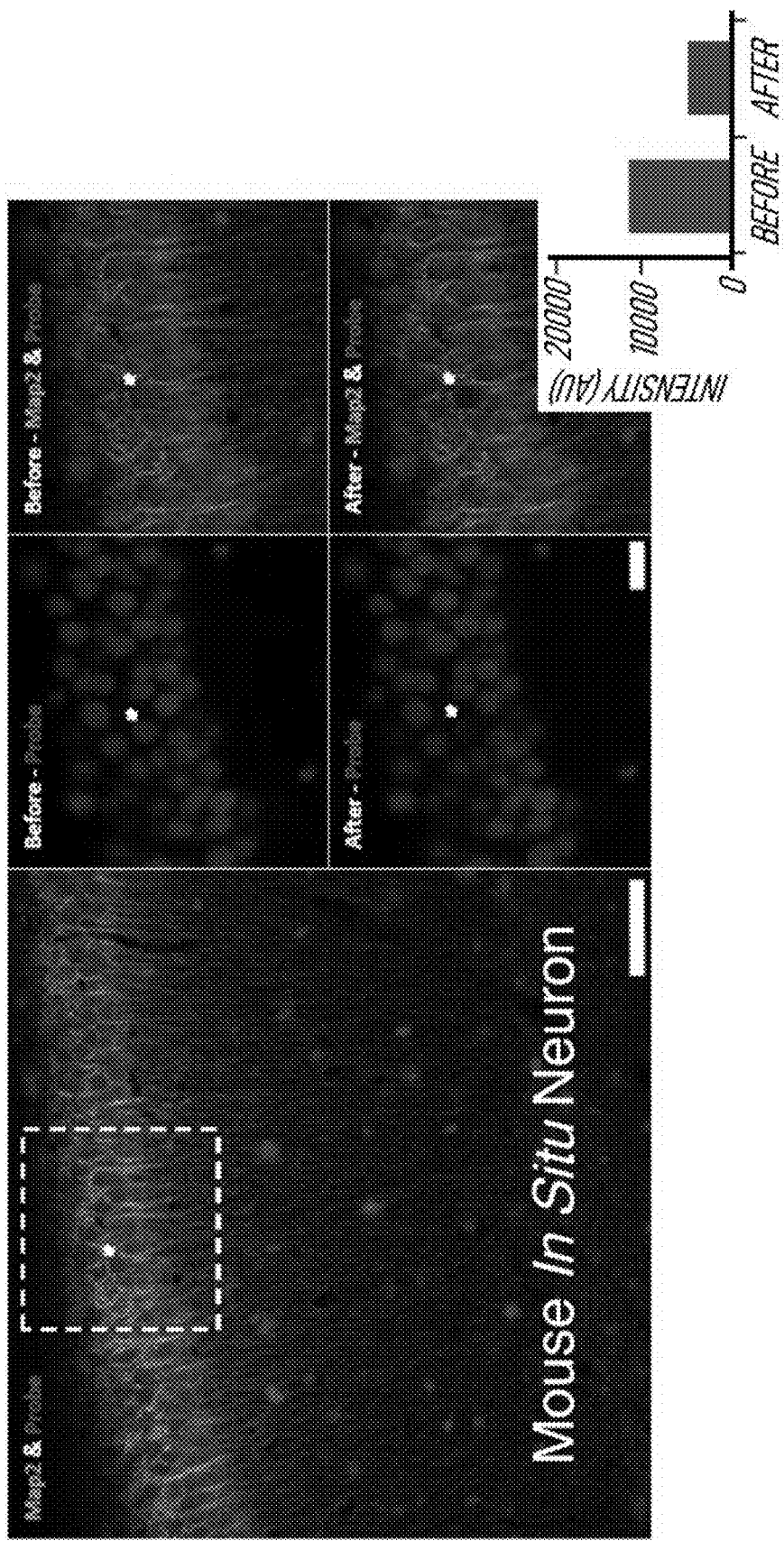

Example 5—In Situ Mouse Brain Tissue Section and Dispersed Single Neuron Analysis To identify open-chromatin sites in individual neurons localized in site in adult mouse brain tissue, where the neurons are in their natural context, CheX-seq was applied to fixed adult brain tissue sections (100 urn) were labeled by immunofluorescence with an antibody that detects neuronal microtubule associated protein 2. (MAP2). CHeX-seq probe was then annealed to the single-stranded DNA in the tissue section (for schematic see FIG. 17A), FIG. 17B shows the CA1 region of the hippocampus labeled for MAP2 immunofluorescence (green) and the CHeX-seq probe (red). The CHeX-seq probe was activated (confirmed by the loss of fluorescent signal) in an individual nucleus (arrow in boxed area of FIG. 17B) after which in situ copying of DNA from single-stranded genomic DNA was performed. The CHeX-primed DNA was removed, amplified, and sequenced. In comparing the open-chromatin CHeX-seq sites from section-localized neurons with the expressed transcriptome from single cells (FIG. 17D), there is a 59% overlap of CHeX-seq sites with expressed RNA, while 88% of the transcriptome overlaps with CHeX-seq reads. This leaves 41% of CHeX-seq sites as not detected in RNA while only 13% of the transcriptome does not show CHeX-seq open-chromatin sites. These data show that there is a large amount of single-stranded open-chromatin in fixed tissue sections that is not represented in the expressed transcriptome, likely corresponding to genes that are ready to be transcribed, DNA replication sites or other types of DNA organizational structures. CHeX-seq reads in the tissue section can be further broken down to show an overlap with the transcriptome of 69% for exonic regions and 65% for intronic regions. This overlap suggests that the chromatin landscape and transcriptome are well correlated in cells that are localized in their natural microenvironment.

Figure 17C:
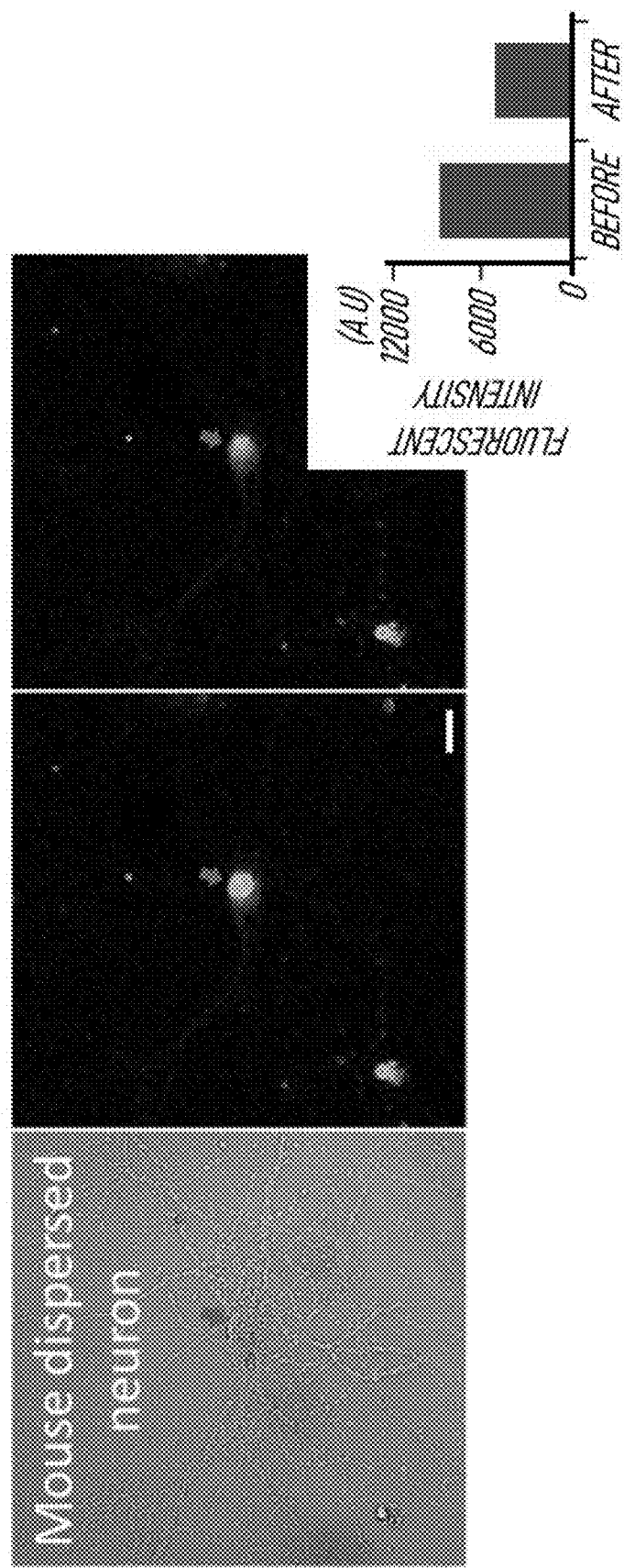
Figure 17D:
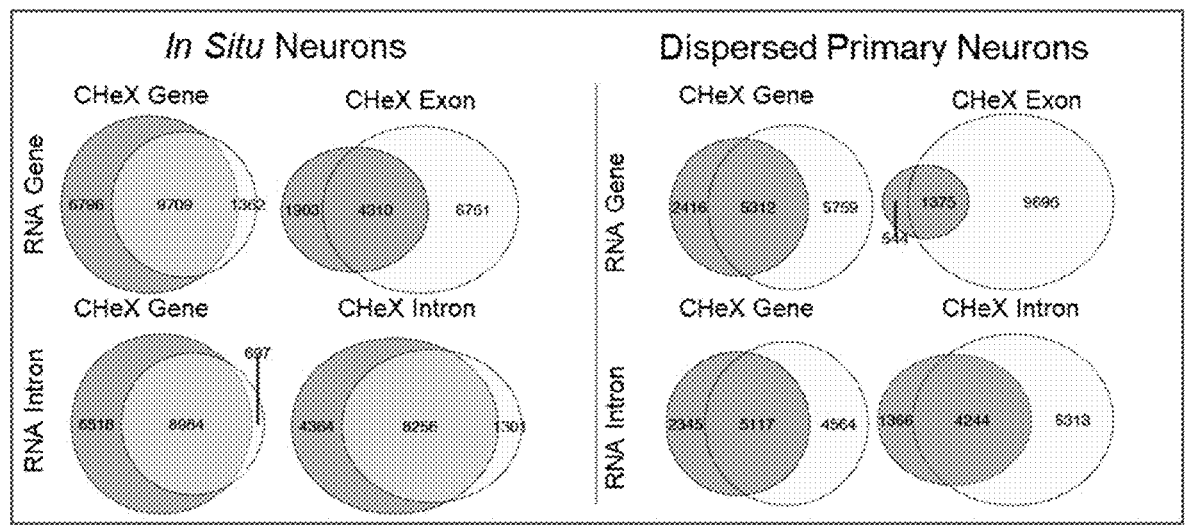

In order to assess the pattern of single-stranded open-chromatin regions in dispersed neuronal cells, single fixed cultured mouse neurons were also examined (FIG. 17C). As adult mouse neurons cannot be cultured and hippocampal cells are difficult to culture, open-chromatin sites were assessed in mouse neonate cortical neurons that were in primary culture for two weeks, during which time they developed dendrites. The dispersed mouse cortical neurons had TSS peaks similar to those observed for K562 cells (FIG. 13D) as well as other cell types (FIGS. 22A-F), showing that they show the same TSS open-chromatin conformation. However, fewer total CHeX-seq reads mapping to the expressed transcriptome were found in the dispersed cortical neurons (5,312) as compared with the in situ hippocampal neurons (9,709) (FIG. 17D). It was found that 88% of the transcriptome mapped onto CHeX-seq reads for the in situ neurons and only 48% for the dispersed neuron transcriptome. However, the percent of CHeX-seq reads that correspond to transcribed RNA is 68% for dispersed cells as compared with 59% for in situ neurons. In general, a higher percentage of CHeX-seq positive regions show evidence of transcription in dispersed cortical neurons as compared to in situ hippocampal cells while a markedly lower percentage of transcribed RNA show CHeX-seq evidence in dispersed culture compared to section. While it is difficult to discern the relative contribution of cell type (although cortical and hippocampal cell transcriptomes are very similar (Zeisel et al., 2018)) and cell age to these data, one potential interpretation is that there are more non-transcription associated open-chromatin sites in brain section neurons than in dispersed neurons.

In comparing the mouse dispersed cortical neuron CHeX-seq data with the averaged transcriptome of single cortical neurons, there is a large overlap of the single-stranded DNA sites with expressed RNA (FIG. 17D, right panel, upper-left). Of the 7,728 CHeX-seq positives, 69% overlap with the transcriptome, leaving 31% of the single-stranded sites with baseline or no detectable transcribed RNA. Concomitant with these data of the 11,071 different transcripts identified in the single cells, 48% correlate with single-strand open-chromatin genes. To assess the systems aspect of this comparison, Gene Ontology (GO) enrichment was assessed in genes in common as well as unique to either assay in dispersed neurons. There are 235 GO Molecular Function terms enriched at a Benjamini-Hochberg (BH) adjusted p-value of <0.1, shared between the open-chromatin analysis and transcriptome, while at the same significance, there are 40 in the CHeX-seq unique genes and 107 in the transcriptome unique genes. Among the shared pathways are those for chromatin binding (p-value: $2.0 \times 10^{-14}$), calmodulin binding (p-value: $1.9 \times 10^{-10}$) and many associated with neuronal function. Evidence for the enrichment of these pathways in both the open chromatin and transcriptome of neurons is not surprising, as they give rise to normal cellular function as well as some of the specialized functions of neurons. The CHeX-seq unique genes show a high propensity for pathways corresponding to regulation of RNA transcription (RNA Polymerase II core promoter, p-value: $1.3 \times 10^{-4}$; transcriptional activation activity, p-value: $4.0 \times 10^{-3}$, enhancer sequence-specific DNA binding, p-value: $6.1 \times 10^{4}$) and oxidative state regulation (oxidoreductase activity, p-value: $3.2 \times 10^{-4}$; heme binding, p-value: $1.3 \times 10^{-4}$). These sites likely need to be open, even when there is little transcribed RNA, so that the cell is ready to rapidly transcribe these RNAs at a time of need. In comparison, the pathways that are enriched in the transcriptome unique genes include several involved in regulation of translation (structural constituent of ribosome, p-value: $4.0 \times 10^{-40}$; rRNA binding, p-value: $1.8 \times 10^{-7}$; translation initiation factor activity, p-value: $6.5 \times 10^{-9}$) and protein fidelity (ubiquitin protein ligase binding, p-value: $1.1 \times 10^{-6}$; unfolded protein binding, p-value: $9.5 \times 10^{-7}$; ubiquitin binding, p-value: $5.8 \times 10^{-6}$), all in keeping with the need of cells for functional protein. Interestingly, there are a number of significantly enriched single-stranded DNA pathways that may be involved in preparing chromatin for opening and transcription (single-stranded DNA binding, p-value: $2.3 \times 10^{-5}$ helicase activity, p-value: $1.2 \times 10^{-3}$). Single-stranded DNA pathways are also found in the shared genes and genes unique to CHeX-seq, but to a much lesser extent.

Figure 17E:
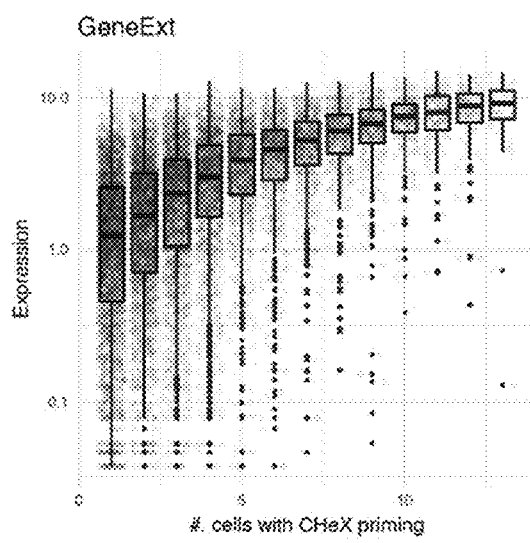
Figure 17F:
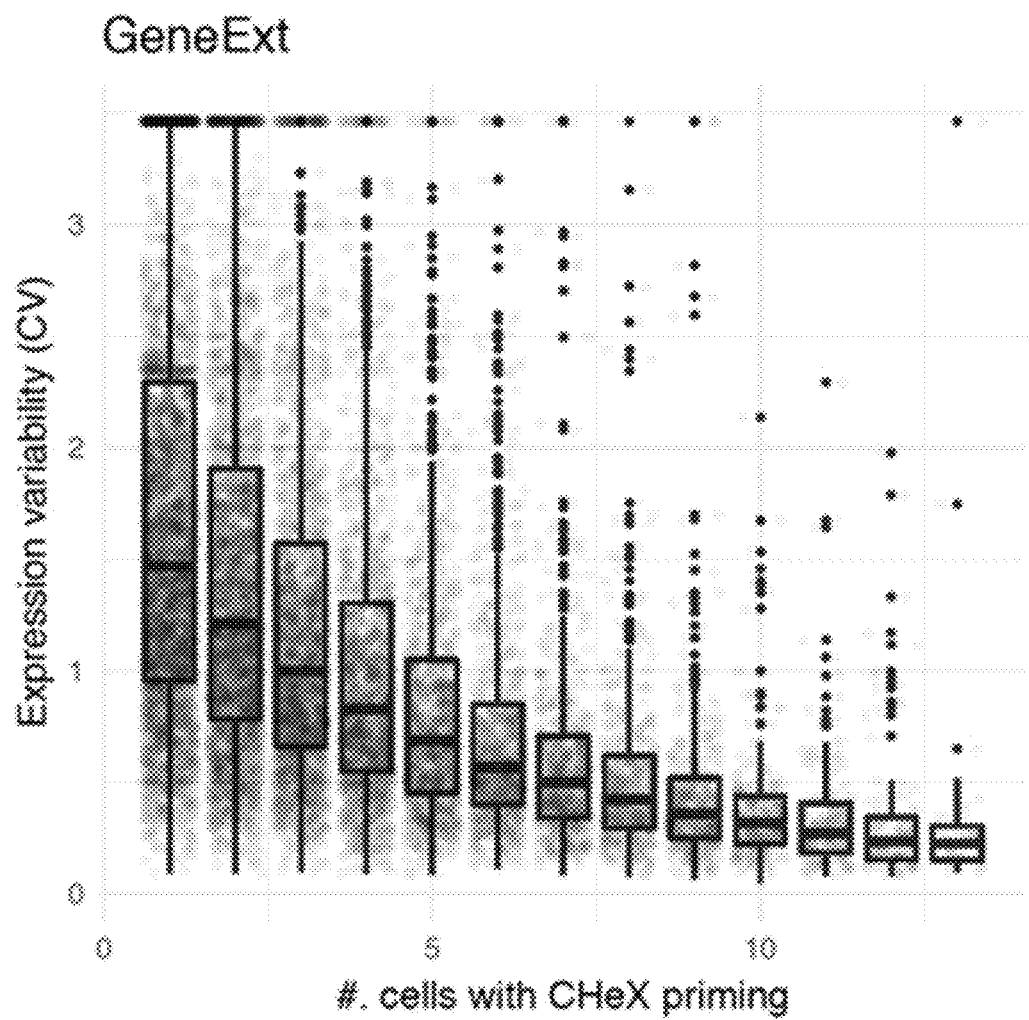

Interestingly, in in situ neurons, there was a significant relationship between the expression level of RNA and the number of CHeX-seq priming sites within that gene (FIG. 17E). These data suggest that the number of CHeX-seq priming sites in a gene is indicative of the amount of transcription from that gene, with more sites suggesting more transcription. This relationship was somewhat surprising, as steady state levels of RNA are dependent upon other factors in addition to transcriptional activity, such as RNA stability. A single open site can correlate with high levels of expression (FIG. 17E, left panel, left-most) but such sites are much fewer in number. The large number of open-chromatin single-stranded sites in highly expressed genes of cells in the tissue section may be reflective of a higher level of activity where a gene is bursting transcriptional activity more frequently and the open-chromatin single-stranded state is maintained for an extended period of time. This is consistent with data showing that the variability in gene expression decreases when there are more CHeX-seq priming sites (FIG. 17F). These data suggest that mean-scaled variability of expression may be inversely related to the quantitative degree and base-pair span of single-stranded DNA regions. Thus, the CHeX-seq priming measure may correlate with temporal constancy of transcription as well as overall production levels, which would be reflective of the cells' higher metabolic needs and requirement for constant high levels of expressed RNAs.

Priming rates in units of extended genic regions, defined as the whole transcribed region (5'UTR, exons, introns, 3'UTR) with an additional 5 kb both upstream and downstream, were examined. For each extended genic region, the priming events from 28 cultured neuronal samples and 15 in situ hippocampal neuronal samples were pooled and Fisher's exact test for differential proportions carried out, given the total reads in each treatment, A total of 86 significantly different priming rates (i.e., single-stranded regions) were found in extended gene regions after multiple test correction (Benjamini-Hochberg adjusted p-value <0.05); there were 50 genic regions with greater CHeX-seq priming rates for dispersed cortical neurons versus in situ hippocampal neurons and 36 genic regions with greater priming rates in situ compared to dispersed culture.

The 50 genic regions with greater priming rates for cortical neurons in dispersed culture included a diverse set of gene functions. It appears that there is a shift in biology upon dispersion, with dispersed cell genes showing more single-strandedness for GO-annotated genes associated with cilium function, membrane function, and nucleotide binding. Since many genes in these functional classes are involved in cell shape in yeast (Hayles et al., 2013), these data suggest that upon cell dispersion, shape-altering genes might be activated. When these 50 genic regions were examined for that correspondence with the single cell transcriptome from dispersed cells, two of the genes that showed higher read recovery in dispersed cells were ACOX3 (Acyl-coenzyme A oxidase 3,an enzyme that functions in the peroxisome (Vanhooren et al., 1996)) and SUDS3 (a subunit of HDAC1-dependent SIN3A co-repressor complex (Fleischer et al., 2003)). SUDS3 is thought to repress transcription by augmenting HDAC1 activity through modulation of chromatin structure. It is possible that SUDS3 protein is increased in dispersed cells and would function to decrease the number of open-chromatin sites upon dispersion. This may be especially true for the large number of non-transcribed. CHeX-seq accessible single-stranded open-chromatin sites identified in section hippocampal neurons.

The 36 genic regions with greater priming rates in in situ hippocampal cells were concentrated on mitochondria-encoded genes, with 27 mitochondrial genes out of the 37 mitochondria-encoded genes showing significant differences (Tables 2A&B). Mitochondrial DNA has been noted in other open-chromatin assays but has generally been removed for nuclear DNA analysis (Montefiori et al., 2017). Mitochondrial DNA is not organized into chromatin, as nuclear DNA is, but rather has a nucleoid structure (containing single-stranded DNA regions) that is dynamically regulated and transcribed (Marom et al., 2019; Kucej et al., 2008; Tomaska et al., 2001). For these genic regions, the neurons from the fixed section showed an average of 15.7 CHeX-seq priming events per gene per cell, ranging from 6.8 events/cell to 32.1 events/cell. Compared to these values, only 0,016 average priming events per cell per mitochondrial-encoded gene were found for neurons from culture. Since CHeX-seq priming is limited by the interval of single-stranded regions, a very large number of priming events per genic region was not expected in general, and these events are hypothesized to represent the single-stranded DNA found in multiple mitochondria in a given cell. These results indicate that mitochondrial activity, mitochondria replication, and/or gene transcription, may be reduced in neurons in culture. There were four cells (single-cell samples) in tissue sections that also had almost no CHeX-seq priming in these 27 mitochondrial gene regions, while showing strong signal from other genic regions suggesting that the mitochondrial DNA activity states are heterogeneous between individual cells.

Tables 2A&B. Genes that are differentially primed in single mouse neurons analyzed in tissue sections and dispersed cell culture. The proportional test was used to identify differentially CHeX-primer primed genes with BH corrected p-value of <0.05. For each gene, the group-wise sum is computed, and then compared with the grand sum where all genes are pooled. The Fisher exact test was applied to the contingency table to test the proportions.

TABLE 2A

|  | sCHeX099 | sCHeX100 | sCHeX101 | sCHeX102 | sCHeX103 | sCHeX104 | pCHeX135 | sCHeX105 | sCHeX106 | sCHeX107 | sCHeX108 |
|---|---|---|---|---|---|---|---|---|---|---|---|
| Gm9843 | 1 | 0 | 0 | 1 | 1 | 1 | 0 | 1 | 0 | 0 | 0 |
| Smg5 | 0 | 0 | 0 | 0 | 1 | 0 | 1 | 0 | 1 | 0 | 1 |
| Suds3 | 1 | 1 | 0 | 2 | 1 | 1 | 1 | 0 | 0 | 1 | 0 |
| Vmn1r-ps25 | 0 | 1 | 0 | 0 | 1 | 1 | 0 | 0 | 1 | 1 | 1 |
| Des | 0 | 1 | 1 | 0 | 1 | 1 | 0 | 0 | 1 | 0 | 1 |
| Gm15978 | 1 | 0 | 0 | 1 | 1 | 0 | 0 | 0 | 1 | 0 | 0 |
| Dscr3 | 2 | 0 | 0 | 2 | 1 | 1 | 1 | 0 | 0 | 0 | 0 |
| Nup160 | 0 | 0 | 0 | 0 | 0 | 0 | 1 | 2 | 1 | 0 | 0 |
| Gm15179 | 0 | 1 | 1 | 1 | 1 | 1 | 0 | 0 | 1 | 0 | 1 |
| Rab36 | 0 | 0 | 0 | 1 | 1 | 2 | 0 | 1 | 1 | 0 | 0 |
| Gm4737 | 1 | 0 | 1 | 1 | 1 | 1 | 1 | 1 | 1 | 1 | 0 |
| Gm11762 | 1 | 0 | 0 | 1 | 1 | 1 | 0 | 0 | 1 | 1 | 1 |
| Nptx1 | 1 | 0 | 0 | 1 | 1 | 1 | 0 | 0 | 1 | 1 | 1 |
| Gm23027 | 1 | 1 | 1 | 1 | 1 | 1 | 1 | 0 | 1 | 1 | 0 |
| Gm10275 | 0 | 1 | 0 | 0 | 1 | 1 | 0 | 0 | 2 | 2 | 0 |
| Acox3 | 1 | 1 | 1 | 1 | 1 | 1 | 1 | 0 | 0 | 1 | 0 |
| Olfr735 | 0 | 0 | 0 | 1 | 1 | 0 | 1 | 1 | 1 | 1 | 1 |
| Lck | 2 | 0 | 1 | 2 | 1 | 1 | 1 | 1 | 1 | 1 | 1 |
| Ifrd2 | 1 | 1 | 1 | 1 | 1 | 1 | 0 | 1 | 1 | 1 | 1 |
| Gm26402 | 1 | 0 | 0 | 1 | 1 | 1 | 1 | 0 | 1 | 0 | 1 |
| Irf2bp2 | 1 | 1 | 1 | 1 | 1 | 1 | 0 | 1 | 1 | 1 | 1 |
| 3110021N24 | 1 | 1 | 0 | 1 | 1 | 1 | 1 | 1 | 1 | 0 | 1 |
| Klhl21 | 0 | 0 | 0 | 1 | 1 | 1 | 1 | 0 | 0 | 0 | 1 |
| Vac14 | 0 | 0 | 0 | 1 | 0 | 0 | 0 | 1 | 1 | 1 | 1 |
| 4921531C22 | 1 | 0 | 0 | 1 | 0 | 0 | 4 | 2 | 1 | 2 | 0 |
| D1Ertd622e | 2 | 1 | 0 | 1 | 2 | 2 | 0 | 0 | 0 | 0 | 0 |
| Fam208b | 0 | 1 | 0 | 1 | 1 | 1 | 0 | 0 | 0 | 0 | 0 |
| Gab1 | 0 | 0 | 1 | 1 | 1 | 1 | 2 | 1 | 1 | 0 | 1 |
| 1700012I11R | 2 | 1 | 0 | 1 | 1 | 2 | 1 | 1 | 0 | 0 | 0 |
| Pkd1l1 | 0 | 0 | 0 | 0 | 1 | 1 | 0 | 0 | 1 | 1 | 1 |
| 1700042O10 | 1 | 1 | 0 | 0 | 0 | 0 | 1 | 1 | 1 | 1 | 1 |
| Cdc26 | 1 | 1 | 1 | 0 | 1 | 1 | 1 | 1 | 1 | 1 | 1 |
| Prpf4 | 1 | 1 | 1 | 0 | 1 | 1 | 1 | 1 | 1 | 1 | 1 |
| Ggt5 | 1 | 0 | 0 | 1 | 1 | 1 | 1 | 0 | 1 | 0 | 1 |
| Ttc7 | 1 | 0 | 0 | 1 | 1 | 1 | 1 | 0 | 1 | 0 | 1 |
| Cfh | 1 | 1 | 0 | 1 | 1 | 1 | 1 | 0 | 1 | 0 | 1 |
| Gm4221 | 1 | 1 | 1 | 1 | 1 | 1 | 2 | 0 | 1 | 1 | 1 |
| Vps13d | 1 | 0 | 1 | 1 | 1 | 2 | 1 | 0 | 1 | 1 | 1 |
| Ppp6r3 | 1 | 2 | 1 | 1 | 1 | 1 | 1 | 1 | 1 | 0 | 0 |
| K230010J24R | 2 | 1 | 1 | 1 | 1 | 1 | 1 | 0 | 1 | 1 | 0 |
| Yeats2 | 1 | 1 | 1 | 1 | 1 | 1 | 1 | 0 | 1 | 1 | 0 |
| Fam135b | 1 | 1 | 1 | 1 | 1 | 3 | 0 | 0 | 0 | 2 | 1 |
| Agtpbp1 | 1 | 2 | 0 | 1 | 0 | 3 | 2 | 0 | 0 | 0 | 1 |
| Rcsd1 | 1 | 1 | 0 | 1 | 0 | 0 | 1 | 1 | 1 | 0 | 1 |
| Fam172a | 1 | 1 | 0 | 2 | 1 | 1 | 3 | 1 | 1 | 1 | 1 |
| Rbms1 | 1 | 1 | 1 | 2 | 2 | 1 | 4 | 1 | 1 | 1 | 0 |
| Zcchc11 | 2 | 2 | 0 | 0 | 2 | 1 | 1 | 0 | 1 | 0 | 1 |
| Trpm6 | 2 | 1 | 1 | 2 | 0 | 2 | 2 | 1 | 2 | 2 | 1 |
| Cdkal1 | 1 | 1 | 1 | 1 | 2 | 2 | 2 | 1 | 1 | 0 | 1 |
| Gm11168 | 7 | 1 | 2 | 3 | 1 | 2 | 36 | 0 | 0 | 1 | 0 |
| Gm26870 | 10 | 6 | 2 | 8 | 5 | 3 | 106 | 0 | 0 | 1 | 0 |
| Gm10720 | 0 | 1 | 0 | 3 | 1 | 0 | 10 | 0 | 0 | 0 | 0 |
| mt-Nd2 | 0 | 0 | 0 | 0 | 0 | 0 | 2 | 0 | 0 | 0 | 0 |
| mt-Nd1 | 0 | 0 | 0 | 0 | 0 | 0 | 2 | 0 | 0 | 0 | 0 |
| Gm10722 | 0 | 0 | 0 | 1 | 0 | 0 | 6 | 0 | 0 | 1 | 0 |
| Gm107171 | 0 | 1 | 0 | 0 | 1 | 0 | 18 | 0 | 0 | 0 | 0 |
| mt-Rnr2 | 0 | 0 | 0 | 0 | 0 | 0 | 2 | 0 | 0 | 0 | 0 |
| mt-Tv | 0 | 0 | 0 | 0 | 0 | 0 | 2 | 0 | 0 | 0 | 0 |
| mt-Rnr1 | 0 | 0 | 0 | 0 | 0 | 0 | 2 | 0 | 0 | 0 | 0 |
| mt-Tf | 0 | 0 | 0 | 0 | 0 | 0 | 2 | 0 | 0 | 0 | 0 |
| Gm10719 | 0 | 0 | 0 | 1 | 0 | 0 | 1 | 0 | 0 | 0 | 0 |
| Gm10718 | 0 | 0 | 0 | 0 | 0 | 0 | 0 | 0 | 0 | 0 | 0 |
| Gm17535 | 0 | 0 | 0 | 0 | 0 | 0 | 0 | 0 | 0 | 0 | 0 |

TABLE 2A-continued

| | | | | | | | | | | | |
|---|---|---|---|---|---|---|---|---|---|---|---|
| mt-Cytb | 0 | 0 | 0 | 0 | 0 | 0 | 0 | 0 | 0 | 0 | 0 |
| mt-Tt | 0 | 0 | 0 | 0 | 0 | 0 | 0 | 0 | 0 | 0 | 0 |
| mt-Tp | 0 | 0 | 0 | 0 | 0 | 0 | 0 | 0 | 0 | 0 | 0 |
| mt-Nd6 | 0 | 0 | 0 | 0 | 0 | 0 | 0 | 0 | 0 | 0 | 0 |
| mt-Te | 0 | 0 | 0 | 0 | 0 | 0 | 0 | 0 | 0 | 0 | 0 |
| Gm10715 | 0 | 0 | 0 | 0 | 0 | 0 | 0 | 0 | 0 | 0 | 0 |
| mt-Nd5 | 0 | 0 | 0 | 0 | 0 | 0 | 0 | 0 | 0 | 0 | 0 |
| mt-Tl2 | 0 | 0 | 0 | 0 | 0 | 0 | 0 | 0 | 0 | 0 | 0 |
| mt-Th | 0 | 0 | 0 | 0 | 0 | 0 | 0 | 0 | 0 | 0 | 0 |
| mt-Nd4 | 0 | 0 | 0 | 0 | 0 | 0 | 0 | 0 | 0 | 0 | 0 |
| mt-Ts2 | 0 | 0 | 0 | 0 | 0 | 0 | 0 | 0 | 0 | 0 | 0 |
| mt-Co1 | 0 | 0 | 0 | 0 | 0 | 0 | 0 | 0 | 0 | 0 | 0 |
| mt-Tc | 0 | 0 | 0 | 0 | 0 | 0 | 0 | 0 | 0 | 0 | 0 |
| mt-Tn | 0 | 0 | 0 | 0 | 0 | 0 | 0 | 0 | 0 | 0 | 0 |
| mt-Ty | 0 | 0 | 0 | 0 | 0 | 0 | 0 | 0 | 0 | 0 | 0 |
| mt-Ta | 0 | 0 | 0 | 0 | 0 | 0 | 0 | 0 | 0 | 0 | 0 |
| mt-Atp8 | 0 | 0 | 0 | 0 | 0 | 0 | 0 | 0 | 0 | 0 | 0 |
| mt-Co2 | 0 | 0 | 0 | 0 | 0 | 0 | 0 | 0 | 0 | 0 | 0 |
| mt-Td | 0 | 0 | 0 | 0 | 0 | 0 | 0 | 0 | 0 | 0 | 0 |
| mt-Tk | 0 | 0 | 0 | 0 | 0 | 0 | 0 | 0 | 0 | 0 | 0 |
| mt-Ts1 | 0 | 0 | 0 | 0 | 0 | 0 | 0 | 0 | 0 | 0 | 0 |
| mt-Atp6 | 0 | 0 | 0 | 0 | 0 | 0 | 0 | 0 | 0 | 0 | 0 |
| Tmem79 | 0 | 0 | 0 | 0 | 2 | 0 | 0 | 0 | 1 | 0 | 1 |

| | sCHeX109 | sCHeX110 | sCHeX111 | sCHeX112 | sCHeX113 | sCHeX114 | sCHeX116 | sCHeX117 | sCHeX120 | sCHeX121 | sCHeX122 |
|---|---|---|---|---|---|---|---|---|---|---|---|
| Gm9843 | 1 | 0 | 1 | 1 | 1 | 0 | 0 | 0 | 0 | 0 | 0 |
| Smg5 | 0 | 0 | 0 | 2 | 2 | 0 | 0 | 0 | 0 | 0 | 0 |
| Suds3 | 0 | 0 | 0 | 0 | 0 | 0 | 0 | 0 | 1 | 1 | 0 |
| Vmn1r-ps25 | 0 | 0 | 1 | 1 | 1 | 0 | 0 | 0 | 0 | 0 | 1 |
| Des | 0 | 0 | 0 | 0 | 0 | 0 | 0 | 0 | 0 | 1 | 0 |
| Gm15978 | 0 | 1 | 0 | 1 | 0 | 1 | 1 | 1 | 1 | 1 | 1 |
| Dscr3 | 1 | 0 | 0 | 0 | 0 | 0 | 0 | 0 | 0 | 0 | 0 |
| Nup160 | 0 | 0 | 0 | 0 | 0 | 0 | 0 | 0 | 0 | 2 | 2 |
| Gm15179 | 0 | 0 | 0 | 0 | 0 | 0 | 0 | 0 | 0 | 1 | 0 |
| Rab36 | 0 | 0 | 1 | 0 | 1 | 0 | 1 | 0 | 0 | 0 | 0 |
| Gm4737 | 1 | 0 | 0 | 0 | 0 | 0 | 1 | 0 | 0 | 0 | 0 |
| Gm11762 | 2 | 1 | 0 | 0 | 0 | 0 | 0 | 0 | 0 | 0 | 0 |
| Nptx1 | 2 | 1 | 0 | 0 | 0 | 0 | 0 | 0 | 0 | 0 | 0 |
| Gm23027 | 1 | 0 | 0 | 0 | 1 | 0 | 1 | 0 | 1 | 0 | 0 |
| Gm10275 | 2 | 0 | 1 | 0 | 2 | 0 | 1 | 0 | 0 | 0 | 0 |
| Acox3 | 0 | 0 | 0 | 0 | 0 | 0 | 0 | 0 | 1 | 1 | 0 |
| Olfr735 | 1 | 1 | 1 | 1 | 0 | 0 | 0 | 0 | 0 | 1 | 0 |
| Lck | 1 | 0 | 1 | 0 | 1 | 0 | 0 | 0 | 1 | 0 | 1 |
| Ifrd2 | 1 | 1 | 1 | 1 | 0 | 0 | 1 | 0 | 1 | 1 | 1 |
| Gm26402 | 1 | 0 | 1 | 1 | 1 | 0 | 0 | 0 | 0 | 0 | 0 |
| Irf2bp2 | 1 | 1 | 0 | 0 | 1 | 1 | 1 | 0 | 0 | 0 | 1 |
| 3110021N24 | 0 | 1 | 0 | 1 | 0 | 0 | 0 | 0 | 0 | 0 | 0 |
| Klhl21 | 1 | 0 | 0 | 0 | 1 | 0 | 1 | 0 | 0 | 0 | 0 |
| Vac14 | 0 | 1 | 1 | 1 | 1 | 0 | 1 | 0 | 0 | 0 | 0 |
| 4921531C22 | 1 | 0 | 0 | 1 | 1 | 0 | 0 | 0 | 0 | 0 | 0 |
| D1Ertd622e | 2 | 1 | 2 | 0 | 3 | 0 | 0 | 0 | 0 | 0 | 0 |
| Fam208b | 0 | 0 | 0 | 0 | 1 | 0 | 0 | 0 | 0 | 0 | 0 |
| Gab1 | 0 | 0 | 1 | 0 | 1 | 0 | 0 | 0 | 0 | 1 | 1 |
| 1700012I11R | 0 | 0 | 1 | 1 | 1 | 0 | 0 | 0 | 0 | 0 | 0 |
| Pkd1l1 | 1 | 1 | 0 | 0 | 1 | 0 | 1 | 0 | 0 | 0 | 0 |
| 1700042O10 | 1 | 0 | 1 | 1 | 1 | 0 | 1 | 1 | 0 | 1 | 0 |
| Cdc26 | 1 | 1 | 3 | 1 | 3 | 1 | 1 | 1 | 1 | 1 | 1 |
| Prpf4 | 1 | 1 | 3 | 1 | 3 | 1 | 1 | 1 | 1 | 1 | 1 |
| Ggt5 | 1 | 0 | 1 | 1 | 1 | 0 | 0 | 0 | 0 | 0 | 0 |
| Ttc7 | 1 | 0 | 1 | 1 | 1 | 0 | 0 | 0 | 0 | 0 | 0 |
| Cfh | 1 | 0 | 1 | 0 | 1 | 0 | 0 | 0 | 0 | 0 | 0 |
| Gm4221 | 1 | 0 | 0 | 0 | 2 | 1 | 1 | 0 | 0 | 0 | 1 |
| Vps13d | 0 | 0 | 2 | 1 | 4 | 0 | 1 | 0 | 0 | 1 | 1 |
| Ppp6r3 | 0 | 0 | 0 | 0 | 1 | 1 | 1 | 0 | 0 | 1 | 0 |
| K230010J24R | 1 | 0 | 1 | 0 | 1 | 0 | 1 | 0 | 1 | 0 | 0 |
| Yeats2 | 1 | 0 | 0 | 0 | 2 | 0 | 1 | 0 | 1 | 0 | 1 |
| Fam135b | 0 | 0 | 2 | 0 | 2 | 0 | 2 | 1 | 0 | 0 | 1 |
| Agtpbp1 | 1 | 1 | 1 | 0 | 0 | 0 | 0 | 1 | 1 | 0 | 0 |
| Rcsd1 | 1 | 0 | 1 | 0 | 2 | 1 | 0 | 0 | 0 | 0 | 0 |
| Fam172a | 1 | 0 | 1 | 1 | 2 | 1 | 1 | 1 | 1 | 1 | 1 |
| Rbms1 | 2 | 0 | 1 | 1 | 1 | 0 | 1 | 0 | 0 | 1 | 0 |
| Zcchc11 | 1 | 1 | 2 | 0 | 2 | 0 | 0 | 0 | 0 | 0 | 0 |
| Trpm6 | 0 | 1 | 2 | 1 | 1 | 1 | 0 | 0 | 1 | 0 | 1 |
| Cdkal1 | 1 | 0 | 2 | 3 | 5 | 1 | 1 | 1 | 0 | 1 | 1 |
| Gm11168 | 0 | 0 | 0 | 0 | 0 | 0 | 0 | 0 | 0 | 0 | 0 |
| Gm26870 | 0 | 0 | 0 | 0 | 0 | 0 | 0 | 0 | 0 | 0 | 0 |
| Gm10720 | 0 | 0 | 0 | 0 | 0 | 0 | 0 | 0 | 0 | 0 | 0 |
| mt-Nd2 | 0 | 0 | 0 | 0 | 0 | 0 | 0 | 0 | 0 | 0 | 0 |
| mt-Nd1 | 0 | 0 | 0 | 0 | 0 | 0 | 0 | 0 | 0 | 0 | 0 |

TABLE 2A-continued

|  |  |  |  |  |  |  |  |  |  |  |  |
|---|---|---|---|---|---|---|---|---|---|---|---|
| Gm10722 | 0 | 0 | 0 | 0 | 0 | 0 | 0 | 0 | 0 | 0 | 0 |
| Gm107171 | 0 | 0 | 0 | 0 | 0 | 0 | 0 | 0 | 0 | 0 | 0 |
| mt-Rnr2 | 0 | 0 | 0 | 0 | 0 | 0 | 0 | 0 | 0 | 0 | 0 |
| mt-Tv | 0 | 0 | 0 | 0 | 0 | 0 | 0 | 0 | 0 | 0 | 0 |
| mt-Rnr1 | 0 | 0 | 0 | 0 | 0 | 0 | 0 | 0 | 0 | 0 | 0 |
| mt-Tf | 0 | 0 | 0 | 0 | 0 | 0 | 0 | 0 | 0 | 0 | 0 |
| Gm10719 | 0 | 0 | 0 | 0 | 0 | 0 | 0 | 0 | 0 | 0 | 0 |
| Gm10718 | 0 | 0 | 0 | 0 | 0 | 0 | 0 | 0 | 0 | 0 | 0 |
| Gm17535 | 0 | 0 | 0 | 0 | 0 | 0 | 0 | 0 | 0 | 0 | 0 |
| mt-Cytb | 0 | 0 | 0 | 0 | 0 | 0 | 0 | 0 | 0 | 0 | 0 |
| mt-Tt | 0 | 0 | 0 | 0 | 0 | 0 | 0 | 0 | 0 | 0 | 0 |
| mt-Tp | 0 | 0 | 0 | 0 | 0 | 0 | 0 | 0 | 0 | 0 | 0 |
| mt-Nd6 | 0 | 0 | 0 | 0 | 0 | 0 | 0 | 0 | 0 | 0 | 0 |
| mt-Te | 0 | 0 | 0 | 0 | 0 | 0 | 0 | 0 | 0 | 0 | 0 |
| Gm10715 | 0 | 0 | 0 | 0 | 0 | 0 | 0 | 0 | 0 | 0 | 0 |
| mt-Nd5 | 0 | 0 | 0 | 0 | 0 | 0 | 0 | 0 | 0 | 0 | 0 |
| mt-Tl2 | 0 | 0 | 0 | 0 | 0 | 0 | 0 | 0 | 0 | 0 | 0 |
| mt-Th | 0 | 0 | 0 | 0 | 0 | 0 | 0 | 0 | 0 | 0 | 0 |
| mt-Nd4 | 0 | 0 | 0 | 0 | 0 | 0 | 0 | 0 | 0 | 0 | 0 |
| mt-Ts2 | 0 | 0 | 0 | 0 | 0 | 0 | 0 | 0 | 0 | 0 | 0 |
| mt-Co1 | 0 | 0 | 0 | 0 | 0 | 0 | 0 | 0 | 0 | 0 | 0 |
| mt-Tc | 0 | 0 | 0 | 0 | 0 | 0 | 0 | 0 | 0 | 0 | 0 |
| mt-Tn | 0 | 0 | 0 | 0 | 0 | 0 | 0 | 0 | 0 | 0 | 0 |
| mt-Ty | 0 | 0 | 0 | 0 | 0 | 0 | 0 | 0 | 0 | 0 | 0 |
| mt-Ta | 0 | 0 | 0 | 0 | 0 | 0 | 0 | 0 | 0 | 0 | 0 |
| mt-Atp8 | 0 | 0 | 0 | 0 | 0 | 0 | 0 | 0 | 0 | 0 | 0 |
| mt-Co2 | 0 | 0 | 0 | 0 | 0 | 0 | 0 | 0 | 0 | 0 | 0 |
| mt-Td | 0 | 0 | 0 | 0 | 0 | 0 | 0 | 0 | 0 | 0 | 0 |
| mt-Tk | 0 | 0 | 0 | 0 | 0 | 0 | 0 | 0 | 0 | 0 | 0 |
| mt-Ts1 | 0 | 0 | 0 | 0 | 0 | 0 | 0 | 0 | 0 | 0 | 0 |
| mt-Atp6 | 0 | 0 | 0 | 0 | 0 | 0 | 0 | 0 | 0 | 0 | 0 |
| Tmem79 | 0 | 0 | 0 | 2 | 2 | 0 | 0 | 0 | 0 | 0 | 0 |

TABLE 2B

|  | sCHeX123 | sCHeX126 | sCHeX127 | sCHeX128 | sCHeX129 | sCHeX130 | pCHeX154 |
|---|---|---|---|---|---|---|---|
| Gm9843 | 0 | 0 | 1 | 1 | 1 | 0 | 0 |
| Smg5 | 0 | 0 | 0 | 1 | 0 | 0 | 0 |
| Suds3 | 0 | 0 | 1 | 1 | 1 | 2 | 0 |
| Vmn1r-ps25 | 0 | 1 | 1 | 1 | 1 | 0 | 0 |
| Des | 0 | 1 | 1 | 1 | 1 | 0 | 0 |
| Gm15978 | 0 | 1 | 0 | 1 | 1 | 1 | 0 |
| Dscr3 | 0 | 0 | 0 | 0 | 0 | 1 | 0 |
| Nup160 | 0 | 1 | 0 | 0 | 0 | 0 | 0 |
| Gm15179 | 0 | 1 | 1 | 1 | 1 | 0 | 0 |
| Rab36 | 1 | 0 | 1 | 1 | 0 | 0 | 0 |
| Gm4737 | 1 | 1 | 1 | 0 | 1 | 1 | 0 |
| Gm11762 | 0 | 0 | 2 | 1 | 0 | 2 | 0 |
| Nptx1 | 0 | 0 | 2 | 1 | 0 | 2 | 0 |
| Gm23027 | 0 | 1 | 1 | 1 | 1 | 0 | 0 |
| Gm10275 | 0 | 0 | 1 | 2 | 0 | 2 | 0 |
| Acox3 | 0 | 0 | 0 | 1 | 1 | 1 | 0 |
| Olfr735 | 1 | 0 | 0 | 1 | 0 | 1 | 0 |
| Lck | 1 | 0 | 0 | 1 | 0 | 1 | 0 |
| Ifrd2 | 0 | 0 | 1 | 1 | 1 | 1 | 0 |
| Gm26402 | 1 | 0 | 1 | 1 | 0 | 0 | 0 |
| Irf2bp2 | 1 | 1 | 1 | 1 | 1 | 1 | 0 |
| 3110021N24 | 0 | 0 | 0 | 0 | 0 | 0 | 1 |
| Klhl21 | 0 | 1 | 1 | 1 | 0 | 0 | 0 |
| Vac14 | 1 | 0 | 0 | 1 | 1 | 0 | 1 |
| 4921531C22 | 0 | 0 | 0 | 1 | 0 | 0 | 0 |
| D1Ertd622e | 0 | 2 | 2 | 2 | 0 | 1 | 0 |
| Fam208b | 0 | 1 | 1 | 2 | 2 | 1 | 0 |
| Gab1 | 1 | 1 | 1 | 1 | 0 | 0 | 0 |
| 1700012I11R | 0 | 0 | 0 | 1 | 0 | 0 | 3 |
| Pkd1l1 | 0 | 1 | 0 | 1 | 1 | 1 | 0 |
| 1700042O10 | 0 | 0 | 1 | 1 | 1 | 1 | 0 |
| Cdc26 | 1 | 1 | 1 | 1 | 1 | 1 | 1 |
| Prpf4 | 1 | 1 | 1 | 1 | 1 | 1 | 1 |
| Ggt5 | 1 | 0 | 1 | 1 | 0 | 0 | 1 |
| Ttc7 | 1 | 0 | 1 | 1 | 0 | 0 | 1 |
| Cfh | 0 | 1 | 1 | 1 | 1 | 1 | 0 |
| Gm4221 | 1 | 1 | 1 | 2 | 0 | 0 | 3 |
| Vps13d | 1 | 0 | 1 | 0 | 0 | 1 | 4 |
| Ppp6r3 | 0 | 1 | 1 | 1 | 0 | 1 | 2 |
| K230010J24R | 0 | 1 | 1 | 1 | 1 | 0 | 4 |

TABLE 2B-continued

| | | | | | | | |
|---|---|---|---|---|---|---|---|
| Yeats2 | 0 | 1 | 1 | 1 | 1 | 0 | 1 |
| Fam135b | 1 | 0 | 1 | 1 | 2 | 1 | 1 |
| Agtpbp1 | 1 | 1 | 0 | 1 | 0 | 0 | 2 |
| Rcsd1 | 1 | 1 | 1 | 1 | 1 | 0 | 0 |
| Fam172a | 0 | 1 | 1 | 1 | 1 | 1 | 2 |
| Rbms1 | 1 | 1 | 1 | 2 | 1 | 1 | 7 |
| Zcchc11 | 0 | 1 | 1 | 2 | 0 | 1 | 3 |
| Trpm6 | 1 | 0 | 0 | 2 | 1 | 0 | 3 |
| Cdkal1 | 1 | 1 | 1 | 1 | 1 | 1 | 5 |
| Gm11168 | 0 | 0 | 2 | 4 | 0 | 0 | 121 |
| Gm26870 | 0 | 0 | 4 | 11 | 0 | 0 | 553 |
| Gm10720 | 0 | 0 | 0 | 2 | 0 | 0 | 83 |
| mt-Nd2 | 0 | 0 | 0 | 0 | 0 | 0 | 24 |
| mt-Nd1 | 0 | 0 | 0 | 0 | 0 | 0 | 22 |
| Gm10722 | 0 | 0 | 1 | 1 | 0 | 0 | 88 |
| Gm107171 | 0 | 0 | 0 | 0 | 0 | 0 | 202 |
| mt-Rnr2 | 0 | 0 | 0 | 0 | 0 | 0 | 52 |
| mt-Tv | 0 | 0 | 0 | 0 | 0 | 0 | 52 |
| mt-Rnr1 | 0 | 0 | 0 | 0 | 0 | 0 | 64 |
| mt-Tf | 0 | 0 | 0 | 0 | 0 | 0 | 64 |
| Gm10719 | 0 | 0 | 0 | 0 | 0 | 0 | 158 |
| Gm10718 | 0 | 0 | 0 | 0 | 0 | 0 | 100 |
| Gm17535 | 0 | 0 | 0 | 0 | 0 | 0 | 76 |
| mt-Cytb | 0 | 0 | 0 | 0 | 0 | 0 | 93 |
| mt-Tt | 0 | 0 | 0 | 0 | 0 | 0 | 93 |
| mt-Tp | 0 | 0 | 0 | 0 | 0 | 0 | 93 |
| mt-Nd6 | 0 | 0 | 0 | 0 | 0 | 0 | 92 |
| mt-Te | 0 | 0 | 0 | 0 | 0 | 0 | 92 |
| Gm10715 | 0 | 0 | 0 | 0 | 0 | 0 | 51 |
| mt-Nd5 | 0 | 0 | 0 | 0 | 0 | 0 | 82 |
| mt-Tl2 | 0 | 0 | 0 | 0 | 0 | 0 | 42 |
| mt-Th | 0 | 0 | 0 | 0 | 0 | 0 | 41 |
| mt-Nd4 | 0 | 0 | 0 | 0 | 0 | 0 | 42 |
| mt-Ts2 | 0 | 0 | 0 | 0 | 0 | 0 | 41 |
| mt-Co1 | 0 | 0 | 0 | 0 | 0 | 0 | 18 |
| mt-Tc | 0 | 0 | 0 | 0 | 0 | 0 | 17 |
| mt-Tn | 0 | 0 | 0 | 0 | 0 | 0 | 17 |
| mt-Ty | 0 | 0 | 0 | 0 | 0 | 0 | 17 |
| mt-Ta | 0 | 0 | 0 | 0 | 0 | 0 | 17 |
| mt-Atp8 | 0 | 0 | 0 | 0 | 0 | 0 | 16 |
| mt-Co2 | 0 | 0 | 0 | 0 | 0 | 0 | 16 |
| mt-Td | 0 | 0 | 0 | 0 | 0 | 0 | 16 |
| mt-Tk | 0 | 0 | 0 | 0 | 0 | 0 | 16 |
| mt-Ts1 | 0 | 0 | 0 | 0 | 0 | 0 | 16 |
| mt-Atp6 | 0 | 0 | 0 | 0 | 0 | 0 | 15 |
| Tmem79 | 0 | 0 | 0 | 0 | 0 | 0 | 0 |

| | sCHeX141 | sCHeX142 | sCHeX143 | pCHeX155 | sCHeX144 | sCHeX145 | sCHeX146 |
|---|---|---|---|---|---|---|---|
| Gm9843 | 0 | 0 | 0 | 0 | 0 | 0 | 0 |
| Smg5 | 0 | 0 | 0 | 0 | 0 | 0 | 0 |
| Suds3 | 0 | 0 | 0 | 0 | 0 | 0 | 0 |
| Vmn1r-ps25 | 0 | 0 | 0 | 0 | 0 | 0 | 0 |
| Des | 0 | 0 | 1 | 0 | 0 | 0 | 0 |
| Gm15978 | 1 | 0 | 0 | 0 | 0 | 0 | 0 |
| Dscr3 | 0 | 0 | 0 | 0 | 0 | 1 | 1 |
| Nup160 | 0 | 0 | 0 | 1 | 0 | 0 | 0 |
| Gm15179 | 0 | 1 | 1 | 0 | 0 | 0 | 0 |
| Rab36 | 0 | 0 | 0 | 0 | 0 | 0 | 0 |
| Gm4737 | 0 | 0 | 0 | 1 | 0 | 1 | 0 |
| Gm11762 | 0 | 0 | 0 | 0 | 0 | 0 | 0 |
| Nptx1 | 0 | 0 | 0 | 0 | 0 | 0 | 0 |
| Gm23027 | 0 | 0 | 0 | 1 | 0 | 0 | 0 |
| Gm10275 | 0 | 0 | 0 | 0 | 0 | 0 | 0 |
| Acox3 | 0 | 0 | 0 | 1 | 0 | 1 | 0 |
| Olfr735 | 1 | 0 | 0 | 0 | 0 | 0 | 0 |
| Lck | 0 | 1 | 0 | 1 | 0 | 0 | 0 |
| Ifrd2 | 1 | 0 | 1 | 0 | 1 | 0 | 0 |
| Gm26402 | 0 | 0 | 1 | 0 | 0 | 0 | 0 |
| Irf2bp2 | 1 | 2 | 1 | 1 | 0 | 0 | 0 |
| 3110021N24 | 0 | 0 | 0 | 0 | 0 | 0 | 0 |
| Klhl21 | 1 | 0 | 1 | 0 | 0 | 0 | 0 |
| Vac14 | 0 | 1 | 0 | 0 | 0 | 0 | 0 |
| 4921531C22 | 1 | 2 | 0 | 0 | 0 | 0 | 0 |
| D1Ertd622e | 0 | 0 | 0 | 0 | 0 | 0 | 0 |
| Fam208b | 0 | 0 | 0 | 0 | 1 | 0 | 0 |
| Gab1 | 0 | 2 | 0 | 0 | 0 | 0 | 2 |
| 1700012I11R | 0 | 0 | 0 | 0 | 0 | 1 | 0 |
| Pkd1l1 | 0 | 2 | 0 | 0 | 0 | 1 | 0 |
| 1700042O10 | 1 | 0 | 0 | 0 | 0 | 2 | 0 |

TABLE 2B-continued

| | | | | | | | |
|---|---|---|---|---|---|---|---|
| Cdc26 | 1 | 1 | 1 | 1 | 1 | 0 | 2 |
| Prpf4 | 1 | 1 | 1 | 1 | 1 | 0 | 2 |
| Ggt5 | 0 | 0 | 1 | 1 | 0 | 1 | 0 |
| Ttc7 | 0 | 0 | 1 | 1 | 0 | 1 | 0 |
| Cfh | 0 | 1 | 1 | 0 | 3 | 0 | 0 |
| Gm4221 | 0 | 2 | 0 | 0 | 2 | 1 | 1 |
| Vps13d | 0 | 3 | 1 | 3 | 0 | 0 | 2 |
| Ppp6r3 | 2 | 1 | 1 | 1 | 1 | 0 | 0 |
| K230010J24R | 1 | 1 | 0 | 3 | 0 | 1 | 0 |
| Yeats2 | 1 | 3 | 0 | 0 | 0 | 2 | 0 |
| Fam135b | 1 | 2 | 0 | 2 | 0 | 2 | 5 |
| Agtpbp1 | 2 | 0 | 1 | 1 | 1 | 2 | 0 |
| Rcsd1 | 3 | 3 | 1 | 1 | 1 | 1 | 1 |
| Fam172a | 2 | 1 | 2 | 4 | 1 | 3 | 3 |
| Rbms1 | 1 | 4 | 2 | 0 | 3 | 2 | 2 |
| Zcchc11 | 2 | 2 | 2 | 1 | 0 | 0 | 1 |
| Trpm6 | 3 | 3 | 2 | 3 | 4 | 5 | 2 |
| Cdkal1 | 8 | 7 | 2 | 5 | 3 | 6 | 3 |
| Gm11168 | 32 | 61 | 16 | 34 | 72 | 146 | 152 |
| Gm26870 | 165 | 281 | 71 | 161 | 333 | 640 | 645 |
| Gm10720 | 20 | 43 | 7 | 17 | 43 | 85 | 84 |
| mt-Nd2 | 7 | 7 | 8 | 4 | 8 | 15 | 12 |
| mt-Nd1 | 7 | 11 | 8 | 6 | 9 | 12 | 10 |
| Gm10722 | 27 | 51 | 10 | 24 | 61 | 103 | 109 |
| Gm107171 | 66 | 101 | 26 | 69 | 115 | 237 | 239 |
| mt-Rnr2 | 26 | 26 | 4 | 22 | 11 | 14 | 5 |
| mt-Tv | 26 | 26 | 4 | 22 | 11 | 14 | 5 |
| mt-Rnr1 | 29 | 32 | 9 | 23 | 18 | 15 | 11 |
| mt-Tf | 30 | 33 | 10 | 23 | 18 | 15 | 13 |
| Gm10719 | 51 | 87 | 17 | 47 | 99 | 173 | 175 |
| Gm10718 | 41 | 55 | 12 | 43 | 59 | 110 | 113 |
| Gm17535 | 26 | 30 | 11 | 22 | 48 | 87 | 90 |
| mt-Cytb | 40 | 47 | 32 | 26 | 21 | 24 | 18 |
| mt-Tt | 39 | 47 | 32 | 26 | 21 | 22 | 18 |
| mt-Tp | 39 | 47 | 32 | 26 | 21 | 18 | 18 |
| mt-Nd6 | 40 | 43 | 32 | 24 | 19 | 24 | 18 |
| mt-Te | 40 | 43 | 32 | 24 | 19 | 24 | 18 |
| Gm10715 | 18 | 22 | 8 | 14 | 30 | 63 | 62 |
| mt-Nd5 | 31 | 37 | 30 | 21 | 19 | 20 | 17 |
| mt-Tl2 | 16 | 19 | 28 | 5 | 10 | 14 | 14 |
| mt-Th | 16 | 19 | 28 | 5 | 9 | 14 | 14 |
| mt-Nd4 | 17 | 19 | 28 | 5 | 9 | 14 | 13 |
| mt-Ts2 | 16 | 19 | 28 | 5 | 9 | 14 | 14 |
| mt-Co1 | 7 | 5 | 7 | 4 | 6 | 11 | 10 |
| mt-Tc | 6 | 5 | 7 | 4 | 6 | 11 | 10 |
| mt-Tn | 6 | 5 | 7 | 4 | 6 | 11 | 10 |
| mt-Ty | 6 | 5 | 7 | 4 | 6 | 11 | 10 |
| mt-Ta | 6 | 5 | 7 | 4 | 6 | 11 | 10 |
| mt-Atp8 | 6 | 5 | 7 | 3 | 6 | 11 | 10 |
| mt-Co2 | 6 | 5 | 7 | 3 | 6 | 11 | 10 |
| mt-Td | 6 | 5 | 7 | 3 | 6 | 11 | 10 |
| mt-Tk | 6 | 5 | 7 | 3 | 6 | 11 | 10 |
| mt-Ts1 | 6 | 5 | 7 | 3 | 6 | 11 | 10 |
| mt-Atp6 | 6 | 5 | 7 | 3 | 6 | 10 | 10 |
| Tmem79 | 0 | 0 | 0 | 0 | 0 | 0 | 0 |

| | sCHeX147 | sCHeX148 | sCHeX149 | sCHeX150 | sCHeX151 | sCHeX152 | sCHeX153 |
|---|---|---|---|---|---|---|---|
| Gm9843 | 0 | 0 | 0 | 0 | 0 | 1 | 0 |
| Smg5 | 0 | 1 | 0 | 0 | 0 | 0 | 0 |
| Suds3 | 1 | 1 | 0 | 0 | 0 | 0 | 0 |
| Vmn1r-ps25 | 0 | 0 | 0 | 0 | 0 | 1 | 1 |
| Des | 0 | 0 | 1 | 0 | 0 | 0 | 0 |
| Gm15978 | 0 | 2 | 0 | 0 | 0 | 0 | 0 |
| Dscr3 | 0 | 0 | 0 | 0 | 0 | 0 | 0 |
| Nup160 | 0 | 1 | 0 | 0 | 0 | 0 | 0 |
| Gm15179 | 0 | 0 | 1 | 0 | 0 | 0 | 0 |
| Rab36 | 0 | 1 | 0 | 0 | 0 | 1 | 1 |
| Gm4737 | 1 | 0 | 1 | 0 | 0 | 0 | 0 |
| Gm11762 | 0 | 1 | 0 | 1 | 0 | 0 | 2 |
| Nptx1 | 0 | 1 | 0 | 1 | 0 | 0 | 2 |
| Gm23027 | 0 | 1 | 1 | 1 | 1 | 0 | 0 |
| Gm10275 | 0 | 2 | 2 | 1 | 0 | 0 | 1 |
| Acox3 | 0 | 3 | 0 | 0 | 0 | 0 | 0 |
| Olfr735 | 0 | 1 | 0 | 0 | 1 | 2 | 1 |
| Lck | 1 | 2 | 1 | 0 | 1 | 1 | 0 |
| Ifrd2 | 1 | 1 | 1 | 0 | 1 | 1 | 1 |
| Gm26402 | 0 | 1 | 0 | 1 | 1 | 1 | 1 |
| Irf2bp2 | 0 | 2 | 1 | 0 | 1 | 1 | 0 |
| 3110021N24 | 1 | 1 | 1 | 0 | 0 | 0 | 1 |

TABLE 2B-continued

| | | | | | | | |
|---|---|---|---|---|---|---|---|
| Klhl21 | 0 | 1 | 0 | 0 | 1 | 1 | 0 |
| Vac14 | 0 | 1 | 0 | 0 | 1 | 1 | 1 |
| 4921531C22 | 2 | 2 | 0 | 0 | 0 | 0 | 0 |
| D1Ertd622e | 0 | 4 | 0 | 3 | 0 | 2 | 2 |
| Fam208b | 0 | 2 | 0 | 2 | 1 | 0 | 0 |
| Gab1 | 0 | 2 | 0 | 0 | 1 | 1 | 1 |
| 1700012I11R | 0 | 1 | 0 | 0 | 0 | 1 | 1 |
| Pkd1l1 | 1 | 2 | 0 | 0 | 0 | 1 | 0 |
| 1700042O10 | 0 | 1 | 2 | 1 | 1 | 1 | 1 |
| Cdc26 | 2 | 2 | 1 | 1 | 1 | 1 | 2 |
| Prpf4 | 3 | 1 | 2 | 1 | 1 | 1 | 2 |
| Ggt5 | 0 | 1 | 0 | 1 | 1 | 1 | 1 |
| Ttc7 | 0 | 1 | 0 | 1 | 1 | 1 | 1 |
| Cfh | 1 | 1 | 1 | 1 | 0 | 1 | 1 |
| Gm4221 | 1 | 3 | 3 | 0 | 0 | 2 | 0 |
| Vps13d | 1 | 0 | 1 | 1 | 1 | 1 | 1 |
| Ppp6r3 | 3 | 1 | 1 | 1 | 0 | 0 | 1 |
| K230010J24R | 0 | 2 | 1 | 2 | 1 | 0 | 0 |
| Yeats2 | 3 | 4 | 2 | 1 | 1 | 0 | 0 |
| Fam135b | 4 | 2 | 2 | 0 | 1 | 0 | 2 |
| Agtpbp1 | 2 | 3 | 1 | 2 | 1 | 0 | 1 |
| Rcsd1 | 1 | 1 | 2 | 1 | 1 | 0 | 1 |
| Fam172a | 2 | 2 | 8 | 0 | 1 | 2 | 1 |
| Rbms1 | 4 | 3 | 2 | 2 | 0 | 1 | 1 |
| Zcchc11 | 2 | 4 | 0 | 3 | 1 | 2 | 3 |
| Trpm6 | 6 | 2 | 2 | 4 | 1 | 1 | 2 |
| Cdkal1 | 9 | 6 | 2 | 1 | 1 | 1 | 3 |
| Gm11168 | 175 | 85 | 159 | 23 | 0 | 22 | 1 |
| Gm26870 | 742 | 360 | 705 | 82 | 1 | 80 | 21 |
| Gm10720 | 100 | 48 | 105 | 13 | 0 | 20 | 5 |
| mt-Nd2 | 25 | 11 | 13 | 0 | 0 | 0 | 0 |
| mt-Nd1 | 31 | 17 | 12 | 0 | 0 | 0 | 0 |
| Gm10722 | 126 | 74 | 110 | 19 | 0 | 17 | 2 |
| Gm107171 | 267 | 132 | 249 | 29 | 1 | 23 | 10 |
| mt-Rnr2 | 49 | 26 | 6 | 0 | 0 | 0 | 0 |
| mt-Tv | 52 | 27 | 10 | 0 | 0 | 0 | 0 |
| mt-Rnr1 | 73 | 45 | 15 | 0 | 0 | 0 | 0 |
| mt-Tf | 72 | 45 | 15 | 0 | 0 | 0 | 0 |
| Gm10719 | 202 | 94 | 191 | 27 | 0 | 29 | 8 |
| Gm10718 | 132 | 58 | 122 | 18 | 1 | 13 | 4 |
| Gm17535 | 94 | 51 | 102 | 5 | 0 | 10 | 3 |
| mt-Cytb | 100 | 57 | 35 | 0 | 0 | 0 | 0 |
| mt-Tt | 97 | 57 | 30 | 0 | 0 | 0 | 0 |
| mt-Tp | 98 | 57 | 30 | 0 | 0 | 0 | 0 |
| mt-Nd6 | 91 | 50 | 33 | 0 | 0 | 0 | 0 |
| mt-Te | 91 | 50 | 33 | 0 | 0 | 0 | 0 |
| Gm10715 | 66 | 38 | 71 | 5 | 0 | 8 | 2 |
| mt-Nd5 | 81 | 46 | 33 | 0 | 0 | 0 | 0 |
| mt-Tl2 | 46 | 27 | 23 | 0 | 0 | 0 | 0 |
| mt-Th | 42 | 24 | 23 | 0 | 0 | 0 | 0 |
| mt-Nd4 | 43 | 23 | 23 | 0 | 0 | 0 | 0 |
| mt-Ts2 | 43 | 24 | 23 | 0 | 0 | 0 | 0 |
| mt-Co1 | 23 | 9 | 11 | 0 | 0 | 0 | 0 |
| mt-Tc | 21 | 9 | 11 | 0 | 0 | 0 | 0 |
| mt-Tn | 21 | 9 | 11 | 0 | 0 | 0 | 0 |
| mt-Ty | 21 | 9 | 11 | 0 | 0 | 0 | 0 |
| mt-Ta | 21 | 9 | 11 | 0 | 0 | 0 | 0 |
| mt-Atp8 | 21 | 8 | 11 | 0 | 0 | 0 | 0 |
| mt-Co2 | 21 | 8 | 11 | 0 | 0 | 0 | 0 |
| mt-Td | 21 | 8 | 11 | 0 | 0 | 0 | 0 |
| mt-Tk | 21 | 8 | 11 | 0 | 0 | 0 | 0 |
| mt-Ts1 | 21 | 8 | 11 | 0 | 0 | 0 | 0 |
| mt-Atp6 | 21 | 8 | 11 | 0 | 0 | 0 | 0 |
| Tmem79 | 0 | 0 | 0 | 0 | 0 | 0 | 0 |

Example 6—Mouse and Human Astrocytes Promoter Openness

Figure 23A:
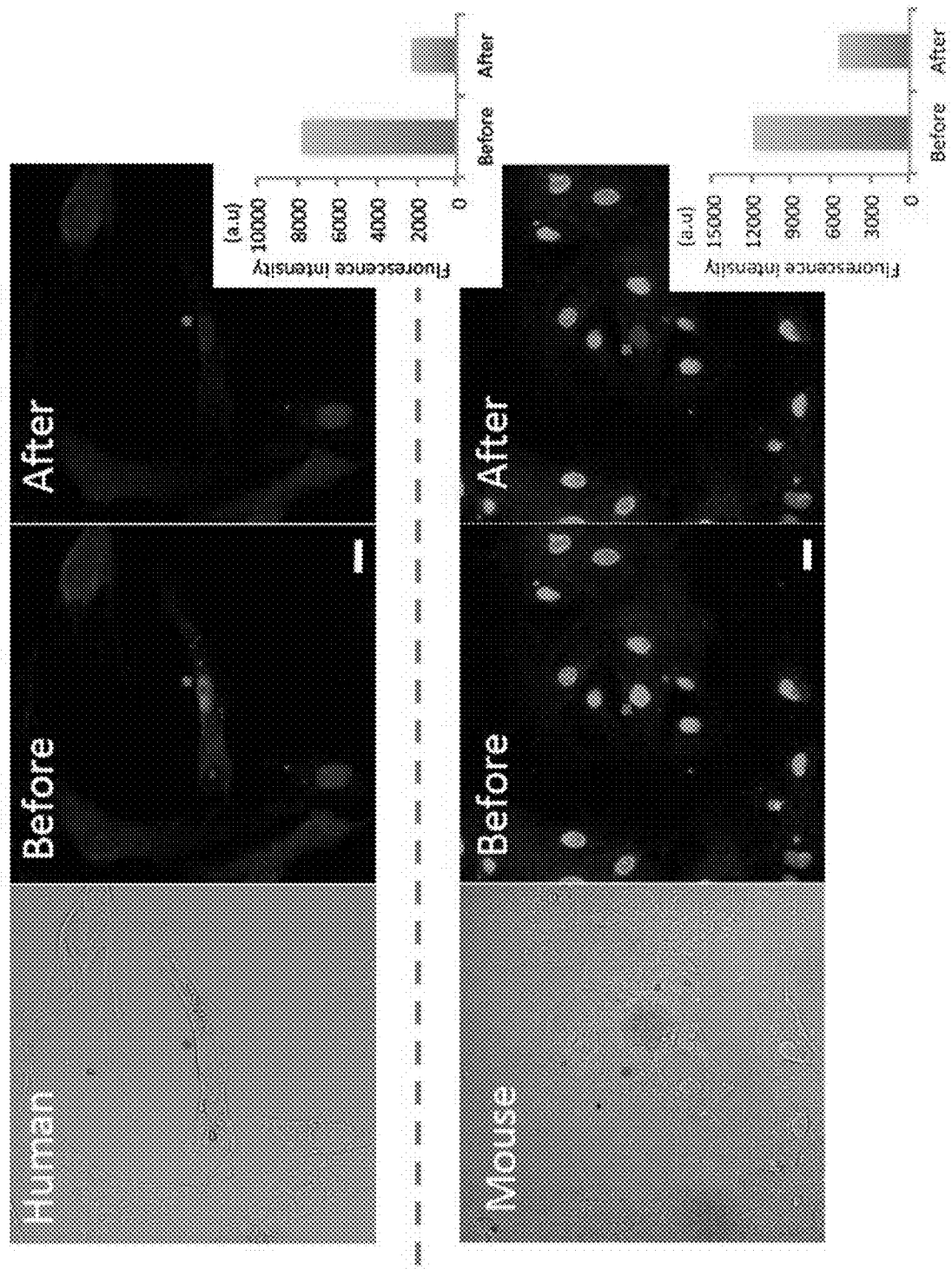
FIGS. 23A-B. CHeX-seq applied to primary astrocyte cultures from mouse and human samples.
Figure 23B:
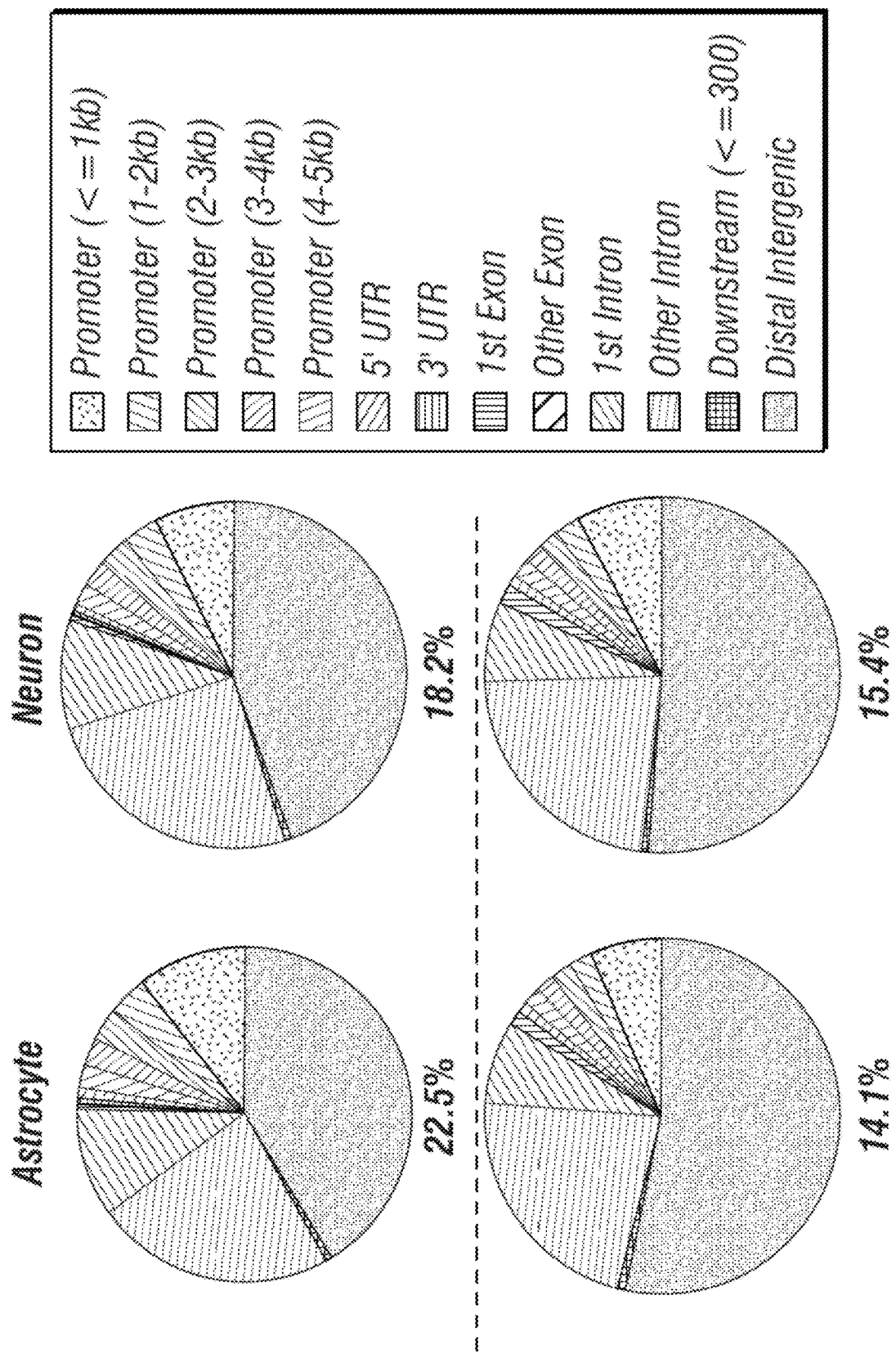

The assay was further performed on neonatal mouse and adult human astrocytes that were in culture for two weeks to compare against neurons of the same species and age (FIG. 23A). Mapping the CHeX-seq reads to the annotated gene model, astrocytes have a higher proportion of CHeX-seq reads in the promoter region of genes than neurons from the same species (FIG. 23B). These data are in accord with earlier studies (Thurman et al., 2012) showing that the chromatin landscape of dividing cells (astrocytes) has more DNase I sensitive open chromatin around the promoter region of genes than terminally differentiated cells (neurons). This is particularly intriguing as the cells cross a wide age span with the mouse cells being neonatal and the human cells were from subjects ranging in age from 50-70 yrs. As noted above, promoter-proximal CHeX-seq priming is more indicative of gene transcription.

Example 7—Open-Chromatin Landscape Across the Mouse Genome

Figure 18:
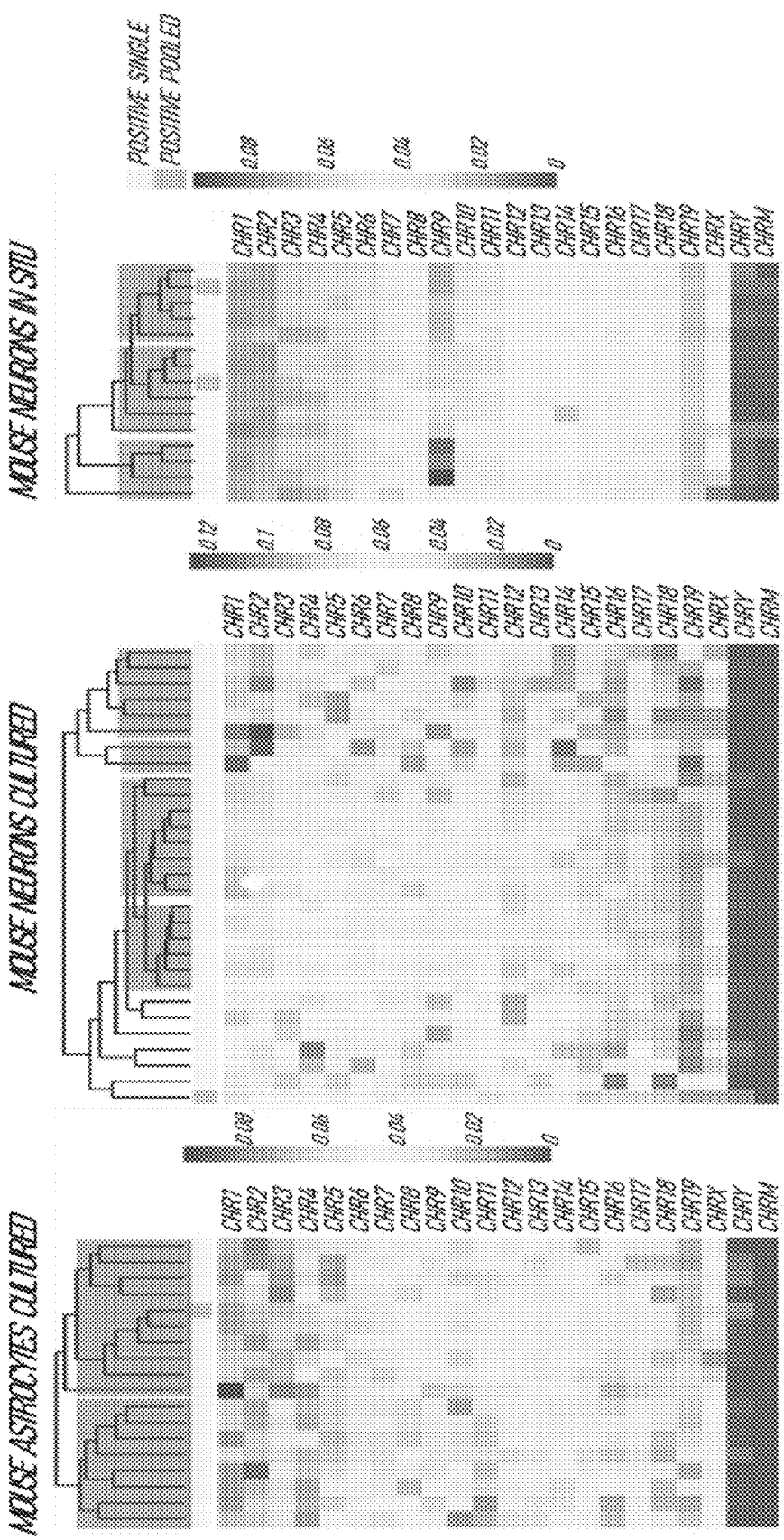
FIG. 18. Chromosomal Landscape of Single Stranded Open-Chromatin Between Cell Types. Distribution of CHeX priming sites by chromosome; color: fraction of priming frequency per chromosome. (Left panel) mouse astrocyte culture, (Middle panel) mouse dispersed neuron cells, (Right panel) mouse neuron section.

As CHeX-seq provides a whole genome view of single-stranded open-chromatin, whether there was differential chromosome accessibility between mouse neurons and astrocytes was tested. In FIG. 18 the CHeX-seq read density for all of the chromosomes (rows) for each of the individual cells (columns) is plotted as a heatmap. Two things come to the fore in looking at these data: 1) the different cell types show different single-stranded open-chromatin densities across the chromosomes, and 2) within a cell type there are groupings of cells that likely correspond to subtypes of the parent cell type. The in situ localized hippocampal neurons (FIG. 18, far right panel) have a greater density of reads on chromosomes I, 2, and 9 then the dispersed cortical neurons or astrocytes. Further there are three subgroupings of these in situ neurons with one group showing less chromosome 9 read density (green rectangles highlighting dendrogram groupings). The astrocytes likewise can be grouped into at least three groups (FIG. 18, far left panel) with one of the discriminators being the density of open-chromatin on chromosome 11. As there are cells from multiple animals in each of the groupings, the groupings are not due to batch effects. These data highlight the ability to characterize cell types based upon open-chromatin status. Why the chromosomal open-chromatin landscape exhibits differences between cells is unclear, but these data reflect the dynamism of the genome. Future studies will elicit a more finely, detailed map of single stranded open-chromatin DNA dynamics.

Figure 11:
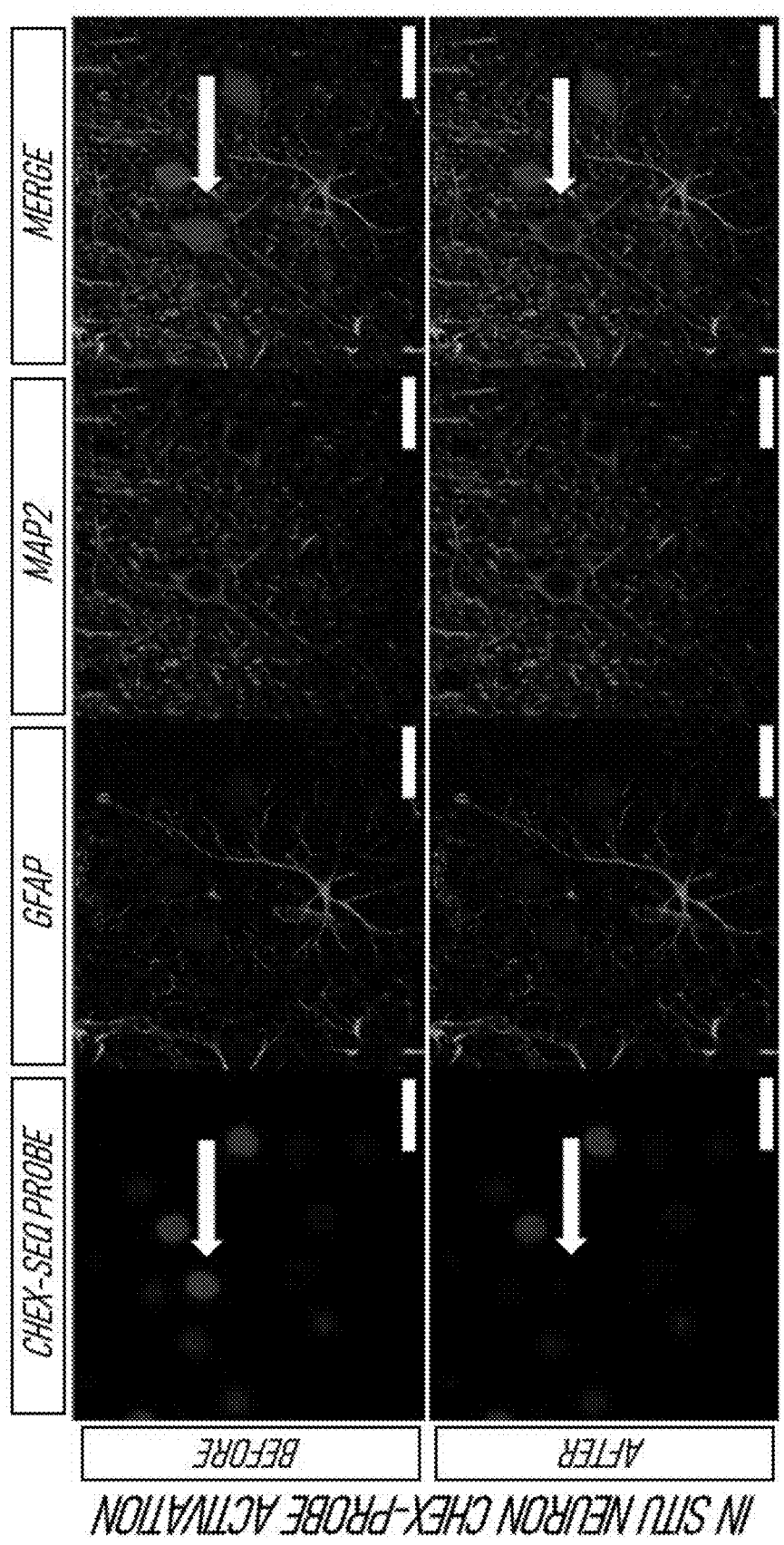
FIG. 11. CHeX-seq oligonucleotide annealing and activation in fixed mouse cortical brain sections. The 130 micron thick sections were fixed with 4% paraformaldehyde for 10 min. The GFAP and Map2 antibodies were applied for overnight. This was followed by addition of fluorescently labeled species specific secondary antibodies. The sections were then incubated with 170 nM CHeX-seq oligonucleotides for 60 min. After washing, individual cells bearing either GFAP or Map2 staining were irradiated with 405 laser line at 80% power. This was followed by cDNA synthesis in situ initiated by addition of DNA polymerase and synthesis buffer. The chicken polyclonal anti-GFAP antibody (Abcam, #ab4674). Rabbit monoclonal anti-Map2 antibody was a gift from Craig Garner, Stanford. Scale bar=20 micron, neuron images are 2× and glial cell 1×. Two mags shown to highlight specificity of CHeX-seq activation.

Example 8—CHeX-Seq and LT-TISA in Immunologically Identified Cells in Fixed Tissue Sections Tissue sections through the mouse brain were used in the performance of the CHeX-seq and LT-TISA procedures upon cells in the fixed slice. Three cell types were assessed including neurons (all neurons with MAP2 (Izant & McIntosh, 1980) staining, inhibitory neurons identified by GAD (Xu et al., 2010) staining, and cholinergic neurons identified by choline acetyltransferase (ChAT) (Houser et al., 1985) staining), glial cells identified by GFAP (Eng et al., 2000) staining, and endothelial cells identified by immunostaining with endothelial barrier antigen (EBA) (Ghabriel et al., 2000). Antibodies to each of these antigens are readily available and have proven to be useful in staining the outline and cytoplasm of their designated cell types. As shown in FIG. 11 sections were stained with antibodies to two or more antigens simultaneously followed by CHeX-seq and/or LT-TISA oligonucleotide hybridization. Shown in FIG. 11, three fluorophores (two for the MAP2 and GFAP antibodies and one for the CHeX-seq oligonucleotide) were used, and as such the fluorescence emission spectrum was distinct for the different fluorophores so that they could be distinguished. Various optimizations will be undertaken, including varying section thickness, varying fixatives and fixation times, incubation times for the various chemical detectors, optimization of the CHeX-seq and LT-TISA cDNA synthesis protocols, and optimization of optical washing so that multiple cells can be analyzed.

Some embodiments include analysis of the chromatin landscape using CHeX-seq analysis in neurons and glia under control conditions followed by fluoxetine treated cells. Pooled cells of a particular cell type are initially assessed followed by single cells to assess variation in responsiveness between cells. These same treatments are performed by multiplexing LT-TISA of cytoplasmic RNA with CHeX-seq, so that both chromatin status and cytoplasmic RNA abundances will be determined. For this, primary cell cultures are be made from mice treated with fluoxetine for 14 days, which is the time required for the clinical effects to be apparent. Single neurons from these primary cultures are taken through CHeX-seq. Once the CHeX-seq baseline data is generated, CHeX-seq are combined with LT-TISA cytoplasmic RNA detection to assess the correlation between RNA abundances and the open-single stranded chromatin status of the treated cells.

Example 9—3D Chromatin-Niche Characterization Around Selected Genes

Figure 12:
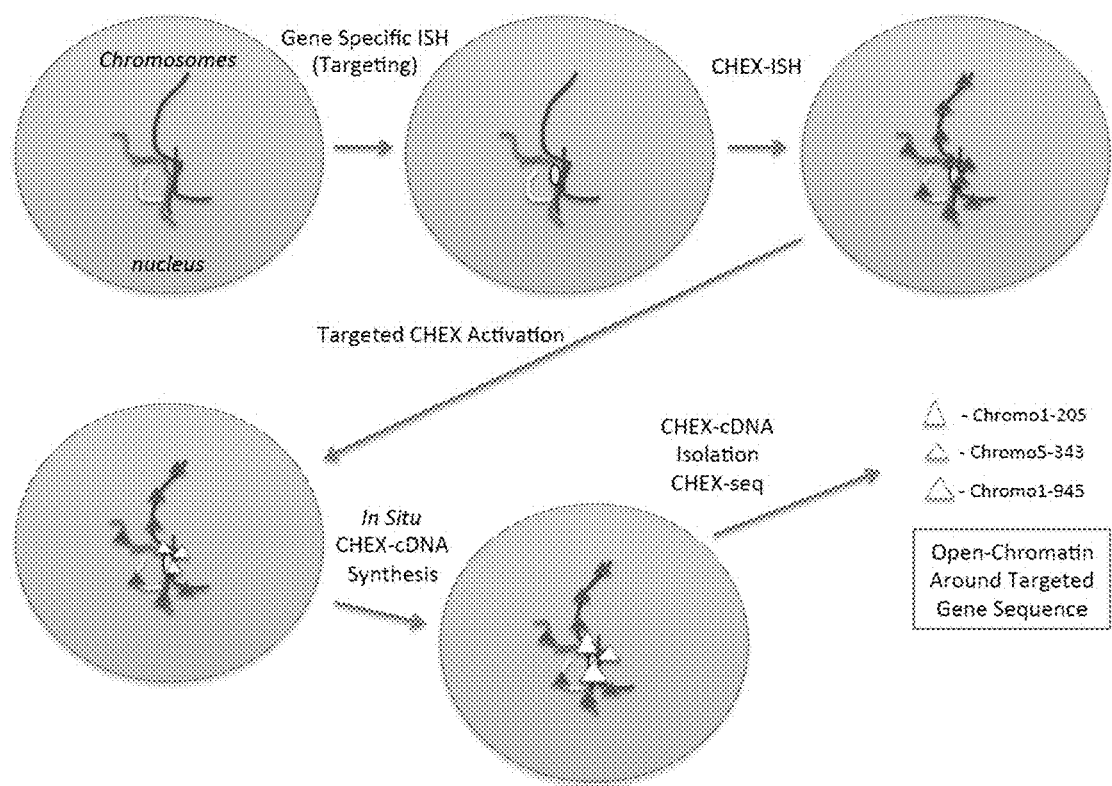
FIG. 12. Schematic of CHeX-seq enabled 3D chromatin niche structural analysis around specific genes. The illustrated method will allow identification of the chromatin regulatory sites that modulate a specific genes expression. The genomic location of the gene of interest will be identified by in situ hybridization using HCR. This will provide a beacon on which to focus the CHeX-seq oligonucleotide activation laser so that only the CHeX-seq oligonucleotides near the site of FISH probe signal will be activated.

In some embodiments, time courses of 3D chromatin change around specific genes associated with depression and known to be fluoxetine responsive may be assessed (FIG. 12). Enhancer elements and other genomic/chromatin regulatory regions that modulate these particular genes will be detectable, as their effects are thought to be exerted by virtue of the genomic organization positioning the regulatory elements close to the gene being regulated. In particular, with the base knowledge of chromatin responsiveness to 14 days of fluoxetine treatment, specifically responsive genes are selected for more detailed analysis of the time-course for 3D chromatin niche modification around those genes. Total CHeX-seq highlights all of the open areas of chromatin but it is impossible to map what open areas are near one another other than through cis-gene localization. As chromosome packing can position genes from distant chromosomal areas including different chromosomes near a gene of interest it is important to define the chromosomal areas near a gene of regulatory interest. Further, monitoring of chromatin niche dynamics over time from initiation of fluoxetine treatment through 2 weeks will detail how these important regulatory niches change over time. In this gene specific iteration of CHeX-seq, fixed cells/tissue is used for fluorescent in situ hybridization to detect the location of specific neuronal genes. This specific gene FISH signal is used to target the multi-photon activation of the CHeX-seq oligonucleotides only at the FISH spotlighted gene.

In one such set of experiments, a FISH probe directed to the open chromatin region near the TSS of the CREB gene, which others have shown is regulated by antidepressant activity, is used (Zhang et al., 2015; Duman, 2013). This probe will produce a fluorescent signal at the CREB TSS that can be imaged. After CREB TSS FISH, the CHeX-seq oligonucleotides is added that will diffuse throughout the tissue and bind to open areas of the cellular chromatin. To specifically assess the chromatin structure around the CREB gene TSS, the CREB FISH is imaged followed by use of two-photon irradiation to locally activate the CHeX-seq oligonucleotides at the site of CREB TSS FISH fluorescence (FIG. 6). The CHeX-seq oligonucleotides activated near the CREB gene be extended from its 3' hydroxyl, thereby allowing for DNA synthesis at single-stranded open chromatin sites near the CREB TSS. This gene niche specific CHeX-seq procedure will identify sequences corresponding to chromatin regions near the site of CREB FISH, which will be candidates for genomic modulator elements (including enhancers) of CREB gene transcription. This approach is generalizable to any in situ hybridization specified genomic DNA site. In addition, it is amenable to higher throughput data generation using optical washing. This assay may also developed for other genetic loci associated with antidepressant drug effects.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references and any other references cited in the present application, to the extent that they provide exemplary procedural or other details supplementary to those set forth herein, are specifically incorporated herein by reference.

Barnes et al., "Crystal Structure of a Transcribing RNA Polymerase II Complex Reveals a Complete Transcription Bubble," *Mol. Cell*, 59:258-269, 2015.

Berton et al., "Essential role of BDNF in the mesolimbic dopamine pathway in social defeat stress," *Science*, 311: 864-868, 2006.

Bieberstein et al., "First exon length controls active chromatin signatures and transcription," *Cell Rep.*, 2:62-68, 2012.

Bjursell et al., "Long regions of single-stranded DNA in human cells," *Nature*, 280:420-423, 1979.

Borrelli et al., "Decoding the epigenetic language of neuronal plasticity," *Neuron*, 60:961-974, 2008.

Boyle et al., "High-resolution mapping and characterization of open chromatin across the genome," *Cell*, 132:311-322, 2008.

Buchhalter & Dichter, "Electrophysiological comparison of pyramidal and stellate nonpyramidal neurons in dissociated cell culture of rat hippocampus," *Brain Res. Bull.*, 26:333-338, 1991.

Buenrostro et al., "Transposition of native chromatin for fast and sensitive epigenomic profiling of open chromatin, DNA-binding proteins and nucleosome position," *Nat. Methods*, 10:1213-1218, 2013.

Buenrostro et al., "Single-cell chromatin accessibility reveals principles of regulatory variation," *Nature*, 523: 486-490, 2015.

Chen et al., "Variant GADL1 and response to lithium therapy in bipolar I disorder," *N. Engl. J. Med.*, 370:119-128, 2014.

Choi et al., "Programmable in situ amplification for multiplexed imaging of mRNA expression," *Nat. Biotechnol.*, 28:1208-1212, 2010.

Choi et al., "Mapping a multiplexed zoo of mRNA expression," *Development*, 143:3632-3637, 2016.

Clark et al., "scNMT-seq enables joint profiling of chromatin accessibility DNA methylation and transcription in single cells," *Nat. Commun.*, 9:781, 2018.

Core et al., "Analysis of nascent RNA identifies a unified architecture of initiation regions at mammalian promoters and enhancers," *Nat. Genet.*, 46:1311-1320, 2014.

Cornelison & Wold, "Single-cell analysis of regulatory gene expression in quiescent and activated mouse skeletal muscle satellite cells," *Developmental Biology*, 191:270-283, 1997.

Costa et al., "Epigenetic targets in GABAergic neurons to treat schizophrenia," *Adv. Pharmacol.*, 54:95-117, 2006.

Crino et al., "Embryonic neuronal markers in tuberous sclerosis: single-cell molecular pathology," *Proc. Natl. Acad. Sci. U.S.A.*, 93:14152-14157, 1996.

Cusanovich et al., "Multiplex single cell profiling of chromatin accessibility by combinatorial cellular indexing," *Science*, 348:910-914, 2015.

Danko et al., "Identification of active transcriptional regulatory elements from GRO-seq data," *Nat. Methods*, 12:433-438, 2015.

Dekker et al., "Exploring the three-dimensional organization of genomes: interpreting chromatin interaction data," *Nat. Rev. Genet.*, 14:390-403, 2013.

de la Torre-Ubieta & Bonni, "Transcriptional regulation of neuronal polarity and morphogenesis in the mammalian brain," *Neuron*, 72:22-40, 2011.

de Wit & de Laat, "A decade of 3C technologies: insights into nuclear organization," *Genes Dev.*, 26:11-24, 2012.

Dueck et al., "Deep sequencing reveals cell-type-specific patterns of single-cell transcriptome variation," *Genome Biol.*, 16:122, 2015.

Dueck et al., "Variation is function: Are single cell differences functionally important?: Testing the hypothesis that single cell variation is required for aggregate function," *Bioessays*, 38:172-180, 2016.

Duman, "Remodeling chromatin and synapses in depression," *Nat. Med.*, 19:267, 2013.

Eberwine et al., "Complementary DNA synthesis in situ: methods and applications," *Methods Enzymol.*, 216:80-100, 1992.

Eberwine et al., "Analysis of gene expression in single live neurons," *Proc. Natl. Acad. Sci. U.S.A.*, 89:3010-3014, 1992.

Ellis et al., "Transcriptome analysis of cortical tissue reveals shared sets of downregulated genes in autism and schizophrenia," *Transl. Psychiatry*, 6:e817, 2016.

Eng et al., "Glial fibrillary acidic protein: GFAP-thirty-one years (1969-2000)," *Neurochem. Res.*, 25:1439-1451, 2000.

Feng et al., "Identifying ChIP-seq enrichment using MACS," *Nat. Protoc.*, 7:1728-1740, 2012.

Fishilevich et al., "GeneHancer: genome-wide integration of enhancers and target genes in GeneCards," *Database* (Oxford), 2017:bax028, 2017.

Fleischer et al., "Identification and characterization of three new components of the mSin3A corepressor complex," *Mol. Cell Biol.*, 23:3456-3467, 2003.

Frankle et al., "The synaptic hypothesis of schizophrenia," *Neuron*, 39:205-216, 2003.

Fullard et al., "Open chromatin profiling of human postmortem brain infers functional roles for non-coding schizophrenia loci," *Hum. Mol. Genet.*, 26:1942-1951, 2017.

Ghabriel et al., "Immunological targeting of the endothelial barrier antigen (EBA) in vivo leads to opening of the blood-brain barrier," *Brain Res.*, 878:127-135, 2000.

Gribble et al., "Cytogenetics of the chronic myeloid leukemia-derived cell line K562: karyotype clarification by multicolor fluorescence in situ hybridization, comparative genomic hybridization, and locus-specific fluorescence in situ hybridization," *Cancer Genet. Cytogenet.*, 118:1-8, 2000.

Guidotti et al., "Epigenetic GABAergic targets in schizophrenia and bipolar disorder," *Neuropharmacology*, 60:1007-1016, 2011.

Hashimshony et al., "CEL-Seq: single-cell RNA-Seq by multiplexed linear amplification," *Cell Rep.*, 2:666-673, 2012.

Hayles et al., "A genome-wide resource of cell cycle and cell shape genes of fission yeast," *Open Biol.*, 3: 130053, 2013.

Hegedus et al., "Endogenous single-strand DNA breaks at RNA polymerase II promoters in *Saccharomyces cerevisiae*," *Nucleic Acids Res.*, 46:10649-10668, 2018.

Heinz et al., "Simple combinations of lineage-determining transcription factors prime cis-regulatory elements required for macrophage and B cell identities," *Mol. Cell.*, 38:576-589, 2010.

Heller et al., "Locus-specific epigenetic remodeling controls addiction- and depression-related behaviors," *Nat. Neurosci.*, 17:1720-1727, 2014.

Houser et al., "Immunocytochemical localization of choline acetyltransferase in rat cerebral cortex: a study of cholinergic neurons and synapses," *J. Comp. Neurol.*, 234:17-34, 1985.

Huang & Akbarian, "GAD1 mRNA expression and DNA methylation in prefrontal cortex of subjects with schizophrenia," *PLoS One*, 2:e809, 2007.

Insel & Wang, "Rethinking mental illness," *JAMA*, 303: 1970-1971, 2010.

Islam et al., "Characterization of the single-cell transcriptional landscape by highly multiplex RNA-seq," *Genome Res.*, 21:1160-1167, 2011.

Islam et al., "Highly multiplexed and strand-specific single-cell RNA 5' end sequencing," *Nat. Protoc.*, 7:813-828, 2012.

Izant & McIntosh, "Microtubule-associated proteins: a monoclonal antibody to MAP2 binds to differentiated neurons," *Proc. Natl. Acad. Sci. U.S.A.*, 77:4741-4745, 1980.

Kent et al., "The human genome browser at UCSC," *Genome Res.*, 12:996-1006, 2002.

Khan & Zhang, "dbSUPER: a database of super-enhancers in mouse and human genome," *Nucleic Acids Res.*, 44:D164-171, 2016.

Kim & Eberwine, "RNA: state memory and mediator of cellular phenotype," *Trends Cell Biol.*, 20:311-318, 2010.

Kolovos et al., "Targeted Chromatin Capture (T2C): a novel high resolution high throughput method to detect genomic interactions and regulatory elements," *Epigenetics Chromatin*, 7:10, 2014.

Kouzine et al., "Permanganate/S1 Nuclease Footprinting Reveals Non-B DNA Structures with Regulatory Potential across a Mammalian Genome," *Cell Syst.*, 4:344-356 e347, 2017.

Kozlenkov et al., "Differences in DNA methylation between human neuronal and glial cells are concentrated in enhancers and non-CpG sites," *Nucleic Acids Res.*, 42:109-127, 2014.

Kozlenkov et al., "Substantial DNA methylation differences between two major neuronal subtypes in human brain," *Nucleic Acids Res.*, 44:2593-2612, 2016.

Kucej et al., "Mitochondrial nucleoids undergo remodeling in response to metabolic cues," *J. Cell Sci.*, 121:1861-1868, 2008.

Kumar et al., "Chromatin remodeling is a key mechanism underlying cocaine-induced plasticity in striatum," *Neuron*, 48:303-314, 2005.

Lai et al., "Integrator mediates the biogenesis of enhancer RNAs," *Nature*, 525:399-403, 2015.

Lee et al., "Fluorescent in situ sequencing (FISSEQ) of RNA for gene expression profiling in intact cells and tissues," *Nat. Protoc.*, 10:442-458, 2015.

Lladser et al., "RNA Pol II transcription model and interpretation of GRO-seq data," *J. Math Biol.*, 74:77-97, 2017.

Louder et al., "Structure of promoter-bound TFIID and model of human pre-initiation complex assembly," *Nature*, 531:604-609, 2016.

Marom et al., "mtDNA Chromatin-like Organization Is Gradually Established during Mammalian Embryogenesis," *iScience*, 12:141-151, 2019.

Martinowich et al., "DNA methyl ation-related chromatin remodeling in activity-dependent BDNF gene regulation," *Science*, 302:890-893, 2003.

Maurano et al., "Systematic localization of common disease-associated variation in regulatory DNA," *Science*, 337: 1190-1195, 2012.

McCarthy et al., "De novo mutations in schizophrenia implicate chromatin remodeling and support a genetic overlap with autism and intellectual disability," *Mol. Psychiatry*, 19:652-658, 2014.

Miyashiro et al., "On the nature and differential distribution of mRNAs in hippocampal neurites: implications for neuronal functioning," *Proc. Natl. Acad. Sci. U.S.A.*, 91:10800-10804, 1994.

Miyashiro et al., "RNA cargoes associating with FMRP reveal deficits in cellular functioning in Fmr1 null mice," *Neuron*, 37:417-431, 2003.

Miyashiro & Eberwine, "Identification of RNA cargoes by antibody-positioned RNA amplification," *Cold Spring Harb. Protoc.*, 2015:434-441, 2015.

Mo et al., "Epigenomic Signatures of Neuronal Diversity in the Mammalian Brain," *Neuron*, 86:1369-1384, 2015.

Moffitt & Zhuang, "RNA Imaging with Multiplexed Error-Robust Fluorescence In Situ Hybridization (MERFISH)," *Methods Enzymol.*, 572:1-49, 2016.

Montefiori et al., "Reducing mitochondrial reads in ATAC-seq using CRISPR/Cas9," *Sci. Rep.*, 7:2451, 2017.

Rao et al., "A 3D map of the human genome at kilobase resolution reveals principles of chromatin looping," *Cell*, 159:1665-1680, 2014.

Renthal et al., "Histone deacetylase 5 epigenetically controls behavioral adaptations to chronic emotional stimuli," *Neuron*, 56:517-529, 2007.

Rotem et al., "Single-cell ChIP-seq reveals cell subpopulations defined by chromatin state," *Nat. Biotechnol.*, 33:1165-1172, 2015.

Roussos et al., "A role for noncoding variation in schizophrenia," *Cell Rep.*, 9:1417-1429, 2014.

Ruzicka et al., "Circuit- and Diagnosis-Specific DNA Methylation Changes at gamma-Aminobutyric Acid-Related Genes in Postmortem Human Hippocampus in Schizophrenia and Bipolar Disorder," *JAMA Psychiatry*, 72:541-551, 2015.

SantaLucia & Hicks, "The thermodynamics of DNA structural motifs," *Annu. Rev. Biophys. Biomol. Struct.*, 33:415-440, 2004.

Scheer et al., "High sensitivity immunolocalization of double and single-stranded DNA by a monoclonal antibody," *Eur. J Cell Biol.*, 43:358-371, 1987.

Seifuddin et al., "Systematic review of genome-wide gene expression studies of bipolar disorder," *BMC Psychiatry*, 13:213, 2013.

Shah et al., "seqFISH Accurately Detects Transcripts in Single Cells and Reveals Robust Spatial Organization in the Hippocampus," *Neuron*, 94:752-758 el, 2017.

Sharma et al., "Valproic acid and chromatin remodeling in schizophrenia and bipolar disorder: preliminary results from a clinical population," Schizophr. Res., 88:227-231, 2006.

Sherwood et al., "Discovery of directional and nondirectional pioneer transcription factors by modeling DNase profile magnitude and shape," Nat. Biotechnol., 32:171-178, 2014.

Simonis et al., "Nuclear organization of active and inactive chromatin domains uncovered by chromosome conformation capture-on-chip (4C)," Nat. Genet., 38:1348-1354, 2006.

Spaethling et al., "Primary Cell Culture of Live Neurosurgically Resected Aged Adult Human Brain Cells and Single Cell Transcriptomics," Cell Rep., 18:791-803, 2017.

Sun et al., "ACF chromatin-remodeling complex mediates stress-induced depressive-like behavior," Nat. Med., 21:1146-1153, 2015.

Szlachta et al., "Alternative DNA secondary structure formation affects RNA polymerase II promoter-proximal pausing in human," Genome Biol., 19:89, 2018.

Tay et al., "Single-cell NF-kappaB dynamics reveal digital activation and analogue information processing," Nature, 466:267-271, 2010.

Tecott et al., "In situ transcription: specific synthesis of complementary DNA in fixed tissue sections," Science, 240:1661-1664, 1988.

Thurman et al., "The accessible chromatin landscape of the human genome," Nature, 489:75-82, 2012.

Tomaska et al., "Mitochondrial single-stranded DNA-binding proteins: in search for new functions," Biol. Chem., 382:179-186, 2001.

Tsankova et al., "Epigenetic regulation in psychiatric disorders," Nat. Rev. Neurosci., 8:355-367, 2007.

Van Gelder et al., "Amplified RNA synthesized from limited quantities of heterogeneous cDNA," Proc. Natl. Acad. Sci. U.S.A., 87:1663-1667, 1990.

Vanhooren et al., "Mammalian peroxisomal acyl-CoA oxidases. I. Molecular characterization of rat pristanoyl-CoA oxidase," Ann. N. Y. Acad. Sci., 804:674-675, 1996.

Varodayan & Harrison, "HSF1 transcriptional activity mediates alcohol induction of Vamp2 expression and GABA release," Front. Integr. Neurosci., 7:89, 2013.

Vasquez et al., "Manipulating the mammalian genome by homologous recombination," Proc. Natl. Acad. Sci. U.S.A., 98:8403-8410, 2001.

Vialou et al., "Epigenetic mechanisms of depression and antidepressant action," Annu. Rev. Pharmacol. Toxicol., 53:59-87, 2013.

Visel et al., "VISTA Enhancer Browser—a database of tissue-specific human enhancers," Nucleic Acids Res., 35:D88-92, 2007.

Wang et al., "A source of the single-stranded DNA substrate for activation-induced deaminase during somatic hypermutation," Nat. Commun., 5:4137, 2014.

Wei et al., "Functional consequences of bidirectional promoters," Trends Genet., 27:267-276, 2011.

Wu et al., "Quantitative assessment of single-cell RNA-sequencing methods," Nat. Methods, 11:41-46, 2014.

Xiao et al., "The DNA methylome and transcriptome of different brain regions in schizophrenia and bipolar disorder," PLoS One, 9:e95875, 2014.

Xu et al., "Immunochemical characterization of inhibitory mouse cortical neurons: three chemically distinct classes of inhibitory cells," J. Comp. Neurol., 518:389-404, 2010.

Yu et al., "Chromatin dynamics during the differentiation of long-term hematopoietic stem cells to multipotent progenitors," Blood Adv., 1:887-898, 2017.

Zeisel et al., "Molecular Architecture of the Mouse Nervous System," Cell, 174:999-1014 e1022, 2018.

Zhang et al., "Increased Variability of Genomic Transcription in Schizophrenia," Sci. Rep., 5:17995, 2015.

Zhao et al., "CrossMap: a versatile tool for coordinate conversion between genome assemblies," Bioinformatics, 30:1006-1007, 2014.

Zhou & Paull, "Direct measurement of single-stranded DNA intermediates in mammalian cells by quantitative polymerase chain reaction," Anal Biochem., 479:48-50, 2015.

Zhu et al., "Genome-wide chromatin state transitions associated with developmental and environmental cues," Cell, 152:642-654, 2013.

Ziller et al., "Dissecting neural differentiation regulatory networks through epigenetic footprinting," Nature, 518:355-359, 2015.

What is claimed is:

1. A method for identifying regions of open DNA in a cell, the method comprising:
   (a) introducing a population of oligonucleotide molecules into the cell, wherein each molecule comprises, from 5' to 3', an amplification segment, an index barcode segment, a hybridization segment, and a reversibly terminating nucleotide;
   (b) incubating the cell under conditions to allow for the hybridization segments of the population of oligonucleotide molecules to anneal to regions of open DNA;
   (c) activating at least a portion of the annealed oligonucleotide molecules to expose an extendable 3' hydroxy group; and
   (d) synthesizing cDNAs from the open DNA by extending the activated oligonucleotide molecules from their extendable 3' hydroxy groups.

2. The method of claim 1, wherein the amplification segment is an RNA polymerase promoter.

3. The method of claim 1, wherein the amplification segment is a primer binding site.

4. The method of claim 1, wherein the amplification segment comprises between about seven and about fifty nucleotides.

5. The method of claim 1, wherein the hybridization segments comprise a degenerate nucleotide sequence.

6. The method of claim 1, wherein each nucleic acid molecule in the population comprises a unique hybridization segment sequence.

7. The method of claim 1, wherein the hybridization segments comprise one or more known nucleotide sequence.

8. The method of claim 7, wherein each known nucleotide sequence is complementary to a target genomic or mitochondrial DNA sequence.

9. The method of claim 1, wherein the hybridization segments comprise between about seven and about thirty nucleotides.

10. The method of claim 1, wherein the hybridization segments comprise about fifteen nucleotides.

11. The method of claim 1, wherein the index barcode segment is positioned between the amplification segment and the hybridization segment.

12. The method of claim 11, further comprising a spacer segment positioned between the amplification segment and the index barcode segment.

13. The method of claim 1, wherein the reversibly terminating nucleotide is a photoactivatable terminating nucleotide.

14. The method of claim 13, wherein the photoactivatable terminating nucleotide comprises a structure of the formula:

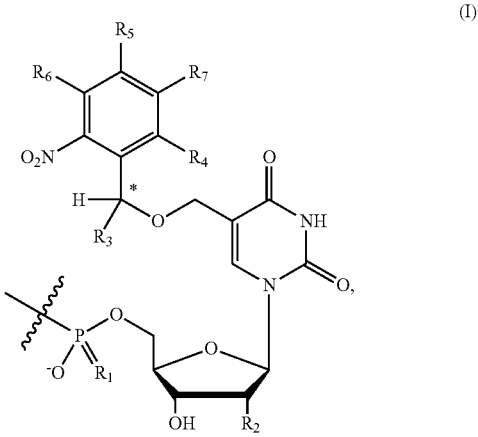

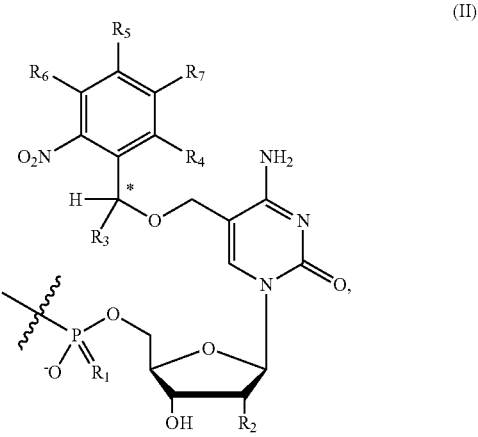

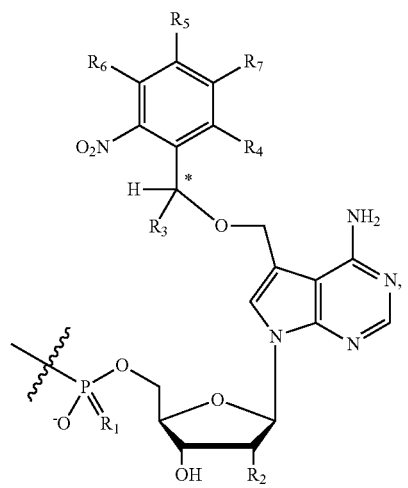

(III)

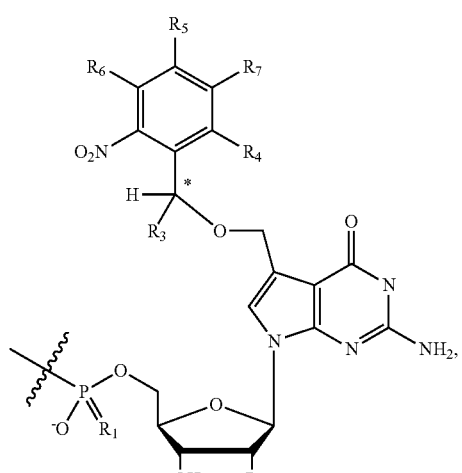

(IV)

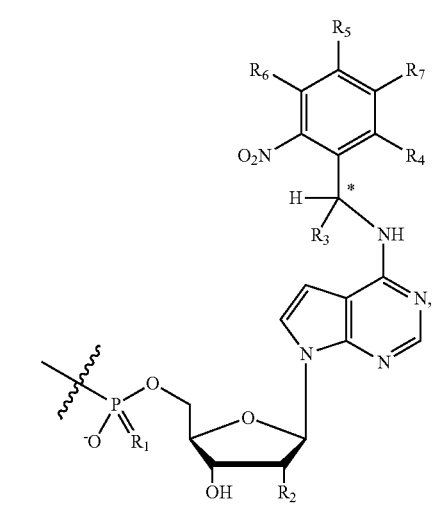

(V)

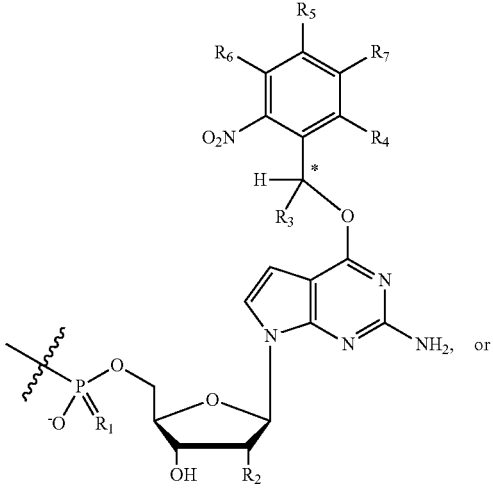

(VI)

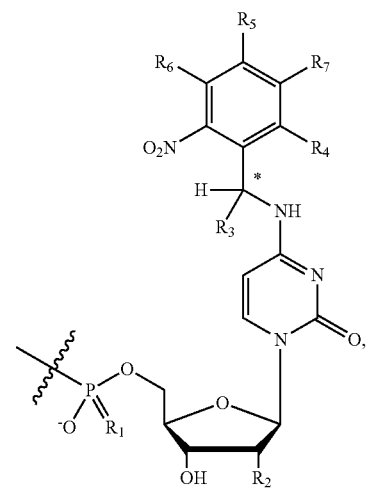

(VII)

wherein:

$R_1$ is O or S;

$R_2$ is hydrogen or hydroxy;

$R_3$ is alkyl$_{(C \leq 8)}$ or substituted alkyl$_{(C \leq 8)}$;

$R_4$ is hydrogen, hydroxy, halo, amino, nitro, cyano, azido or mercapto;

alkyl$_{(C \leq 56)}$, acyl$_{(C \leq 56)}$, alkoxy$_{(C \leq 6)}$, acyloxy$_{(C \leq 56)}$, alkylamino$_{(C \leq 6)}$, dialkyl-amino$_{(C \leq 6)}$, amido$_{(C \leq 6)}$, or a substituted version of any of these groups;

$R_5$, $R_6$, and $R_7$ are each independently:

hydrogen, hydroxy, halo, amino, nitro, cyano, azido or mercapto;

alkyl$_{(C \leq 6)}$, alkenyl$_{(C \leq 6)}$, alkynyl$_{(C \leq 6)}$, aryl$_{(C \leq 6)}$, aralkyl$_{(C \leq 8)}$, heteroaryl$_{(C \leq 6)}$, acyl$_{(C \leq 56)}$, alkoxy$_{(C \leq 56)}$, acyloxy$_{(C \leq 6)}$, alkylamino$_{(C \leq 6)}$, dialkyl-amino$_{(C \leq 6)}$, amido$_{(C \leq 6)}$, or a substituted version of any of these groups;

a group of formula:

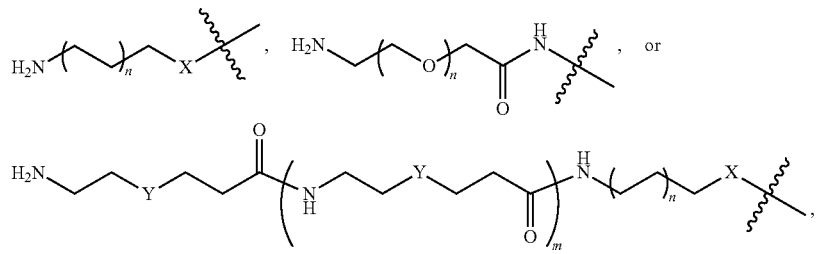

wherein
X is
—O—, —S—, or —NH—; or
alkanediyl$_{(C \leq 12)}$, alkenediyl$_{(C \leq 12)}$, alkynediyl$_{(C \leq 12)}$, or a substituted version of any of these groups;
Y is —O—, —NH—, alkanediyl$_{(C \leq 12)}$ or substituted alkane-diyl$_{(C \leq 12)}$;
n is an integer from 0-6; and
m is an integer from 0-6; or
a -linker-reporter;
or a tautomer or optical isomer thereof.

15. The method of claim 14, wherein R$_7$ is methoxy.

16. The method of claim 15, wherein the photoactivatable terminating nucleotide comprises a structure of the formula:

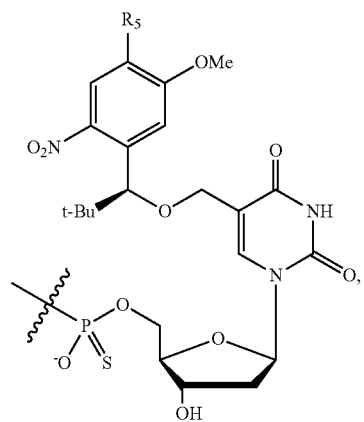

wherein R$_5$ is a -linker-reporter.

17. The method of claim 16, wherein the photoactivatable terminating nucleotide comprises a structure of the formula:

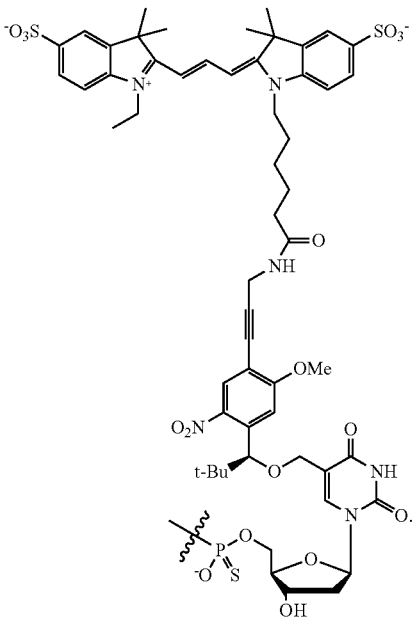

18. The method of claim 1, wherein the open DNA is open chromatin, wherein activation comprises exposing the nucleus to ultraviolet light.

19. The method of claim 18, wherein activation is performed at a particular site within the nucleus.

20. The method of claim 19, wherein the particular site is identified based on localization of a gene of interest.

21. The method of claim 20, wherein the gene of interest is localized using in situ hybridization.

22. The method of claim 21, wherein activation at the gene of interest comprises exposing the particular site to multi-photon excitation based on the in situ hybridization signal.

23. The method of claim 1, wherein the method further comprises determining whether regions of open DNA are transcriptionally active, wherein the method further comprises, after process (d):
(e) incubating the cell under conditions which substantially allow only unextended oligonucleotides to denature from the open DNA;
(f) inactivating or removing the denatured unextended oligonucleotides;
(g) introducing a second population of oligonucleotide molecules into the cell, wherein each molecule comprises, from 5' to 3', an amplification segment, an index barcode segment that is distinct from the index barcode segment of the oligonucleotide molecules introduced in process (a), a hybridization segment, and a reversibly terminating nucleotide;

(h) incubating the cell under conditions to allow for the hybridization segments of the population of oligonucleotide molecules to anneal to expressed RNAs;

(i) activating at least a portion of the annealed oligonucleotide molecules to expose an extendable 3' hydroxy group; and (j) synthesizing cDNAs from the expressed RNAs by extending the activated oligonucleotide molecules from their extendable 3' hydroxy groups.

24. The method of claim 23, wherein activation comprises exposing the cytoplasm to ultraviolet light.

* * * * *